US012597513B2

(12) United States Patent
Goldstein et al.

(10) Patent No.: US 12,597,513 B2
(45) Date of Patent: *\*Apr. 7, 2026**

(54) METHOD AND DEVICE FOR AUDIO RECORDING

(71) Applicant: ST FamTech, LLC, Delray Beach, FL (US)

(72) Inventors: Steven W. Goldstein, Delray Beach, FL (US); John Usher, Devon (GB); Marc Andre Boillot, Plantation, FL (US)

(73) Assignee: ST FamTech, LLC, Delray Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/372,697

(22) Filed: Sep. 26, 2023

(65) Prior Publication Data

US 2024/0013904 A1 Jan. 11, 2024

Related U.S. Application Data

(60) Continuation of application No. 17/973,536, filed on Oct. 26, 2022, which is a continuation of application (Continued)

(51) Int. Cl.
*G16H 40/60* (2018.01)
*A61B 5/00* (2006.01)
(Continued)

(52) U.S. Cl.
CPC ........... *G16H 40/60* (2018.01); *A61B 5/0205* (2013.01); *A61B 5/1117* (2013.01);
(Continued)

(58) Field of Classification Search
CPC .......... H04N 11/00; G01H 3/14; H04R 29/00; H04R 29/004; H04R 3/005; H04R 5/033;
(Continued)

(56) References Cited

U.S. PATENT DOCUMENTS 2,803,308 A 8/1957 Mattia
3,028,454 A 4/1962 Kohorn
(Continued)

FOREIGN PATENT DOCUMENTS

AU 2006200446 2/2006
CA 2215764 11/1996
(Continued)

OTHER PUBLICATIONS

Samsung Electronics Co., Ltd., and Samsung Electronics, America, Inc., v. Staton Techiya, LLC, IPR2022-00282, Dec. 21, 2021.
(Continued)

*Primary Examiner* — Ahmad F. Matar
*Assistant Examiner* — Sabrina Diaz
(74) *Attorney, Agent, or Firm* — Akerman LLP; Peter A. Chiabotti

(57) ABSTRACT

An earpiece, with two ambient sound microphones and an ear canal microphone detects whether the user is speaking and if so then detects an event, saving audio to memory.

20 Claims, 11 Drawing Sheets

Related U.S. Application Data

No. 17/061,722, filed on Oct. 2, 2020, now Pat. No. 11,605,456, which is a continuation of application No. 16/781,286, filed on Feb. 4, 2020, now Pat. No. 10,856,092, which is a continuation of application No. 16/260,454, filed on Jan. 29, 2019, now Pat. No. 10,616,702, which is a continuation of application No. 15/790,771, filed on Oct. 23, 2017, now Pat. No. 10,212,528, which is a continuation of application No. 15/137,730, filed on Apr. 25, 2016, now Pat. No. 9,900,718, which is a continuation of application No. 14/576,236, filed on Dec. 19, 2014, now Pat. No. 9,323,899, which is a continuation of application No. 14/048,324, filed on Oct. 8, 2013, now Pat. No. 8,918,141, which is a division of application No. 13/556,509, filed on Jul. 24, 2012, now Pat. No. 8,582,782, which is a continuation of application No. 12/024,842, filed on Feb. 1, 2008, now Pat. No. 8,254,591.

(60) Provisional application No. 60/887,800, filed on Feb. 1, 2007.

(51) Int. Cl.

| | |
|---|---|
| *A61B 5/0205* | (2006.01) |
| *A61B 5/11* | (2006.01) |
| *A61B 5/145* | (2006.01) |
| *G16H 10/20* | (2018.01) |
| *G16H 20/10* | (2018.01) |
| *G16H 50/20* | (2018.01) |
| *G16H 50/30* | (2018.01) |
| *H04M 1/65* | (2006.01) |
| *H04R 1/10* | (2006.01) |
| *H04R 25/00* | (2006.01) |
| *H04R 29/00* | (2006.01) |
| *A61B 5/021* | (2006.01) |
| *A61B 5/024* | (2006.01) |

(52) U.S. Cl.
CPC ........ *A61B 5/14542* (2013.01); *A61B 5/6817* (2013.01); *G16H 10/20* (2018.01); *G16H 20/10* (2018.01); *G16H 50/20* (2018.01); *G16H 50/30* (2018.01); *H04M 1/65* (2013.01); *H04R 1/1091* (2013.01); *H04R 25/70* (2013.01); *H04R 29/004* (2013.01); *A61B 5/021* (2013.01); *A61B 5/024* (2013.01); *H04R 2201/109* (2013.01); *H04R 2410/05* (2013.01); *H04R 2499/11* (2013.01)

(58) Field of Classification Search
CPC .... H04R 5/02; H04R 5/0335; H04R 2420/07; H04R 5/04; H04R 9/063; H04R 1/1083; H04R 1/1008; H04R 1/1041; H04R 1/1016; H04R 1/24; H04R 1/26; H04R 1/403; H04R 1/1066; H04R 1/1091; H04R 25/70; H04R 2201/109; H04R 2410/05; H04R 2499/11; H04S 7/40; A61F 2011/145; A61F 11/08; G10K 11/1788; H04M 1/65; A61B 5/0205; A61B 5/1117; A61B 5/14542; A61B 5/6817; A61B 5/021; A61B 5/024; G16H 40/60; G16H 50/30; G16H 50/20; G16H 20/10
USPC .............................. 381/74, 56, 72, 182, 370
See application file for complete search history.

(56) References Cited

U.S. PATENT DOCUMENTS

| | | |
|---|---|---|
| 3,729,598 A | 4/1973 | Tegt |
| 3,876,843 A | 4/1975 | Moen |
| 4,041,256 A | 8/1977 | Ohta |
| 4,054,749 A | 10/1977 | Suzuki et al. |
| 4,088,849 A | 5/1978 | Usami et al. |
| 4,455,677 A | 6/1984 | Fox |
| 4,533,795 A | 8/1985 | Baumhauer |
| 4,555,677 A | 11/1985 | Beesley |
| 4,596,902 A | 6/1986 | Gilman |
| 4,827,458 A | 5/1989 | D'Alayer de Costemore D'Arc |
| 4,891,841 A | 1/1990 | Bohn |
| 4,941,187 A | 7/1990 | Slater |
| 4,947,432 A | 8/1990 | Topholm |
| 4,947,440 A | 8/1990 | Bateman et al. |
| 5,002,151 A | 3/1991 | Oliveira et al. |
| 5,027,410 A | 6/1991 | Williamson et al. |
| 5,033,090 A | 7/1991 | Weinrich |
| 5,182,774 A | 1/1993 | Bourk |
| 5,202,927 A | 4/1993 | Topholm |
| 5,204,906 A | 4/1993 | Nohara |
| 5,208,867 A | 5/1993 | Stites, III |
| 5,251,263 A | 10/1993 | Andrea |
| 5,259,033 A | 11/1993 | Goodings |
| 5,267,321 A | 11/1993 | Langberg |
| 5,276,740 A | 1/1994 | Inanaga et al. |
| 5,298,692 A | 3/1994 | Ikeda |
| 5,317,273 A | 5/1994 | Hanson |
| 5,327,506 A | 7/1994 | Stites |
| 5,345,430 A | 9/1994 | Moe |
| 5,390,254 A | 2/1995 | Adelman |
| 5,430,826 A | 7/1995 | Webster |
| 5,473,684 A | 12/1995 | Bartlett |
| 5,479,522 A | 12/1995 | Lindemann |
| 5,524,056 A | 6/1996 | Killion et al. |
| 5,526,819 A | 6/1996 | Martin |
| 5,528,739 A | 6/1996 | Lucas et al. |
| 5,539,831 A | 7/1996 | Harley |
| 5,550,923 A | 8/1996 | Hotvet |
| 5,557,659 A | 9/1996 | Hyde-Thomson |
| 5,577,511 A | 11/1996 | Killion |
| 5,606,621 A | 2/1997 | Reiter et al. |
| 5,632,002 A | 5/1997 | Hashimoto et al. |
| 5,636,351 A | 6/1997 | Lee |
| 5,647,011 A | 7/1997 | Garvis |
| 5,649,055 A | 7/1997 | Gupta |
| 5,692,059 A | 11/1997 | Kruger |
| 5,740,262 A | 4/1998 | Yoshida et al. |
| 5,748,754 A | 5/1998 | Maag et al. |
| 5,764,778 A | 6/1998 | Zurek |
| 5,787,187 A | 7/1998 | Bouchard |
| 5,799,273 A | 8/1998 | Mitchell et al. |
| 5,826,064 A | 10/1998 | Loring et al. |
| 5,862,065 A | 1/1999 | Muthusamy |
| 5,887,070 A | 3/1999 | Iseberg |
| 5,903,868 A | 5/1999 | Yuen et al. |
| 5,909,667 A | 6/1999 | Leontiades et al. |
| 5,920,835 A | 7/1999 | Huzenlaub et al. |
| 5,923,624 A | 7/1999 | Groeger |
| 5,930,751 A | 7/1999 | Cohrs et al. |
| 5,933,506 A | 8/1999 | Aoki |
| 5,933,510 A | 8/1999 | Bryant |
| 5,937,070 A | 8/1999 | Todter |
| 5,946,050 A | 8/1999 | Wolff |
| 5,953,392 A | 9/1999 | Rhie et al. |
| 5,956,681 A | 9/1999 | Yamakita |
| 6,005,525 A | 12/1999 | Kivela |
| 6,021,205 A | 2/2000 | Yamada |
| 6,021,207 A | 2/2000 | Puthuff et al. |
| 6,021,325 A | 2/2000 | Hall |
| 6,028,514 A | 2/2000 | Lemelson et al. |
| 6,048,320 A | 4/2000 | Brainard, II |
| 6,056,698 A | 5/2000 | Iseberg |
| 6,069,963 A | 5/2000 | Martin |
| 6,072,645 A | 6/2000 | Sprague |
| 6,094,492 A | 7/2000 | Boesen |

(56)                    References Cited

U.S. PATENT DOCUMENTS

| | | | |
|---|---|---|---|
| 6,094,494 | A | 7/2000 | Haroldson |
| 6,101,256 | A | 8/2000 | Steelman |
| 6,118,877 | A | 9/2000 | Lindemann |
| 6,118,878 | A | 9/2000 | Jones |
| 6,141,426 | A | 10/2000 | Stobba |
| 6,151,571 | A | 11/2000 | Pertrushin |
| 6,160,758 | A | 12/2000 | Spiesberger |
| 6,163,338 | A | 12/2000 | Johnson et al. |
| 6,163,508 | A | 12/2000 | Kim et al. |
| 6,173,259 | B1 | 1/2001 | Bijl |
| 6,175,633 | B1 | 1/2001 | Morrill |
| 6,198,971 | B1 | 3/2001 | Leysieffer |
| 6,226,389 | B1 | 5/2001 | Lemelson et al. |
| 6,263,147 | B1 | 7/2001 | Tognazzini |
| 6,269,161 | B1 | 7/2001 | McLaughlin |
| 6,298,323 | B1 | 10/2001 | Kaemmerer |
| 6,308,158 | B1 | 10/2001 | Kuhnen et al. |
| 6,311,092 | B1 | 10/2001 | Yamada |
| 6,338,038 | B1 | 1/2002 | Hanson |
| 6,359,993 | B2 | 3/2002 | Brimhall |
| 6,400,652 | B1 | 6/2002 | Goldberg et al. |
| 6,405,165 | B1 | 6/2002 | Blum et al. |
| 6,408,272 | B1 | 6/2002 | White et al. |
| 6,415,034 | B1 | 7/2002 | Hietanen |
| 6,424,721 | B1 | 7/2002 | Hohn |
| 6,445,799 | B1 | 9/2002 | Taenzer |
| 6,456,975 | B1 | 9/2002 | Chang |
| 6,463,413 | B1 | 10/2002 | Applebaum |
| 6,475,163 | B1 | 11/2002 | Smits |
| 6,483,899 | B2 | 11/2002 | Agraharam et al. |
| 6,490,557 | B1 | 12/2002 | Jeppesen |
| 6,513,621 | B1 | 2/2003 | Deslauriers et al. |
| 6,526,148 | B1 | 2/2003 | Jourjine |
| 6,526,381 | B1 | 2/2003 | Wilson |
| 6,554,761 | B1 | 4/2003 | Puria |
| 6,567,524 | B1 | 5/2003 | Svean et al. |
| 6,593,848 | B1 | 7/2003 | Atkins |
| 6,597,787 | B1 | 7/2003 | Lindgren |
| 6,606,598 | B1 | 8/2003 | Holthouse |
| 6,639,987 | B2 | 10/2003 | McIntosh |
| 6,647,123 | B2 | 11/2003 | Kandel |
| 6,647,368 | B2 | 11/2003 | Nemirovski |
| 6,648,368 | B2 | 11/2003 | Nemirovski |
| RE38,351 | E | 12/2003 | Iseberg et al. |
| 6,658,122 | B1 | 12/2003 | Westermann |
| 6,661,886 | B1 | 12/2003 | Huart |
| 6,661,901 | B1 | 12/2003 | Svean et al. |
| 6,671,379 | B2 | 12/2003 | Nemirovski |
| 6,671,643 | B2 | 12/2003 | Kachler |
| 6,674,862 | B1 | 1/2004 | Magilen |
| 6,687,339 | B2 | 2/2004 | Martin |
| 6,687,377 | B2 | 2/2004 | Voix et al. |
| 6,687,671 | B2 | 2/2004 | Gudorf et al. |
| 6,717,991 | B1 | 4/2004 | Gustafsson |
| 6,725,194 | B1 | 4/2004 | Bartosik et al. |
| 6,728,385 | B2 | 4/2004 | Kval et al. |
| 6,738,482 | B1 | 5/2004 | Jaber |
| 6,738,485 | B1 | 5/2004 | Boesen |
| 6,748,238 | B1 | 6/2004 | Lau |
| 6,754,359 | B1 | 6/2004 | Svean et al. |
| 6,760,754 | B1 | 7/2004 | Isaacs et al. |
| 6,775,206 | B2 | 8/2004 | Karhu |
| 6,782,106 | B1 | 8/2004 | Kong et al. |
| 6,785,394 | B1 | 8/2004 | Olsen |
| 6,789,060 | B1 | 9/2004 | Wolfe et al. |
| 6,804,638 | B2 | 10/2004 | Fiedler |
| 6,804,643 | B1 | 10/2004 | Kiss |
| 6,826,286 | B1 | 11/2004 | Arndt et al. |
| 6,837,857 | B2 | 1/2005 | Stirnemenn |
| 6,879,692 | B2 | 4/2005 | Nielsen |
| 6,910,013 | B2 | 6/2005 | Allegro |
| 6,912,289 | B2 | 6/2005 | Vonlanthen |
| 6,941,161 | B1 | 9/2005 | Bobisuthi |
| 6,987,992 | B2 | 1/2006 | Hundal |
| 7,003,099 | B1 | 2/2006 | Zhang |
| 7,003,123 | B2 | 2/2006 | Kanevsky |
| 7,020,297 | B2 | 3/2006 | Fang |
| 7,037,274 | B2 | 5/2006 | Thornton |
| 7,039,195 | B1 | 5/2006 | Svean |
| 7,039,585 | B2 | 5/2006 | Wilmot |
| 7,043,037 | B2 | 5/2006 | Lichtblau |
| 7,050,592 | B1 | 5/2006 | Iseberg |
| 7,050,966 | B2 | 5/2006 | Schneider |
| 7,050,971 | B1 | 5/2006 | Kaufholz |
| 7,072,482 | B2 | 7/2006 | Van et al. |
| 7,082,393 | B2 | 7/2006 | Lahr |
| 7,092,532 | B2 | 8/2006 | Luo |
| 7,103,188 | B1 | 9/2006 | Jones |
| 7,107,109 | B1 | 9/2006 | Nathan et al. |
| 7,110,554 | B2 | 9/2006 | Brennan |
| 7,130,437 | B2 | 10/2006 | Stonikas et al. |
| 7,158,643 | B2 | 1/2007 | Lavoie et al. |
| 7,158,933 | B2 | 1/2007 | Balan |
| 7,162,041 | B2 | 1/2007 | Haapapuro |
| 7,174,022 | B1 | 2/2007 | Zhan |
| 7,177,433 | B2 | 2/2007 | Sibbald |
| 7,181,020 | B1 | 2/2007 | Riley |
| 7,181,030 | B2 | 2/2007 | Rasmussen |
| 7,209,569 | B2 | 4/2007 | Boesen |
| 7,215,766 | B2 | 5/2007 | Wurtz |
| 7,223,245 | B2 | 5/2007 | Zoth |
| 7,246,058 | B2 | 7/2007 | Burnett |
| 7,277,722 | B2 | 10/2007 | Rosenzweig |
| 7,280,849 | B1 | 10/2007 | Bailey |
| 7,312,699 | B2 | 12/2007 | Chornenky |
| 7,346,504 | B2 | 3/2008 | Liu |
| 7,359,504 | B1 | 4/2008 | Reuss |
| 7,383,178 | B2 | 6/2008 | Visser |
| 7,395,090 | B2 | 7/2008 | Alden |
| 7,430,299 | B2 | 9/2008 | Armstrong et al. |
| 7,430,300 | B2 | 9/2008 | Vosburgh |
| 7,433,463 | B2 | 10/2008 | Alves |
| 7,433,714 | B2 | 10/2008 | Howard et al. |
| 7,444,353 | B1 | 10/2008 | Chen |
| 7,450,730 | B2 | 11/2008 | Berg et al. |
| 7,464,029 | B2 | 12/2008 | Visser |
| 7,477,754 | B2 | 1/2009 | Rasmussen |
| 7,477,756 | B2 | 1/2009 | Wickstrom et al. |
| 7,477,922 | B2 | 1/2009 | Lewis |
| 7,502,484 | B2 | 3/2009 | Ngia |
| 7,512,245 | B2 | 3/2009 | Rasmussen |
| 7,519,193 | B2 | 4/2009 | Fretz |
| 7,529,379 | B2 | 5/2009 | Zurek |
| 7,532,734 | B2 | 5/2009 | Pham |
| 7,536,006 | B2 | 5/2009 | Patel |
| 7,562,020 | B2 | 7/2009 | Le et al. |
| 7,574,917 | B2 | 8/2009 | Von Dach |
| 7,590,254 | B2 | 9/2009 | Olsen |
| 7,617,099 | B2 | 11/2009 | Yang |
| 7,623,823 | B2 | 11/2009 | Zito |
| 7,634,094 | B2 | 12/2009 | Reber |
| 7,659,827 | B2 | 2/2010 | Gunderson |
| 7,680,465 | B2 | 3/2010 | Issa |
| 7,702,482 | B2 | 4/2010 | Graepel |
| 7,710,654 | B2 | 5/2010 | Ashkenazi |
| 7,715,568 | B2 | 5/2010 | Nakano |
| 7,715,577 | B2 | 5/2010 | Allen et al. |
| 7,729,912 | B1 | 6/2010 | Bacchiani et al. |
| 7,756,281 | B2 | 7/2010 | Goldstein et al. |
| 7,756,283 | B2 | 7/2010 | Bramslow |
| 7,756,285 | B2 | 7/2010 | Sjursen et al. |
| 7,773,743 | B2 | 8/2010 | Stokes |
| 7,773,759 | B2 | 8/2010 | Alves |
| 7,773,763 | B2 | 8/2010 | Pedersen |
| 7,774,202 | B2 | 8/2010 | Spengler et al. |
| 7,778,434 | B2 | 8/2010 | Juneau et al. |
| 7,801,318 | B2 | 9/2010 | Bartel |
| 7,801,726 | B2 | 9/2010 | Ariu |
| 7,804,974 | B2 | 9/2010 | Paludan-Muller |
| 7,813,520 | B2 | 10/2010 | Dach |
| 7,817,808 | B2 | 10/2010 | Konchitsky |
| 7,844,070 | B2 | 11/2010 | Abolfathi |
| 7,844,248 | B2 | 11/2010 | Sotack |
| 7,853,031 | B2 | 12/2010 | Hamacher |

(56) References Cited

U.S. PATENT DOCUMENTS

| | | | |
|---|---|---|---|
| 7,861,008 | B2 | 12/2010 | Batson et al. |
| 7,861,723 | B2 | 1/2011 | Dedrick |
| 7,869,606 | B2 | 1/2011 | Fichtl |
| 7,903,825 | B1 | 3/2011 | Melanson |
| 7,903,826 | B2 | 3/2011 | Boersma |
| 7,903,833 | B2 | 3/2011 | Goldberg |
| 7,920,557 | B2 | 4/2011 | Moote |
| 7,925,007 | B2 | 4/2011 | Stokes |
| 7,929,713 | B2 | 4/2011 | Victorian |
| 7,933,423 | B2 | 4/2011 | Jensen |
| 7,936,885 | B2 | 5/2011 | Frank |
| 7,953,241 | B2 | 5/2011 | Jorgensen |
| 7,983,433 | B2 | 7/2011 | Nemirovski |
| 7,983,907 | B2 | 7/2011 | Visser |
| 7,986,791 | B2 | 7/2011 | Bostick |
| 7,986,802 | B2 | 7/2011 | Ziller |
| 7,995,773 | B2 | 8/2011 | Mao |
| 8,014,553 | B2 | 9/2011 | Radivojevic et al. |
| 8,018,337 | B2 | 9/2011 | Jones et al. |
| 8,019,091 | B2 | 9/2011 | Burnett |
| 8,027,481 | B2 | 9/2011 | Beard |
| 8,045,840 | B2 | 10/2011 | Murata et al. |
| 8,047,207 | B2 | 11/2011 | Perez |
| 8,050,143 | B2 | 11/2011 | Nicholas |
| 8,068,627 | B2 | 11/2011 | Zhan |
| 8,077,872 | B2 | 12/2011 | Dyer |
| 8,081,780 | B2 | 12/2011 | Goldstein et al. |
| 8,085,943 | B2 | 12/2011 | Bizjak |
| 8,086,093 | B2 | 12/2011 | Stuckman |
| 8,111,839 | B2 | 2/2012 | Goldstein et al. |
| 8,111,840 | B2 | 2/2012 | Haulick |
| 8,111,849 | B2 | 2/2012 | Tateno |
| 8,116,472 | B2 | 2/2012 | Mizuno |
| 8,116,489 | B2 | 2/2012 | Mejia |
| 8,121,301 | B2 | 2/2012 | Suzuki |
| 8,140,325 | B2 | 3/2012 | Kanevsky |
| 8,144,881 | B2 | 3/2012 | Crockett |
| 8,144,891 | B2 | 3/2012 | Her |
| 8,150,044 | B2 | 4/2012 | Goldstein et al. |
| 8,150,084 | B2 | 4/2012 | Jessen |
| 8,160,261 | B2 | 4/2012 | Schulein |
| 8,160,273 | B2 | 4/2012 | Visser |
| 8,162,846 | B2 | 4/2012 | Epley |
| 8,180,078 | B2 | 5/2012 | Zellner |
| 8,184,823 | B2 | 5/2012 | Itabashi |
| 8,186,478 | B1 | 5/2012 | Grason |
| 8,189,803 | B2 | 5/2012 | Bergeron |
| 8,194,864 | B2 | 6/2012 | Goldstein et al. |
| 8,194,865 | B2 | 6/2012 | Goldstein |
| 8,199,919 | B2 | 6/2012 | Goldstein et al. |
| 8,199,942 | B2 | 6/2012 | Mao |
| 8,204,435 | B2 | 6/2012 | Seshadri |
| 8,208,609 | B2 | 6/2012 | Harris |
| 8,208,642 | B2 | 6/2012 | Edwards |
| 8,208,644 | B2 | 6/2012 | Goldstein et al. |
| 8,208,652 | B2 | 6/2012 | Keady |
| 8,209,181 | B2 | 6/2012 | Heckerman et al. |
| 8,213,629 | B2 | 7/2012 | Goldstein |
| 8,218,784 | B2 | 7/2012 | Schulein |
| 8,221,861 | B2 | 7/2012 | Keady |
| 8,229,127 | B2 | 7/2012 | Jorgensen et al. |
| 8,229,128 | B2 | 7/2012 | Keady |
| 8,229,148 | B2 | 7/2012 | Rasmssen |
| 8,229,513 | B2 | 7/2012 | Ibe |
| 8,251,925 | B2 | 8/2012 | Staab et al. |
| 8,254,586 | B2 | 8/2012 | Voix |
| 8,254,591 | B2 * | 8/2012 | Goldstein ............ H04R 1/1091 381/313 |
| 8,270,629 | B2 | 9/2012 | Bothra |
| 8,270,634 | B2 | 9/2012 | Harney |
| 8,306,235 | B2 | 11/2012 | Mahowald |
| 8,312,960 | B2 | 11/2012 | Keady |
| 8,315,400 | B2 | 11/2012 | Goldstein et al. |
| 8,322,222 | B2 | 12/2012 | Goldberg |
| 8,340,309 | B2 | 12/2012 | Burnett |
| 8,351,634 | B2 | 1/2013 | Khenkin |
| 8,369,901 | B2 | 2/2013 | Haulick |
| 8,374,361 | B2 | 2/2013 | Moon |
| 8,385,560 | B2 | 2/2013 | Solbeck |
| 8,391,534 | B2 | 3/2013 | Ambrose et al. |
| 8,401,198 | B2 | 3/2013 | Oh et al. |
| 8,401,200 | B2 | 3/2013 | Tiscareno |
| 8,411,880 | B2 | 4/2013 | Wang |
| 8,437,492 | B2 | 5/2013 | Goldstein et al. |
| 8,447,370 | B2 | 5/2013 | Ueda |
| 8,462,969 | B2 | 6/2013 | Claussen |
| 8,462,974 | B2 | 6/2013 | Jeong |
| 8,472,616 | B1 | 6/2013 | Jiang |
| 8,477,955 | B2 | 7/2013 | Engle et al. |
| 8,488,799 | B2 | 7/2013 | Goldstein et al. |
| 8,493,204 | B2 | 7/2013 | Wong et al. |
| 8,515,089 | B2 | 8/2013 | Nicholson |
| 8,522,916 | B2 | 9/2013 | Keady |
| 8,548,181 | B2 | 10/2013 | Kraemer |
| 8,550,206 | B2 | 10/2013 | Keady et al. |
| 8,554,350 | B2 | 10/2013 | Keady et al. |
| 8,577,062 | B2 | 11/2013 | Goldstein |
| 8,594,341 | B2 | 11/2013 | Rothschild |
| 8,600,067 | B2 | 12/2013 | Usher et al. |
| 8,611,548 | B2 | 12/2013 | Bizjak |
| 8,611,560 | B2 | 12/2013 | Goldstein |
| 8,625,818 | B2 | 1/2014 | Stultz |
| 8,625,819 | B2 | 1/2014 | Goldstein |
| 8,631,801 | B2 | 1/2014 | Keady |
| 8,649,540 | B2 | 2/2014 | Killion et al. |
| 8,652,040 | B2 | 2/2014 | LeBoeuf |
| 8,657,064 | B2 | 2/2014 | Staab et al. |
| 8,678,011 | B2 | 3/2014 | Goldstein et al. |
| 8,693,704 | B2 | 4/2014 | Kim |
| 8,718,288 | B2 | 5/2014 | Woods |
| 8,718,305 | B2 | 5/2014 | Usher |
| 8,718,313 | B2 | 5/2014 | Keady |
| 8,744,091 | B2 | 6/2014 | Chen et al. |
| 8,750,295 | B2 | 6/2014 | Liron |
| 8,774,433 | B2 | 7/2014 | Goldstein |
| 8,774,435 | B2 | 7/2014 | Ambrose et al. |
| 8,792,669 | B2 | 7/2014 | Harsch |
| 8,798,278 | B2 | 8/2014 | Isabelle |
| 8,798,279 | B2 | 8/2014 | Ranta |
| 8,798,289 | B1 | 8/2014 | Every |
| 8,804,974 | B1 | 8/2014 | Melanson |
| 8,848,939 | B2 | 9/2014 | Keady et al. |
| 8,851,372 | B2 | 10/2014 | Zhou |
| 8,855,343 | B2 | 10/2014 | Usher |
| 8,903,113 | B2 | 12/2014 | Gebert |
| 8,917,880 | B2 | 12/2014 | Goldstein et al. |
| 8,917,892 | B2 | 12/2014 | Poe |
| 8,917,894 | B2 | 12/2014 | Goldstein |
| 8,942,370 | B2 | 1/2015 | Li |
| 8,942,405 | B2 | 1/2015 | Jones et al. |
| 8,948,428 | B2 | 2/2015 | Kates |
| 8,983,081 | B2 | 3/2015 | Bayley |
| 8,992,710 | B2 | 3/2015 | Keady |
| 9,002,023 | B2 | 4/2015 | Gauger |
| 9,013,351 | B2 | 4/2015 | Park |
| 9,037,458 | B2 | 5/2015 | Park et al. |
| 9,053,697 | B2 | 6/2015 | Park |
| 9,076,427 | B2 | 7/2015 | Alderson |
| 9,112,701 | B2 | 8/2015 | Sano |
| 9,113,240 | B2 | 8/2015 | Ramakrishman |
| 9,113,267 | B2 | 8/2015 | Usher et al. |
| 9,123,323 | B2 | 9/2015 | Keady |
| 9,123,343 | B2 | 9/2015 | Kurki-Suonio |
| 9,124,982 | B2 | 9/2015 | Goldstein et al. |
| 9,135,797 | B2 | 9/2015 | Couper et al. |
| 9,135,809 | B2 | 9/2015 | Chang |
| 9,137,597 | B2 | 9/2015 | Usher |
| 9,138,353 | B2 | 9/2015 | Keady |
| 9,142,207 | B2 | 9/2015 | Hendrix |
| 9,165,567 | B2 | 10/2015 | Visser |
| 9,185,481 | B2 | 11/2015 | Goldstein et al. |
| 9,191,732 | B2 | 11/2015 | Wurtz |
| 9,191,740 | B2 | 11/2015 | McIntosh |
| 9,196,247 | B2 | 11/2015 | Harada |

(56) References Cited

U.S. PATENT DOCUMENTS

| | | |
|---|---|---|
| 9,216,237 B2 | 12/2015 | Keady |
| 9,270,244 B2 | 2/2016 | Usher et al. |
| 9,288,592 B2 | 3/2016 | Basseas |
| 9,338,568 B2 | 5/2016 | van Hal |
| 9,357,288 B2 | 5/2016 | Goldstein |
| 9,369,814 B2 | 6/2016 | Victorian |
| 9,445,183 B2 | 9/2016 | Dahl |
| 9,462,100 B2 | 10/2016 | Usher |
| 9,491,542 B2 | 11/2016 | Usher |
| 9,497,423 B2 | 11/2016 | Moberly |
| 9,539,147 B2 | 1/2017 | Keady et al. |
| 9,554,733 B2 | 1/2017 | Henriksen et al. |
| 9,609,424 B2 | 3/2017 | Goldstein |
| 9,628,896 B2 | 4/2017 | Ichimura |
| 9,653,869 B1 | 5/2017 | Hersman |
| 9,684,778 B2 | 6/2017 | Tharappel |
| 9,685,921 B2 | 6/2017 | Smith |
| 9,757,069 B2 | 9/2017 | Keady et al. |
| 9,763,003 B2 | 9/2017 | Usher |
| 9,779,716 B2 | 10/2017 | Gadonniex |
| 9,781,530 B2 | 10/2017 | Usher et al. |
| 9,843,854 B2 | 12/2017 | Keady |
| 9,894,452 B1 | 2/2018 | Termeulen |
| 9,943,185 B2 | 4/2018 | Chen |
| 10,012,529 B2 | 7/2018 | Goldstein et al. |
| 10,045,107 B2 | 8/2018 | Kirsch et al. |
| 10,142,332 B2 | 11/2018 | Ravindran |
| 10,190,904 B2 | 1/2019 | Goldstein et al. |
| 10,284,939 B2 | 5/2019 | Radin |
| 10,297,246 B2 | 5/2019 | Asada |
| 10,365,883 B2 | 7/2019 | Goldstein et al. |
| 10,413,197 B2 | 9/2019 | LeBoeuf |
| 10,506,320 B1 | 12/2019 | Lott |
| 10,709,339 B1 | 7/2020 | Lusted |
| 10,760,948 B2 | 9/2020 | Goldstein |
| 10,848,827 B2 | 11/2020 | Sengupta et al. |
| 10,917,711 B2 | 2/2021 | Higgins |
| 10,966,015 B2 | 3/2021 | Usher |
| 10,970,375 B2 | 4/2021 | Shila |
| 10,979,836 B2 | 4/2021 | Usher et al. |
| 11,006,198 B2 | 5/2021 | Lott |
| 11,012,770 B2 | 5/2021 | Hatfield et al. |
| 11,039,259 B2 | 6/2021 | Goldstein et al. |
| 11,051,704 B1 | 7/2021 | Tran |
| 11,057,701 B2 | 7/2021 | Goldstein et al. |
| 11,115,750 B2 | 9/2021 | Monsarrant-Chanon |
| 11,122,357 B2 | 9/2021 | Burnett |
| 11,172,298 B2 | 11/2021 | Carrigan |
| 11,217,237 B2 | 1/2022 | Usher et al. |
| 11,244,666 B2 | 2/2022 | Goldstein et al. |
| 11,277,682 B2 | 3/2022 | Usher |
| 11,277,700 B2 | 3/2022 | Goldstein |
| 11,294,619 B2 | 4/2022 | Usher et al. |
| 11,383,158 B2 | 7/2022 | Bonanno |
| 11,393,486 B1 | 7/2022 | Woodruff et al. |
| 11,610,587 B2 | 3/2023 | Goldstein et al. |
| 11,659,315 B2 | 5/2023 | Perez et al. |
| 11,665,493 B2 | 5/2023 | Usher et al. |
| 11,710,473 B2 | 7/2023 | Goldstein et al. |
| 11,750,965 B2 | 9/2023 | Usher et al. |
| 2001/0041559 A1 | 11/2001 | Salabaschew |
| 2001/0046304 A1 | 11/2001 | Rast |
| 2002/0003889 A1 | 1/2002 | Fischer |
| 2002/0009203 A1 | 1/2002 | Erten |
| 2002/0018798 A1 | 2/2002 | Sewing et al. |
| 2002/0026311 A1 | 2/2002 | Okitsu |
| 2002/0057817 A1 | 5/2002 | Darbut |
| 2002/0069056 A1 | 6/2002 | Nofsinger |
| 2002/0076057 A1 | 6/2002 | Voix |
| 2002/0076059 A1 | 6/2002 | Joynes |
| 2002/0085690 A1 | 7/2002 | Davidson et al. |
| 2002/0098878 A1 | 7/2002 | Mooney |
| 2002/0106091 A1 | 8/2002 | Furst et al. |
| 2002/0111798 A1 | 8/2002 | Huang |
| 2002/0116541 A1 | 8/2002 | Parker et al. |
| 2002/0118798 A1 | 8/2002 | Langhart et al. |
| 2002/0123893 A1 | 9/2002 | Woodward |
| 2002/0133513 A1 | 9/2002 | Townsend et al. |
| 2002/0141599 A1 | 10/2002 | Trajkovic |
| 2002/0141602 A1 | 10/2002 | Nemirovski |
| 2002/0143534 A1 | 10/2002 | Hol |
| 2002/0165719 A1 | 11/2002 | Wang |
| 2002/0169596 A1 | 11/2002 | Brill et al. |
| 2002/0169615 A1 | 11/2002 | Kruger et al. |
| 2002/0191799 A1 | 12/2002 | Nordqvist |
| 2002/0191952 A1 | 12/2002 | Fiore |
| 2002/0193130 A1 | 12/2002 | Yang |
| 2003/0008633 A1 | 1/2003 | Bartosik |
| 2003/0026438 A1 | 2/2003 | Ray |
| 2003/0032447 A1 | 2/2003 | Bulthuis |
| 2003/0033152 A1 | 2/2003 | Cameron |
| 2003/0035551 A1 | 2/2003 | Light |
| 2003/0048882 A1 | 3/2003 | Smith |
| 2003/0050777 A1 | 3/2003 | Walker |
| 2003/0055627 A1 | 3/2003 | Balan |
| 2003/0061032 A1 | 3/2003 | Gonopolskiy |
| 2003/0065512 A1 | 4/2003 | Walker |
| 2003/0065620 A1 | 4/2003 | Gailey et al. |
| 2003/0069002 A1 | 4/2003 | Hunter |
| 2003/0083879 A1 | 5/2003 | Cyr et al. |
| 2003/0083883 A1 | 5/2003 | Cyr et al. |
| 2003/0110040 A1 | 6/2003 | Holland et al. |
| 2003/0130016 A1 | 7/2003 | Matsuura |
| 2003/0138118 A1 | 7/2003 | Stahl |
| 2003/0152359 A1 | 8/2003 | Kim |
| 2003/0156725 A1 | 8/2003 | Boone |
| 2003/0161097 A1 | 8/2003 | Le et al. |
| 2003/0165246 A1 | 9/2003 | Kvaloy et al. |
| 2003/0165319 A1 | 9/2003 | Barber |
| 2003/0198357 A1 | 10/2003 | Schneider |
| 2003/0198359 A1 | 10/2003 | Killion et al. |
| 2003/0200096 A1 | 10/2003 | Asai |
| 2003/0228019 A1 | 12/2003 | Eichler |
| 2003/0228023 A1 | 12/2003 | Burnett |
| 2004/0008850 A1 | 1/2004 | Gustavsson |
| 2004/0019482 A1 | 1/2004 | Holub |
| 2004/0042103 A1 | 3/2004 | Mayer |
| 2004/0047474 A1 | 3/2004 | Vries |
| 2004/0047486 A1 | 3/2004 | Van Doom |
| 2004/0049385 A1 | 3/2004 | Lovance et al. |
| 2004/0086138 A1 | 5/2004 | Kuth |
| 2004/0088162 A1 | 5/2004 | He et al. |
| 2004/0109579 A1 | 6/2004 | Izuchi et al. |
| 2004/0109668 A1 | 6/2004 | Stuckman |
| 2004/0125965 A1 | 7/2004 | Alberth et al. |
| 2004/0128136 A1 | 7/2004 | Irani |
| 2004/0133421 A1 | 7/2004 | Burnett |
| 2004/0150717 A1 | 8/2004 | Page |
| 2004/0160573 A1 | 8/2004 | Jannard |
| 2004/0165742 A1 | 8/2004 | Shennib |
| 2004/0179694 A1 | 9/2004 | Alley |
| 2004/0185804 A1 | 9/2004 | Kanamori |
| 2004/0190737 A1 | 9/2004 | Kuhnel et al. |
| 2004/0196992 A1 | 10/2004 | Ryan |
| 2004/0202333 A1 | 10/2004 | Csermak |
| 2004/0202339 A1 | 10/2004 | O'Brien |
| 2004/0202340 A1 | 10/2004 | Armstrong et al. |
| 2004/0203351 A1 | 10/2004 | Shearer et al. |
| 2004/0252852 A1 | 12/2004 | Taenzer |
| 2004/0258263 A1 | 12/2004 | Saxton et al. |
| 2004/0264938 A1 | 12/2004 | Felder |
| 2005/0008167 A1 | 1/2005 | Gleissner |
| 2005/0028212 A1 | 2/2005 | Laronne |
| 2005/0033384 A1 | 2/2005 | Sacha |
| 2005/0033571 A1 | 2/2005 | Huang |
| 2005/0047611 A1 | 3/2005 | Mao |
| 2005/0049854 A1 | 3/2005 | Reding et al. |
| 2005/0058300 A1 | 3/2005 | Suzuki |
| 2005/0058313 A1 | 3/2005 | Victorian |
| 2005/0060142 A1 | 3/2005 | Visser |
| 2005/0068171 A1 | 3/2005 | Kelliher |
| 2005/0070337 A1 | 3/2005 | Byford |
| 2005/0071158 A1 | 3/2005 | Byford |
| 2005/0071626 A1 | 3/2005 | Bear |

(56)　　　　　References Cited

U.S. PATENT DOCUMENTS

| | | |
|---|---|---|
| 2005/0077102 A1 | 4/2005 | Banter et al. |
| 2005/0078838 A1 | 4/2005 | Simon |
| 2005/0078842 A1 | 4/2005 | Vonlanthen |
| 2005/0090295 A1 | 4/2005 | Ali |
| 2005/0096764 A1 | 5/2005 | Weiser |
| 2005/0096899 A1 | 5/2005 | Padhi et al. |
| 2005/0102142 A1 | 5/2005 | Soufflet et al. |
| 2005/0114124 A1 | 5/2005 | Liu |
| 2005/0123146 A1 | 6/2005 | Voix et al. |
| 2005/0134710 A1 | 6/2005 | Nomura |
| 2005/0157891 A1 | 7/2005 | Johansen |
| 2005/0163289 A1 | 7/2005 | Caspi et al. |
| 2005/0175194 A1 | 8/2005 | Anderson |
| 2005/0182620 A1 | 8/2005 | Kabi et al. |
| 2005/0207605 A1 | 9/2005 | Dehe |
| 2005/0215907 A1 | 9/2005 | Toda |
| 2005/0216531 A1 | 9/2005 | Blandford |
| 2005/0222820 A1 | 10/2005 | Chung |
| 2005/0227674 A1 | 10/2005 | Kopra |
| 2005/0254640 A1 | 11/2005 | Ohki |
| 2005/0254676 A1 | 11/2005 | Rass |
| 2005/0258942 A1 | 11/2005 | Manasseh |
| 2005/0260978 A1 | 11/2005 | Rader |
| 2005/0264425 A1 | 12/2005 | Sato |
| 2005/0281422 A1 | 12/2005 | Armstrong |
| 2005/0281423 A1 | 12/2005 | Armstrong |
| 2005/0283369 A1 | 12/2005 | Clausner et al. |
| 2005/0288057 A1 | 12/2005 | Lai et al. |
| 2006/0013410 A1 | 1/2006 | Wurtz |
| 2006/0018496 A1 | 1/2006 | Niederdrank et al. |
| 2006/0053007 A1 | 3/2006 | Niemisto |
| 2006/0064037 A1 | 3/2006 | Shalon et al. |
| 2006/0067551 A1 | 3/2006 | Cartwright et al. |
| 2006/0074895 A1 | 4/2006 | Belknap |
| 2006/0083387 A1 | 4/2006 | Emoto |
| 2006/0083388 A1 | 4/2006 | Rothschild |
| 2006/0083390 A1 | 4/2006 | Kaderavek |
| 2006/0083395 A1 | 4/2006 | Allen et al. |
| 2006/0088176 A1 | 4/2006 | Werner |
| 2006/0092043 A1 | 5/2006 | Lagassey |
| 2006/0095199 A1 | 5/2006 | Lagassey |
| 2006/0116175 A1 | 6/2006 | Chu |
| 2006/0116877 A1 | 6/2006 | Pickering |
| 2006/0120545 A1 | 6/2006 | Rasmussen |
| 2006/0126821 A1 | 6/2006 | Sahashi |
| 2006/0126865 A1 | 6/2006 | Blarney |
| 2006/0140425 A1 | 6/2006 | Berg |
| 2006/0147063 A1 | 7/2006 | Chen |
| 2006/0153394 A1 | 7/2006 | Beasley |
| 2006/0154642 A1 | 7/2006 | Scannell, Jr. |
| 2006/0167687 A1 | 7/2006 | Kates |
| 2006/0173563 A1 | 8/2006 | Borovitski |
| 2006/0182287 A1 | 8/2006 | Schulein |
| 2006/0182295 A1 | 8/2006 | Dijkstra et al. |
| 2006/0184983 A1 | 8/2006 | Casey |
| 2006/0188075 A1 | 8/2006 | Peterson |
| 2006/0188105 A1 | 8/2006 | Baskerville et al. |
| 2006/0195322 A1 | 8/2006 | Broussard et al. |
| 2006/0204014 A1 | 9/2006 | Iseberg et al. |
| 2006/0223547 A1 | 10/2006 | Chin et al. |
| 2006/0233413 A1 | 10/2006 | Nam |
| 2006/0241948 A1 | 10/2006 | Abrash et al. |
| 2006/0258325 A1 | 11/2006 | Tsutaichi |
| 2006/0262935 A1 | 11/2006 | Goose |
| 2006/0262938 A1 | 11/2006 | Gauger |
| 2006/0262944 A1 | 11/2006 | Rasmussen et al. |
| 2006/0264176 A1 | 11/2006 | Hong |
| 2006/0274166 A1 | 12/2006 | Lee |
| 2006/0285709 A1 | 12/2006 | Barthel |
| 2006/0287014 A1 | 12/2006 | Matsuura |
| 2007/0003090 A1 | 1/2007 | Anderson |
| 2007/0009122 A1 | 1/2007 | Hamacher |
| 2007/0009127 A1 | 1/2007 | Harald |
| 2007/0014423 A1 | 1/2007 | Darbut et al. |
| 2007/0019817 A1 | 1/2007 | Siltmann |
| 2007/0021148 A1 | 1/2007 | Mahini |
| 2007/0021958 A1 | 1/2007 | Visser et al. |
| 2007/0027676 A1 | 2/2007 | Chambers et al. |
| 2007/0036377 A1 | 2/2007 | Stirnemann |
| 2007/0041589 A1 | 2/2007 | Patel et al. |
| 2007/0043563 A1 | 2/2007 | Comerford et al. |
| 2007/0076896 A1 | 4/2007 | Hosaka |
| 2007/0086600 A1 | 4/2007 | Boesen |
| 2007/0092087 A1 | 4/2007 | Bothra |
| 2007/0100637 A1 | 5/2007 | McCune |
| 2007/0127660 A1 | 6/2007 | Roberts et al. |
| 2007/0143820 A1 | 6/2007 | Pawlowski |
| 2007/0147635 A1 | 6/2007 | Dijkstra |
| 2007/0160243 A1 | 7/2007 | Dijkstra |
| 2007/0165875 A1 * | 7/2007 | Rezvani ............... H04M 1/6066 |
| | | 381/74 |
| 2007/0172087 A1 | 7/2007 | Olsen |
| 2007/0177743 A1 | 8/2007 | Mertens |
| 2007/0185601 A1 | 8/2007 | Lee |
| 2007/0189544 A1 | 8/2007 | Rosenberg |
| 2007/0194893 A1 | 8/2007 | Deyoe |
| 2007/0201705 A1 | 8/2007 | Dorogusker et al. |
| 2007/0206825 A1 | 9/2007 | Thomasson |
| 2007/0223717 A1 | 9/2007 | Boersma |
| 2007/0225035 A1 | 9/2007 | Gauger |
| 2007/0230734 A1 | 10/2007 | Beard |
| 2007/0233487 A1 | 10/2007 | Cohen |
| 2007/0239294 A1 | 10/2007 | Brueckner |
| 2007/0253569 A1 | 11/2007 | Bose |
| 2007/0255435 A1 | 11/2007 | Cohen |
| 2007/0260460 A1 | 11/2007 | Hyatt |
| 2007/0274531 A1 | 11/2007 | Camp |
| 2007/0281744 A1 | 12/2007 | Andreasson |
| 2007/0291953 A1 | 12/2007 | Ngia et al. |
| 2008/0037801 A1 | 2/2008 | Alves et al. |
| 2008/0063228 A1 | 3/2008 | Mejia |
| 2008/0069369 A1 | 3/2008 | Dyer |
| 2008/0079571 A1 | 4/2008 | Samadani |
| 2008/0089530 A1 | 4/2008 | Bostick et al. |
| 2008/0091421 A1 | 4/2008 | Gustavsson |
| 2008/0101638 A1 | 5/2008 | Ziller |
| 2008/0107282 A1 | 5/2008 | Asada |
| 2008/0107297 A1 | 5/2008 | Fischer et al. |
| 2008/0123866 A1 | 5/2008 | Rule |
| 2008/0129520 A1 | 6/2008 | Lee |
| 2008/0130908 A1 | 6/2008 | Cohen |
| 2008/0137873 A1 | 6/2008 | Goldstein |
| 2008/0145032 A1 | 6/2008 | Lindroos |
| 2008/0152167 A1 | 6/2008 | Taenzer |
| 2008/0152169 A1 | 6/2008 | Asada |
| 2008/0159547 A1 | 7/2008 | Schuler |
| 2008/0162133 A1 | 7/2008 | Couper et al. |
| 2008/0165988 A1 | 7/2008 | Terlizzi et al. |
| 2008/0175411 A1 | 7/2008 | Greve |
| 2008/0181419 A1 | 7/2008 | Goldstein et al. |
| 2008/0201138 A1 | 8/2008 | Visser |
| 2008/0221880 A1 | 9/2008 | Cerra et al. |
| 2008/0240458 A1 | 10/2008 | Goldstein et al. |
| 2008/0257047 A1 | 10/2008 | Pelecanos |
| 2008/0260180 A1 | 10/2008 | Goldstein |
| 2008/0269926 A1 | 10/2008 | Xiang |
| 2009/0010456 A1 | 1/2009 | Goldstein et al. |
| 2009/0016501 A1 | 1/2009 | May |
| 2009/0016541 A1 | 1/2009 | Goldstein |
| 2009/0024234 A1 | 1/2009 | Archibald |
| 2009/0034748 A1 | 2/2009 | Sibbald |
| 2009/0046867 A1 | 2/2009 | Clemow |
| 2009/0067661 A1 | 3/2009 | Keady |
| 2009/0071487 A1 | 3/2009 | Keady |
| 2009/0076821 A1 | 3/2009 | Brenner |
| 2009/0085873 A1 | 4/2009 | Betts |
| 2009/0087003 A1 | 4/2009 | Zurek |
| 2009/0122996 A1 | 5/2009 | Klein |
| 2009/0175474 A1 | 7/2009 | Salvetti |
| 2009/0180631 A1 | 7/2009 | Michael |
| 2009/0192688 A1 | 7/2009 | Padmanabhan |
| 2009/0227888 A1 | 9/2009 | Salmi |
| 2009/0238386 A1 | 9/2009 | Usher |
| 2009/0274314 A1 | 11/2009 | Arndt |

(56) References Cited

U.S. PATENT DOCUMENTS

| | | |
|---|---|---|
| 2009/0286515 A1 | 11/2009 | Othmer |
| 2010/0061564 A1 | 3/2010 | Clemow et al. |
| 2010/0119077 A1 | 5/2010 | Platz et al. |
| 2010/0150367 A1 | 6/2010 | Mizuno |
| 2010/0166203 A1 | 7/2010 | Peissig |
| 2010/0223223 A1 | 9/2010 | Sandler |
| 2010/0241256 A1 | 9/2010 | Goldstein et al. |
| 2010/0286490 A1 | 11/2010 | Koverzin |
| 2010/0296668 A1 | 11/2010 | Lee et al. |
| 2010/0316033 A1 | 12/2010 | Atwal |
| 2010/0328224 A1 | 12/2010 | Kerr et al. |
| 2011/0026724 A1 | 2/2011 | Doclo |
| 2011/0055256 A1 | 3/2011 | Phillips |
| 2011/0079227 A1 | 4/2011 | Turcot et al. |
| 2011/0096939 A1 | 4/2011 | Ichimura |
| 2011/0116643 A1 | 5/2011 | Tiscareno |
| 2011/0125063 A1 | 5/2011 | Shalon |
| 2011/0135120 A1 | 6/2011 | Larsen |
| 2011/0187640 A1 | 8/2011 | Jacobsen et al. |
| 2011/0264447 A1 | 10/2011 | Visser et al. |
| 2011/0288860 A1 | 11/2011 | Schevciw |
| 2011/0293103 A1 | 12/2011 | Park et al. |
| 2011/0299695 A1 | 12/2011 | Nicholson |
| 2012/0076317 A1 | 3/2012 | Fratti |
| 2012/0170412 A1 | 7/2012 | Calhoun |
| 2013/0098706 A1 | 4/2013 | Keady |
| 2013/0136285 A1 | 5/2013 | Naumann |
| 2013/0149192 A1 | 6/2013 | Keady |
| 2013/0219345 A1 | 8/2013 | Saukko et al. |
| 2013/0251172 A1 | 9/2013 | Mosseri |
| 2014/0003644 A1 | 1/2014 | Keady et al. |
| 2014/0010378 A1 | 1/2014 | Voix |
| 2014/0023203 A1 | 1/2014 | Rotschild |
| 2014/0026665 A1 | 1/2014 | Keady |
| 2014/0089672 A1 | 3/2014 | Luna |
| 2014/0122092 A1 | 5/2014 | Goldstein |
| 2014/0126748 A1 | 5/2014 | Usher et al. |
| 2014/0148101 A1 | 5/2014 | Seshadri |
| 2014/0163976 A1 | 6/2014 | Park |
| 2014/0166122 A1 | 6/2014 | Goldstein et al. |
| 2014/0205123 A1 | 7/2014 | Lafort et al. |
| 2014/0270200 A1 | 9/2014 | Usher et al. |
| 2014/0373854 A1 | 12/2014 | Keady |
| 2015/0150728 A1 | 6/2015 | Duvall |
| 2015/0170645 A1 | 6/2015 | Di et al. |
| 2015/0195641 A1 | 7/2015 | Di et al. |
| 2015/0215701 A1 | 7/2015 | Usher |
| 2015/0358730 A1 | 12/2015 | Kirsch |
| 2016/0012714 A1 | 1/2016 | Patenaude |
| 2016/0015568 A1 | 1/2016 | Keady |
| 2016/0019024 A1 | 1/2016 | Suzuki et al. |
| 2016/0050483 A1 | 2/2016 | Kulavik et al. |
| 2016/0058378 A1 | 3/2016 | Wisby et al. |
| 2016/0104452 A1 | 4/2016 | Guan et al. |
| 2016/0127818 A1 | 5/2016 | Ambrose |
| 2016/0192077 A1 | 6/2016 | Keady |
| 2016/0249128 A1 | 8/2016 | Goldstein |
| 2016/0277854 A1 | 9/2016 | Puria |
| 2016/0295311 A1 | 10/2016 | Keady et al. |
| 2017/0134865 A1 | 5/2017 | Goldstein et al. |
| 2017/0142511 A1 | 5/2017 | Dennis |
| 2017/0223451 A1 | 8/2017 | Kirsch |
| 2018/0054668 A1 | 2/2018 | Keady |
| 2018/0115818 A1 | 4/2018 | Asada et al. |
| 2018/0132048 A1 | 5/2018 | Usher et al. |
| 2018/0160211 A1 | 6/2018 | Kirsch et al. |
| 2018/0220239 A1 | 8/2018 | Keady et al. |
| 2018/0233125 A1 | 8/2018 | Mitchell |
| 2019/0038224 A1 | 2/2019 | Zhang |
| 2019/0082272 A9 | 3/2019 | Goldstein et al. |
| 2019/0387305 A1 | 12/2019 | Keady |
| 2020/0379717 A1 | 12/2020 | Mazur et al. |
| 2020/0380945 A1 | 12/2020 | Woodruff et al. |
| 2021/0014597 A1 | 1/2021 | Andersen |
| 2021/0152924 A1 | 5/2021 | Keady |
| 2022/0061767 A1 | 3/2022 | Goldstein et al. |

FOREIGN PATENT DOCUMENTS

| | | | |
|---|---|---|---|
| DE | 4312155 | | 10/1994 |
| DE | 102012221233 | | 3/2014 |
| DE | 102013203334 | | 5/2014 |
| EP | 0495653 | A1 | 7/1992 |
| EP | 0643881 | | 12/1998 |
| EP | 0935236 | | 8/1999 |
| EP | 1415505 | | 12/2002 |
| EP | 1033063 | B1 | 5/2003 |
| EP | 1320281 | | 6/2003 |
| EP | 0692169 | | 7/2003 |
| EP | 1483591 | | 11/2003 |
| EP | 1385324 | | 1/2004 |
| EP | 1385324 | A1 | 1/2004 |
| EP | 1401240 | | 3/2004 |
| EP | 1570244 | | 6/2004 |
| EP | 1489596 | | 12/2004 |
| EP | 1519625 | A2 | 3/2005 |
| EP | 1594344 | | 9/2005 |
| EP | 1638079 | | 3/2006 |
| EP | 1640972 | | 3/2006 |
| EP | 1640972 | A1 | 3/2006 |
| EP | 1674061 | | 6/2006 |
| EP | 1681903 | | 7/2006 |
| EP | 1800950 | | 6/2007 |
| EP | 1841283 | | 10/2007 |
| EP | 1322268 | B1 | 1/2009 |
| EP | 1313417 | B1 | 2/2009 |
| EP | 1313418 | B1 | 3/2009 |
| EP | 2749043 | | 7/2014 |
| EP | 2991381 | | 4/2019 |
| EP | 3068142 | | 9/2019 |
| FR | 2560520 | | 9/1985 |
| GB | 1518299 | | 7/1978 |
| GB | 2082820 | | 8/1980 |
| GB | 2441835 | | 8/2008 |
| JP | 02-097362 | A | 4/1990 |
| JP | 5145623 | | 6/1993 |
| JP | H05199590 | | 8/1993 |
| JP | H05336599 | | 12/1993 |
| JP | H0877468 | | 3/1996 |
| JP | H10162283 | | 6/1998 |
| JP | H10294989 | | 11/1998 |
| JP | 297362 | | 9/1999 |
| JP | 12878298 | | 11/1999 |
| JP | H11331990 | | 11/1999 |
| JP | 3085237 | | 7/2000 |
| JP | 2001045585 | | 2/2001 |
| JP | 2001054184 | | 2/2001 |
| JP | 2002-204500 | A | 7/2002 |
| JP | 3353701 | | 12/2002 |
| JP | 3353701 | B2 | 12/2002 |
| JP | 2003304599 | | 10/2003 |
| JP | 3556987 | | 5/2004 |
| JP | 2005064744 | | 3/2005 |
| JP | 2005130205 | | 5/2005 |
| JP | 2005168888 | | 6/2005 |
| JP | 2005227511 | | 8/2005 |
| JP | 2005260944 | | 9/2005 |
| JP | 2005295175 | | 10/2005 |
| JP | 2006107044 | | 4/2006 |
| JP | 2004289762 | | 2/2007 |
| JP | 2009003040 | | 1/2009 |
| JP | 2017147677 | | 8/2017 |
| KR | 20020086433 | | 11/2002 |
| KR | 100366231 | | 12/2002 |
| KR | 20030013732 | | 2/2003 |
| KR | 20030058432 | | 7/2003 |
| KR | 20030068021 | | 8/2003 |
| KR | 20030069471 | | 8/2003 |
| KR | 101154948 | | 7/2006 |
| KR | 100607492 | | 8/2006 |
| KR | 100783099 | | 12/2007 |
| KR | 101194923 | | 10/2012 |

(56) References Cited

FOREIGN PATENT DOCUMENTS

| TW | 200615862 | | 5/2006 |
|----|-----------|---|--------|
| WO | WO1986000133 | | 1/1986 |
| WO | 93/26084 | A1 | 12/1993 |
| WO | WO9326085 | | 12/1993 |
| WO | WO1993026085 | | 12/1993 |
| WO | WO1997025790 | | 7/1997 |
| WO | WO1998054878 | | 12/1998 |
| WO | WO1999043185 | | 8/1999 |
| WO | WO2001001731 | | 1/2001 |
| WO | WO2001057852 | | 8/2001 |
| WO | 01/89083 | A1 | 11/2001 |
| WO | WO2002013522 | | 2/2002 |
| WO | 02/17835 | A1 | 3/2002 |
| WO | WO2002017836 | | 3/2002 |
| WO | WO2002093891 | | 11/2002 |
| WO | WO2002101720 | | 12/2002 |
| WO | WO2003023766 | | 3/2003 |
| WO | WO2003073790 | | 9/2003 |
| WO | WO2004016037 | | 2/2004 |
| WO | WO2006026812 | | 3/2004 |
| WO | WO2007028250 | | 3/2004 |
| WO | WO2004114722 | | 12/2004 |
| WO | WO2005029468 | | 3/2005 |
| WO | WO2005073875 | | 8/2005 |
| WO | WO2005107320 | | 11/2005 |
| WO | WO2006034029 | | 3/2006 |
| WO | 2006/036262 | A2 | 4/2006 |
| WO | 2006/037156 | A1 | 4/2006 |
| WO | WO2006037156 | | 4/2006 |
| WO | WO2006054205 | | 5/2006 |
| WO | WO2006054698 | | 5/2006 |
| WO | WO2006074082 | | 7/2006 |
| WO | 2006/097099 | A1 | 9/2006 |
| WO | WO2006114101 | | 11/2006 |
| WO | WO2007007916 | | 1/2007 |
| WO | WO2007017809 | | 2/2007 |
| WO | WO2007017810 | | 2/2007 |
| WO | 2007/073818 | A1 | 7/2007 |
| WO | WO2007073818 | | 7/2007 |
| WO | WO2007082579 | | 7/2007 |
| WO | WO2007092660 | | 8/2007 |
| WO | WO2007147077 | | 12/2007 |
| WO | WO2008017326 | | 2/2008 |
| WO | WO2008050583 | | 5/2008 |
| WO | 2008/067454 | A2 | 6/2008 |
| WO | WO2008096125 | | 8/2008 |
| WO | 2009/023633 | A1 | 2/2009 |
| WO | WO2009023633 | | 2/2009 |
| WO | WO2009023784 | | 2/2009 |
| WO | WO2009097009 | | 8/2009 |
| WO | WO2011110901 | | 9/2011 |
| WO | WO2011161487 | | 12/2011 |
| WO | WO2012097150 | | 7/2012 |

OTHER PUBLICATIONS

*Samsung Electronics Co., Ltd., and Samsung Electronics, America, Inc., v. Staton Techiya, LLC,* IPR2022-00242, Dec. 23, 2021.
*Samsung Electronics Co., Ltd., and Samsung Electronics, America, Inc., v. Staton Techiya, LLC,* IPR2022-00243, Dec. 23, 2021.
*Samsung Electronics Co., Ltd., and Samsung Electronics, America, Inc., v. Staton Techiya, LLC,* IPR2022-00234, Dec. 21, 2021.
*Samsung Electronics Co., Ltd., and Samsung Electronics, America, Inc., v. Staton Techiya, LLC,* IPR2022-00253, Jan. 18, 2022.
*Samsung Electronics Co., Ltd., and Samsung Electronics, America, Inc., v. Staton Techiya, LLC,* IPR2022-00324, Jan. 13, 2022.
*Samsung Electronics Co., Ltd., and Samsung Electronics, America, Inc., v. Staton Techiya, LLC,* IPR2022-00281, Jan. 18, 2022.
*Samsung Electronics Co., Ltd., and Samsung Electronics, America, Inc., v. Staton Techiya, LLC,* IPR2022-00302, Jan. 13, 2022.
*Samsung Electronics Co., Ltd., and Samsung Electronics, America, Inc., v. Staton Techiya, LLC,* IPR2022-00369, Feb. 18, 2022.
*Samsung Electronics Co., Ltd., and Samsung Electronics, America, Inc., v. Staton Techiya, LLC,* IPR2022-00388, Feb. 18, 2022.
*Samsung Electronics Co., Ltd., and Samsung Electronics, America, Inc., v. Staton Techiya, LLC,* IPR2022-00410, Feb. 18, 2022.
*Samsung Electronics Co., Ltd., and Samsung Electronics, America, Inc., v. Staton Techiya, LLC,* IPR2022-01078, Jun. 9, 2022.
*Samsung Electronics Co., Ltd., and Samsung Electronics, America, Inc., v. Staton Techiya, LLC,* IPR2022-01099, Jun. 9, 2022.
*Samsung Electronics Co., Ltd., and Samsung Electronics, America, Inc., v. Staton Techiya, LLC,* IPR2022-01106, Jun. 9, 2022.
*Samsung Electronics Co., Ltd., and Samsung Electronics, America, Inc., v. Staton Techiya, LLC,* IPR2022-01098, Jun. 9, 2022.
U.S. Appl. No. 90/015,146, Samsung Electronics Co., Ltd. and Samsung Electronics, America, Inc., Request for Ex Parte Reexamination of U.S. Pat. No. 10,979,836.
U.S. Appl. No. 90/019,169, Samsung Electronics Co., Ltd. and Samsung Electronics, America, Inc., Request for Ex Parte Reexamination of U.S. Pat. No. 11,244,666.
*Samsung Electronics Co., Ltd., And Samsung Electronics, America, Inc., v. Staton Techiya, LLC,* IPR2022-00559, Feb. 9, 2024.
Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Appendix 1A-1C for U.S. Pat. No. 8,111,839 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Appendix 2A-2C for U.S. Pat. No. 8,254,591 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Appendix 3A-3C for U.S. Pat. No. 8,315,400 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Appendix 4A-4C for U.S. Pat. No. 9,124,982 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Appendix 5A-5C for U.S. Pat. No. 9,270,244 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Appendix 6A-6C for U.S. Pat. No. 9,491,542 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Appendix 7A-7C for U.S. Pat. No. 9,609,424 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Appendix 8A-8C for U.S. Pat. No. 10,405,082 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Appendix 9A-9Cfor U.S. Pat. No. 8,111,839 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Appendix 10A-10C for U.S. Pat. No. 10,979,836 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

(56) References Cited

OTHER PUBLICATIONS

Appendix 11A-11C for U.S. Pat. No. 11,039,259 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Appendix 12A-12C for U.S. Pat. No. 11,057,701 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Appendix 13A-13C for U.S. Pat. No. 11,217,237 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Appendix 14A-14C for U.S. Pat. No. 11,244,666 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A1 (Nacre QuietPro) to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A2 (Silynx QuietOps) to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A3 (Motorola H5) to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A4 (Jawbone Aliph) to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A5 (Snooper) to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A6 (NCH Swift) to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A7 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served 18, 2022.

Ex. A8 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A9 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A10 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A11 (NaturalRecorder) to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A12 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A13 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A14 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A15 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A16 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A17 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A18 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A19 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A20 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A21 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A22 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A23 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A24 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A25 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A26 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A27 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A28 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. A29 to Samsung's Invalidity Contentions and P.R. 3-3 And 3-4 Disclosures for U.S. Pat. Nos. 8,111,839, 8,254,591, 8,315,400,

(56) References Cited

OTHER PUBLICATIONS 9,124,982, 9,270,244, 9,491,542, 9,609,424, 10,405,082, 10,966,015 (Case No. 2:22-CV-00053-JRG-RSP), served May 18, 2022.
Ex. A30 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. A31 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. A32 (Olympus WS-320M) to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. A33 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. A34 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. A35 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B1 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B2 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B3 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B4 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B5 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B6 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B7 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B8 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B9 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B10 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B11 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B12 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B13 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B14 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B15 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B16 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B17 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B18 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. B19 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. C1 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. C2 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. C3 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. C4 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. C5 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. C6 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. C7 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. C8 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. C9 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. C10 to Samsung's Invalidity Contentions and P.R. 3-3 And 3-4 Disclosures for U.S. Pat. Nos. 8,111,839, 8,254,591, 8,315,400,

(56)　　　References Cited

OTHER PUBLICATIONS 9,124,982, 9,270,244, 9,491,542, 9,609,424, 10,405,082, 10,966,015 (Case No. 2:22-CV-00053-JRG-RSP), served May 18, 2022.
Ex. C11 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. C12 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. C13 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. C14 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. C15 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D1 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D2 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D3 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D4 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D5 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D6 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D7 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D8 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D9 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D10 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D11 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D12 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D13 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D14 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D15 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D16 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D17 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D18 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D19 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D20 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D21 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D22 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D23 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D24 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D25 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D26 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D27 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D28 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D29 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D30 to Samsung's Invalidity Contentions and P.R. 3-3 And 3-4 Disclosures for U.S. Pat. Nos. 8,111,839, 8,254,591, 8,315,400,

(56)  References Cited

OTHER PUBLICATIONS 9,124,982, 9,270,244, 9,491,542, 9,609,424, 10,405,082, 10,966,015 (Case No. 2:22-CV-00053-JRG-RSP), served May 18, 2022.
Ex. D31 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. D32 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E1 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E2 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E3 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E4 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E5 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E6 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E7 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E8 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E9 (corrected) to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E9 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E10 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E11 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E12 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E13 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E14 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E15 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E16 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E17 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. E18 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F1 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F2 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F3 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F4 (corrected) to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F4 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F5 (corrected) to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F5 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F6 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F7 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F8 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F9 (corrected) to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F9 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F10 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

(56) References Cited

OTHER PUBLICATIONS

Ex. F11 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F12 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F13 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F14 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F15 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F16 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F17 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. F18 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G1 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G2 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G3 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G4 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G5 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G6 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G7 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G8 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G9 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G10 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G11 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G12 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G13 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G14 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G15 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G16 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G17 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G18 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G19 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G20 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G21 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G22 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G23 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G24 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G25 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G26 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G27 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

(56)     References Cited

OTHER PUBLICATIONS

Ex. G28 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G29 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G30 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G31 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G32 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G33 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G34 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. G35 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H1 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H2 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H3 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H4 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H5 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H6 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H7 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H8 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H9 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H10 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H11 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H12 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H15 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H16 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H17 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H18 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H19 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. H20 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. I1 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. I2 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. I3 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. I4 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. I5 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. I6 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. I7 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. I8 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. I9 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

(56) References Cited

OTHER PUBLICATIONS

Ex. I10 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. I11 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. I12 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. I15 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. I16 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18 2022.
Ex. I17 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. I18 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J1 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J2 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J3 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J4 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J5 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J6 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J7 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J8 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J9 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J10 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J11 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J12 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J13 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J14 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J15 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J16 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J17 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J18 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J19 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J20 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J21 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J22 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J23 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J24 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J25 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J26 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J27 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.
Ex. J28 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

(56)                    References Cited

OTHER PUBLICATIONS

Ex. J29 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Ex. J30 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022.

Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K1 (Calhoun) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K2 (Cerra) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K3 (Chen '353) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K4 (Comerford) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K5 (Couper) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K6 (Emoto) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K7 (Zaykovskiy) to Samsung's Invalidity Contentions and P.R. 3-3 And 3-4. Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K8 (Hunter) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K9 (Jones) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K10 (Kelliher) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K11 (Kopra) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K12 (Lagassey '043) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K13 (Lemelson) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K14 (Pickering) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K15 (Schuler) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K16 (Soufflet) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K17 (White) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K18 (BlueAnt V1) to Samsung's Invalidity Contentions and P.R. 3-3 And 3- 4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K19 (LG Chocolate) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K20 (Midomi) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K21 (Promptu) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K22 (Samsung SCH-a950) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K23 (W850) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K24 (EARS) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K25 (Motorola Pebl) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K26 (Silynx QuietOps) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K27 (NACRE QuietPro) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K28 (Shazam) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K29 (Vlingo) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit K30 (Yoon) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit L1 (Alves 801) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit L2 (Burnett 421) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

(56)  References Cited

OTHER PUBLICATIONS

Exhibit L3 (Hietanen) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit L4 (Huang 798) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit L5 (Jaber) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit L6 (LG HBM-730) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit L7 (Nokia BH-600) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit L8 (Nokia BH-900) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit L9 (Pedersen) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit L10 (QuietOps) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit L11 (QuietPro) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit L12 (Visser '958) to Samsung's Invalidity Contentions and P.R. 3-3 And 3-Disclosures for U.S. Pat. Nos. 11,039,259, 11,057,701, 11,217,237, and 11,244,666 (Case No. 2:22-CV-00053-JRG-RSP), served Jul. 6, 2022.
Exhibit L13 (Zhang 099) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit L14 (Byford) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit L15 (Mejia '156) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit L16 (Yang '130) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M1 (Armstrong) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M2 (Boersma) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M3 (Dijsktra 972) to Samsung's Invalidity Contentions and P.R. 3-3 And 3-Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M4 (Hamacher 031) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M5 (Hietanen) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M6 (Hotvet) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M7 (Kondo 701) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M8 (Kvaløy) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M9 (Light) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M10 (Melanson) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M11 (Nemirovski 368) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M12 (Platz 077) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M13 (Rasmussen 245) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M14 (Svean 359) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M15 (Victorian 625) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M16 (Zurek 379) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M17 (Jawbone) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M18 (QuietOps) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M19 (NACRE QuietPro) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M20 (SenSay) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit M21 (Andrea) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

(56)        References Cited

OTHER PUBLICATIONS

Exhibit M22 (Darbut) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit M23 (Ramakrishnan) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N1 (Platz 077) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N2 (Kvaløy) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N3 (Inanaga) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N4 (Rosenberg) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N5 (Visser 958) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N6 (Terlizzi) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N7 (Light) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N8 (Boersma) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N9 (McCune) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N10 (Bose) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N11 (Emoto) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N12 (Dijkstra 243) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N13 (Cohen 908) to Samsung's Invalidity Contentions and P.R. 3-3 And 3-4 Disclosures for U.S. Patent Nos. 11,039,259, 11,057,701, 11,217,237, and 11,244,666 (Case No. 2:22-CV-00053-JRG-RSP), served Jul. 6, 2022.

Exhibit N14 (Rast) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N15 (Bothra 629) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N16 (Victorian 625) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N17 (Engle) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N18 (Svean 359) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N19 (Hotvet) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N20 (Killion 056) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N21 (Bothra 087) to Samsung's Invalidity Contentions and P.R. 3-3 And 3-4 Disclosures for U.S. Pat. Nos. 1,039,259, 11,057,701, 11,217,237, and 11,244,666 (Case No. 2:22-CV-00053-JRG-RSP), served Jul. 6, 2022.

Exhibit N22 (Melanson) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N23 (Andrea) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N24 (Hohman) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N25 (Bergeron) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N26 (Frank) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N27 (Darbut 423) to Samsung's Invalidity Contentions and P.R. 3-3 And 3-Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N28 (QuietPro) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N29 (QuietOps) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N30 (Jawbone) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N31 (EarSet 2) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N32 (Etymotic ER-6) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

Exhibit N33 (Zen) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.

(56) References Cited

OTHER PUBLICATIONS

Exhibit N34 (Motorola H605) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N35 (Peltor Lite-Com II) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N36 (Discovery 655) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N37 (MX200 Series) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N38 (Sony S700) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N39 (H5 Miniblue) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N40 (3D Active Ambient IEM) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N41 (Armstrong 422) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N42 (Hohn) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N43 (Mejia 228) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N44 (Nemirovski 368) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N45 (Thomasson) to Samsung's Invalidity Contentions and P.R. 3-3 And 3-Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N46 (Zurek 003) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N47 (Kurcan) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N48 (Rafaely) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N49 (Vaidyanathan) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N50 (Westerlund) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
Exhibit N51 (Zhang) to Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022.
3M/Acaro Technologies' E-A-RFitTM Validation System ("E-A-RFit"), Sep. 10, 2015 WayBack Machine capture of 3M's website depicts a brochure describing the E-A-RFit and "Individual Fit Testing Using F-Mire." https://web.archive.org/web/20150910084252/http:/multimedia.3m.com/mws/media/10622 67O/earfit-dual-ear-brochure- us.pdf?fn=EARfit%20Dual-Ear%20Brochure%20US.pdf (SAM-TECH_00052333—SAM-TECH_00052336; SAM-TECH_00052339—SAM-TECH_00052339).
3M/Acaro Technologies' E-A-RFitTM Validation System ("E-A-RFit"), 2010 brochure from 3M's website describes the E-A-RFit and identifies model 393-1000 as an available mode. https://multimedia.3m.com/mws/media/62914 9O/3m-e-a-rfit-validation-system- brochure.pdf (SAM-TECH_00052186).
3M/Aearo Technologies' E-A-RFitTM Validation System ("E-A-RFit"), Abstract titled "New from ISEA member 3M Company (www.3m.com] is the E-A-Rfit Validation System a quantitative hearing protector fittest", published in Jul. 2012. New from ISEA member 3M Company (www.3m.com] is the E-A-Rfit Validation System a quantitative hearing protector fittest, EHS today, vol. 5, Issue 7, ISSN 1945-9599, Gale Group Trade & Industry Database (Jul. 2012), available at https://dialog.proquest.com/professional/docview/1095272736?accountid=154502 (SAM-TECH_00052203).
3M/Aearo Technologies' E-A-RFitTM Validation System ("E-A-RFit"), Apr. 24, 2007 article published by E.H. Berger from Aearo Technologies discusses E-A-RFit and notes that "[t]he E-A-RfitTM Validation System is a quick and accurate method of estimating real-ear attenuation for a given fitting of a pair of earplugs" and "has been designed and built to be an integral part of a comprehensive workplace hearing conservation program." See E.H. Berger, Recommended Applications for the E-A-RFitTM Validation System in a Workplace Hearing Conservation Program, Aearo Company (2007) (SAM-TECH_00056087—SAM-TECH_0005609).
3M/Aearo Technologies' E-A-RFitTM Validation System ("E-A-RFit"), At least by Feb. 9, 2007, A 2010 brochure for the E-A-RFit describes the validation system and lists Model 393-1000 as an available product. https://multimedia.3m.com/mws/media/67382 8O/earfit-brochure.pdf (SAM-TECH_00052179—SAM-TECH_00052184).
Methods Of Developing And Validating A Field—MIRE Approach For Measuring Hearing Protector Attenuation, Berger, Elliott & Voix, Jérémie & Kieper, R., Feb. 9, 2007, in connection with 3M/Aearo Technologies' E-A-RFitTM Validation System ("E-A-RFit"); This article was originally prepared for the 32nd Annual Conference of the National Hearing Conservation Association, held on Feb. 15-17, 2007, in Savannah, Georgia, and published in Spectrum, vol. 24, Suppl. 1.
3M/Acaro Technologies' E-A-RFitTM Validation System ("E-A-RFit"), Mar. 16, 2016 WayBack Machine capture of 3M's website lists the E-A-RFit for purchase. https://web.archive.org/web/20160316180537/http://www.3m.com/3M/en_US/company- us/all-3m-products/~/All-3M-Products/Personal-Protective- Equipment/Hearing- Protection/Safety/Worker-Health-Safety/E- A-R-Fit-Validation-Tools/?N=5002385+8709322+8711017+8711405+8720539+8720546+8720770+3294857497&rt=r3 (SAM-TECH_00052201).
3M/Acaro Technologies' E-A-RFitTM Validation System ("E-A-RFit"), Mar. 20, 2016 WayBack Machine capture of 3M's website describes the Validation System and protection that the system offers. https://web.archive.org/web/20160320080156/http:/www.3m.com/3M/en_US/company-us/all-3m-products/~/All-3M-Equipment/Hearing- Protection/Safety/Worker-Health- Safety/?N=5002385+8709322+8711017+8711405+8720539+8720546+3294857497&rt=r3 (SAM-TECH_00052278; SAM—TECH_00052292).
3M/Aearo Technologies' E-A-RFitTM Validation System ("E-A-RFit"), Sep. 4, 2015 WayBack Machine capture of 3M's website contains an image of the E-A-RFit and states "[t]he 3M™ E-A-Rfit™ Dual Ear Validation System makes it easy to measure every employee's unique level of protection and takes the guesswork out managing compliance in your hearing conservation program." https://

(56)                    References Cited

OTHER PUBLICATIONS web.archive.org/web/20150904132810/http:/solutions.3m.com/wps/portal/3M/en_US/3M-PPE-Safety-Solutions/Personal-Protective-Equipment/safety-management/safety-training/hearing-protection-fit-testing/?WT.mc_id=www.3m.com/EARfitDe mo/ (SAM-TECH_00052276; SAM-Tech _; SAM-TECH_00052274).

A binaural processor for missing data speech recognition in the presence of noise and small-room reverberation, Kalle Palomäki, Guy Brown & Deliang Wang, Speech Communication, 43, 361-378.

A compact multi-sensor headset for hands-free communication, Liu, Zicheng & Seltzer, Michael & Acero, A. & Tashev, Ivan & Zhang, Zhengyou & Sinclair, Michael, IEEE Workshop on Applications of Signal Processing to Audio and Acoustics, 138-141. 10.1109/ASPAA.2005.1540188.

A Dual-Mode Human-Machine Interface for Robotic Control Based on Acoustic Sensitivity of the Aural Cavity—Ravi Vaidyanathan, et al., Feb. 2006.

A Local Active Noise Control System for Locomotive Drivers, internoise 2000, the 29th International Congress and Exhibition on Noise Control Enginerring, Nielsen, Saebo, Ottesen, Reinen, Sorsdal, Aug. 2000.

A MFCC-based CELP speech coder for server-based speech recognition in network environments, Yoon, Jae Sam, Gil Ho Lee, and Hong Kook Kim, IEICE Transactions on Fundamentals of Electronics, Communications and Computer Sciences 90.3, 626-632, Mar. 2007.

A Modified Coherence Based Method for Dual Microphone Speech Enhancement, M. Rahmani, et al., Signal Processing and Communications, 2007.

A New Two-Sensor Active Noise Cancellation Algorithm, K.C. Zangi, 1993 IEEE International Conference on Acoustics, Speech, and Signal Processing, Minneapolis, MN, USA, 1993, pp. 351-354 vol. 2, doi: 10.

A Pattern Recognition Approach to Voiced-Unvoiced-Silence Classification with Applications to Speech Recognition, B. Atal and L. Rabiner, IEEE Transactions on Acoustics, Speech, and Signal Processing, vol. 24, No. 3, pp. 201-212, Jun. 1976.

Active Noise Attenuation Using LQG/LTR Control, Garcia, José & Bortoloto, Edson & Ribeiro, Jean & Garcia, Eletrônica de Potência. 9. 23-27, Eletrônica de Potência. 9. 23-27. 10.18618/REP.2005.2.023027, Nov. 2004.

Active Noise Cancellation for Headphones Used in High Noise Environments Using Conventional Analog Circuitry, Mark C. Flohr, May 1, 1987.

Active Noise Control System for Headphone Applications Sen M. Kuo, et al. 2006.

Active Noise Control: Low-Frequency Techniques for Suppressing Acoustic Noise Leap Forward with Signal Processing, S.J. Elliott and P.A. Nelson, Oct. 1993.

Active Noise Reduction Headphone Measurement: Comparison Of Physical And Psychophysical Protocols And Effects Of Microphone Placement, Perala, Apr. 10, 2006.

Active noise Reduction in an ear terminal, Ottesen, The Journal of the Acoustical Society of America, vol. 105, Issue 2, Feb. 1999.

Adaptive Feedback Active Noise Control Headset: Implementation, Evaluation, and its Extensions, Woon S. Gan, et al. 2005.

Adaptive Filtering in the Frequency Domain, M. Dentino, J. McCool & B. Widrow, Proceedings of the IEEE, vol. 66, No. 12, pp. 1658-1659, Dec. 1978.

Adaptive Noise Cancellation in a Multimicrophone System for Distortion Product Otoacoustic Emission Acquisition, Rafael E. Delgado, et al., 2000.

Adaptive Noise Cancelling In Headsets, Per Rubak, Henrik D. Green & Lars G. Johansen, Proceedings of IEEE Nordic Signal Processing Symposium, NORSIG'96, Sep. 24-27, 1996, Espoo, Finland.

Adaptive noise cancelling: Principles and applications, B. Widrow, et al., Proceedings of the IEEE, vol. 63, No. 12, pp. 1692-1716, Dec. 1975.

Air- and Bone-Conductive Integrated Microphones for Robust Speech Detection and Enhancement, Yanli Zheng, et al., 2003 IEEE Workshop on Automatic Speech Recognition and Understanding.

An Integrated Audio And Active Noise Control Headsets, W. S. Gan & S. M. Kuo, IEEE Transactions on Consumer Electronics, vol. 48, No. 2, pp. 242-247, May 2002.

Apple's AirPods Pro ("AirPods Pro"), Article on Apple's website published Apr. 15, 2020 mentions the AirPods Pro has an Ear Tip Fit test available. https://support.apple.com/en-us/HT210633 (SAM-TECH_00072120—SAM-TECH_00072123).

Apple's AirPods Pro ("AirPods Pro"), article published by Dan Seifert on Mar. 29, 2019 reviews the AirPods Pro and states Apple is selling the second-gen AirPods in two ways: with the new wireless charging case for $199 or with the standard case for the same $159 as before. https://www.theverge.com/2019/3/29/1828601 2/apple-airpods-2-new-2nd-gen-review-price-specs-features; (SAM-TECH_00057262—SAM-TECH_00057275).

Apple's AirPods Pro ("AirPods Pro"), Dec. 21, 2019 WayBack Machine capture of Apple's website displays an image of the AirPods Pro and states "[u]se the Ear Tip Fit Test to create the optimal listening experience—you'll get the right tip size for your ears, and the best seal for noise cancellation." https://web.archive.org/web/20191221170719/ https://www.apple.com/airpods-pro/ (SAM-TECH_00054447; SAM-TECH_00054134).

Apple's AirPods Pro ("AirPods Pro"),Nov. 2, 2019 article by Karisa Bell published on mashable.com discusses whether Apple's AirPods Pro are compatible with Androids. https://mashable.com/article/do-airpods-pro- work-with-android. (SAM-TECH_00052378—SAM-TECH_00052390).

Nov. 3, 2019 article published by Imran Hussain discusses how to use the ear tip fit test with the AirPods Pro and an iOS device such as the iphone 11 for the best fit. https://www.esquire.com/lifestyle/a29612084/apple-airpods-pro-active-noise-cancellation-review/ (SAM-TECH_00052413—SAM-TECH_00052424).

Oct. 20, 2019 article by Tim Hardwick discussing how to perform an ear tip fit test using Apple's AirPods Pro with Apple's iPhone 11. https://www.macrumors.com/how- to/perform-ear-tip-fit-test-airpods-pro/; (SAM-TECH_00052357—SAM-TECH_00052370).

Apple's AirPods Pro ("AirPods Pro"),Oct. 29, 2019 artcile by Sarah Rense also discusses testing out the AirPods Pro with active-noise cancellation. https://www.esquire.com/lifestyle/a29612084/apple-airpods-pro-active-noise-cancellation-review/ (SAM-TECH_00058067—SAM-TECH_00058080).

Apple's AirPods Pro ("AirPods Pro"),The specs of the AirPods Pro can be found here https://web.archive.org/web/20191224065355/ https://www.apple.com/airpods-pro/specs/ (SAM-TECH_00052343—SAM-TECH_00052352; SAM-TECH_00053159).

Apple's iPhone 11 (iPhone 11), Oct. 11, 2019 article published by Jake Peterson discusses the eartip fit test using AirPods Pro and an iPhone running iOS 13.2. https://ios.gadgethacks.com/how-to/make- your-airpods-pro-fit-better-by-testing-rubber-tips-0210500/ (SAM-TECH_00056564—SAM-TECH_00056569).

Apple's iPhone 11 (iPhone 11), Press release from Apple's website dated Sep. 10, 2019 states "Apple introduces dual camera iPhone 11" and that "Customers in the US, Puerto Rico, the US Virgin Islands and more than 30 other countries and regions will be able to pre-order iPhone 11 beginning at 5 a.m. PDT on Friday, Sep. 13 with availability beginning Friday, Sep. 20." https://www.apple.com/newsroom/2019/09/a pple-introduces-dual-camera-iphone-11/ (SAM-TECH_00056571—SAM-TECH_00056588).

Apple's iPhone 11 (iPhone 11), Sep. 15, 2019 WayBack Machine capture of Apple's website has an image of the iphone 11 and lists it for sale on the website. https://web.archive.org/web/20190915061032 /https://www.apple.com/shop/buy-iphone/iphone-11; (SAM-TECH_00055106—SAM-TECH_00055123).

Apple's iPhone 11 (iPhone 11), WayBack Machine capture from Sep. 16, 2019 of Apple's website, displays the iPhone and states "Available 9.20." https://web.archive.org/web/20190916102733/ https://www.apple.com/iphone-11/specs/. (SAM-TECH_00056907).

Audiometric Ear Canal Probe with Active Ambient Noise Control, B. Rafaely & M. Furst, IEEE Transactions on Speech and Audio Processing, vol. 4, No. 3, pp. 224-230, May 1996.

(56)                    References Cited

OTHER PUBLICATIONS

Bang and Olufsen EarSet 2 Bluetooth Headset, At least by 2006, https://www.beoworld.org/prod_details.asp?pid=733 (SAM-TECH_00094798).
Bang and Olufsen EarSet 2 Bluetooth Headset, At least by 2006, https://www.dexigner.com/news/9935 (SAM-TECH_00094865).
Brian Hobbs et al., Wideband Hearing, Intelligibility, and Sound Protection, Jan. 10, 2008 Final Report AFRL-RH-WP-TR-2009-0031 at 2 (SAM-TECH_00053002-116).
Build These Noise-Cancelling Headphones, Jules Ryckebusch, 1997.
Combined feedback-feedforward active noise-reducing headset—The effect of the acoustics on broadband performance, Boaz Rafaely & Matthew Jones, J. Acoust. Soc. Am. Sep. 1, 2002; 112 (3): 981-989.
Dec. 25, 2005 WayBack Machine Capture of Maico's website has an image of the Maico MI26 and discusses the products features. https://web.archive.org/web/20051225200404/http:/www.maico-diagnostics.com/eprise/main/Maico/Products/ Files/MI26/SpecSheet.MI24-26.NEW.pdf (SAM-TECH_00051161—SAM-TECH_00051162).
Direct filtering for air- and bone-conductive microphones, Zicheng Liu, Zhengyou Zhang, A. Acero, J. Droppo and Xuedong Huang , IEEE 6th Workshop on Multimedia Signal Processing, 2004., Siena, Italy, 2004, pp. 363-366.
DSP Software Development Techniques for Embedded and Real-Time Systems, Robert Oshana, 2006.
E-3 In-Flight Acoustic Exposure Studies and Mitigation Via Active Noise Reduction Headset, Frank Mobley, John Allen Hall, & Donald Yeager, Dec. 2002.
Efficient Tracking of the Cross-Correlation Coefficient, AARTS, IEEE Transactions on Speech and Audio Processing, vol. 10, No. 6, Sep. 2002.
Etymotic ER-6 Earphones, At least by Feb. 7, 2005, https://www.cnet.com/reviews/etymoti c-er-6-review/ (SAM-TECH_00095121).
Etymotic ER-6 Earphones, At least by Feb. 7, 2005, https://www.etymotic.com/ephp/er6i- ts.aspx (SAM-TECH_00095178).
Etymotic's ER-33 Occlusion Effect Meter ("ER-33"), Apr. 9, 2001 WayBack Machine capture of Etymotic's website contains an image of the ER-33 and states that "[t]he ER-33 Occlusion Effect Meter quickly quantifies the occlusion effect and earmold leakage" and was on sale for $350.00. https://web.archive.org/web/20010404224259/ https://www.etymotic.com/ (SAM-TECH_00054976).
Etymotic's ER-33 Occlusion Effect Meter ("ER-33"), Aug. 2003 article by H. Gustav Mueller in the Hearing Journal, Mueller describes the ER-33 as a product manufactured by Etymotic that "costs no more than a few bottles of good wine." See H. Gustav Mueller, There's less talking in barrels, but the occlusion effect is still with us, 56 Hearing J. 10, 14 (2003) (SAM-TECH_00054761—SAM-TECH_00054764).
Etymotic's ER-33 Occlusion Effect Meter ("ER-33"), Dec. 5, 2004 article submitted by Wayne J. Staab to The Hearing Review, discusses the ER-33 and notes "[t]he occlusion effect was measured with the ER-33 Occlusion Effect meter (Figure 5) using a probe tube extending 2 mm beyond the receiver tip. The ER-33 is a hand-held device that measures both the magnitude of the occlusion effect and the leakage around an earmold." https://hearingreview.com/practice- building/practice-management/measuring- the-occlusion-effect-in-a-deep-fitting- hearing-device (SAM-TECH_00060339—SAM-TECH_00060350).
Etymotic's ER-33 Occlusion Effect Meter ("ER-33"), Mar. 3, 2005 capture of Etymotic's website contains a description of the ER-33 which includes a sale price for $350.00. https://web.archive.org/web/20050303170952/ http://www.etymotic.com/pro/er33.asp (SAM-TECH_00054986).
Etymotic's ER-33 Occlusion Effect Meter ("ER-33"), Mar. 4, 2005 WayBack Machine capture of Etymotic's website contains a user manual for the ER-33 which was on sale at that time. https://web.

archive.org/web/20050304030715/ http://www.etymotic.com/pdf/er33-oem- usermanual.pdf (SAM-TECH_00055001; SAM-TECH_00060165).
Excerpts from Discrete-Time Signal Processing, Third Edition, Alan V. Oppenheim & Ronald W. Schafer, Aug. 18, 2009.
Experimentation To Address Appropriate Test Techniques For Measuring The Attenuation Provided By Double ANR Hearing Protectors, Susan E. Mercy, Christopher Tubb and Soo H. James, New Directions for Improving Audio Effectiveness (pp. 18-1-18-14). Meeting Proceedings RTO-MP-HFM-123, Paper 18. Neuilly-sur-seine, France: RTO.
Fit-Testing of Hearing Protection, WITT, The Hearing Review.
Gennum Zen Digital Wireless Headset ("Zen"), At least by 2004, CNET Article—Gennum Zen Bluetooth Headset Review (SAM-TECH_00098419).
Gennum Zen Digital Wireless Headset ("Zen"), At least by 2004, Gennum Zen User Manual (SAM-TECH_00098432).
Gennum Zen Digital Wireless Headset ("Zen"), At least by 2004, Globe and Mail Article—Gennum Z-E-N Headset for Bluetooth (SAM-TECH_00098485).
Huseyin Dogan, Trym Holter, & Ingrid Svagard, Trial of a special end user terminal that aids field operators during emergency rescue operations, Proceedings of the 3rd International ISCRAM China Workshop, Harbin, China, at 4 (Aug. 2008) discusses the PARAT as well (SAM-TECH_00051920—SAM-TECH_00051931).
In-Ear Microphone Speech Data Recognition using HMMs, R. S. Kurcan, M. P. Fargues and R. Vaidyanathan, 2006 IEEE 12th Digital Signal Processing Workshop & 4th IEEE Signal Processing Education Workshop, Teton National Park, WY, USA, 2006.
In-Ear Microphone Speech Data Segmentation and Recognition using Neural Networks, G. Bulbuller, Monique Fargues & Ravi Vaidyanathan, IEEE 12th Digital Signal Processing Workshop and 4th IEEE Signal Processing Education Workshop, 2006.
In-Ear Microphone Techniques For Severe Noise Situations, N. Westerlund, M. Dahl, I. Claesson, Nov. 2005.
Interaction Techniques Using Prosodic Features of Speech and Audio Localization, Alex Olwal & Steven Feiner, Jan. 5, 2011.
Isolated Word Recognition from In-Ear Microphone Data Using Hidden Markov Models (HMM), Remzi Serdar Kurcan, Mar. 2006.
Jawbone Aliph, At least by Sep. 9, 2004, https://www.capecodtimes.com/story/news/20 06/12/24/new-earphones-let-you-go/50845129007 (SAM-TECH_00062054).
Jawbone Aliph, At least by Sep. 9, 2004, https://www.cnet.com/reviews/aliph-jawbone-bluetooth-headset-review/ (SAM-TECH_00060121).
Jawbone Aliph, At least by Sep. 9, 2004, https://www.wired.com/2004/09/military- headset-reaches-masses (SAM-TECH_00062036).
Jawbone Aliph, At least by Sep. 9, 2004, Jawbone User Manual (SAM-TECH_00061992).
Learning-Based Three Dimensional Sound Localization Using a Compact Non-Coplanar Array of Microphones, Kamen Y. Guentchev and John J. Weng, AAAI Technical Report SS-98-02, 1998.
Maico MI26 Tymp/audiometer combo ("Maico MI26"), Aug. 12, 2004 WayBack Machine Capture of Maico's website has an image of the Maico MI26 and lists the Maico MI26 as a product available for purchase. https://web.archive.org/web/20040422090329/http://www.maico-diagnostics.com:80/eprise/main/Maico/US_en/ProductCategories/LST01_Tympanometers (SAM-TECH_00060329—SAM-TECH_00060331).
Mar. 17, 2006 Wayback Machine capture of Maico's website has a user manual available for the Maico MI26 https://web.archive.org/web/20060317092410/ http:/www.maico- diagnostics.com/eprise/main/Maico/Products/ Files/MI26/1162-0322REVD.pdf (SAM-Tech_00051168—SAM-TECH_00051215).
Mar. 17, 2006 WayBack Machine Capture of Maico's website discusses frequently asked questions about the Maico MI26 andis' features. https://web.archive.org/web/20060317092109/ http://www.maico-diagnostics.com/eprise/main/Maico/Products/Files/MI24/FAQ.MI24-26.pdf (SAM-Tech_00051250—SAM-TECH_00051251).
Methods of measuring the attenuation of hearing protection devices, E H Berger, The Journal of the Acoustical Society of America vol. 79,6 (1986).

(56) References Cited

OTHER PUBLICATIONS

Microphone Array for Headset with Spatial Noise Suppressor, Ivan Tashev, Michael Seltzer & Alex Acero, 2005.

Microphone Array Processing for Robust Speech Recognition, Michael L. Seltzer, Jul. 2003.

Motorola H5 Miniblue Bluetooth Headset, Jan. 14, 2005, https://newatlas.com/ces-2006-bluetooth- innovations-abound-inner-ear-headset-bluetooth-keyboard-and-wireless-ipod- companion/4977/ (SAM-TECH_00060368) (Motorola H5 Miniblue Bluetooth Headset).

Motorola H5 Miniblue Bluetooth Headset, Jan. 14, 2005, https://www.cnet.com/tech/mobile/motorola- h5-miniblue-bluetooth-headset/ (SAM-TECH_00060424) (Motorola H5 Miniblue Bluetooth Headset).

Motorola H5 Miniblue Bluetooth Headset, Jan. 14, 2005, https://www.engadget.com/2006-01-04- motorolas-h5-miniblue-bluetooth-headset.html (SAM-TECH_00060628).

Motorola H5 Miniblue Headset ("Miniblue"), Jan. 2006, Motorola H9 Bluetooth Headset User Manual (SAM-TECH_00060509-14).

Motorola H605, At least by 2006, CNET Article—Motorola H605 Bluetooth Headset Review (SAM-TECH_00098639).

Motorola H605, At least by 2006, Motorola H605 User Manual (SAM-TECH_00098719).

Motorola H605, At least by 2006, PhoneArena Article—Motorola H605 Review (SAM-TECH_00098743).

Motorola Miniblue Press Release (https://web.archive.org/web/20060212115000/http://www.motorola.com/motoinfo/product/de tails/0,,133,00.html) (SAM-TECH_00056060).

Motorola's Astro XTS 5000 Digital Portable Radio ("Motorola XTS 5000"), At least by Jun. 2002, Motorola's Detailed Service Manuel has a release date in 2003. See Detailed Service Manuel for Astro XTS 5000 VHF/UHF Range 1/Range 2/700-800 MHZ, Digital Portable Radios (2003) (SAM-TECH_00051382—SAM-TECH_00051711).

Motorola's Astro XTS 5000 Digital Portable Radio ("Motorola XTS 5000"), Jun. 14, 2002 WayBack Machine capture of Motorola Inc.'s website contains an image of the Motorola and states that "[t]he top of the line XTS 5000 portable radio is ready and equipped to meet the needs of demanding environments" and that it is "Motorola's newest maximum performance two-way radio." https://web.archive.org/web/20020614082842/ http://www.motorola.com:80/cgiss/portables/ xts5000.shtml (SAM-TECH_00051718).

Motorola's XTS 2500 Digital Portable Radio ("Motorola XTS 2500"), Motorola XTS 2500's Basic Service Manual dated 2002-2003, see XTS 2500 XTS 1500 MT 1500 700-800 MHz Digital Portable Radios, Basic Service Manual at 70 (SAM_00051287—SAM-TECH_00051374).

Motorola's XTS 2500 Digital Portable Radio ("Motorola XTS 2500"), Nov. 9, 2001, WayBack Machine capture of Motorola's website contains an image of the XTS 2500 and states that "[t]he XTS 2500 portable radio is Motorola's high-performance, small-sized, digital two-way radio." https://web.archive.org/web/20020804062125/ http://www.motorola.com:80/cgiss/portables/ xts2500.shtml (SAM-TECH_00051258).

Multi-Microphone Correlation-Based Processing for Robust Automatic Speech Recognition, Thomas M. Sullivan, Department of Electrical and Computer Engineering Carnegie Mellon University.

Multi-Microphone Signal Acquisition for Speech Recognition Systems, Kevin Fink, EE 586—Speech Recognition Systems, Dec. 16, 1993.

Multi-sensory microphones for robust speech detection, enhancement and recognition, Zhengyou Zhang, Zicheng Liu, M. Sinclair, A. Acero, L. Deng, J. Droppo, Xuedong Huang, Yanli Zheng, 2004 IEEE International Conference on Acoustics, Speech, and Signal Processing 3 (2004).

Nacre QuietPro, In a Mar. 7, 2013 presentation by Blake Martin of Honeywell Safety Products to the Alberta Industrial Fire Protection Association, Mr. Martin identifies "2005" as the "First commercial success for Quietpro." (SAM-TECH_00054652).

Nacre QuietPro, In Aug. 2006, Nacre won U.S. Government Contract No. W912DQ-06-D-0037 to supply the Nacre QuietPro to the U.S. military. U.S. Government Contract No. W912DQ-06-D-0037 (SAM-TECH_00055735).

NacreQuietPro, In proceedings before the U.S. Trademark Trial and Appeal Board, Nacre stated that it "has used in commerce with the United States, long since prior to Apr. 28, 2006, the registered trademark QuietPro on one or more of headphones, earphones . . . " *Nacre AS* v. *Silynx Communications, Inc.*, Sep. 4, 2007 Notice of Opposition. (SAM-TECH_00054696).

Nacre QuietPro, Mar. 9, 2005, Honeywell Quietpro QP100ex Mar. 2013 presentation (SAM-TECH_00063985).

Nacre QuietPro, Mar. 9, 2005, IEEE Explore Article (SAMTECH_00063687).

Nacre QuietPro, Mar. 9, 2005, Nacre QuietPro User Manual v2.0 (SAMTECH_00055181).

Nacre QuietPro, Mar. 9, 2005, New Scientist Article (SAMTECH_00064068).

Nacre QuietPro, Mar. 9, 2005, SoldierMod Article (SAM-TECH_00065729).

Nacre QuietPro, Mar. 9, 2005, Article posted at: https://www.tu.no/artikler/quietproverner-og-forsterker-horselen/261960 (SAM-TECH_00097600).

Nacre QuietPro, Mar. 9, 2005, WayBack Machine capture of Nacre's website contains an image of the Nacre QuietPro and states that "Nacre has secured MNOK 27,5 from a consortium led by Ferd Venture" and that "[m]ost of the money will be spent to boost efforts within sales and marketing of QuietPro in the global military market."

Nacre's PARAT earplug ("Parat"), 1999 article published by one of the PARAT's designers Georg E. Ottensen, discusses the PARAT system and states, "[a]n active ear terminal is beeing designed at SEVTEF Telecom and informatics. The acronym of the consept is PARAT—Personal Active Radio/Audio Terminal." Georg E. Ottesen, Active noise reduction in an ear terminal, The Journal of the Acoustical Society of America 105, 1300 (1999); https://doi.org/10.1121/1.424828, SINTEF Telecom and Informatics, N-7465 (SAM-TECH_00051952—SAM-TECH_00051955).

Nacre's PARAT earplug ("Parat"), Jan. 2004 publication by Fredrik Vraalsen et al., describes how "[p]articular attention has been given to voice interaction in noisy industrial scenarios, utilising the PARAT earplug." Fredrik Vraalsen, Trym Holter, Ingrid Storruste Svagard, and 0yvind Kvennas, A Multimodal Context Aware Mobile Maintenance Terminal For Noisy Environments, SINTEF ICT, N-7465 Trondheim, Norway, 79, 79 (Jan. 2004) (SAM-TECH_00051938—SAM-TECH_00051951).

Noise attenuation and proper insertion of earplugs into ear canals, Markku Toivonen, Rauno Pääkkönen, Seppo Savolainen, Kyösti Lehtomäki, The Annals of occupational hygiene, vol. 46,6 (2002): 527-530.

Oct. 29, 2019 on BusinessToday.in states the AirPods Pro require Apple devices running iOS 13.2 or later, iPadOS 13.2 or later, watchOS 6.1 or later, tvOS 13.2 or later, or macOS Catalina 10.15.1 or later. https://www.businesstoday.in/technology/lau nch/story/apple-airpods-pro-with-noise- cancellation-launched-check-out-price-in- india features-235269-2019-10-29 (SAM- TECH_00061346—SAM-TECH_00061349).

Oct. 31, 2019 article published by Charlie Sorrel discusses the Ear tip fit test for the AirPods Pro in the iPhone settings. https://www.cultofmac.com/662548/airpods-pro-ear-tip-fit-test/; (SAM-TECH_00056870—SAM-TECH_00056881).

Olympus WS-320M, At least by Nov. 25, 2005 (Olympus WS-320M) https://web.archive.org/web/20051125000137mp_, http://www.olympusamerica.com/cpg_se ction/cpg_vr_digitalmusic.asp (SAM-TECH_00051760).

Olympus WS-320M, At least by Nov. 25, 2005 (Olympus WS-320M) https://web.archive.org/web/20060314095402/, http://www.olympusamerica.com/cpg_sectio n/product.asp?product=1195&fl=2 (SAM-TECH_00051767; SAM-TECH_00051753).

Olympus WS-320M, At least by Nov. 25, 2005 Olympus WS-320M Instruction Manual (SAM-TECH_00051833).

Optimal Feedback Control Formulation of the Active Noise Cancellation Problem: Pointwise and Distributed, Kambiz C. Zangi,

(56)                    References Cited

OTHER PUBLICATIONS

RLE Technical Report No. 583, Research Laboratory of Electronics Massachusetts Institute of Technology, May 1994.

Peltor Lite-Com II, At least by 1999, Peltor Lite-Com II Manual (SAM-TECH_00099254).

Peltor Lite-Com II, At least by 1999, Peltor Lite-Com II Brochure (SAM-TECH_00099203).

Performance of dual microphone in-the-ear hearing aids, Michael Valente, Gerald Schuchmant, Lisa G. Potts & Lucille B. Beck, Journal of the American Academy of Audiology, 2000.

Plantronics Discovery 655, At least by 2006, CNET Article—Plantronics Discovery 655 Bluetooth Headset Review (SAM-TECH_00099287).

Plantronics Discovery 655, At least by 2006, Plantronics Discovery 655 Brochure (SAM-TECH_00099296).

Plantronics Discovery 655, At least by 2006, Plantronics Discovery 655 User Guide (SAM-TECH_00099344).

Plantronics Discovery 655, At least by 2006, Silicon Poip Culture Article—Plantronics Discovery 655 (SAM-TECH_00099387).

Plantronics MX200, At least by 2006, Plantronics MX200 Brochure (SAM-TECH_00099419).

Plantronics MX200, At least by 2006, Plantronics MX200 User Guide (SAM-TECH_00099435).

Plantronics MX200, At least by 2006, Plantronics MX250 User Guide (SAM-TECH_00099461).

PocketLint Article—Zen Gennum Bluetooth Headset (SAM-TECH_00098490).

Preferred methods for measuring hearing protector attenuation, Elliott Berger, International Congress on Noise Control Engineering 2005, Internoise 2005.

Products of Interest, Project Muse, Computer Music Journal, vol. 30, No. 3, Fall 2006.

Reducing the Negative Effects of Ear-Canal Occlusion, Samuel S. Job, Department of Electrical and Computer Engineering Brigham Young University, 2002.

Research in Motion's BlackBerry 7520 ("BlackBerry"), At least by 2004, Blackberry 7520 Wireles Handheld Model No. RAL11IN, Version 4.1 User Guide, last modified Mar. 6, 2006 (SAM-TECH_00054461—SAM-TECH_00054618).

Research in Motion's BlackBerry 7520 ("BlackBerry"), Jun. 28, 2006 WayBack Machine capture of the BlackBerry lists it for sale and describes the Blackberry as a "strong addition to the product line-up." https://web.archive.org/web/20060628035351/http://www.blackberry-7520.com (SAM-TECH_00054619; SAM-TECH_00054624; SAM-TECH_00054622).

Research in Motion's BlackBerry 7520 ("BlackBerry"), At least by 2004, BlackBerry Wireless Handheld Getting Started Guide (SAM-TECH_00228841).

Research in Motion's BlackBerry 7520 ("BlackBerry"), Nextel Services Guide for the Blackberry is dated the year 2004; (SAM-TECH_00226708).

SeboTek Hearing Systems' PAC (Post Auricular Canal) Instrument ("Sebotek"), Mar. 19, 2003 WayBack Machine capture of SeboTek's website contains a description of the PAC, which notes that "[t]he PAC is an exciting new hearing system by SeboTek that is significantly different from traditional hearing aids. If offers deep canal fitting, superior acoustics, incredible discreetness, and unmatched comfort." https://web.archive.org/web/20030319140205/http://www.sebotek.com:80/ (SAM-TECH_00052377).

SeboTek Hearing Systems' PAC (Post Auricular Canal) Instrument ("Sebotek"), May 26, 2007 WayBack Machine capture of SeboTek's website contains a description of the PAC, and notes that "Prior to 2003, depending on the level of hearing loss, consumers could choose between four primary styles, none of which offered superior sound quality, comfort or cosmetic appeal. All that changed in 2003, when SeboTek introduced the PAC Voice-Q™ hearing instrument, the first-ever speaker-in-the-canal device." https://web.archive.org/web/20070526135524/http://www.sebotek.com:80/OurProducts/our Products.html (SAM-TECH_00052392).

SeboTek Hearing Systems' PAC (Post Auricular Canal) Instrument ("Sebotek"), Oct. 6, 2003 post by Bruce Gefvert, Director of Sales and Marketing at SeboTek Hearing Systems, on audiologyonline.com discusses the PAC, and states "PAC refers to Post Auricular Canal, an entirely new style of hearing aid that is intended to provide hearing professionals with one more option for treating hearing loss in the mild to severe ranges." https://www.audiologyonline.com/ask-the-experts/sebotek-pac-post-auricular-canal- 601 (SAM_00052353—SAM-TECH_00052356).

SeboTek Hearing Systems' PAC (Post Auricular Canal) Instrument ("Sebotek"), Publication by King Chung in 2004 mentions that "SeboTek VoiceQ and Vivatone have recently launched newly designed behind-the-ear or postauricular canal (PAC, as SeboTek preferred) hearing aids that have receivers situated in the ear canal." See King Chung, Challenges and recent developments in hearing aids. Part II. Feedback and occlusion effect reduction strategies, laser shell manufacturing processes, and other signal processing technologies, 8 Trends Amplif. 125, 150 (2004), available at https://www.ncbi.nlm.nih.gov/pmc/articles/PMC4111464/pdf/10.1177_108471380400800 402.pdf (SAM-TECH_00062067—SAM-TECH_00062106).

Sensaphonics 3D Active Ambient In-Ear Monitor System, At least by 2006, Products of Interest Article (SAM-TECH_00096723).

Sensaphonics 3D Active Ambient In-Ear Monitor System, At least by 2006, Sensaphonics 3D Active Ambient In-Ear Monitor System User Guide (SAM-TECH_00100046).

Sensaphonics 3D Active Ambient In-Ear Monitor System, At least by 2006, Sensaphonics 3D Active Ambient IEM System Article (SAM-TECH_00100065).

Silynx QuietOps, Oct. 4, 2007 Applicant's Answer to Opposer's Notice of Opposition (SAM-TECH_00052371).

Silynx QuietOps, https://defense- update.com/20080513_c4ops.html (SAM-TECH_00057150).

Silynx QuietOps, QuietOps Pocket Guide (Rev. 2.00) (Silynx QuietOps).

Small-footprint keyword spotting using deep neural networks, G. Chen, C. Parada and G. Heigold, 2014 IEEE International Conference on Acoustics, Speech and Signal Processing (ICASSP), Florence, Italy, 2014, pp. 4087-4091.

Sonar-operator active noise reduction insert-earphone: Prototype preliminary test and evaluation, Joseph S. Russotti, Naval Submarine Medical Research Laboratory, Report No. 1225.

Sonomax's Sonomax: SonoCustom and SonoPass ("Sonomax"), Apr. 8, 2006 WayBack Machine capture of Sonomax's website contains an image of the Sonomax and states that "[t]ens of Thousands of people around the world give the SonoCustom a big thumbs up for comfort." https://web.archive.org/web/20060408170243/http://sonomax.com.au/index.cfm/aboutus/so nomax_solution/ (SAM-TECH_00052472; SAM-TECH_00052998).

Sonomax's Sonomax: SonoCustom and SonoPass ("Sonomax"), Jun. 15, 2006 WayBack Machine capture of Sonomax's website contains frequently asked questions about the Sonomax and states that SonoPass, our proprietary Windows-based software, drives the fitting process and provides immediate proof of functionality. https://web.archive.org/web/20060615054356/http://www.sonomax.com.au:80/index.cfm/fa q/ (SAM-TECH_00052643).

Sonomax's Sonomax: SonoCustom and SonoPass ("Sonomax"), Apr. 8, 2006 WayBack Machine capture of Sonomax's website contains an image of the SonoCustom and describes it as a "cost effective, comfortable and resusable earpiece." https://web.archive.org/web/20060408165744/http://sonomax.com.au:80/index.cfm/fittingprocess/ (SAM-TECH_00052436).

Sonomax's Sonomax: SonoCustom and SonoPass ("Sonomax"), Apr. 8, 2006 WayBack Machine capture of Sonomax's website contains an image of the Sonomax and states that "[t]he Sonomax is a hearing protection system that combines a uniquely designed earpiece, the SonoCustom, with an optimised hardware and software application, called SonoPass." https://web.archive.org/web/20060408170221/http://sonomax.com.au:80/index.cfm/testingp rocess/ (SAM-TECH_00052425).

Sonomax's Sonomax: SonoCustom and SonoPass ("Sonomax"), Jun. 15, 2006 WayBack Machine capture of Sonomax's website contains an image of the Sonomax and states that "application

(56)　　　　References Cited

OTHER PUBLICATIONS provides employers the unique ability to quantify and track hearing protection performance and produce detailed reports." https://web.archive.org/web/20060615054658/http://www.sonomax.com.au/index.cfm/testi ngprocess/ (SAM-TECH_00052589).

Sony S700 Walkman, At least by Oct. 13, 2006, EAFIT Article—The Sony Walkman (SAM-TECH_00099514).

Sony S700 Walkman, At least by Oct. 13, 2006, IDG Article—Sony's New Walkman Players Pack Noise Canceling (SAM-TECH_00099533).

Sony S700 Walkman, At least by Oct. 13, 2006, Sony Walkman User Manual (SAM-TECH_00099557).

Sony S700 Walkman, At least by Oct. 13, 2006, Stuff Article—Sony NW-S700 Review (SAM-TECH_00099579).

Sound Source Localization and Separation, Biniyam Tesfaye Taddese, Mathematics, Statistics, and Computer Science Honors Projects (2006).

Speaker Turn Segmentation Based on Between-Channel Differences, Daniel P.W. Ellis & Jerry C. Liu, LabRosa, Dept. of Electrical Engineering, Columbia University.

Spectral analysis of speech by linear prediction, J. Makhoul, IEEE Transactions on Audio and Electroacoustics, vol. 21, No. 3, pp. 140-148, Jun. 1973.

Speech Input Hardware Investigation for Future Dismounted Soldier Computer Systems, Jeffrey C. Bos & David W. Tack, DRDC Toronto CR 2005-064, May 1, 2005.

Speech Modeling with Magnitude-Normalized Complex Spectra and Its Application to Multisensory Speech Enhancement, A. Subramanya, Z. Zhang, Z. Liu and A. Acero, 2006 IEEE International Conference on Multimedia and Expo, Toronto, ON, Canada, 2006, pp. 1157-1160.

Speech Recognition in Severely Disturbed Environments Combining Ear-Mic and Active Noise Control, N. Westerlund, M. Dahl, I. Claesson, Published 2002, Engineering, Computer Science.

Survey of the Speech Recognition Techniques for Mobile Devices, Dmitry Zaykovskiy, Department of Information Technology, SPECOM'2006, St. Petersburg, Jun. 2006.

Techniques and applications for wearable augmented reality audio, Härmä, Aki & Turku, Julia & Tikander, Miikka & Karjalainen, M & Lokki, Tapio & Nironen, H & Vesa, Sampo (2003).

The Effect of Hearing Aid Microphone Location on the Intelligibility of Hearing Aid—Transduced Speech, John Robert Franks, Dec. 1975.

Using Audio-Based Signal Processing to Passively Monitor Road Traffic, Orla Duffner, Centre for Digital Video Processing and School of Electronic Engineering Dublin City University, Jul. 2006.

Verifying the attenuation of earplugs in situ: Method validation using artificial head and numerical simulations, Annelies Bockstael, Bram De Greve, Timothy Van Renterghem, Dick Botteldooren, Wendy D'Haenens, Hannah Keppler, Leen Maes, Birgit Philips, Freya Swinnen, Bart Vinck, The Journal of the Acoustical Society of America; 124 (2): 973-981, Aug. 1, 2008.

Olwal, A. and Feiner S. Interaction Techniques Using Prosodic Features of Speech and Audio Localization. Proceedings of IUI 2005 (International Conference on Intelligent User Interfaces), San Diego, CA, Jan. 9-12, 2005, p. 284-286.

Bernard Widrow, John R. Glover Jr., John M. McCool, John Kaunitz, Charles S. Williams, Robert H. Hearn, James R. Zeidler, Eugene Dong Jr, and Robert C. Goodlin, Adaptive Noise Cancelling: Principles and Applications, Proceedings of the IEEE, vol. 63, No. 12, Dec. 1975.

Mauro Dentino, John M. McCool, and Bernard Widrow, Adaptive Filtering in the Frequency Domain, Proceedings of the IEEE, vol. 66, No. 12, Dec. 1978.

'400 Patent Family Tree, Exhibit—1009, Filed on Dec. 10, 2021—Cited in IPR2022-00282, challenging U.S. Pat. No. 8,315,400.

Nov. 3, 2022 [16] Notice of Deposition of David Kleinschmidt, Exhibit—16, Filed on Nov. 3, 2022—Cited in IPR2022-00282, challenging U.S. Pat. No. 8,315,400.

Aarts, Exhibit—1015, Filed on Jan. 14, 2022—Cited in IPR2022-00410, challenging U.S. Pat. No. 10,979,836.

Adaptive Filtering (Dentino), Exhibit—1012, Filed on Dec. 10, 2021—Cited in IPR2022-00282, challenging U.S. Pat. No. 8,315,400.

Adaptive Filtering Algorithims (Diniz), Exhibit—1013, Filed on Dec. 10, 2021—Cited in IPR2022-00282, challenging U.S. Pat. No. 8,315,400.

Adaptive Noise Cancelling (Widrow), Exhibit—1011, Filed on Dec. 10, 2021—Cited in IPR2022-00282, challenging U.S. Pat. No. 8,315,400.

AirPods (1st generation)—Technical Specifications, Exhibit—2009, Filed on Sep. 13, 2022—Cited in IPR2022-00243, challenging U.S. Pat. No. 8,111,839.

Amended Complaint, Techiya v. Samsung, E.D. Tex., Exhibit—1014, Filed on Jan. 14, 2022—Cited in IPR2022-00410, challenging U.S. Pat. No. 10,979,836.

Amended Complaint, Techiya v. Samsung, E.D. Tex., Exhibit—1014, Filed on Dec. 21, 2021—Cited in IPR2022-00302, challenging U.S. Pat. No. 9,609,424.

Amended Complaint, Techiya v. Samsung, E.D. Tex., Exhibit—1017, Filed on Jan. 4, 2022—Cited in IPR2022-00388, challenging U.S. Pat. No. 10,966,015.

Amended Complaint, Techiya v. Samsung, E.D. Tex., Exhibit—1017, Filed on Dec. 30, 2021—Cited in IPR2022-00369, challenging U.S. Pat. No. 10,405,082.

Amended Docket Control Order, DN 156 from E.D. Tex. 21-cv-00413, Exhibit—1029, Filed on Nov. 15, 2022—Cited in IPR2022-01098, challenging U.S. Pat. No. 11,217,237.

Amended Docket Control Order, DN 156 from E.D. Tex., Exhibit—1023, Filed on Nov. 10, 2022—Cited in IPR2022-01099, challenging U.S. Pat. No. 11,244,666.

Amended Docket Control Order, DN 156 from E.D. Tex., Exhibit—1026, Filed on Nov. 10, 2022—Cited in IPR2022-01078, challenging U.S. Pat. No. 11,057,701.

Amended Docket Control Order, DN 156 from E.D. Tex., Exhibit—1032, Filed on Nov. 10, 2022—Cited in IPR2022-01106, challenging U.S. Pat. No. 11,039,259.

Amended Notice of Deposition of Les E. Atlas, Ph.D., Exhibit—15, Filed on Mar. 14, 2023—Cited in IPR2022-01106, challenging U.S. Pat. No. 11,039,259.

Amendment in U.S. Appl. No. 11/616,973, dated Apr. 13, 2015, Exhibit—2009, Filed on Oct. 11, 2022—Cited in IPR2022-01106, challenging U.S. Pat. No. 11,039,259.

Anderson Declaration ISO MSJ of No Infringement of '259 Patent, Exhibit—2019, Filed on Aug 14, 2023—Cited in IPR2022-01106, challenging U.S. Pat. No. 11,039,259.

Anderson Non-Infringement Report (excerpt, redacted), Exhibit—2020, Filed on Aug. 14, 2023—Cited in IPR2022-01106, challenging U.S. Pat. No. 11,039,259.

Anderson Rebuttal Report (Redacted, Excerpt), Exhibit—2017, Filed on Apr. 10, 2023—Cited in IPR2022-01106, challenging U.S. Pat. No. 11,039,259.

Android Central, The History of True Wireless Earbuds, Exhibit—2009, Filed on Oct. 17, 2022—Cited in IPR2022-00324, challenging U.S. Pat. No. 8,254,591.

Android Central, The History of True Wireless Earbuds, Exhibit—2011, Filed on Sep. 13, 2022—Cited in IPR2022-00243, challenging U.S. Pat. No. 8,111,839.

C.V. of Richard Stern, Ph.D., Exhibit—1003, Filed on Jan. 4, 2022—Cited in IPR2022-00388, challenging U.S. Pat. No. 10,966,015.

C.V. of Richard Stern, Ph.D., Exhibit—1003, Filed on Dec. 10, 2021—Cited in IPR2022-00282, challenging U.S. Pat. No. 8,315,400.

CDC, What Noises Cause Hearing Loss?, Exhibit—2009, Filed on Sep. 13, 2022—Cited in IPR2022-00242, challenging U.S. Pat. No. 8,111,839.

Christopher J. Struck CV, Exhibit—2002, Filed on Apr. 13, 2022—Cited in IPR2022-00302, challenging U.S. Pat. No. 9,609,424.

Claim Construction Order, Exhibit—2008, Filed on Feb. 22, 2023—Cited in IPR2022-00253, challenging U.S. Pat. No. 9,491,542.

Claim Construction Order, Exhibit—2008, Filed on Apr. 18, 2023—Cited in IPR2022-00281, challenging U.S. Pat. No. 9,270,244.

Claim Construction Order, Exhibit—2013, Filed on Apr. 10, 2023—Cited in IPR2022-01106, challenging U.S. Pat. No. 11,039,259.

(56) References Cited

OTHER PUBLICATIONS

Complaint, DN 1 from E.D. Tex. 21-cv-00413, Exhibit—1022, Filed on Nov. 10, 2022—Cited in IPR2022-01099, challenging U.S. Pat. No. 11,244,666.
Complaint, DN 1 from E.D. Tex. 21-cv-00413, Exhibit—1025, Filed on Nov. 10, 2022—Cited in IPR2022-01078, challenging U.S. Pat. No. 11,057,701.
Complaint, DN 1 from E.D. Tex. 21-cv-00413, Exhibit—1028, Filed on Nov. 15, 2022—Cited in IPR2022-01098, challenging U.S. Pat. No. 11,217,237.
Complaint, DN 1 from E.D. Tex. 21-cv-00413, Exhibit—1031, Filed on Nov. 10, 2022—Cited in IPR2022-01106, challenging U.S. Pat. No. 11,039,259.
Complaint, E.D. Tex. 22-53, Exhibit—1020, Filed on Jun. 14, 2022—Cited in IPR2022-00369, challenging U.S. Pat. No. 10,405,082.
Complaint, E.D. Tex. 22-53, Exhibit—1020, Filed on Jun. 14, 2022—Cited in IPR2022-00388, challenging U.S. Pat. No. 10,966,015.
Complaint, E.D. Tex. 22-53, Exhibit—1021, Filed on Jun. 14, 2022—Cited in IPR2022-00410, challenging U.S. Pat. No. 10,979,836.
Complaint, E.D. Tex., 22-cv-53, Exhibit—1024, Filed on May 10, 2022—Cited in IPR2022-00302, challenging U.S. Pat. No. 9,609,424.
Complaint, E.D. Tex., 22-cv-53, Exhibit—1032, Filed on May 11, 2022—Cited in IPR2022-00324, challenging U.S. Pat. No. 8,254,591.
Complaint, *Techiya* v. *Samsung*, E.D. Tex., Exhibit—1008, Filed on Jan. 14, 2022—Cited in IPR2022-00410, challenging U.S. Pat. No. 10,979,836.
Complaint, *Techiya* v. *Samsung*, E.D. Tex., Exhibit—1008, Filed on Dec. 21, 2021—Cited in IPR2022-00302, challenging U.S. Pat. No. 9,609,424.
Consolidation Order, E.D. Tex. 21-413 & 22-53, Exhibit—1021, Filed on Jun. 14, 2022—Cited in IPR2022-00369, challenging U.S. Pat. No. 10,405,082.
Consolidation Order, E.D. Tex. 21-413 & 22-53, Exhibit—1021, Filed on Jun. 14, 2022—Cited in IPR2022-00388, challenging U.S. Pat. No. 10,966,015.
Consolidation Order, E.D. Tex. 21-413 & 22-53, Exhibit—1022, Filed on Jun. 14, 2022—Cited in IPR2022-00410, challenging U.S. Pat. No. 10,979,836.
Consolidation Order, E.D. Tex., Exhibit—1025, Filed on May 10, 2022—Cited in IPR2022-00302, challenging U.S. Pat. No. 9,609,424.
Consolidation Order, E.D. Tex., Exhibit—1033, Filed on May 11, 2022—Cited in IPR2022-00324, challenging U.S. Pat. No. 8,254,591.
Corrected Declaration of Richard Stern, Ph.D., Exhibit—1002, Filed on Jan. 4, 2022—Cited in IPR2022-00388, challenging U.S. Pat. No. 10,966,015.
Corrected Declaration of Richard Stern, Ph.D., Exhibit—1002, Filed on Dec. 10, 2021—Cited in IPR2022-00282, challenging U.S. Pat. No. 8,315,400.
Corrected Petition for Inter Partes Review of U.S. Pat. No. 8,111,839, Exhibit—11, Filed on Feb. 3, 2022—Cited in IPR2022-00243, challenging U.S. Pat. No. 8,111,839.
Corrected Petition for Inter Partes Review of U.S. Pat. No. 8,111,839, Exhibit—12, Filed on Feb. 3, 2022—Cited in IPR2022-00242, challenging U.S. Pat. No. 8,111,839.
Corrected Petition for IPR of U.S. Pat. No. 8,315,400, Exhibit—4, Filed on Dec. 10, 2021—Cited in IPR2022-00282, challenging U.S. Pat. No. 8,315,400.
Curriculum Vitae of Christopher J. Struck, Exhibit—2002, Filed on Oct. 7, 2022—Cited in IPR2022-01078, challenging U.S. Pat. No. 11,057,701.
Curriculum Vitae of Christopher J. Struck, Exhibit—2002, Filed on Oct. 7, 2022—Cited in IPR2022-01098, challenging U.S. Pat. No. 11,217,237.
Curriculum Vitae of David Kleinschmidt, Exhibit—2002, Filed on Oct. 11, 2022—Cited in IPR2022-01106, challenging U.S. Pat. No. 11,039,259.
Curriculum Vitae of David Kleinschmidt, Exhibit—2002, Filed on Oct. 7, 2022—Cited in IPR2022-01099, challenging U.S. Pat. No. 11,244,666.

CV for Marshall Buck, Ph.D., Exhibit—2002, Filed on May 18, 2022—Cited in IPR2022-00369, challenging U.S. Pat. No. 10,405,082.
CV of Chris Kyriakakis, Ph.D., Exhibit—1003, Filed on Dec. 21, 2021—Cited in IPR2022-00302, challenging U.S. Pat. No. 9,609,424.
CV of Christopher J. Struck, Exhibit—2002, Filed on May 18, 2022—Cited in IPR2022-00410, challenging U.S. Pat. No. 10,979,836.
CV of Daniel P. Anagnos, Exhibit—2002, Filed on Mar. 23, 2022—Cited in IPR2022-00242, challenging U.S. Pat. No. 8,111,839.
CV of Daniel P. Anagnos, Exhibit—2002, Filed on Mar. 23, 2022—Cited in IPR2022-00243, challenging U.S. Pat. No. 8,111,839.
CV of Daniel P. Anagnos; Exhibit—2002, Filed on Mar. 21, 2022—Cited in IPR2022-00234, challenging U.S. Pat. No. 9124982.
CV of Dr. Chris Kyriakakis, Exhibit—1003, Filed on Jan. 14, 2022—Cited in IPR2022-00410, challenging U.S. Pat. No. 10,979,836.
CV of Les E. Atlas, Ph.D., Exhibit—1003, Filed on Dec. 20, 2021—Cited in IPR2022-00324, challenging U.S. Pat. No. 8,254,591.
CV of Les E. Atlas, Ph.D., Exhibit—1004, Filed on Dec. 13, 2021—Cited in IPR2022-00242, challenging U.S. Pat. No. 8,111,839.
CV of Les E. Atlas, Ph.D., Exhibit—1004, Filed on Dec. 13, 2021—Cited in IPR2022-00243, challenging U.S. Pat. No. 8,111,839.
CV of Marshall Buck, Ph.D., Exhibit—2002, Filed on May 18, 2022—Cited in IPR2022-00388, challenging U.S. Pat. No. 10,966,015.
CV of Nathaniel Polish, Ph.D., Exhibit—1003, Filed on Dec. 17, 2021—Cited in IPR2022-00253, challenging U.S. Pat. No. 9,491,542.
CV of Nathaniel Polish, Ph.D., Exhibit—1003, Filed on Dec. 21, 2021—Cited in IPR2022-00281, challenging U.S. Pat. No. 9,270,244.
CV of of Les E. Atlas, Ph.D.; Exhibit—1003, Filed on Dec. 13, 2021—Cited in IPR2022-00234, challenging U.S. Pat. No. 9124982.
CV of Richard Stern, Ph.D., Exhibit—1003, Filed on Dec. 30, 2021—Cited in IPR2022-00369, challenging U.S. Pat. No. 10,405,082.
Daniel P. Anagnos CV, Exhibit—2002, Filed on Apr. 13, 2022—Cited in IPR2022-00324, challenging U.S. Pat. No. 8,254,591.
David Kleinschmidt CV, Exhibit—2002, Filed on Mar. 21, 2022—Cited in IPR2022-00282, challenging U.S. Pat. No. 8,315,400.
David Kleinschmidt CV, Exhibit—2002, Filed on Apr. 18, 2022—Cited in IPR2022-00253, challenging U.S. Pat. No. 9,491,542.
David Kleinschmidt CV, Exhibit—2002, Filed on Apr. 18, 2022—Cited in IPR2022-00281, challenging U.S. Pat. No. 9,270,244.
Decision Denying Institution of Inter Partes Review 35 U.S.C. § 314, Exhibit—10, Filed on Jan. 3, 2023—Cited in IPR2022-01099, challenging U.S. Pat. No. 11,244,666.
Decision Denying Institution of Inter Partes Review 35 U.S.C. § 314, Exhibit—11, Filed on Jan. 3, 2023—Cited in IPR2022-01098, challenging U.S. Pat. No. 11,217,237.
Decision Granting Institution of Inter Partes Review 35 U.S.C. sec 314, Exhibit—10, Filed on Dec. 29, 2022—Cited in IPR2022-01078, challenging U.S. Pat. No. 11,057,701.
Declaration of Chris Kyriakakis, Ph.D., Exhibit—1002, Filed on Dec. 21, 2021—Cited in IPR2022-00302, challenging U.S. Pat. No. 9,609,424.
Declaration of Christopher J. Struck in Support of Patent Owner's Preliminary Response, Exhibit—2001, Filed on Oct. 7, 2022—Cited in IPR2022-01078, challenging U.S. Pat. No. 11,057,701.
Declaration of Christopher J. Struck in Support of Patent Owner's Preliminary Response, Exhibit—2001, Filed on Oct. 7, 2022—Cited in IPR2022-01098, challenging U.S. Pat. No. 11,217,237.
Declaration of Christopher J. Struck in Support of Patent Owner's Preliminary Response, Exhibit—2001, Filed on Apr. 13, 2022—Cited in IPR2022-00302, challenging U.S. Pat. No. 9,609,424.
Declaration of Christopher J. Struck in Support of Patent Owner's Preliminary Response, Exhibit—2001, Filed on May 18, 2022—Cited in IPR2022-00410, challenging U.S. Pat. No. 10,979,836.
Declaration of Christopher J. Struck in Support of Patent Owner's Response, Exhibit—2006, Filed on Oct. 17, 2022—Cited in IPR2022-00302, challenging U.S. Pat. No. 9,609,424.
Declaration of Christopher Struck in Support of POR, Exhibit—2013, Filed on Mar. 23, 2023—Cited in IPR2022-01078, challenging U.S. Pat. No. 11,057,701.
Declaration of Daniel P. Anagnos in Support of Patent Owner Response; Exhibit—2006, Filed on Sep. 9, 2022—Cited in IPR2022-00234, challenging U.S. Pat. No. 9124982.

(56)                    References Cited

OTHER PUBLICATIONS

Declaration of Daniel P. Anagnos in Support of Patent Owner's Preliminary Response, Exhibit—2001, Filed on Apr. 13, 2022—Cited in IPR2022-00324, challenging U.S. Pat. No. 8,254,591.

Declaration of Daniel P. Anagnos in Support of Patent Owner's Response, Exhibit—2006, Filed on Oct. 17, 2022—Cited in IPR2022-00324, challenging U.S. Pat. No. 8,254,591.

Declaration of Daniel P. Anagnos in Support of Patent Owner's Response, Exhibit—2006, Filed on Sep. 13, 2022—Cited in IPR2022-00242, challenging U.S. Pat. No. 8,111,839.

Declaration of Daniel P. Anagnos in Support of Patent Owner's Response, Exhibit—2006, Filed on Sep. 13, 2022—Cited in IPR2022-00243, challenging U.S. Pat. No. 8,111,839.

Declaration of Daniel P. Anagnos, Exhibit—2001, Filed on Mar. 23, 2022—Cited in IPR2022-00242, challenging U.S. Pat. No. 8,111,839.

Declaration of Daniel P. Anagnos, Exhibit—2001, Filed on Mar. 23, 2022—Cited in IPR2022-00243, challenging U.S. Pat. No. 8,111,839.

Declaration of Daniel P. Anagnos; Exhibit—2001, Filed on Mar. 21, 2022—Cited in IPR2022-00234, challenging U.S. Pat. No. 9,124,982.

Declaration of David Kleinschmidt in Support of Patent Owner's Preliminary Response, Exhibit—2001, Filed on Oct. 11, 2022—Cited in IPR2022-01106, challenging U.S. Pat. No. 11,039,259.

Declaration of David Kleinschmidt in Support of Patent Owner's Preliminary Response, Exhibit—2001, Filed on Oct. 7, 2022—Cited in IPR2022-01099, challenging U.S. Pat. No. 11,244,666.

Declaration of David Kleinschmidt in Support of Patent Owner's Preliminary Response, Exhibit—2001, Filed on Mar. 21, 2022—Cited in IPR2022-00282, challenging U.S. Pat. No. 8,315,400.

Declaration of David Kleinschmidt in Support of Patent Owner's Preliminary Response, Exhibit—2001, Filed on Apr. 18, 2022—Cited in IPR2022-00253, challenging U.S. Pat. No. 9,491,542.

Declaration of David Kleinschmidt in Support of Patent Owner's Preliminary Response, Exhibit—2001, Filed on Apr. 18, 2022—Cited in IPR2022-00281, challenging U.S. Pat. No. 9,270,244.

Declaration of David Kleinschmidt in Support of Patent Owner's Response, Exhibit—2006, Filed on Oct. 19, 2022—Cited in IPR2022-00253, challenging U.S. Pat. No. 9,491,542.

Declaration of David Kleinschmidt in Support of Patent Owner's Response, Exhibit—2006, Filed on Oct. 19, 2022—Cited in IPR2022-00281, challenging U.S. Pat. No. 9,270,244.

Declaration of David Kleinschmidt in Support of Patent Owner's Response, Exhibit—009, Filed on Sep. 9, 2022—Cited in IPR2022-00282, challenging U.S. Pat. No. 8,315,400.

Declaration of Dr. Chris Kyriakakis, Exhibit—1002, Filed on Jan. 14, 2022—Cited in IPR2022-00410, challenging U.S. Pat. No. 10,979,836.

Declaration of Dr. David Anderson Regarding Claim Construction dated Oct. 21, 2022, Exhibit—2011, Filed on Nov. 8, 2022—Cited in IPR2022-00388, challenging U.S. Pat. No. 10,966,015.

Declaration of Dr. Eric Tarr, Exhibit—2001, Filed on Dec. 6, 2024—Cited in IPR2024-00559, challenging U.S. Pat. No. 11,610,587.

Declaration of Les E. Atlas, Ph.D., Exhibit—1002, Filed on Dec. 13, 2021—Cited in IPR2022-00242, challenging U.S. Pat. No. 8,111,839.

Declaration of Les E. Atlas, Ph.D., Exhibit—1002, Filed on Dec. 20, 2021—Cited in IPR2022-00324, challenging U.S. Pat. No. 8,254,591.

Declaration of Les E. Atlas, Ph.D., Exhibit—1003, Filed on Dec. 13, 2021—Cited in IPR2022-00243, challenging U.S. Pat. No. 8,111,839.

Declaration of Les E. Atlas, Ph.D.; Exhibit—1002, Filed on Dec. 13, 2021—Cited in IPR2022-00234, challenging U.S. Pat. No. 9,124,982.

Declaration of Marshall Buck in Support of Patent Owner's Preliminary Response, Exhibit—2001, Filed on May 18, 2022—Cited in IPR2022-00369, challenging U.S. Pat. No. 10,405,082.

Declaration of Marshall Buck in Support of Patent Owner's Preliminary Response, Exhibit—2001, Filed on May 18, 2022—Cited in IPR2022-00388, challenging U.S. Pat. No. 10,966,015.

Declaration of Marshall D. Buck, Ph.D. in Support of Patent Owner Response, Exhibit—2008, Filed on Nov. 8, 2022—Cited in IPR2022-00369, challenging U.S. Pat. No. 10,405,082.

Declaration of Marshall D. Buck, Ph.D. in Support of Patent Owner's Response, Exhibit—2008, Filed on Nov. 8, 2022—Cited in IPR2022-00388, challenging U.S. Pat. No. 10,966,015.

Declaration of Nathaniel Polish, Ph.D., Exhibit—1002, Filed on Dec. 17, 2021—Cited in IPR2022-00253, challenging U.S. Pat. No. 9,491,542.

Declaration of Nathaniel Polish, Ph.D., Exhibit—1002, Filed on Dec. 21, 2021—Cited in IPR2022-00281, challenging U.S. Pat. No. 9,270,244.

Declaration of Richard Stern, Ph.D., Exhibit—1002, Filed on Dec. 10, 2021—Cited in IPR2022-00282, challenging U.S. Pat. No. 8,315,400.

Declaration of Richard Stern, Ph.D., Exhibit—1002, Filed on Dec. 30, 2021—Cited in IPR2022-00369, challenging U.S. Pat. No. 10,405,082.

Declaration of Roy Falik In Support of Motion for the Pro Hac Vice Admission, Exhibit—2001, Filed on Jul. 5, 2024—Cited in IPR2024-01003, challenging U.S. Pat. No. 9,191,083.

Declaration of Roy Falik In Support of Motion for the Pro Hac Vice Admission, Exhibit—2001, Filed on Jul. 5, 2024—Cited in IPR2024-01004, challenging U.S. Pat. No. 9,614,943.

Declaration of Roy Falik In Support of Motion for the Pro Hac Vice AdmissionExhibit2001,Jul. 5, 2024—Cited in IPR2024-01033, challenging U.S. Pat. No. 8,434,966.

Declaration of Roy Falik, Exhibit—2001, Filed on Jul. 18, 2024—Cited in IPR2024-01031, challenging U.S. Pat. No. 7,049,850.

Declaration of Roy Falik, Exhibit—2001, Filed on Jul. 18, 2024—Cited in IPR2024-01034, challenging U.S. Pat. No. 9,279,263.

Declaration of Scott Delman with attached exhibit, Exhibit—1024, Filed on Dec. 21, 2021—Cited in IPR2022-00281, challenging U.S. Pat. No. 9,270,244.

Deposition Transcript of David Kleinschmidt, dated Jun. 9, 2023, Exhibit—1034, Filed on Jun. 30, 2023—Cited in IPR2022-01106, challenging U.S. Pat. No. 11,039,259.

Determining All Challenged Claims Unpatentable 35 U.S.C. § 318(a), Exhibit—31, Filed on Aug. 11, 2023—Cited in IPR2022-00388, challenging U.S. Pat. No. 10,966,015.

Determining All Challenged Claims Unpatentable 35 U.S.C. § 318(a), Exhibit—32, Filed on Aug. 11, 2023—Cited in IPR2022-00369, challenging U.S. Pat. No. 10,405,082.

Determining All Challenged Claims Unpatentable 35 U.S.C. § 318(a), Exhibit—26, Filed on Nov. 13, 2023—Cited in IPR2022-01078, challenging U.S. Pat. No. 11,057,701.

Determining Some Challenged Claims Unpatentable 35 U.S.C. § 318(a), Exhibit—37, Filed on Jul. 7, 2023—Cited in IPR2022-00302, challenging U.S. Pat. No. 9,609,424.

Docket Control Order, E.D. Tex., Exhibit—1014, Filed on Apr. 20, 2022—Cited in IPR2022-00282, challenging U.S. Pat. No. 8,315,400.

Docket Control Order, E.D. Tex., Exhibit—1043, Filed on Apr. 20, 2022—Cited in IPR2022-00242, challenging U.S. Pat. No. 8,111,839.

Docket Control Order, E.D. Tex., Exhibit—1043, Filed on Apr. 20, 2022—Cited in IPR2022-00243, challenging U.S. Pat. No. 8,111,839.

Docket Control Order, E.D. Tex.; Exhibit—1033, Filed on Apr. 20, 2022—Cited in IPR2022-00234, challenging U.S. Pat. No. 9124982.

Edwards, The Future of Hearing Aid Technology, Exhibit—2008, Filed on Sep. 13, 2022—Cited in IPR2022-00243, challenging U.S. Pat. No. 8,111,839.

EX 1032—Protective Order (*Staton Techiya, LLC* v. *Samsung Electronics Co.*, Ltd, 21-CV-00413-JRG-RSP), Exhibit—1032, Filed on Apr. 13, 2023—Cited in IPR2022-00302, challenging U.S. Pat. No. 9,609,424.

Ex 1045—Nov. 18, 2022, Deposition Transcript of Daniel P Anagnos, Exhibit—1045, Filed on Dec. 6, 2022—Cited in IPR2022-00242, challenging U.S. Pat. No. 8,111,839.

Ex 1045—Nov. 18, 2022, Deposition Transcript of Daniel P Anagnos, Exhibit—1045, Filed on Dec. 6, 2022—Cited in IPR2022-00243, challenging U.S. Pat. No. 8,111,839.

Ex 1046—Patent Owner's Response in IPR2022-00243, Paper 21, Exhibit—1046, Filed on Dec. 6, 2022—Cited in IPR2022-00242, challenging U.S. Pat. No. 8,111,839.

Ex 1047—Patent Owner Response for IPR2022-00234, Paper 17, Exhibit—1047, Filed on Dec. 6, 2022—Cited in IPR2022-00242, challenging U.S. Pat. No. 8,111,839.

(56) References Cited

OTHER PUBLICATIONS

Ex 1047—Patent Owner Response for IPR2022-00234, Paper 17, Exhibit—1047, Filed on Dec, 6, 2022—Cited in IPR2022-00243, challenging U.S. Pat. No. 8,111,839.

Ex 1048—Institution Decision for IPR2022-00234, Paper 12, Exhibit—1048, Filed on Dec. 6, 2022—Cited in IPR2022-00242, challenging U.S. Pat. No. 8,111,839.

Ex 1049—File History for 382 Patent, Exhibit—1049, Filed on Dec. 6, 2022—Cited in IPR2022-00242, challenging U.S. Pat. No. 8,111,839.

Ex 1053—Excerpts from The Authoritative Dictionary of IEEE Standards Terms, Exhibit—1053, Filed on Dec. 6, 2022—Cited in IPR2022-00242, challenging U.S. Pat. No. 8,111,839.

Ex 1054—Supplemental Declaration of Les E Atlas PhD (Atlas-Supp), Exhibit—1054, Filed on Dec. 6, 2022—Cited in IPR2022-00243, challenging U.S. Pat. No. 8, 111,839.

Ex. 1002—Declaration of Dr. Les Atlas, Ph.D., Exhibit—1002, Filed on Jun. 9, 2022—Cited in IPR2022-01106, challenging U.S. Pat. No. 11,039,259.

Ex. 1002—Declaration of Nathaniel Polish, Ph.D., Exhibit—1002, Filed on Jun. 9, 2022—Cited in IPR2022-01098, challenging U.S. Pat. No. 11,217,237.

Ex. 1002—Declaration of Nathaniel Polish, Ph.D., Exhibit—1002, Filed on Jun. 9, 2022—Cited in IPR2022-01099, challenging U.S. Pat. No. 11,244,666.

Ex. 1002—Kyriakakis DeclarationExhibit1002,Jun. 18, 2024—Cited in IPR2024-01033, challenging U.S. Pat. No. 8,434,966.

Ex. 1002 Declaration of Chris Kyriakakis, Exhibit—1002, Filed on Jul. 1, 2024—Cited in IPR2024-01034, challenging U.S. Pat. No. 9,279,263.

Ex. 1002 Declaration of Dr. Richard M. Stern, Exhibit—1002, Filed on Jun. 9, 2022—Cited in IPR2022-01078, challenging U.S. Pat. No. 11,057,701.

Ex. 1003—CV of Dr. Les Atlas, Ph.D., Exhibit—1003, Filed on Jun. 9, 2022—Cited in IPR2022-01106, challenging U.S. Pat. No. 11,039,259.

Ex. 1003—CV of Nathaniel Polish, Ph.D., Exhibit—1003, Filed on Jun. 9, 2022—Cited in IPR2022-01098, challenging U.S. Pat. No. 11,217,237.

Ex. 1003—CV of Nathaniel Polish, Ph.D., Exhibit—1003, Filed on Jun. 9, 2022—Cited in IPR2022-01099, challenging U.S. Pat. No. 11,244,666.

Ex. 1003—Kyriakakis CVExhibit1003,Jun. 18, 2024—Cited in IPR2024-01033, challenging U.S. Pat. No. 8,434,966.

Ex. 1003 Chris Kyriakakis CV, Exhibit—1003, Filed on Jul. 1, 2024—Cited in IPR2024-01034, challenging U.S. Pat. No. 9,279,263.

Ex. 1003 CV of Dr. Richard M. Stern, Exhibit—1003, Filed on Jun. 9, 2022—Cited in IPR2022-01078, challenging U.S. Pat. No. 11,057,701.

Ex. 1004—U.S. Appl. No. 16/571,973 File History for 259, Exhibit—1004, Filed on Jun. 9, 2022—Cited in IPR2022-01106, challenging U.S. Pat. No. 11,039,259.

Ex. 1004—File History for U.S. Pat. No. 11,750,965Exhibit1004,Jun. 18, 2024—Cited in IPR2024-01033, challenging U.S. Pat. No. 8,434,966.

Ex. 1004—File History of U.S. Pat. No. 11,217,237, Exhibit—1004, Filed on Jun. 9, 2022—Cited in IPR2022-01098, challenging U.S. Pat. No. 11,217,237.

Ex. 1004—File History of U.S. Pat. No. 11,244,666, Exhibit—1004, Filed on Jun. 9, 2022—Cited in IPR2022-01099, challenging U.S. Pat. No. 11,244,666.

Ex. 1004 File History for U.S. Pat. No. 11,665,493, Exhibit—1004, Filed on Jul. 1, 2024—Cited in IPR2024-01034, challenging U.S. Pat. No. 9,279,263.

Ex. 1004 File History of U.S. Pat. No. 11,057,701, Exhibit—1004, Filed on Jun. 9, 2022—Cited in IPR2022-01078, challenging U.S. Pat. No. 11,057,701.

Ex. 1005—U.S. Appl. No. 13/917,079 File History part 1 of 2, Exhibit—1005, Filed on Jun. 9, 2022—Cited in IPR2022-01106, challenging U.S. Pat. No. 11,039,259.

Ex. 1005—U.S. Appl. No. 13/917,079 File History part 2 of 2, Exhibit—1005, Filed on Jun. 9, 2022—Cited in IPR2022-01106, challenging U.S. Pat. No. 11,039,259.

Ex. 1005 U.S. Appl. No. 61/098,250, Exhibit—1005, Filed on Jul. 1, 2024—Cited in IPR2024-01034, challenging U.S. Pat. No. 9,279,263.

Ex. 1006—U.S. Appl. No. 12/555,570 File History, Exhibit—1006, Filed on Jun. 9, 2022—Cited in IPR2022-01106, challenging U.S. Pat. No. 11,039,259.

Ex. 1006—U.S. Appl. No. 12/115,349 File History, Exhibit—1006, Filed on Jun. 9, 2022—Cited in IPR2022-01078, challenging U.S. Pat. No. 11,057,701.

Ex. 1006 U.S. Appl. No. 12/555,864, Exhibit—1006, Filed on Jul. 1, 2024—Cited in IPR2024-01034, challenging U.S. Pat. No. 9,279,263.

Ex. 1007—U.S. Appl. No. 61/096,128 File History, Exhibit—1007, Filed on Jun. 9, 2022—Cited in IPR2022-01106, challenging U.S. Pat. No. 11,039,259.

Ex. 1007 U.S. Appl. No. 60/916,271 File History, Exhibit—1007, Filed on Jun. 9, 2022—Cited in IPR2022-01078, challenging U.S. Pat. No. 11,057,701.

Ex. 1008—JP3353701B2 to Kondo with Translation, Exhibit—1008, Filed on Jun. 9, 2022—Cited in IPR2022-01098, challenging U.S. Pat. No. 11,217,237.

Ex. 1009 Translation of JPA 2002-204500 (Hayashi), Exhibit—1009, Filed on Jul. 1, 2024—Cited in IPR2024-01034, challenging U.S. Pat. No. 9,279,263.

Ex. 1010—Redline—965 versus parentExhibit1010,Jun. 18, 2024—Cited in IPR2024-01033, challenging U.S. Pat. No. 8,434,966.

Ex. 1012—U.S. Appl. No. 60/893,617Exhibit1012,Jun. 18, 2024—Cited in IPR2024-01033, challenging U.S. Pat. No. 8,434,966.

Ex. 1013—150139_14109987 NOA referred to in 965 NOAExhibit1013,Jun. 18, 2024—Cited in IPR2024-01033, challenging U.S. Pat. No. 8,434,966.

Ex. 1013 Deterministic Broad-Band Signal (Chu), Exhibit—1013, Filed on Jul. 1, 2024—Cited in IPR2024-01034, challenging U.S. Pat. No. 9,279,263.

Ex. 1013 IPR2022-00282 Patent Owner Preliminary Response, Exhibit—1013, Filed on Jun. 9, 2022—Cited in IPR2022-01078, challenging U.S. Pat. No. 11,057,701.

Ex. 1014—Mulgrew 2002, Exhibit—1014, Filed on Jun. 9, 2022—Cited in IPR2022-01099, challenging U.S. Pat. No. 11,244,666.

Ex. 1014—Redline—682 parent versus ultimate parent 812Exhibit1014,Jun. 18, 2024—Cited in IPR2024-01033, challenging U.S. Pat. No. 8,434,966.

Ex. 1014 701 Patent Family Tree, Exhibit—1014, Filed on Jun. 9, 2022—Cited in IPR2022-01078, challenging U.S. Pat. No. 11,057,701.

Ex. 1015-666 Family Tree, Exhibit—1015, Filed on Jun. 9, 2022—Cited in IPR2022-01099, challenging U.S. Pat. No. 11,244,666.

Ex. 1015—Letter re 965 IPR StipulationExhibit1015,Jun. 18, 2024—Cited in IPR2024-01033, challenging U.S. Pat. No. 8,434,966.

Ex. 1015 Complaint, E.D. Tex. 22-53, Exhibit—1015, Filed on Jun. 9, 2022—Cited in IPR2022-01078, challenging U.S. Pat. No. 11,057,701.

Ex. 1016—Complaint, E.D. Tex., 22-53, Exhibit—1016, Filed on Jun. 9, 2022—Cited in IPR2022-01099, challenging U.S. Pat. No. 11,244,666.

Ex. 1016 GSM 6.31, Exhibit—1016, Filed on Jun. 9, 2022—Cited in IPR2022-01078, challenging U.S. Pat. No. 11,057,701.

Ex. 1016 Reply Declaration of Richard Stern, PhD, Exhibit—1016, Filed on Dec. 2, 2022—Cited in IPR2022-00282, challenging U.S. Pat. No. 8,315,400.

Ex. 1017—Amended Complaint, E.D. Tex., 21-413, Exhibit—1017, Filed on Jun. 9, 2022—Cited in IPR2022-01099, challenging U.S. Pat. No. 11,244,666.

Ex. 1017—Rose 2003, Exhibit—1017, Filed on Jun. 9, 2022—Cited in IPR2022-01106, challenging U.S. Pat. No. 11,039,259.

Ex. 1017 David Kleinschmidt Depo Transcript, Exhibit—1017, Filed on Dec. 2, 2022—Cited in IPR2022-00282, challenging U.S. Pat. No. 8,315,400.

Ex. 1017 Final Rejection from Reexam 90_015,146, Exhibit—1017, Filed on Jul. 1, 2024—Cited in IPR2024-01034, challenging U.S. Pat. No. 9,279,263.

Ex. 1017 GSM 6.12, Exhibit—1017, Filed on Jun. 9, 2022—Cited in IPR2022-01078, challenging U.S. Pat. No. 11,057,701.

(56) References Cited

OTHER PUBLICATIONS

Ex. 1018—Confidential Settlement Agreement with Exhibits A-IExhibit1018, Dec. 11, 2024—Cited in IPR2024-01033, challenging U.S. Pat. No. 8,434,966. [Document not publicly available at PTAB].

Ex. 1018—Consolidation Order, E.D. Tex., 21-413 & 22-53, Exhibit—1018, Filed on Jun. 9, 2022—Cited in IPR2022-01099, challenging U.S. Pat. No. 11,244,666.

Ex. 1018 Consolidation Order, E.D. Tex. 21-413 & 22-53, Exhibit—1018, Filed on Jun. 9, 2022—Cited in IPR2022-01078, challenging U.S. Pat. No. 11,057,701.

Ex. 1018 Excerpts from Wiley Electrical & Electronics Engineering Dictionary, Exhibit—1018, Filed on Dec. 2, 2022—Cited in IPR2022-00282, challenging U.S. Pat. No. 8,315,400.

Ex. 1019—Docket Control Order, E.D. Tex., 21-413, Exhibit—1019, Filed on Jun. 9, 2022—Cited in IPR2022-01099, challenging U.S. Pat. No. 11,244,666.

Ex. 1019—Duffner 2006, Exhibit—1019, Filed on Jun. 9, 2022—Cited in IPR2022-01098, challenging U.S. Pat. No. 11,217,237.

Ex. 1019 Docket Control Order, E.D. Tex. 21-413, Exhibit—1019, Filed on Jun. 9, 2022—Cited in IPR2022-01078, challenging U.S. Pat. No. 11,057,701.

Ex. 1019 Dual-Channel MLS-Based Test System (Schneider), Exhibit—1019, Filed on Jul. 1, 2024—Cited in IPR2024-01034, challenging U.S. Pat. No. 9,279,263.

Ex. 1020—Letter re IPR Stipulation, Exhibit—1020, Filed on Jun. 9, 2022—Cited in IPR2022-01099, challenging U.S. Pat. No. 11,244,666.

Ex. 1020 Letter re IPR Stipulation, Exhibit—1020, Filed on Jun. 9, 2022—Cited in IPR2022-01078, challenging U.S. Pat. No. 11,057,701.

Ex. 1021—Complaint. E.D. Tex., 22-00053, Exhibit—1021, Filed on Jun. 9, 2022—Cited in IPR2022-01098, challenging U.S. Pat. No. 11,217,237.

Ex. 1021—Hsu 2005, Exhibit—1021, Filed on Jun. 9, 2022—Cited in IPR2022-01106, challenging U.S. Pat. No. 11,039,259.

Ex. 1021—Stipulation Letter, Exhibit—1021, Filed on Jun. 9, 2022—Cited in IPR2022-00253, challenging U.S. Pat. No. 9,491,542.

Ex. 1021 Amended Complaint, E.D. Tex. 21-413, Exhibit—1021, Filed on Jun. 9, 2022—Cited in IPR2022-01078, challenging U.S. Pat. No. 11,057,701.

Ex. 1021 Claim Construction Order, ED Tex, Exhibit—1021, Filed on Jul. 1, 2024—Cited in IPR2024-01034, challenging U.S. Pat. No. 9,279,263.

Ex. 1022—Amended Complaint, E.D.Tex., 21-00413, Exhibit—1022, Filed on Jun. 9, 2022—Cited in IPR2022-01098, challenging U.S. Pat. No. 11,217,237.

Ex. 1022—Complaint, E.D. Tex., Exhibit—1022, Filed on May 20, 2022—Cited in IPR2022-00253, challenging U.S. Pat. No. 9,491,542.

Ex. 1022 Letter to Techiya re 493 IPR Stipulation, Exhibit—1022, Filed on Jul. 1, 2024—Cited in IPR2024-01034, challenging U.S. Pat. No. 9,279,263.

Ex. 1023—Consolidation Order, E.D. Tex., Exhibit—1023, Filed on May 20, 2022—Cited in IPR2022-00253, challenging U.S. Pat. No. 9,491,542.

Ex. 1023—Consolidation Order, E.D.Tex., 21-00413 & 22-00053, Exhibit—1023, Filed on Jun. 9, 2022—Cited in IPR2022-01098, challenging U.S. Pat. No. 11,217,237.

Ex. 1023 Techiya Appeal Brief from Reexam 90_015, 146, Exhibit—1023, Filed on Jul. 1, 2024—Cited in IPR2024-01034, challenging U.S. Pat. No. 9,279,263.

Ex. 1024—259 Family Tree, Exhibit—1024, Filed on Jun. 9, 2022—Cited in IPR2022-01106, challenging U.S. Pat. No. 11,039,259.

Ex. 1024—Docket Control Order, E.D. Tex., 21-00413, Exhibit—1024, Filed on Jun. 9, 2022—Cited in IPR2022-01098, challenging U.S. Pat. No. 11,217,237.

Ex. 1024 Judicial Caseload Profile, Exhibit—1024, Filed on Jul. 1, 2024—Cited in IPR2024-01034, challenging U.S. Pat. No. 9,279,263.

Ex. 1025—Complaint, E.D. Tex. 22-53, Exhibit—1025, Filed on Jun. 9, 2022—Cited in IPR2022-01106, challenging U.S. Pat. No. 11,039,259.

Ex. 1025—Letter re IPR Stipulation, Exhibit—1025, Filed on Jun. 9, 2022—Cited in IPR2022-01098, challenging U.S. Pat. No. 11,217,237.

Ex. 1025—Stipulation Letter, Exhibit—1025, Filed on May 27, 2022—Cited in IPR2022-00281, challenging U.S. Pat. No. 9,270,244.

Ex. 1026—237 Family Tree, Exhibit—1026, Filed on Jun. 9, 2022—Cited in IPR2022-01098, challenging U.S. Pat. No. 11,217,237.

Ex. 1026—Amended Complaint, E.D. Tex. 21-413, Exhibit—1026, Filed on Jun. 9, 2022—Cited in IPR2022-01106, challenging U.S. Pat. No. 11,039,259.

Ex. 1026—Complaint, E.D. Tex., Exhibit—1026, Filed on May 27, 2022—Cited in IPR2022-00281, challenging U.S. Pat. No. 9,270,244.

Ex. 1026—Confidential Settlement Agreement, Exhibit—1026, Filed on Dec. 9, 2024—Cited in IPR2024-01034, challenging U.S. Pat. No. 9,279,263. [Document not publicly available at PTAB].

Ex. 1027—Confidential Settlement Agreement with Exhibits A-I, Exhibit—1027, Filed on Dec. 11, 2024—Cited in IPR2024-01034, challenging U.S. Pat. No. 9,279,263. [Document not publicly available at PTAB].

Ex. 1027—Consolidation Order, E.D. Tex., Exhibit—1027, Filed on May 27, 2022—Cited in IPR2022-00281, challenging U.S. Pat. No. 9,270,244.

Ex. 1027—Docket Control Order, E.D. Tex. 21-413, Exhibit—1027, Filed on Jun. 9, 2022—Cited in IPR2022-01106, challenging U.S. Pat. No. 11,039,259.

Ex. 1027—Transcript of Deposition of Christopher Struck, Exhibit—1027, Filed on Jan. 10, 2023—Cited in IPR2022-00302, challenging U.S. Pat. No. 9,609,424.

Ex. 1028—Consolidation Order, E.D. Tex. 21-413 & 22-53, Exhibit—1028, Filed on Jun. 9, 2022—Cited in IPR2022-01106, challenging U.S. Pat. No. 11,039,259.

Ex. 1028—Errata Sheet for Deposition of Christopher Struck, Exhibit—1028, Filed on Jan. 10, 2023—Cited in IPR2022-00302, challenging U.S. Pat. No. 9,609,424.

Ex. 1029—Letter re IPR Stipulation, Exhibit—1029, Filed on Jun. 9, 2022—Cited in IPR2022-01106, challenging U.S. Pat. No. 11,039,259.

Ex. 1029—Patent Owner's Opening Claim Construction Brief, E.D. Tex., Exhibit—1029, Filed on Jan. 10, 2023—Cited in IPR2022-00302, challenging U.S. Pat. No. 9,609,424.

Ex. 1029 Petitioners' Oral Hearing Demonstratives, Exhibit—1029, Filed on Sep. 26, 2023—Cited in IPR2022-01078, challenging U.S. Pat. No. 11,057,701.

Ex. 1030—Petitioners' Oral Hearing Demonstratives, Exhibit—1030, Filed on Apr. 11, 2023—Cited in IPR2022-00302, challenging U.S. Pat. No. 9,609,424.

Ex. 1033—Confidential Deposition of Christopher Struck, E.D. Tex., Exhibit—1033, Filed on May 15, 2023—Cited in IPR2022-00302, challenging U.S. Pat. No. 9,609,424. [Document not publicly available at PTAB].

Ex. 1034—Redacted Deposition of Christopher Struck, E.D. Tex., Exhibit—1034, Filed on May 15, 2023—Cited in IPR2022-00302, challenging U.S. Pat. No. 9,609,424.

Ex. 1037—Petitioners' Oral Hearing Demonstratives, Exhibit—1037, Filed on Oct. 11, 2023—Cited in IPR2022-01106, challenging U.S. Pat. No. 11,039,259.

Ex. 3001, Exhibit—3001, Filed on Nov. 8, 2024—Cited in IPR2024-01003, challenging U.S. Pat. No. 9,191,083.

Ex. 3001, Exhibit—3001, Filed on Nov. 8, 2024—Cited in IPR2024-01004, challenging U.S. Pat. No. 9,614,943.

Ex. 3001, Exhibit—3001, Filed on Nov. 8, 2024—Cited in IPR2024-01031, challenging U.S. Pat. No. 7,049,850.

Ex. 3001, Exhibit—3001, Filed on Nov. 8, 2024—Cited in IPR2024-01033, challenging U.S. Pat. No. 8,434,966.

Ex. 3001, Exhibit—3001, Filed on Nov. 8, 2024—Cited in IPR2024-01034, challenging U.S. Pat. No. 9,279,263.

Ex. 3001, Exhibit—3001, Filed on Apr. 6, 2023—Cited in IPR2022-00388, challenging U.S. Pat. No. 10,966,015.

EX1002—Declaration of Christopher Schmandt, Exhibit—1002, Filed on Feb. 9, 2024—Cited in IPR2024-00559, challenging U.S. Pat. No. 11,610,587.

(56)     References Cited

OTHER PUBLICATIONS

EX1002—Declaration of Nathaniel Polish, Exhibit—1002, Filed on Jun. 24, 2024—Cited in IPR2024-01031, challenging U.S. Pat. No. 7,049,850.

EX1002—Kyriakakis Declaration, Exhibit—1002, Filed on Jun. 12, 2024—Cited in IPR2024-01003, challenging U.S. Pat. No. 9,191,083.

EX1002—Kyriakakis Declaration, Exhibit—1002, Filed on Jun. 12, 2024—Cited in IPR2024-01004, challenging U.S. Pat. No. 9,614,943.

EX1003—Nathaniel Polish CV, Exhibit—1003, Filed on Jun. 25, 2024—Cited in IPR2024-01031, challenging U.S. Pat. No. 7,049,850.

EX1003—Kyriakakis CV, Exhibit—1003, Filed on Jun. 12, 2024—Cited in IPR2024-01003, challenging U.S. Pat. No. 9,191,083.

EX1003—Kyriakakis CV, Exhibit—1003, Filed on Jun. 12, 2024—Cited in IPR2024-01004, challenging U.S. Pat. No. 9,614,943.

EX1003—Schmandt CV, Exhibit—1003, Filed on Feb. 9, 2024—Cited in IPR2024-00559, challenging U.S. Pat. No. 11,610,587.

EX1004—File History for U.S. Pat. No. 11,659,315—Part 1 of 2, Exhibit—1004, Filed on Jun. 25, 2024—Cited in IPR2024-01031, challenging U.S. Pat. No. 7,049,850.

EX1004—File History for U.S. Pat. No. 11,659,315—Part 2 of 2, Exhibit—1004, Filed on Jun. 25, 2024—Cited in IPR2024-01031, challenging U.S. Pat. No. 7,049,850.

EX1004—File History for U.S. Pat. No. 11,710,473_Part 1 of 3, Exhibit—1004, Filed on Jun. 12, 2024—Cited in IPR2024-01003, challenging U.S. Pat. No. 9,191,083.

EX1004—File History for U.S. Pat. No. 11,710,473_Part 1 of 3, Exhibit—1004, Filed on Jun. 12, 2024—Cited in IPR2024-01004, challenging U.S. Pat. No. 9,614,943.

EX1004—File History for U.S. Pat. No. 11,710,473_Part 2 of 3, Exhibit—1004, Filed on Jun. 12, 2024—Cited in IPR2024-01003, challenging U.S. Pat. No. 9,191,083.

EX1004—File History for U.S. Pat. No. 11,710,473_Part 2 of 3, Exhibit—1004, Filed on Jun. 12, 2024—Cited in IPR2024-01004, challenging U.S. Pat. No. 9,614,943.

EX1004—File History for U.S. Pat. No. 11,710,473_Part 3 of 3, Exhibit—1004, Filed on Jun. 12, 2024—Cited in IPR2024-01003, challenging U.S. Pat. No. 9,191,083.

EX1004—File History for U.S. Pat. No. 11,710,473_Part 3 of 3, Exhibit—1004, Filed on Jun. 12, 2024—Cited in IPR2024-01004, challenging U.S. Pat. No. 9,614,943.

EX1004—U.S. Pat. No. 11,610,587 Part 1 of 2, Exhibit—1004, Filed on Feb. 9, 2024—Cited in IPR2024-00559, challenging U.S. Pat. No. 11,610,587.

EX1004—U.S. Pat. No. 11,610,587 Part 2 of 2, Exhibit—1004, Filed on Feb. 9, 2024—Cited in IPR2024-00559, challenging U.S. Pat. No. 11,610,587.

EX1005—U.S. Appl. No. 60/885,917, Exhibit—1005, Filed on Jun. 12, 2024—Cited in IPR2024-01003, challenging U.S. Pat. No. 9,191,083.

EX1005—U.S. Appl. No. 60/885,917, Exhibit—1005, Filed on Jun. 12, 2024—Cited in IPR2024-01004, challenging U.S. Pat. No. 9,614,943.

EX1005—U.S. Appl. No. 61/737,932 Provisional, Exhibit—1005, Filed on Jun. 25, 2024—Cited in IPR2024-01031, challenging U.S. Pat. No. 7,049,850.

EX1005—U.S. Appl. No. 61/098,914 (Provisional Application), Exhibit—1005, Filed on Feb. 9, 2024—Cited in IPR2024-00559, challenging U.S. Pat. No. 11,610,587.

EX1006—U.S. Appl. No. 16/266,829 (829 App), Exhibit—1006, Filed on Jun. 25, 2024—Cited in IPR2024-01031, challenging U.S. Pat. No. 7,049,850.

EX1006—U.S. Appl. No. 17/321,892, Exhibit—1006, Filed on Jun. 12, 2024—Cited in IPR2024-01003, challenging U.S. Pat. No. 9,191,083.

EX1006—U.S. Appl. No. 17/321,892, Exhibit—1006, Filed on Jun. 12, 2024—Cited in IPR2024-01004, challenging U.S. Pat. No. 9,614,943.

EX1006—U.S. Appl. No. 17/203,731, Exhibit—1006, Filed on Feb. 9, 2024—Cited in IPR2024-00559, challenging U.S. Pat. No. 11,610,587.

EX1007—315 Patent Family Tree, Exhibit—1007, Filed on Jun. 25, 2024—Cited in IPR2024-01031, challenging U.S. Pat. No. 7,049,850.

EX1008—Docket Control Order, Exhibit—1008, Filed on Jun. 25, 2024—Cited in IPR2024-01031, challenging U.S. Pat. No. 7,049,850.

EX1008—File History for U.S. Pat. No. 11,244,666, Exhibit—1008, Filed on Jun. 12, 2024—Cited in IPR2024-01003, challenging U.S. Pat. No. 9,191,083.

EX1008—File History for U.S. Pat. No. 11,244,666, Exhibit—1008, Filed on Jun. 12, 2024—Cited in IPR2024-01004, challenging U.S. Pat. No. 9,614,943.

EX1009—Letter from Nikhil Krishnan to Thomas J. Friel, Jr., Exhibit—1009, Filed on Jun. 25, 2024—Cited in IPR2024-01031, challenging U.S. Pat. No. 7,049,850.

EX1009—U.S. Appl. No. 90/019,169 RE of U.S. Pat. No. 11,244,666_Part 1 of 5, Exhibit—1009, Filed on Jun. 12, 2024—Cited in IPR2024-01003, challenging U.S. Pat. No. 9,191,083.

EX1009—U.S. Appl. No. 90/019,169 RE of U.S. Pat. No. 11,244,666_Part 1 of 5, Exhibit—1009, Filed on Jun. 12, 2024—Cited in IPR2024-01004, challenging U.S. Pat. No. 9,614,943.

EX1009—U.S. Appl. No. 90/019,169 RE of U.S. Pat. No. 11,244,666_Part 2 of 5, Exhibit—1009, Filed on Jun. 12, 2024—Cited in IPR2024-01003, challenging U.S. Pat. No. 9,191,083.

EX1009—U.S. Appl. No. 90/019,169 RE of U.S. Pat. No. 11,244,666_Part 2 of 5, Exhibit—1009, Filed on Jun. 12, 2024—Cited in IPR2024-01004, challenging U.S. Pat. No. 9,614,943.

EX1009—U.S. Appl. No. 90/019,169 RE of U.S. Pat. No. 11,244,666_Part 3 of 5, Exhibit—1009, Filed on Jun. 12, 2024—Cited in IPR2024-01003, challenging U.S. Pat. No. 9,191,083.

EX1009—U.S. Appl. No. 90/019,169 RE of U.S. Pat. No. 11,244,666_Part 3 of 5, Exhibit—1009, Filed on Jun. 12, 2024—Cited in IPR2024-01004, challenging U.S. Pat. No. 9,614,943.

EX1009—U.S. Appl. No. 90/019,169 RE of U.S. Pat. No. 11,244,666_Part 4 of 5, Exhibit—1009, Filed on Jun. 12, 2024—Cited in IPR2024-01003, challenging U.S. Pat. No. 9,191,083.

EX1009—U.S. Appl. No. 90/019,169 RE of U.S. Pat. No. 11,244,666_Part 4 of 5, Exhibit—1009, Filed on Jun. 12, 2024—Cited in IPR2024-01004, challenging U.S. Pat. No. 9,614,943.

EX1009—U.S. Appl. No. 90/019,169 RE of U.S. Pat. No. 11,244,666_Part 5 of 5, Exhibit—1009, Filed on Jun. 12, 2024—Cited in IPR2024-01003, challenging U.S. Pat. No. 9,191,083.

EX1009—U.S. Appl. No. 90/019,169 RE of U.S. Pat. No. 11,244,666_Part 5 of 5, Exhibit—1009, Filed on Jun. 12, 2024—Cited in IPR2024-01004, challenging U.S. Pat. No. 9,614,943.

EX1010—473 Patent Family Tree, Exhibit—1010, Filed on Jun. 12, 2024—Cited in IPR2024-01003, challenging U.S. Pat. No. 9,191,083.

EX1010—473 Patent Family Tree, Exhibit—1010, Filed on Jun. 12, 2024—Cited in IPR2024-01004, challenging U.S. Pat. No. 9,614,943.

EX1011—Claim Construction Order, ED Tex, Exhibit—1011, Filed on Jun. 12, 2024—Cited in IPR2024-01003, challenging U.S. Pat. No. 9,191,083.

EX1011—Claim Construction Order, ED Tex, Exhibit—1011, Filed on Jun. 12, 2024—Cited in IPR2024-01004, challenging U.S. Pat. No. 9,614,943.

EX1012—Docket Control Order, ED Tex, Exhibit—1012, Filed on Jun. 12, 2024—Cited in IPR2024-01003, challenging U.S. Pat. No. 9,191,083.

EX1012—Docket Control Order, ED Tex, Exhibit—1012, Filed on Jun. 12, 2024—Cited in IPR2024-01004, challenging U.S. Pat. No. 9,614,943.

EX1013—Letter from Nikhil Krishnan to Thomas J Friel, Jr, Exhibit—1013, Filed on Jun. 12, 2024—Cited in IPR2024-01003, challenging U.S. Pat. No. 9,191,083.

EX1013—Letter from Nikhil Krishnan to Thomas J Friel, Jr, Exhibit—1013, Filed on Jun. 12, 2024—Cited in IPR2024-01004, challenging U.S. Pat. No. 9,614,943.

EX1016—Stay Order from E.D. Tex.Exhibit1016, Nov. 20, 2024—Cited in IPR2024-01033, challenging U.S. Pat. No. 8,434,966.

EX1019—U.S. Appl. No. 60/841,990 (Rosenberg Provisional) (annotated), Exhibit—1019, Filed on Jun. 12, 2024—Cited in IPR2024-01003, challenging U.S. Pat. No. 9,191,083.

EX1023—Preliminary Constructions, E.D. Tex., Exhibit—1023, Filed on Jan. 31, 2023—Cited in IPR2022-00369, challenging U.S. Pat. No. 10,405,082.

(56) References Cited

OTHER PUBLICATIONS

EX1023—Preliminary Constructions, E.D. Tex., Exhibit—1023, Filed on Jan. 31, 2023—Cited in IPR2022-00388, challenging U.S. Pat. No. 10,966,015.
EX1024—Cohen, Exhibit—1024, Filed on Feb. 9, 2024—Cited in IPR2024-00559, challenging U.S. Pat. No. 11,610,587.
EX1024—Transcript of Deposition of Marshall Buck, Exhibit—1024, Filed on Jan. 31, 2023—Cited in IPR2022-00369, challenging U.S. Pat. No. 10,405,082.
EX1024—Transcript of Deposition of Marshall Buck, Exhibit—1024, Filed on Jan. 31, 2023—Cited in IPR2022-00388, challenging U.S. Pat. No. 10,966,015.
EX1025—Blattner et al, Earcons and Icons, Exhibit—1025, Filed on Jun. 25, 2024—Cited in IPR2024-01031, challenging U.S. Pat. No. 7,049,850.
Ex1025—Deposition Transcript of David Kleinschmidt, Exhibit—1025, Filed on Jan. 11, 2023—Cited in IPR2022-00253, challenging U.S. Pat. No. 9,491,542.
EX1025—Stay Order from E.D. Tex., Exhibit—1025, Filed on Nov. 20, 2024—Cited in IPR2024-01034, challenging U.S. Pat. No. 9,279,263.
EX1025—Tanenbaum, Exhibit—1025, Filed on Feb. 9, 2024—Cited in IPR2024-00559, challenging U.S. Pat. No. 11,610,587.
EX1025 Petitioners' Oral Hearing Demonstratives, Exhibit—1025, Filed on May 9, 2023—Cited in IPR2022-00369, challenging U.S. Pat. No. 10,405,082.
EX1025 Petitioners' Oral Hearing Demonstratives, Exhibit—1025, Filed on May 9, 2023—Cited in IPR2022-00388, challenging U.S. Pat. No. 10,966,015.
Ex1026—Cessation from Merriam-Webster's Collegiate Dictionary, 10th Ed, Exhibit—1026, Filed on Nov. 11, 2023—Cited in IPR2022-00253, challenging U.S. Pat. No. 9,491,542.
EX1026—Computer Dictionary 2nd Ed, Exhibit—1026, Filed on Feb. 9, 2024—Cited in IPR2024-00559, challenging U.S. Pat. No. 11,610,587.
Ex1027—Cessation from New World Dictionary, 2d College Ed, Exhibit—1027, Filed on Jan. 11, 2023—Cited in IPR2022-00253, challenging U.S. Pat. No. 9,491,542.
EX1028—Basu, Exhibit—1028, Filed on Jun. 12, 2024—Cited in IPR2024-01003, challenging U.S. Pat. No. 9,191,083.
EX1028—Basu, Smart Headphones, Exhibit—1028, Filed on Jun. 12, 2024—Cited in IPR2024-01004, challenging U.S. Pat. No. 9,614,943.
Ex1028—Supplemental Declaration of Nathanial Polish, Ph.D., Exhibit—1028, Filed on Jan. 11, 2023—Cited in IPR2022-00253, challenging U.S. Pat. No. 9,491,542.
EX1029—Declaration of Nathanial Polish, Exhibit—1029, Filed on Jan. 11, 2023—Cited in IPR2022-00281, challenging U.S. Pat. No. 9,270,244.
EX1029—Mueller, Transparent Hearing, Exhibit—1029, Filed on Jun. 12, 2024—Cited in IPR2024-01003, challenging U.S. Pat. No. 9,191,083.
EX1029—Mueller, Transparent Hearing, Exhibit—1029, Filed on Jun. 12, 2024—Cited in IPR2024-01004, challenging U.S. Pat. No. 9,614,943.
EX1030—Deposition Transcript of David Kleinschmidt, Exhibit—1030, Filed on Jan. 11, 2023—Cited in IPR2022-00281, challenging U.S. Pat. No. 9,270,244.
EX1031—587 Patent Family Tree, Exhibit—1031, Filed on Feb. 9, 2024—Cited in IPR2024-00559, challenging U.S. Pat. No. 11,610,587.
EX1031—Basu, et al., Smart Headphones, Exhibit—1031, Filed on Jun. 25, 2024—Cited in IPR2024-01031, challenging U.S. Pat. No. 7,049,850.
EX1031—Cessation from Merriam-Webster's Collegiate Dictionary, 10th Ed, Exhibit—1031, Filed on Jan. 11, 2023—Cited in IPR2022-00281, challenging U.S. Pat. No. 9,270,244.
EX1031—Patent Rule 4-3 Joint Claim Construction and Prehearing Statement, E.D. Tx, Exhibit—1031, Filed on Mar. 7, 2023—Cited in IPR2022-00253, challenging U.S. Pat. No. 9,491,542.

EX1032—Cessation from New World Dictionary, 2d College Ed, Exhibit—1032, Filed on Jan. 11, 2023—Cited in IPR2022-00281, challenging U.S. Pat. No. 9,270,244.
EX1032—Ex. A-01_U.S. Appl. No. 11/610,587 Samsung Infringement Claim Chart, Exhibit—1032, Filed on Feb. 9, 2024—Cited in IPR2024-00559, challenging U.S. Pat. No. 11,610,587.
EX1032—Excerpts from Microsoft Computer Dictionary, 4th ed, Exhibit—1032, Filed on Jun. 25, 2024—Cited in IPR2024-01031, challenging U.S. Pat. No. 7,049,850.
Ex1032—Petitioners' Oral Hearing Demonstratives, Exhibit—1032, Filed on Apr. 12, 2023—Cited in IPR2022-00253, challenging U.S. Pat. No. 9,491,542.
EX1033—Order Granting Proposed Docket Control Order, Exhibit—1033, Filed on Feb. 9, 2024—Cited in IPR2024-00559, challenging U.S. Pat. No. 11,610,587.
EX1033—Pending from Merriam-Webster's Collegiate Dictionary, 10th Ed, Exhibit—1033, Filed on Jan. 11, 2023—Cited in IPR2022-00281, challenging U.S. Pat. No. 9,270,244.
EX1034—Computer Dictionary 2nd Ed, Exhibit—1034, Filed on Jun. 12, 2024—Cited in IPR2024-01003, challenging U.S. Pat. No. 9,191,083.
EX1034—D Del Statistics, Exhibit—1034, Filed on Feb. 9, 2024—Cited in IPR2024-00559, challenging U.S. Pat. No. 11,610,587.
EX1034—Pause from Merriam-Webster's Collegiate Dictionary, 10th Ed, Exhibit—1034, Filed on Jan. 11, 2023—Cited in IPR2022-00281, challenging U.S. Pat. No. 9,270,244.
EX1035—Deposition Transcript for Daniel P. Anagnos, Exhibit—1035, Filed on Jan. 10, 2023—Cited in IPR2022-00324, challenging U.S. Pat. No. 8,254,591.
EX1035—File History of U.S. Pat. No. 10,635,382; Exhibit—1035, Filed on Dec. 2, 2022—Cited in IPR2022-00234, challenging U.S. Pat. No. 9,124,982.
EX1035—Letter to Techiya re 587 IPR Stipulation, Exhibit—1035, Filed on Feb. 9, 2024—Cited in IPR2024-00559, challenging U.S. Pat. No. 11,610,587.
EX1035—National Judicial Caseload Profile, Exhibit—1035, Filed on Mar. 7, 2023—Cited in IPR2024-01031, challenging U.S. Pat. No. 7,049,850.
EX1035—Patent Rule 4-3 Joint Claim Construction and Prehearing Statement, E.D. TX, Exhibit—1035, Filed on Mar. 7, 2023—Cited in IPR2022-00281, challenging U.S. Pat. No. 9,270,244.
EX1035—Tanenbaum Excerpt, Exhibit—1035, Filed on Jun. 12, 2024—Cited in IPR2024-01003, challenging U.S. Pat. No. 9,191,083.
EX1036—LinkedIn Profile for Harish Jonnalagadda, Exhibit—1036, Filed on Jan. 10, 2023—Cited in IPR2022-00324, challenging U.S. Pat. No. 8,254,591.
EX1036—Oshana excerpt, Exhibit—1036, Filed on Jun. 12, 2024—Cited in IPR2024-01003, challenging U.S. Pat. No. 9,191,083.
EX1036—Oshana excerpt, Exhibit—1036, Filed on Jun. 12, 2024—Cited in IPR2024-01004, challenging U.S. Pat. No. 9,614,943.
EX1036—Petitioners' Oral Hearing Demonstratives, Exhibit—1036, Filed on Apr. 13, 2023—Cited in IPR2022-00281, challenging U.S. Pat. No. 9,270,244.
EX1036—Stay Order from E.D. Tex., Exhibit—1036, Filed on Nov. 20, 2024—Cited in IPR2024-01031, challenging U.S. Pat. No. 7,049,850.
EX1037—Confidential Settlement Agrement with Exhibits A-I, Exhibit—1037, Filed on Dec. 11, 2024—Cited in IPR2024-00559, challenging U.S. Pat. No. 11,610,587. [Document not publicly available at PTAB].
EX1038—Confidential Settlement Agreement with Exhibits A-I, Exhibit—1038, Filed on Dec. 11, 2024—Cited in IPR2024-01031, challenging U.S. Pat. No. 7,049,850. [Document not publicly available at PTAB].
EX1038—Handbook for Sound Engineers_Part 1 of 2, Exhibit—1038, Filed on Jun. 12, 2024—Cited in IPR2024-01003, challenging U.S. Pat. No. 9,191,083.
EX1038—Handbook for Sound Engineers_Part 2 of 2, Exhibit—1038, Filed on Jun. 12, 2024—Cited in IPR2024-01003, challenging U.S. Pat. No. 9,191,083.
EX1040—IPR2022-00234, Ex 2001, Declaration of Daniel P Anagnos; Exhibit—1040, Filed on Dec. 2, 2022—Cited in IPR2022-00234, challenging U.S. Pat. No. 9,124,982.

(56) References Cited

OTHER PUBLICATIONS

EX1041—Nov. 18, 2022, Deposition Transcript of Daniel P Anagnos; Exhibit—1041, Filed on Dec. 2, 2022—Cited in IPR2022-00234, challenging U.S. Pat. No. 9,124,982.
EX1041—Supplemental Declaration of Les E. Atlas, Ph.D., Exhibit—1041, Filed on Jan. 10, 2023—Cited in IPR2022-00324, challenging U.S. Pat. No. 8,254,591.
EX1042—Excerpts from the Authoritative Dictionary of IEEE Standards Terms; Exhibit—1042, Filed on Dec. 2, 2022—Cited in IPR2022-00234, challenging U.S. Pat. No. 9,124,982.
Ex1042—Petitioners' Oral Hearing Demonstratives, Exhibit—1042, Filed on Apr. 4, 2023—Cited in IPR2022-00324, challenging U.S. Pat. No. 8,254,591.
EX1043—Institution Decision, IPR2022-00234, Paper 16; Exhibit—1043, Filed on Dec. 2, 2022—Cited in IPR2022-00234, challenging U.S. Pat. No. 9,124,982.
EX1044—Patent Owner Response, IPR2022-00234, Paper 22; Exhibit—1044, Filed on Dec. 2, 2022—Cited in IPR2022-00234, challenging U.S. Pat. No. 9,124,982.
EX1045—Excerpt of Prosecution History of U.S. Appl. No. 17/483,190, Exhibit—1045, Filed on Jun. 12, 2024—Cited in IPR2024-01003, challenging U.S. Pat. No. 9,191,083.
EX1056—U.S. Pat. No. 11,710,473 Samsung Infringement Claim Chart, Ex. A-06, Exhibit—1056, Filed on Jun. 12, 2024—Cited in IPR2024-01003, challenging U.S. Pat. No. 9,191,083.
EX1056—U.S. Pat. No. 11,710,473 Samsung Infringement Claim Chart, Ex. A-06, Exhibit—1056, Filed on Jun. 12, 2024—Cited in IPR2024-01004, challenging U.S. Pat. No. 9,614,943.
EX1058—Kuo, Active Noise Control, Exhibit—1058, Filed on Jun. 12, 2024—Cited in IPR2024-01004, challenging U.S. Pat. No. 9,614,943.
Ex1058—Petitioners' Oral Hearing Demonstratives, Exhibit—1058, Filed on Mar. 16, 2023—Cited in IPR2022-00242, challenging U.S. Pat. No. 8,111,839.
Ex1058—Petitioners' Oral Hearing Demonstratives, Exhibit—1058, Filed on Mar. 16, 2023—Cited in IPR2022-00243, challenging U.S. Pat. No. 8,111,839.
EX1059—Stay Order from E.D. Tex., Exhibit—1059, Filed on Nov. 20, 2024—Cited in IPR2024-01003, challenging U.S. Pat. No. 9,191,083.
EX1059—Stay Order from E.D. Tex., Exhibit—1059, Filed on Nov. 20, 2024—Cited in IPR2024-01004, challenging U.S. Pat. No. 9,614,943.
EX1061—Confidential Settlement Agreement with Exhibits A-I, Exhibit—1061, Filed on Dec. 11, 2024—Cited in IPR2024-01004, challenging U.S. Pat. No. 9,614,943. [Document not publicly available at PTAB].
EX1061—Confidential Settlement Agrement with Exhibits A-I, Exhibit—1061, Filed on Dec. 11, 2024—Cited in IPR2024-01003, challenging U.S. Pat. No. 9,191,083. [Document not publicly available at PTAB].
Excerpt from Computer Dictionary, 2d ed., Exhibit—1027, Filed on Dec. 13, 2021—Cited in IPR2022-00242, challenging U.S. Pat. No. 8,111,839.
Excerpt from Computer Dictionary, 2d ed., Exhibit—1027, Filed on Dec. 13, 2021—Cited in IPR2022-00243, challenging U.S. Pat. No. 8,111,839.
Excerpt from Computer Dictionary, 2d ed.; Exhibit—1029, Filed on Dec. 13, 2021—Cited in IPR2022-00234, challenging U.S. Pat. No. 9124982.
Excerpt from Dictionary of Scientific and Technical Terms, 5th ed., Exhibit—1026, Filed on Dec. 20, 2021—Cited in IPR2022-00324, challenging U.S. Pat. No. 8,254,591.
Excerpt from McGraw Hill Dictionary of Scientific and Technical Terms, 5th ed., Exhibit—1025, Filed on Dec. 13, 2021—Cited in IPR2022-00242, challenging U.S. Pat. No. 8,111,839.
Excerpt from McGraw-Hill Dictionary of Scientific and Technical Terms, 5th ed., Exhibit—1025, Filed on Dec. 13, 2021—Cited in IPR2022-00243, challenging U.S. Pat. No. 8,111,839.

Excerpt from Oshana; Exhibit—1030, Filed on Dec. 13, 2021—Cited in IPR2022-00234, challenging U.S. Pat. No. 9,124,982.
Excerpt of File History of U.S. Appl. No. 12/100,281; Exhibit—1006, Filed on Dec. 13, 2021—Cited in IPR2022-00234, challenging U.S. Pat. No. 9,124,982.
Excerpt of File History of U.S. Appl. No. 13/352,694; Exhibit—1007, Filed on Dec. 13, 2021—Cited in IPR2022-00234, challenging U.S. Pat. No. 9,124,982.
Excerpts from Federal Court Management Statistics, Exhibit—1022, Filed on Jul. 1, 2022—Cited in IPR2022-00369, challenging U.S. Pat. No. 10,405,082.
Excerpts from Federal Court Management Statistics, Exhibit—1022, Filed on Jul. 1, 2022—Cited in IPR2022-00388, challenging U.S. Pat. No. 10,966,015.
Excerpts from Federal Court Management Statistics, Exhibit—1023, Filed on Jul. 1, 2022—Cited in IPR2022-00410, challenging U.S. Pat. No. 10,979,836.
Excerpts from Federal Court Management Statistics, Exhibit—1024, Filed on Jul. 1, 2022—Cited in IPR2022-00253, challenging U.S. Pat. No. 9,491,542.
Excerpts from Federal Court Management Statistics, Exhibit—1026, Filed on Jul. 1, 2022—Cited in IPR2022-00302, challenging U.S. Pat. No. 9,609,424.
Excerpts from Federal Court Management Statistics, Exhibit—1028, Filed on Jul. 1, 2022—Cited in IPR2022-00281, challenging U.S. Pat. No. 9,270,244.
Excerpts from Federal Court Management Statistics, Exhibit—1034, Filed on Jul. 1, 2022—Cited in IPR2022-00324, challenging U.S. Pat. No. 8,254,591.
Excerpts from McGraw-Hill Dictionary of Scientific and Technical Terms, 5th ed.; Exhibit—1021, Filed on Dec. 13, 2021—Cited in IPR2022-00234, challenging U.S. Pat. No. 9,124,982.
Excerpts from Openheim, Exhibit—1016, Filed on Jan. 4, 2022—Cited in IPR2022-00388, challenging U.S. Pat. No. 10,966,015.
Excerpts from Oppenheim & Schafer, 3rd ed., Exhibit—1016, Filed on Dec. 30, 2021—Cited in IPR2022-00369, challenging U.S. Pat. No. 10,405,082.
Excerpts from Oshana, Exhibit—1027, Filed on Dec. 20, 2021—Cited in IPR2022-00324, challenging U.S. Pat. No. 8,254,591.
Excerpts from Oshana, Exhibit—1028, Filed on Dec. 13, 2021—Cited in IPR2022-00242, challenging U.S. Pat. No. 8,111,839.
Excerpts from Oshana, Exhibit—1028, Filed on Dec. 13, 2021—Cited in IPR2022-00243, challenging U.S. Pat. No. 8,111,839.
Exhibit 3001, Exhibit—3001, Filed on Jan. 5, 2023—Cited in IPR2022-00282, challenging U.S. Pat. No. 8,315,400.
Exhibit 3001, Exhibit—3001, Filed on Nov. 3, 2022—Cited in IPR2022-01078, challenging U.S. Pat. No. 11,057,701.
Exhibit 3001, Exhibit—3001, Filed on Nov. 3, 2022—Cited in IPR2022-01106, challenging U.S. Pat. No. 11,039,259.
Exhibit 3001, Exhibit—3001, Filed on Apr. 6, 2023—Cited in IPR2022-00369, challenging U.S. Pat. No. 10,405,082.
Expunged, Exhibit—1002, Filed on Jan. 4, 2022—Cited in IPR2022-00388, challenging U.S. Pat. No. 10,966,015. [Document expunged from PTAB record].
Expunged, Exhibit—1006, Filed on Dec. 13, 2021—Cited in IPR2022-00242, challenging U.S. Pat. No. 8,111,839.
Expunged, Exhibit—1006, Filed on Dec. 13, 2021—Cited in IPR2022-00243, challenging U.S. Pat. No. 8,111,839.
Expunged, Exhibit—1031, Filed on Apr. 13, 2023—Cited in IPR2022-00302, challenging U.S. Pat. No. 9,609,424.
Expunged, Exhibit—1036, Filed on Dec. 9, 2024—Cited in IPR2024-00559, challenging U.S. Pat. No. 11,610,587. [Document expunged from PTAB record].
Expunged, Exhibit—1037, Filed on Dec. 9, 2024—Cited in IPR2024-01031, challenging U.S. Pat. No. 7,049,850. [Document expunged from PTAB record].
Expunged, Exhibit—1060, Filed on Dec. 9, 2024—Cited in IPR2024-01003, challenging U.S. Pat. No. 9,191,083. [Document expunged from PTAB record].
Expunged, Exhibit—1060, Filed on Dec. 9, 2024—Cited in IPR2024-01004, challenging U.S. Pat. No. 9,614,943. [Document expunged from PTAB record].

(56) References Cited

OTHER PUBLICATIONS

Expunged, Exhibit—11, Filed on Jan. 18, 2023—Cited in IPR2022-01099, challenging U.S. Pat. No. 11,244,666. [Document expunged from PTAB record].

Expunged, Exhibit—12, Filed on Jan. 18, 2023—Cited in IPR2022-01098, challenging U.S. Pat. No. 11,217,237. [Document expunged from PTAB record].

Expunged, Exhibit—2008, Filed on Feb. 22, 2023—Cited in IPR2022-00281, challenging U.S. Pat. No. 9,270,244.

Expunged, Exhibit—3, Filed on Dec. 10, 2021—Cited in IPR2022-00282, challenging U.S. Pat. No. 8,315,400. [Document expunged from PTAB record].

Expunged, Exhibit—3, Filed on Jun. 9, 2022—Cited in IPR2022-01098, challenging U.S. Pat. No. 11,217,237. [Document expunged from PTAB record].

Expunged, Exhibit—3002, Filed on Apr. 6, 2023—Cited in IPR2022-00388, challenging U.S. Pat. No. 10,966,015. [Document expunged from PTAB record].

Expunged, Exhibit—37, Filed on Aug. 15, 2023—Cited in IPR2022-00243, challenging U.S. Pat. No. 8,111,839.

ExpungedExhibit1017, Dec. 9, 2024—Cited in IPR2024-01033, challenging U.S. Pat. No. 8,434,966. [Document expunged from PTAB record].

Extract from Federal Court Management Statistics, Exhibit—1021, Filed on Nov. 10, 2022—Cited in IPR2022-01099, challenging U.S. Pat. No. 11,244,666.

Extract from Federal Court Management Statistics, Exhibit—1024, Filed on Nov. 10, 2022—Cited in IPR2022-01078, challenging U.S. Pat. No. 11,057,701.

Extract from Federal Court Management Statistics, Exhibit—1027, Filed on Nov. 15, 2022—Cited in IPR2022-01098, challenging U.S. Pat. No. 11,217,237.

Extract from Federal Court Management Statistics, Exhibit—1030, Filed on Nov. 10, 2022—Cited in IPR2022-01106, challenging U.S. Pat. No. 11,039,259.

Federal Court Management Statistics (excerpt), Exhibit—2004, Filed on Jul. 1, 2022—Cited in IPR2022-00253, challenging U.S. Pat. No. 9,491,542.

Federal Court Management Statistics (excerpt), Exhibit—2004, Filed on Jul. 1, 2022—Cited in IPR2022-00281, challenging U.S. Pat. No. 9,270,244.

Federal Court Management Statistics (excerpt), Exhibit—2004, Filed on Jul. 1, 2022—Cited in IPR2022-00302, challenging U.S. Pat. No. 9,609,424.

Federal Court Management Statistics (excerpt), Exhibit—2004, Filed on Jul. 1, 2022—Cited in IPR2022-00324, challenging U.S. Pat. No. 8,254,591.

Federal Court Management Statistics (excerpt), Exhibit—2005, Filed on Jul. 1, 2022—Cited in IPR2022-00369, challenging U.S. Pat. No. 10,405,082.

Federal Court Management Statistics (excerpt), Exhibit—2005, Filed on Jul. 1, 2022—Cited in IPR2022-00410, challenging U.S. Pat. No. 10,979,836.

Federal Court Management Statistics (excerpt), Exhibit—2006, Filed on Jul. 1, 2022—Cited in IPR2022-00388, challenging U.S. Pat. No. 10,966,015.

File History for U.S. Pat. No. 9,491,542, Exhibit—1004, Filed on Dec. 17, 2021—Cited in IPR2022-00253, challenging U.S. Pat. No. 9,491,542.

File History of U.S. Appl. No. 16/168,752, Exhibit—2005, Filed on May 18, 2022—Cited in IPR2022-00388, challenging U.S. Pat. No. 10,966,015.

File History of U.S. Appl. No. 12/555,864, Exhibit—1012, Filed on Jan. 14, 2022—Cited in IPR2022-00410, challenging U.S. Pat. No. 10,979,836.

File History of U.S. Appl. No. 14/054,015, Exhibit—1011, Filed on Jan. 14, 2022—Cited in IPR2022-00410, challenging U.S. Pat. No. 10,979,836.

File History of U.S. Appl. No. 14/827,332, Exhibit—1010, Filed on Jan. 14, 2022—Cited in IPR2022-00410, challenging U.S. Pat. No. 10,979,836.

File History of U.S. Appl. No. 15/700,511, Exhibit—1009, Filed on Jan. 14, 2022—Cited in IPR2022-00410, challenging U.S. Pat. No. 10,979,836.

File History of U.S. Appl. No. 16/414,136, Exhibit—1013, Filed on Jan. 14, 2022—Cited in IPR2022-00410, challenging U.S. Pat. No. 10,979,836.

File History of U.S. Pat. No. 8,111,839, Exhibit—1005, Filed on Dec. 13, 2021—Cited in IPR2022-00242, challenging U.S. Pat. No. 8,111,839.

File History of U.S. Pat. No. 8,111,839, Exhibit—1005, Filed on Dec. 13, 2021—Cited in IPR2022-00243, challenging U.S. Pat. No. 8,111,839.

File History of U.S. Pat. No. 8,254,591, Exhibit—1004, Filed on Dec. 20, 2021—Cited in IPR2022-00324, challenging U.S. Pat. No. 8,254,591.

File History of U.S. Pat. No. 9,124,982; Exhibit—1004, Filed on Dec. 13, 2021—Cited in IPR2022-00234, challenging U.S. Pat. No. 9,124,982.

File History of U.S. Pat. No. 10,405,082, Exhibit—1004, Filed on Dec. 30, 2021—Cited in IPR2022-00369, challenging U.S. Pat. No. 10,405,082.

File History of U.S. Pat. No. 10,966,015, Exhibit—1005, Filed on Jan. 4, 2022—Cited in IPR2022-00388, challenging U.S. Pat. No. 10,966,015.

File History of U.S. Pat. No. 10,979,836,, U.S. Appl. No. 16/838,277, Exhibit—1004, Filed on Jan. 14, 2022—Cited in IPR2022-00410, challenging U.S. Pat. No. 10,979,836.

File History of U.S. Pat. No. 8,315,400, Exhibit—1004, Filed on Dec. 10, 2021—Cited in IPR2022-00282, challenging U. S. Patent No. 8,315,400.

File History of U.S. Pat. No. 8,774,433, Exhibit—1009, Filed on Dec. 20, 2021—Cited in IPR2022-00302, challenging U.S. Pat. No. 9,609,424.

File History of U.S. Pat. No. 9,270,244, Exhibit—1004, Filed on Dec. 21, 2021—Cited in IPR2022-00281, challenging U.S. Pat. No. 9,270,244.

File History of U.S. Pat. No. 9,332,364, Exhibit—1005, Filed on Dec. 21, 2021—Cited in IPR2022-00302, challenging U.S. Pat. No. 9,609,424.

File History of U.S. Pat. No. 9,609,424, Exhibit—1004, Filed on Dec. 21, 2021—Cited in IPR2022-00302, challenging U.S. Pat. No. 9,609,424.

File History of U.S. Appl. No. 60/910,808; Exhibit—1005, Filed on Dec. 13, 2021—Cited in IPR2022-00234, challenging U.S. Pat. No. 9,124,982.

File History of U.S. Appl. No. 61/098,250, Exhibit—1005, Filed on Jan. 14, 2022—Cited in IPR2022-00410, challenging U.S. Pat. No. 10,979,836.

File History of U.S. Appl. No. 60/619,517 (Allen Provisional), Exhibit—1020, Filed on Dec. 21, 2021—Cited in IPR2022-00302, challenging U.S. Pat. No. 9,609,424.

File History of U.S. Appl. No. 60/866,420, Exhibit—1010, Filed on Dec. 21, 2021—Cited in IPR2022-00302, challenging U.S. Pat. No. 9,609,424.

Final Written Decision, IPR2022-00282 (Paper No. 28, Jun. 14, 2023), Exhibit—1035, Filed on Jun. 30, 2023—Cited in IPR2022-01106, challenging U.S. Pat. No. 11,039,259.

Final Written Decision: Final Written Decision Determining All Challenged Claims Unpatentable 35 U.S.C. sec. 318a, Exhibit—32, Filed on Jan. 5, 2024—Cited in IPR2022-01106, challenging U.S. Pat. No. 11,039,259.

Final Written Decision: original, Exhibit—28, Filed on Jun.14, 2023—Cited in IPR2022-00282, challenging U.S. Pat. No. 8,315,400.

Final Written Decision: original, Exhibit—31, Filed on Jul. 13, 2023—Cited in IPR2022-00281, challenging U.S. Pat. No. 9,270,244.

Final Written Decision: original, Exhibit—33, Filed on Jul. 10, 2023—Cited in IPR2022-00324, challenging U.S. Pat. No. 8,254,591.

Final Written Decision: original, Exhibit—33, Filed on Jul. 14, 2023—Cited in IPR2022-00253, challenging U.S. Pat. No. 9,491,542.

(56) References Cited

OTHER PUBLICATIONS

Final Written Decision: original, Exhibit—36, Filed on Jun. 16, 2023—Cited in IPR2022-00242, challenging U.S. Pat. No. 8,111,839.

Final Written Decision: original; Exhibit—29, Filed on Jun. 14, 2023—Cited in IPR2022-00234, challenging U.S. Pat. No. 9,124,982.

Final Written Decision: Judgment Final Written Decision Determining All Challenged Claims Unpatentable 35 U.S. C. § 318(a), Exhibit—35, Filed on Jun. 20, 2023—Cited in IPR2022-00243, challenging U.S. Pat. No. 8,111,839.

First Amended Complaint, Staton *Techiya* v. *Samsung*, E.D. Tex., Exhibit—1008, Filed on Dec. 10, 2021—Cited in IPR2022-00282, challenging U.S. Pat. No. 8,315,400.

First Amended Complaint, *Techiya* v. *Samsung*, E.D. Tex., Exhibit—1018, Filed on Dec. 21, 2021—Cited in IPR2022-00281, challenging U.S. Pat. No. 9,270,244.

First Amended Complaint, *Techiya* v. *Samsung*, E.D. Tex., Exhibit—1020, Filed on Dec. 17, 2021—Cited in IPR2022-00253, challenging U.S. Pat. No. 9,491,542.

First Amended Complaint, *Techiya* v. *Samsung*, E.D. Tex., Exhibit—1029, Filed on Dec. 20, 2021—Cited in IPR2022-00324, challenging U.S. Pat. No. 8,254,591.

First Amended Complaint, *Techiya* v. *Samsung*, E.D. Tex., Exhibit—1040, Filed on Dec. 13, 2021—Cited in IPR2022-00242, challenging U.S. Pat. No. 8,111,839.

First Amended Complaint, *Techiya* v. *Samsung*, E.D. Tex., Exhibit—1040, Filed on Dec. 13, 2021—Cited in IPR2022-00243, challenging U.S. Pat. No. 8,111,839.

First Amended Complaint, *Techiya* v. *Samsung*, E.D. Tex.; Exhibit—1040, Filed on Dec. 13, 2021—Cited in IPR2022-00234, challenging U.S. Pat. No. 9,124,982.

Granting Institution of Inter Partes Review 35 U.S.C. § 314, Exhibit—13, Filed on Jul. 15, 2022—Cited in IPR2022-00253, challenging U.S. Pat. No. 9,491,542.

Granting Institution of Inter Partes Review 35 U.S.C. § 314, Exhibit—13, Filed on Jul. 15, 2022—Cited in IPR2022-00281, challenging U.S. Pat. No. 9,270,244.

Granting Institution of Inter Partes Review 35 U.S.C. § 314, Exhibit—13, Filed on Aug. 16, 2022—Cited in IPR2022-00388, challenging U.S. Pat. No. 10,966,015.

Granting Institution of Inter Partes Review 35 U.S.C. § 314, Exhibit—14, Filed on Aug. 16, 2022—Cited in IPR2022-00369, challenging U.S. Pat. No. 10,405,082.

Harman Q&As about Microphone Windscreens, Exhibit—2013, Filed on Sep. 13, 2022—Cited in IPR2022-00242, challenging U.S. Pat. No. 8,111, 839.

Harman, Q&As about Microphone Screens; Exhibit—2012, Filed on Sep. 9, 2022—Cited in IPR2022-00234, challenging U.S. Pat. No. 9,124,982.

IEEE Dictionary of Standards Terms (excerpts), Exhibit—2006, Filed on Mar. 21, 2022—Cited in IPR2022-00282, challenging U.S. Pat. No. 8,315,400.

Institution Decision: Deny, Exhibit—12, Filed on Aug. 12, 2022—Cited in IPR2022-00410, challenging U.S. Pat. No. 10,979,836.

Institution Decision: Grant, Exhibit—10, Filed on Jan. 9, 2023—Cited in IPR2022-01106, challenging U.S. Pat. No. 11,039,259.

Institution Decision: Grant, Exhibit—12, Filed on Jun. 17, 2022—Cited in IPR2022-00282, challenging U.S. Pat. No. 8,315,400.

Institution Decision: Grant, Exhibit—12, Filed on Jun. 17, 2022—Cited in IPR2022-00302, challenging U.S. Pat. No. 9,609,424.

Institution Decision: Grant, Exhibit—12, Filed on Jun. 17, 2022—Cited in IPR2022-00324, challenging U.S. Pat. No. 8,254,591.

Institution Decision: Grant, Exhibit—15, Filed on Jun. 21, 2022—Cited in IPR2022-00243, challenging U.S. Pat. No. 8,111,839.

Institution Decision: Grant Exhibit—16, Filed on Jun. 21, 2022—Cited in IPR2022-00242, challenging U.S. Pat. No. 8,111,839.

Institution Decision: Grant, Exhibit—8, Filed on Aug. 16, 2024—Cited in IPR2024-00559, challenging U.S. Pat. No. 11,610,587.

Institution Decision: Grant; Exhibit—12, Filed on Jun. 17, 2022—Cited in IPR2022-00234, challenging U.S. Pat. No. 9,124,982.

Joint Motion to Consolidate; Exhibit—2005, Filed on Apr. 29, 2022—Cited in IPR2022-00234, challenging U.S. Pat. No. 9,124,982.

Joint Motion to Terminate Proceeding, Exhibit—17, Filed on Dec. 9, 2024—Cited in IPR2024-00559, challenging U.S. Pat. No. 11,610,587.

Joint Request to Treat Settlement Agreement as Business Confidential Information, Exhibit—14, Filed on Dec. 9, 2024—Cited in IPR2024-01003, challenging U.S. Pat. No. 9,191,083.

Joint Request to Treat Settlement Agreement as Business Confidential Information, Exhibit—14, Filed on Dec. 9, 2024—Cited in IPR2024-01004, challenging U.S. Pat. No. 9,614,943.

Joint Request to Treat Settlement Agreement as Business Confidential Information, Exhibit—14, Filed on Dec. 9, 2024—Cited in IPR2024-01031, challenging U.S. Pat. No. 7,049,850.

Joint Request to Treat Settlement Agreement as Business Confidential Information, Exhibit—15, Filed on Dec. 9, 2024—Cited in IPR2024-01034, challenging U.S. Pat. No. 9,279,263.

Joint Request to Treat Settlement Agreement as Business Confidential Information, Exhibit—18, Filed on Dec. 9, 2024—Cited in IPR2024-00559, challenging U.S. Pat. No. 11,610,587.

Joint Request to Treat Settlement Agreement as Business Confidential InformationPaper13, Dec. 9, 2024—Cited in IPR2024-01033, challenging U.S. Pat. No. 8,434,966.

Joint Statement Regarding Oral Argument, Exhibit—15, Filed on Jul. 29, 2022—Cited in IPR2022-00253, challenging U.S. Pat. No. 9,491,542.

Joint Statement Regarding Oral Argument, Exhibit—15, Filed on Jul. 29, 2022—Cited in IPR2022-00281, challenging U.S. Pat. No. 9,270,244.

Joint Statement Regarding Oral Argument, Exhibit—15, Filed on Jul. 29, 2022—Cited in IPR2022-00302, challenging U.S. Pat. No. 9,609,424.

Joint Statement Regarding Oral Argument, Exhibit—15, Filed on Aug. 24, 2022—Cited in IPR2022-00388, challenging U.S. Pat. No. 10,966,015.

Joint Statement Regarding Oral Argument, Exhibit—16, Filed on Jul. 29,2022—Cited in IPR2022-00324, challenging U.S. Pat. No. 8,254,591.

Joint Statement Regarding Oral Argument, Exhibit—16, Filed on Aug. 24, 2022—Cited in IPR2022-00369, challenging U.S. Pat. No. 10,405,082.

Joint Statement Regarding Oral Argument, Exhibit—18, Filed on Jul. 29, 2022—Cited in IPR2022-00243, challenging U.S. Pat. No. 8,111,839.

Joint Statement Regarding Oral Argument, Exhibit—19, Filed on Jul. 29, 2022—Cited in IPR2022-00242, challenging U.S. Pat. No. 8,111,839.

Joint Stipulation To Modify Due Dates 1-3, Exhibit—10, Filed on Oct. 25,2024—Cited in IPR2024-00559, challenging U.S. Pat. No. 11,610,587.

Joint Stipulation To Modify Due Dates 1-3, Exhibit—12, Filed on Nov. 22, 2024—Cited in IPR2024-00559, challenging U.S. Pat. No. 11,610,587.

Joint Stipulation to Modify Scheduling Order, Exhibit—14, Filed on Mar. 14, 2023—Cited in IPR2022-01106, challenging U.S. Pat. No. 11,039,259.

Joint Stipulation to Modify the Scheduling Order, Exhibit—16, Filed on Aug. 16, 2022—Cited in IPR2022-00253, challenging U.S. Pat. No. 9,491,542.

Joint Stipulation to Modify the Scheduling Order, Exhibit—16, Filed on Aug. 16, 2022—Cited in IPR2022-00281, challenging U.S. Pat. No. 9,270,244.

Joint Stipulation to Modify the Scheduling Order, Exhibit—16, Filed on Aug. 16, 2022—Cited in IPR2022-00302, challenging U.S. Pat. No. 9,609,424.

Joint Stipulation to Modify the Scheduling Order, Exhibit—19, Filed on Aug. 16, 2022—Cited in IPR2022-00324, challenging U.S. Pat. No. 8,254,591.

Kleinschmidt Declaration in Support of Patent Owner Response, Exhibit—2018, Filed on Apr. 10, 2023—Cited in IPR2022-01106, challenging U.S. Pat. No. 11,039,259.

(56)                    References Cited

OTHER PUBLICATIONS

LEAP Practitioner Request and Verification Form (Patent Owner), Exhibit—29, Filed on Feb. 28, 2023—Cited in IPR2022-00243, challenging U.S. Pat. No. 8,111,839.

LEAP Practitioner Request and Verification Form (Patent Owner), Exhibit—30, Filed on Feb. 28, 2023—Cited in IPR2022-00242, challenging U.S. Pat. No. 8,111,839.

LEAP Practitioner Request and Verification Form (Petitioner), Exhibit—30, Filed on Mar. 13, 2023—Cited in IPR2022-00243, challenging U.S. Pat. No. 8,111,839.

LEAP Practitioner Request and Verification Form (Petitioner), Exhibit—31, Filed on Mar. 13, 2023—Cited in IPR2022-00242, challenging U.S. Pat. No. 8,111,839.

Letter from Petitioners' Counsel to PO's Counsel Apr. 20, 2022, Exhibit—2004, Filed on May 18, 2022—Cited in IPR2022-00369, challenging U.S. Pat. No. 10,405,082.

Letter from Petitioners' Counsel to PO's Counsel Apr. 20, 2022, Exhibit—2004, Filed on May 18, 2022—Cited in IPR2022-00388, challenging U.S. Pat. No. 10,966,015.

Letter from Petitioners' Counsel to PO's Counsel Apr. 20, 2022, Exhibit—2004, Filed on May 18, 2022—Cited in IPR2022-00410, challenging U.S. Pat. No. 10,979,836.

Markman Hearing Transcript (excerpts), Exhibit—2022, Filed on Oct. 19, 2023—Cited in IPR2022-01106, challenging U.S. Pat. No. 11,039,259.

Mauer, Embedded Indexing, Exhibit—2008, Filed on Sep. 13, 2022—Cited in IPR2022-00242, challenging U.S. Pat. No. 8,111,839.

Mauer, Embedded Indexing: Pros and Cons for the Indexer; Exhibit—2008, Filed on Sep. 9, 2022—Cited in IPR2022-00234, challenging U.S. Pat. No. 9,124,982.

McGraw-Hill Dictionary of Scientific and Technical Terms, Exhibit—2010, Filed on Sep. 13, 2022—Cited in IPR2022-00242, challenging U.S. Pat. No. 8,111,839.

McGraw-Hill Dictionary of Scientific and Technical Terms; Exhibit—2009, Filed on Sep. 9, 2022—Cited in IPR2022-00234, challenging U.S. Pat. No. 9,124,982.

Merriam-Webster's Collegiate Dictionary (excerpt), Exhibit—2010, Filed on Oct. 11, 2022—Cited in IPR2022-01106, challenging U.S. Pat. No. 11,039,259.

Montgomery Declaration with Exhibit A, Exhibit—1018, Filed on Jan. 14, 2022—Cited in IPR2022-00410, challenging U.S. Pat. No. 10,979,836.

Motion for Leave to File Corrected Petition, Exhibit—10, Filed on Jan. 31, 2022—Cited in IPR2022-00242, challenging U.S. Pat. No. 8,111,839.

Motion: Motion to dismiss due to settlement (pre-DI), Exhibit—13, Filed on Dec. 9, 2024—Cited in IPR2024-01003, challenging U.S. Pat. No. 9,191,083.

Motion: Motion to dismiss due to settlement (pre-DI), Exhibit—13, Filed on Dec. 9, 2024—Cited in IPR2024-01004, challenging U.S. Pat. No. 9,614,943.

Motion: Motion to dismiss due to settlement (pre-DI), Exhibit—13, Filed on Dec. 9, 2024—Cited in IPR2024-01031, challenging U.S. Pat. No. 7,049,850.

Motion: Motion to dismiss due to settlement (pre-DI), Exhibit—14, Filed on Dec. 9, 2024—Cited in IPR2024-01034, challenging U.S. Pat. No. 9,279,263.

Motion: Motion to dismiss due to settlement (pre-DI)Paper12, Dec. 9, 2024—Cited in IPR2024-01033, challenging U.S. Pat. No. 8,434,966.

Notice : Mandatory Notice, Exhibit—5, Filed on Jul. 16, 2024—Cited in IPR2024-01031, challenging U.S. Pat. No. 7,049,850.

Notice : Mandatory Notice, Exhibit—6, Filed on Jul. 16, 2024—Cited in IPR2024-01034, challenging U.S. Pat. No. 9,279,263.

Notice : Mandatory Notice, Exhibit—7, Filed on Mar. 1, 2024—Cited in IPR2024-00559, challenging U.S. Pat. No. 11,610,587.

Notice : Other—Notice of Ranking, Exhibit—4, Filed on Jul. 1, 2024—Cited in IPR2024-01034, challenging U.S. Pat. No. 9,279,263.

Notice : Power of Attorney for Harman International Industries, Exhibit—3, Filed on Feb. 9, 2024—Cited in IPR2024-00559, challenging U.S. Pat. No. 11,610,587.

Notice : Power of Attorney for Harman International Industries, Inc., Exhibit—3, Filed on Jun. 25, 2024—Cited in IPR2024-01031, challenging U.S. Pat. No. 7,049,850.

Notice : Power of Attorney for Harman International Industries, Inc., Exhibit—3, Filed on Jul. 1, 2024—Cited in IPR2024-01034, challenging U.S. Pat. No. 9,279,263.

Notice : Power of Attorney for Samsung Electronics America, Exhibit—2, Filed on Feb. 9, 2024—Cited in IPR2024-00559, challenging U.S. Pat. No. 11,610,587.

Notice : Power of Attorney for Samsung Electronics America, Inc., Exhibit—2, Filed on Jun. 12, 2024—Cited in IPR2024-01003, challenging U.S. Pat. No. 9,191,083.

Notice : Power of Attorney for Samsung Electronics America, Inc., Exhibit—2, Filed on Jun. 12, 2024—Cited in IPR2024-01004, challenging U.S. Pat. No. 9,614,943.

Notice : Power of Attorney for Samsung Electronics America, Inc., Exhibit—2, Filed on Jun. 25, 2024—Cited in IPR2024-01031, challenging U.S. Pat. No. 7,049,850.

Notice : Power of Attorney for Samsung Electronics America, Inc., Exhibit—2, Filed on Jul. 1, 2024—Cited in IPR2024-01034, challenging U.S. Pat. No. 9,279,263.

Notice : Power of Attorney for Samsung Electronics America, Inc. Paper2,Jun. 18, 2024—Cited in IPR2024-01033, challenging U.S. Pat. No. 8,434,966.

Notice : Power of Attorney for Samsung Electronics Co., Ltd., Exhibit—1, Filed on Feb. 9, 2024—Cited in IPR2024-00559, challenging U.S. Pat. No. 11,610,587.

Notice : Power of Attorney for Samsung Electronics Co., Ltd., Exhibit—1, Filed on Jun. 12, 2024—Cited in IPR2024-01003, challenging U.S. Pat. No. 9,191,083.

Notice : Power of Attorney for Samsung Electronics Co., Ltd., Exhibit—1, Filed on Jun. 12, 2024—Cited in IPR2024-01004, challenging U.S. Pat. No. 9,614,943.

Notice : Power of Attorney for Samsung Electronics Co., Ltd., Exhibit—1, Filed on Jul. 1, 2024—Cited in IPR2024-01034, challenging U.S. Pat. No. 9,279,263.

Notice : Power of Attorney for Samsung Electronics Co., Ltd. Paper1,Jun. 18, 2024—Cited in IPR2024-01033, challenging U.S. Pat. No. 8,434,966.

Notice : Power of Attorney for Samsung Electronics Corp., Exhibit—1, Filed on Jun. 25, 2024—Cited in IPR2024-01031, challenging U.S. Pat. No. 7,049,850.

Notice : Power of Attorney, Exhibit—6, Filed on Mar. 1, 2024—Cited in IPR2024-00559, challenging U.S. Pat. No. 11,610,587.

Notice : Power of Attorney, Exhibit—6, Filed on Jul. 16, 2024—Cited in IPR2024-01031, challenging U.S. Pat. No. 7,049,850.

Notice : Power of Attorney, Exhibit—7, Filed on Jul. 16, 2024—Cited in IPR2024-01034, challenging U.S. Pat. No. 9,279,263.

Notice of Deposition of Chris Kyriakakis, Ph.D., Exhibit—17, Filed on Sep. 13, 2022—Cited in IPR2022-00302, challenging U.S. Pat. No. 9,609,424.

Notice of Deposition of Daniel P Anagnos, Exhibit—21, Filed on Dec. 14, 2022—Cited in IPR2022-00324, challenging U.S. Pat. No. 8,254,591.

Notice of Deposition of David Kleinschmidt, Exhibit—20, Filed on 12/2/2022—Cited in IPR2022-00253, challenging U.S. Pat. No. 9,491,542.

Notice of Deposition of David Kleinschmidt, Exhibit—20, Filed on Dec. 2, 2022—Cited in IPR2022-00281, challenging U.S. Pat. No. 9,270,244.

Notice of Deposition of Les E. Atlas, Ph.D., Exhibit—13, Filed on Mar. 9, 2023—Cited in IPR2022-01106, challenging U.S. Pat. No. 11,039,259.

Notice of Deposition of Les E. Atlas, Ph.D., Exhibit—17, Filed on Aug. 8, 2022—Cited in IPR2022-00324, challenging U.S. Pat. No. 8,254,591.

Notice of Deposition of Les E. Atlas, Ph. D., Exhibit—19, Filed on Aug. 4, 2022—Cited in IPR2022-00243, challenging U.S. Pat. No. 8,111,839.

Notice of Deposition of Les E. Atlas, Ph.D., Exhibit—20, Filed on Aug. 4, 2022—Cited in IPR2022-00242, challenging U.S. Pat. No. 8,111,839.

(56) References Cited

OTHER PUBLICATIONS

Notice of Deposition of Les E. Atlas, Ph.D.; Exhibit..19, Filed on Aug. 4, 2022—Cited in IPR2022-00234, challenging U.S. Pat. No. 9,124,982.
Notice of Deposition of Marshall Buck, Exhibit—19, Filed on Dec. 16, 2022—Cited in IPR2022-00388, challenging U.S. Pat. No. 10,966,015.
Notice of Deposition of Marshall Buck, Exhibit—20, Filed on Dec. 16, 2022—Cited in IPR2022-00369, challenging U.S. Pat. No. 10,405,082.
Notice of Deposition of Nathaniel Polish, Ph.D., Exhibit—18, Filed on Sep. 13, 2022—Cited in IPR2022-00253, challenging U.S. Pat. No. 9,491,542.
Notice of Deposition of Nathaniel Polish, Ph.D., Exhibit—18, Filed on Sep. 13, 2022—Cited in IPR2022-00281, challenging U.S. Pat. No. 9,270,244.
Notice of Deposition of Richard M. Stern, Ph.D., Exhibit—13, Filed on Feb. 28, 2023—Cited in IPR2022-01078, challenging U.S. Pat. No. 11,057,701.
Notice of Deposition of Richard M. Stern, Ph.D., Exhibit—14, Filed on Aug. 5, 2022—Cited in IPR2022-00282, challenging U.S. Pat. No. 8,315,400.
Notice of Deposition of Richard M. Stern, Ph.D., Exhibit—17, Filed on Oct. 14, 2022—Cited in IPR2022-00388, challenging U.S. Pat. No. 10,966,015.
Notice of Deposition of Richard M. Stern, Ph.D., Exhibit—18, Filed on Oct. 14, 2022—Cited in IPR2022-00369, challenging U.S. Pat. No. 10,405,082.
Notice of Filing Date Accorded to Petition, Exhibit—5, Filed on Dec. 23, 2021—Cited in IPR2022-00242, challenging U.S. Pat. No. 8,111,839.
Notice of Filing Date Accorded to Petition, Exhibit—5, Filed on Dec. 23, 2021—Cited in IPR2022-00243, challenging U.S. Pat. No. 8,111,839.
Notice of Ranking, Exhibit—4, Filed on Dec. 13, 2021—Cited in IPR2022-00242, challenging U.S. Pat. No. 8,111,839.
Notice of Ranking, Exhibit—4, Filed on Dec. 13, 2021—Cited in IPR2022-00243, challenging U.S. Pat. No. 8,111,839.
Notice of Ranking, Exhibit—4, Filed on Jun. 12, 2024—Cited in IPR2024-01003, challenging U.S. Pat. No. 9,191,083.
Notice of Ranking, Exhibit—4, Filed on Jun. 12, 2024—Cited in IPR2024-01004, challenging U.S. Pat. No. 9,614,943.
Notice Regarding Transcript of Markman Hearing, Exhibit—29, Filed on Oct. 19, 2023—Cited in IPR2022-01106, challenging U.S. Pat. No. 11,039,259.
Notice: Notice filing date accorded, Exhibit—5, Filed on Dec. 21, 2021—Cited in IPR2022-00282, challenging U.S. Pat. No. 8,315,400.
Notice: Notice filing date accorded, Exhibit—5, Filed on Feb. 27, 2024—Cited in IPR2024-00559, challenging U.S. Pat. No. 11,610,587.
Notice: Notice filing date accorded, Exhibit—5, Filed on Jun. 17, 2024—Cited in IPR2024-01003, challenging U.S. Pat. No. 9,191,083.
Notice: Notice filing date accorded, Exhibit—5, Filed on Jun. 18, 2024—Cited in IPR2024-01004, challenging U.S. Pat. No. 9,614,943.
Notice: Notice filing date accorded, Exhibit—6, Filed on Jan. 13, 2022—Cited in IPR2022-00302, challenging U.S. Pat. No. 9,609,424.
Notice: Notice filing date accorded, Exhibit—6, Filed on Jan. 13, 2022—Cited in IPR2022-00324, challenging U.S. Pat. No. 8,254,591.
Notice: Notice filing date accorded, Exhibit—6, Filed on Jan. 18, 2022—Cited in IPR2022-00253, challenging U.S. Pat. No. 9,491,542.
Notice: Notice filing date accorded, Exhibit—6, Filed on Jan. 18, 2022—Cited in IPR2022-00281, challenging U.S. Pat. No. 9,270,244.
Notice: Notice filing date accorded, Exhibit—6, Filed on Feb. 18, 2022—Cited in IPR2022-00410, challenging U.S. Pat. No. 10,979,836.
Notice: Notice filing date accorded, Exhibit—6, Filed on Jul. 7, 2022—Cited in IPR2022-01078, challenging U.S. Pat. No. 11,057,701.
Notice: Notice filing date accorded, Exhibit—6, Filed on Jul. 7, 2022—Cited in IPR2022-01099, challenging U.S. Pat. No. 11,244,666.
Notice: Notice filing date accorded, Exhibit—6, Filed on Jul. 8, 2022—Cited in IPR2022-01106, challenging U.S. Pat. No. 11,039,259.

Notice: Notice filing date accorded, Exhibit—7, Filed on Feb. 18, 2022—Cited in IPR2022-00388, challenging U.S. Pat. No. 10,966,015.
Notice: Notice filing date accorded, Exhibit—7, Filed on Jul. 7, 2022—Cited in IPR2022-01098, challenging U.S. Pat. No. 11,217,237.
Notice: Notice filing date accorded, Exhibit—8, Filed on Feb. 18, 2022—Cited in IPR2022-00369, challenging U.S. Pat. No. 10,405,082.
Notice: Notice filing date accorded, Exhibit—8, Filed on Jul. 24, 2024—Cited in IPR2024-01031, challenging U.S. Pat. No. 7,049,850.
Notice: Notice filing date accorded, Exhibit—9, Filed on Aug. 16, 2024—Cited in IPR2024-01034, challenging U.S. Pat. No. 9,279,263.
Notice: Notice filing date accorded; Exhibit—4, Filed on Dec. 21, 2021—Cited in IPR2022-00234, challenging U.S. Pat. No. 9,124,982.
Notice: Notice filing date accordedPaper4,Jun. 20, 2024—Cited in IPR2024-01033, challenging U.S. Pat. No. 8,434,966.
Notice: refund approved, Exhibit—13, Filed on Mar. 7, 2023—Cited in IPR2022-01099, challenging U.S. Pat. No. 11,244,666.
Notice: refund approved, Exhibit—14, Filed on Jan. 20, 2023—Cited in IPR2022-00410, challenging U.S. Pat. No. 10,979,836.
Notice: refund approved, Exhibit—14, Filed on Mar. 7, 2023—Cited in IPR2022-01098, challenging U.S. Pat. No. 11,217,237.
Notice: refund approved, Exhibit—18, Filed on Dec. 17, 2024—Cited in IPR2024-01003, challenging U.S. Pat. No. 9,191,083.
Notice: refund approved, Exhibit—18, Filed on Dec. 17, 2024—Cited in IPR2024-01004, challenging U.S. Pat. No. 9,614,943.
Notice: refund approved, Exhibit—18, Filed on Dec. 17, 2024—Cited in IPR2024-01031, challenging U.S. Pat. No. 7,049,850.
Notice: refund approved, Exhibit—19, Filed on Dec. 17, 2024—Cited in IPR2024-01034, challenging U.S. Pat. No. 9,279,263.
Notice: refund approvedPaper17, Dec. 17, 2024—Cited in IPR2024-01033, challenging U.S. Pat. No. 8,434,966.
Olwal 2005, Exhibit—1023, Filed on Dec. 21, 2021—Cited in IPR2022-00281, challenging U.S. Pat. No. 9,270,244.
Order Adopting Claim Construction Order, Exhibit—2015, Filed on Apr. 10, 2023—Cited in IPR2022-01106, challenging U.S. Pat. No. 11,039,259.
Order Clarifying Claim Construction Order, Exhibit—2014, Filed on Apr. 10, 2023—Cited in IPR2022-01106, challenging U.S. Pat. No. 11,039,259.
Order Conditionally Granting Patent Owner's Motion to Withdraw and Substitute Counsel 37 C.F.R. § 42.10, Exhibit—12, Filed on Sep. 9, 2024—Cited in IPR2024-01003, challenging U.S. Pat. No. 9,191,083.
Order Conditionally Granting Patent Owner's Motion to Withdraw and Substitute Counsel 37 C.F.R. § 42.10, Exhibit—12, Filed on Dec. 9, 2024—Cited in IPR2024-01004, challenging U.S. Pat. No. 9,614,943.
Order Conditionally Granting Patent Owner's Motion to Withdraw and Substitute Counsel 37 C.F.R. § 42.10, Exhibit—12, Filed on Dec. 9, 2024—Cited in IPR2024-01031, challenging U.S. Pat. No. 7,049,850.
Order Conditionally Granting Patent Owner's Motion to Withdraw and Substitute Counsel 37 C.F.R. § 42.10, Exhibit—13, Filed on Dec. 9, 2024—Cited in IPR2024-01034, challenging U.S. Pat. No. 9,279,263.
Order Conditionally Granting Patent Owner's Motion to Withdraw and Substitute Counsel 37 C.F.R. § 42.10Paper11, Dec. 9, 2024—Cited in IPR2024-01033, challenging U.S. Pat. No. 8,434,966.
Order Conditionally Granting Patent Owner's Motion to Withdraw and Substitute Counsel, Exhibit—13, Filed on Dec. 5, 2024—Cited in IPR2024-00559, challenging U.S. Pat. No. 11,610,587.
Order Granting Patent Owner's Motions for Pro Hac Vice Admission of Roy Falik 37 C.F.R. § 42.10(c), Exhibit—9, Filed on Sep. 23, 2024—Cited in IPR2024-01031, challenging U.S. Pat. No. 7,049,850.
Order Trial Hearing 37 C.F.R. 42.70, Exhibit—23, Filed on Feb. 6, 2023—Cited in IPR2022-00282, challenging U.S. Pat. No. 8,315,400.
Order Trial Hearing 37 C.F.R. 42.70; Exhibit—24, Filed on Feb. 6, 2023—Cited in IPR2022-00234, challenging U.S. Pat. No. 9124982.
Order Trial Hearing 37 C.F.R. § 42.70, Exhibit—24, Filed on Mar. 1, 2023—Cited in IPR2022-00302, challenging U.S. Pat. No. 9,609,424.
Order Trial Hearing 37 C.F.R. § 42.70, Exhibit—26, Filed on Oct. 10, 2023—Cited in IPR2022-01106, challenging U.S. Pat. No. 11,039,259.

(56)          References Cited

OTHER PUBLICATIONS

Order Trial Hearing 37 C.F.R. § 42.70, Exhibit—26, Filed on Mar. 1, 2023—Cited in IPR2022-00324, challenging U.S. Pat. No. 8,254,591.
Order Trial Hearing 37 C.F.R. sec 42.70, Exhibit—28, Filed on Feb. 8, 2023—Cited in IPR2022-00243, challenging U.S. Pat. No. 8,111,839.
Order Trial Hearing 37 C.F.R. sec 42.70, Exhibit—29, Filed on Feb. 8, 2023—Cited in IPR2022-00242, challenging U.S. Pat. No. 8,111,839.
Order Trial Hearing, Exhibit—25, Filed on Mar. 1, 2023—Cited in IPR2022-00281, challenging U.S. Pat. No. 9,270,244.
Order Vacating Standing Orders, Exhibit—2005, Filed on Jul. 1, 2022—Cited in IPR2022-00253, challenging U.S. Pat. No. 9,491,542.
Order Vacating Standing Orders, Exhibit—2005, Filed on Jul. 1, 2022—Cited in IPR2022-00281, challenging U.S. Pat. No. 9,270,244.
Order Vacating Standing Orders, Exhibit—2005, Filed on Jul. 1, 2022—Cited in IPR2022-00302, challenging U.S. Pat. No. 9,609,424.
Order Vacating Standing Orders, Exhibit—2005, Filed on Jul. 1, 2022—Cited in IPR2022-00324, challenging U.S. Pat. No. 8,254,591.
Order Vacating Standing Orders, Exhibit—2006, Filed on Jul. 1, 2022—Cited in IPR2022-00369, challenging U.S. Pat. No. 10,405,082.
Order Vacating Standing Orders, Exhibit—2006, Filed on Jul. 1, 2022—Cited in IPR2022-00410, challenging U.S. Pat. No. 10,979,836.
Order Vacating Standing Orders, Exhibit—2007, Filed on Jul. 1, 2022—Cited in IPR2022-00388, challenging U.S. Pat. No. 10,966,015.
Order: Conduct of the Proceeding 37 C.F.R. sec. 42.5, Exhibit—18, Filed on Jan. 5, 2023—Cited in IPR2022-00282, challenging U.S. Pat. No. 8,315,400.
Order: Granting Patent Owner's Motion for Pro Hac Vice Admission of Roy Falik 37 C.F.R. § 42.10, Exhibit—10, Filed on Oct. 4, 2024—Cited in IPR2024-01034, challenging U.S. Pat. No. 9,279,263.
Order: Granting Patent Owner's Motions for Admission Pro Hac Vice of Roy Falik 37 C.F.R. § 42.10, Exhibit—9, Filed on Oct. 4, 2024—Cited in IPR2024-01004, challenging U.S. Pat. No. 9,614,943.
Order: Granting Patent Owner's Motions for Admission Pro Hac Vice of Roy Falik 37 C.F.R. § 42.10Paper8, Oct. 4, 2024—Cited in IPR2024-01033, challenging U.S. Pat. No. 8,434,966.
Order: on Motion, Exhibit—9, Filed on Oct. 4, 2024—Cited in IPR2024-01003, challenging U.S. Pat. No. 9,191,083.
Order: Order Setting Oral Argument 37 C.F.R. § 42.70, Exhibit—22, Filed on Aug. 21, 2023—Cited in IPR2022-01078, challenging U.S. Pat. No. 11,057,701.
Order: Other, Exhibit—12, Filed on Feb. 22, 2023—Cited in IPR2022-01078, challenging U.S. Pat. No. 11,057,701.
Order: Panel Change Order, Exhibit—22, Filed on Feb. 10, 2023—Cited in IPR2022-00253, challenging U.S. Pat. No. 9,491,542.
Order: Scheduling Order, Exhibit—13, Filed on Jun. 17, 2022—Cited in IPR2022-00282, challenging U.S. Pat. No. 8,315,400.
Order: Scheduling Order; Exhibit—13, Filed on Jun. 17, 2022—Cited in IPR2022-00234, challenging U.S. Pat. No. 9,124,982.
Order: Trial Hearing (Revised), Exhibit—27, Filed on Mar. 3, 2023—Cited in IPR2022-00324, challenging U.S. Pat. No. 8,254,591.
Order: Trial Hearing—37 CFR 42.70, Exhibit—26, Filed on Mar. 2, 2023—Cited in IPR2022-00253, challenging U.S. Pat. No. 9,491,542.
Order: Hearing Order, Exhibit—26, Filed on Apr. 7, 2023—Cited in IPR2022-00388, challenging U.S. Pat. No. 10,966,015.
Order: Hearing Order, Exhibit—27, Filed on Apr. 7, 2023—Cited in IPR2022-00369, challenging U.S. Pat. No. 10,405,082.
Order: Trial Hearing (Revised), Exhibit—25, Filed on Mar. 3, 2023—Cited in IPR2022-00302, challenging U.S. Pat. No. 9,609,424.
OSHA, Appx A to 1910.95—Noise Exposure Computation, Exhibit—2014, Filed on Sep. 13, 2022—Cited in IPR2022-00242, challenging U.S. Pat. No. 8,111,839.
OSHA, Appx A to 1910.95 - Noise Exposure Computation; Exhibit—2013, Filed on Sep. 9, 2022—Cited in IPR2022-00234, challenging U.S. Pat. No. 9,124,982.
Oshana, Chapters 3-4, Exhibit—1017, Filed on Jan. 14, 2022—Cited in IPR2022-00410, challenging U.S. Pat. No. 10,979,836.
Other: Hearing transcript, Exhibit—25, Filed on Oct. 16, 2023—Cited in IPR2022-01078, challenging U.S. Pat. No. 11,057,701.
Other: Hearing transcript, Exhibit—27, Filed on Apr. 18, 2023—Cited in IPR2022-00282, challenging U.S. Pat. No. 8,315,400.

Other: Hearing transcript, Exhibit—30, Filed on Jul. 25, 2023—Cited in IPR2022-00388, challenging U.S. Pat. No. 10,966,015.
Other: Hearing transcript, Exhibit—31, Filed on Dec. 13, 2023—Cited in IPR2022-01106, challenging U.S. Pat. No. 11,039,259.
Other: Hearing transcript, Exhibit—31, Filed on Jul. 25, 2023—Cited in IPR2022-00369, challenging U.S. Pat. No. 10,405,082.
Other: Hearing transcript, Exhibit—32, Filed on Jul. 3, 2023—Cited in IPR2022-00324, challenging U.S. Pat. No. 8,254,591.
Other: Hearing transcript, Exhibit—32, Filed on Jul. 31, 2023—Cited in IPR2022-00281, challenging U.S. Pat. No. 9,270,244.
Other: Hearing transcript, Exhibit—32, Filed on Jul. 6, 2023—Cited in IPR2022-00253, challenging U.S. Pat. No. 9,491,542.
Other: Hearing transcript, Exhibit—34, Filed on Jun. 1, 2023—Cited in IPR2022-00243, challenging U.S. Pat. No. 8,111,839.
Other: Hearing transcript, Exhibit—34, Filed on Jun. 22, 2023—Cited in IPR2022-00302, challenging U.S. Pat. No. 9,609,424.
Other: Hearing transcript, Exhibit—35, Filed on Ju. 1, 2023—Cited in IPR2022-00242, challenging U.S. Pat. No. 8,111,839.
Other: Hearing transcript, Exhibit—36, Filed on Jul. 6, 2023—Cited in IPR2022-00302, challenging U.S. Pat. No. 9,609,424.
Other: Hearing transcript; Exhibit—28, Filed on Apr. 18, 2023—Cited in IPR2022-00234, challenging U.S. Pat. No. 9124982.
Other: Order Granting Motion for Leave to File Corrected Petition, Exhibit—10, Filed on Feb. 2, 2022—Cited in IPR2022-00243, challenging U.S. Pat. No. 8,111,839.
Other: Order Granting Motion for Leave to File Corrected Petition, Exhibit—11, Filed on Feb. 2, 2022—Cited in IPR2022-00242, challenging U.S. Pat. No. 8,111,839.
Other: Fed Circuit mandate, Exhibit—34, Filed on Jun. 27, 2024—Cited in IPR2022-01106, challenging U.S. Pat. No. 11,039,259.
Other: Fed Circuit mandate, Exhibit—36, Filed on Jun. 27, 2024—Cited in IPR2022-00324, challenging U.S. Pat. No. 8,254,591.
Oxford Dictionary of Elecs and Electrical Eng (excerpts), Exhibit—2005, Filed on Mar. 21, 2022—Cited in IPR2022-00282, challenging U.S. Pat. No. 8,315,400.
P.R. 4-5(d) Joint Claim Construction Chart, Exhibit—2009, Filed on Feb. 22, 2023—Cited in IPR2022-00253, challenging U.S. Pat. No. 9,491,542.
P.R. 4-5(d) Joint Claim Construction Chart, Exhibit—2009, Filed on Feb. 22, 2023—Cited in IPR2022-00281, challenging U.S. Pat. No. 9,270,244.
Panel Change Order, Exhibit—12, Filed on Feb. 3, 2023—Cited in IPR2022-01106, challenging U.S. Pat. No. 11,039,259.
Patent Owner Brief Regarding Interim Procedure for Discretionary Denials, Exhibit—12, Filed on Jul. 1, 2022—Cited in IPR2022-00253, challenging U.S. Pat. No. 9,491,542.
Patent Owner Response; Exhibit—17, Filed on Sep. 9, 2022—Cited in IPR2022-00234, challenging U.S. Pat. No. 9,124,982.
Patent Owner Stanton Techiya LLC's Mandatory NoticePaper6,Jul. 3, 2024—Cited in IPR2024-01033, challenging U.S. Pat. No. 8,434,966.
Patent Owner Staton Techiya, LLC's Mandatory Notice, Exhibit—7, Filed on Jul. 3, 2024—Cited in IPR2024-01004, challenging U.S. Pat. No. 9,614,943.
Patent Owner Staton Techiya, LLC's Mandatory Notices, Exhibit—7, Filed on Jul. 3, 2024—Cited in IPR2024-01003, challenging U.S. Pat. No. 9,191,083.
Patent Owner Staton Techiya, LLC's Motion for the Pro Hac Vice Admission of Roy Falik, Exhibit—8, Filed on Jul. 5, 2024—Cited in IPR2024-01003, challenging U.S. Pat. No. 9,191,083.
Patent Owner Staton Techiya, LLC's Motion for the Pro Hac Vice Admission of Roy Falik, Exhibit—8, Filed on Jul. 5, 2024—Cited in IPR2024-01004, challenging U.S. Pat. No. 9,614,943.
Patent Owner Staton Techiya, LLC's Motion for the Pro Hac Vice Admission of Roy FalikPaper7,Jul. 5, 2024—Cited in IPR2024-01033, challenging U.S. Pat. No. 8,434,966.
Patent Owner Staton Techiya, LLC's Power of Attorney, Exhibit—6, Filed on Jul. 3, 2024—Cited in IPR2024-01003, challenging U.S. Pat. No. 9,191,083.
Patent Owner Staton Techiya, LLC's Power of Attorney, Exhibit—6, Filed on Jul. 3, 2024—Cited in IPR2024-01004, challenging U.S. Pat. No. 9,614,943.
Patent Owner Staton Techiya, LLC's Power of AttorneyPaper5,Jul. 3, 2024—Cited in IPR2024-01033, challenging U.S. Pat. No. 8,434,966.

(56) References Cited

OTHER PUBLICATIONS

Patent Owner's Brief Regarding Interim Procedure for Discretionary Denials, Exhibit—11, Filed on Jul. 1, 2022—Cited in IPR2022-00410, challenging U.S. Pat. No. 10,979,836.

Patent Owner's Brief Regarding Interim Procedure for Discretionary Denials, Exhibit—12, Filed on Jul. 1, 2022—Cited in IPR2022-00281, challenging U.S. Pat. No. 9,270,244.

Patent Owner's Brief Regarding Interim Procedure for Discretionary Denials, Exhibit—12, Filed on Jul. 1, 2022—Cited in IPR2022-00302, challenging U.S. Pat. No. 9,609,424.

Patent Owner's Brief Regarding Interim Procedure for Discretionary Denials, Exhibit—12, Filed on Jul. 1, 2022—Cited in IPR2022-00324, challenging U.S. Pat. No. 8,254,591.

Patent Owner's Brief Regarding Interim Procedure for Discretionary Denials, Exhibit—12, Filed on Jul. 1, 2022—Cited in IPR2022-00388, challenging U.S. Pat. No. 10,966,015.

Patent Owner's Brief Regarding Interim Procedure for Discretionary Denials, Exhibit—13, Filed on Jul. 1, 2022—Cited in IPR2022-00369, challenging U.S. Pat. No. 10,405,082.

Patent Owner's Corrected Notice of Appeal, Exhibit—38, Filed on Aug. 15, 2023—Cited in IPR2022-00243, challenging U.S. Pat. No. 8,111,839.

Patent Owner's Demonstratives, Exhibit—2008, Filed on Apr. 11, 2023—Cited in IPR2022-00302, challenging U.S. Pat. No. 9,609,424.

Patent Owner's Demonstratives, Exhibit—2010, Filed on Apr. 12, 2023—Cited in IPR2022-00253, challenging U.S. Pat. No. 9,491,542.

Patent Owner's Demonstratives, Exhibit—2010, Filed on Apr. 13, 2023—Cited in IPR2022-00281, challenging U.S. Pat. No. 9,270,244.

Patent Owner's Demonstratives, Exhibit—2010, Filed on Apr. 4, 2023—Cited in IPR2022-00324, challenging U.S. Pat. No. 8,254,591.

Patent Owner's Demonstratives, Exhibit—2012, Filed on May 9, 2023—Cited in IPR2022-00369, challenging U.S. Pat. No. 10,405,082.

Patent Owner's Demonstratives, Exhibit—2012, Filed on May 9, 2023—Cited in IPR2022-00388, challenging U.S. Pat. No. 10,966,015.

Patent Owner's Demonstratives, Exhibit—2014, Filed on Mar. 14, 2023—Cited in IPR2022-00282, challenging U.S. Pat. No. 8,315,400.

Patent Owner's Demonstratives, Exhibit—2014, Filed on Sep. 25, 2023—Cited in IPR2022-01078, challenging U.S. Pat. No. 11,057,701.

Patent Owner's Demonstratives, Exhibit—2015, Filed on Mar. 16, 2023—Cited in IPR2022-00242, challenging U.S. Pat. No. 8,111,839.

Patent Owner's Demonstratives, Exhibit—2015, Filed on Mar. 16, 2023—Cited in IPR2022-00243, challenging U.S. Pat. No. 8,111,839.

Patent Owner's Demonstratives, Exhibit—2021, Filed on Oct. 11, 2023—Cited in IPR2022-01106, challenging U.S. Pat. No. 11,039,259.

Patent Owner's Demonstratives; Exhibit—2014, Filed on Mar. 14, 2023—Cited in IPR2022-00234, challenging U.S. Pat. No. 9,124,982.

Patent Owner's Mandatory Notice under 37 C.F.R. 42.8, Exhibit—5, Filed on Jan. 19, 2022—Cited in IPR2022-00388, challenging U.S. Pat. No. 10,966,015.

Patent Owner's Mandatory Notice under 37 C.F.R. 42.8, Exhibit—5, Filed on Jan. 19, 2022—Cited in IPR2022-00410, challenging U.S. Pat. No. 10,979,836.

Patent Owner's Mandatory Notice under 37 C.F.R. 42.8, Exhibit—5, Filed on Dec. 28, 2021—Cited in IPR2022-00253, challenging U.S. Pat. No. 9,491,542.

Patent Owner's Mandatory Notice under 37 C.F.R. 42.8, Exhibit—5, Filed on Dec. 28, 2021—Cited in IPR2022-00281, challenging U.S. Pat. No. 9,270,244.

Patent Owner's Mandatory Notice under 37 C.F.R. 42.8, Exhibit—5, Filed on Dec. 28, 2021—Cited in IPR2022-00302, challenging U.S. Pat. No. 9,609,424.

Patent Owner's Mandatory Notice under 37 C.F.R. 42.8, Exhibit—5, Filed on Dec. 28, 2021—Cited in IPR2022-00324, challenging U.S. Pat. No. 8,254,591.

Patent Owner's Mandatory Notice under 37 C.F.R. 42.8, Exhibit—5, Filed on Jun. 22, 2022—Cited in IPR2022-01078, challenging U.S. Pat. No. 11,057,701.

Patent Owner's Mandatory Notice under 37 C.F.R. 42.8, Exhibit—5, Filed on Jun. 22, 2022—Cited in IPR2022-01099, challenging U.S. Pat. No. 11,244,666.

Patent Owner's Mandatory Notice under 37 C.F.R. 42.8, Exhibit—5, Filed on Jun. 22, 2022—Cited in IPR2022-01106, challenging U.S. Pat. No. 11,039,259.

Patent Owner's Mandatory Notice under 37 C.F.R. 42.8, Exhibit—6, Filed on Jun. 22, 2022—Cited in IPR2022-01098, challenging U.S. Pat. No. 11,217,237.

Patent Owner's Mandatory Notice under 37 C.F.R. 42.8, Exhibit—7, Filed on Dec. 28, 2021—Cited in IPR2022-00242, challenging U.S. Pat. No. 8,111,839.

Patent Owner's Mandatory Notice under 37 C.F.R. 42.8, Exhibit—7, Filed on Dec. 28, 2021—Cited in IPR2022-00243, challenging U.S. Pat. No. 8,111,839.

Patent Owner's Mandatory Notice under 37 C.F.R. 42.8, Exhibit—7, Filed on Dec. 28, 2021—Cited in IPR2022-00282, challenging U.S. Pat. No. 8,315,400.

Patent Owner's Mandatory Notice under 37 C.F.R. 42.8; Exhibit—6, Filed on Dec. 28, 2021—Cited in IPR2022-00234, challenging U.S. Pat. No. 9124982.

Patent Owner's Mandatory Notice under 37 CFR 42.8, Exhibit—6, Filed on Jan. 19, 2022—Cited in IPR2022-00369, challenging U.S. Pat. No. 10,405,082.

Patent Owner's Notice of Appeal, Exhibit—30, Filed on Aug. 11, 2023—Cited in IPR2022-00282, challenging U.S. Pat. No. 8,315,400.

Patent Owner's Notice of Appeal, Exhibit—33, Filed on Mar. 5, 2024—Cited in IPR2022-01106, challenging U.S. Pat. No. 11,039,259.

Patent Owner's Notice of Appeal, Exhibit—33, Filed on Sep. 8, 2023—Cited in IPR2022-00281, challenging U.S. Pat. No. 9,270,244.

Patent Owner's Notice of Appeal, Exhibit—34, Filed on Sep. 8, 2023—Cited in IPR2022-00253, challenging U.S. Pat. No. 9,491,542.

Patent Owner's Notice of Appeal, Exhibit—34, Filed on Sep. 8, 2023—Cited in IPR2022-00324, challenging U.S. Pat. No. 8,254,591.

Patent Owner's Notice of Appeal, Exhibit—38, Filed on Aug. 15, 2023—Cited in IPR2022-00242, challenging U.S. Pat. No. 8,111,839.

Patent Owner's Notice of Appeal; Exhibit—31, Filed on Aug. 11, 2023—Cited in IPR2022-00234, challenging U.S. Pat. No. 9,124,982.

Patent Owner's Notice of Cross-Appeal, Exhibit—39, Filed on Aug. 23, 2023—Cited in IPR2022-00302, challenging U.S. Pat. No. 9,609,424.

Patent Owner's Power of Attorney, Exhibit—4, Filed on Jan. 19, 2022—Cited in IPR2022-00388, challenging U.S. Pat. No. 10,966,015.

Patent Owner's Power of Attorney, Exhibit—4, Filed on Jan. 19, 2022—Cited in IPR2022-00410, challenging U.S. Pat. No. 10,979,836.

Patent Owner's Power of Attorney, Exhibit—4, Filed on Dec. 28, 2021—Cited in IPR2022-00253, challenging U.S. Pat. No. 9,491,542.

Patent Owner's Power of Attorney, Exhibit—4, Filed on Dec. 28, 2021—Cited in IPR2022-00281, challenging U.S. Pat. No. 9,270,244.

Patent Owner's Power of Attorney, Exhibit—4, Filed on Dec. 28, 2021—Cited in IPR2022-00302, challenging U.S. Pat. No. 9,609,424.

Patent Owner's Power of Attorney, Exhibit—4, Filed on Dec. 28, 2021—Cited in IPR2022-00324, challenging U.S. Pat. No. 8,254,591.

Patent Owner's Power of Attorney, Exhibit—4, Filed on Jun. 22, 2022—Cited in IPR2022-01078, challenging U.S. Pat. No. 11,057,701.

Patent Owner's Power of Attorney, Exhibit—4, Filed on Jun. 22, 2022—Cited in IPR2022-01099, challenging U.S. Pat. No. 11,244,666.

Patent Owner's Power of Attorney, Exhibit—4, Filed on Jun. 22, 2022—Cited in IPR2022-01106, challenging U.S. Pat. No. 11,039,259.

Patent Owner's Power of Attorney, Exhibit—5, Filed on Jun. 19, 2022—Cited in IPR2022-00369, challenging U.S. Pat. No. 10,405,082.

Patent Owner's Power of Attorney, Exhibit—5, Filed on Jun. 22, 2022—Cited in IPR2022-01098, challenging U.S. Pat. No. 11,217,237.

Patent Owner's Power of Attorney, Exhibit—6, Filed on Dec. 28, 2021—Cited in IPR2022-00242, challenging U.S. Pat. No. 8,111,839.

Patent Owner's Power of Attorney, Exhibit—6, Filed on Dec. 28, 2021—Cited in IPR2022-00243, challenging U.S. Pat. No. 8,111,839.

Patent Owner's Power of Attorney, Exhibit—6, Filed on Dec. 28, 2021—Cited in IPR2022-00282, challenging U.S. Pat. No. 8,315,400.

Patent Owner's Power of Attorney; Exhibit—5, Filed on Dec. 28, 2021—Cited in IPR2022-00234, challenging U.S. Pat. No. 9,124,982.

Patent Owner's Preliminary Response, Exhibit—12, Filed on Mar. 23, 2022—Cited in IPR2022-00243, challenging U.S. Pat. No. 8,111,839.

(56) References Cited

OTHER PUBLICATIONS

Patent Owner's Preliminary Response, Exhibit—13, Filed on Mar. 23, 2022—Cited in IPR2022-00242, challenging U.S. Pat. No. 8,111,839.

Patent Owner's Preliminary Response, Exhibit—7, Filed on Oct. 11, 2022—Cited in IPR2022-01106, challenging U.S. Pat. No. 11,039,259.

Patent Owner's Preliminary Response, Exhibit—7, Filed on Oct. 7, 2022—Cited in IPR2022-01078, challenging U.S. Pat. No. 11,057,701.

Patent Owner's Preliminary Response, Exhibit—7, Filed on Oct. 7, 2022—Cited in IPR2022-01099, challenging U.S. Pat. No. 11,244,666.

Patent Owner's Preliminary Response, Exhibit—7, Filed on May 18, 2022—Cited in IPR2022-00410, challenging U.S. Pat. No. 10,979,836.

Patent Owner's Preliminary Response, Exhibit—8, Filed on Oct. 7, 2022—Cited in IPR2022-01098, challenging U.S. Pat. No. 11,217,237.

Patent Owner's Preliminary Response, Exhibit—8, Filed on Apr. 13, 2022—Cited in IPR2022-00302, challenging U.S. Pat. No. 9,609,424.

Patent Owner's Preliminary Response, Exhibit—8, Filed on Apr. 13, 2022—Cited in IPR2022-00324, challenging U.S. Pat. No. 8,254,591.

Patent Owner's Preliminary Response, Exhibit—8, Filed on Apr. 18, 2022—Cited in IPR2022-00253, challenging U.S. Pat. No. 9,491,542.

Patent Owner's Preliminary Response, Exhibit—8, Filed on Apr. 18, 2022—Cited in IPR2022-00281, challenging U.S. Pat. No. 9,270,244.

Patent Owner's Preliminary Response, Exhibit—8, Filed on May 18, 2022—Cited in IPR2022-00388, challenging U.S. Pat. No. 10,966,015.

Patent Owner's Preliminary Response, Exhibit—9, Filed on Mar. 21, 2022—Cited in IPR2022-00282, challenging U.S. Pat. No. 8,315,400.

Patent Owner's Preliminary Response, Exhibit—9, Filed on May 18, 2022—Cited in IPR2022-00369, challenging U.S. Pat. No. 10,405,082.

Patent Owner's Preliminary Response; Exhibit—9, Filed on Mar. 21, 2022—Cited in IPR2022-00234, challenging U.S. Pat. No. 9,124,982.

Patent Owner's Preliminary Sur-Reply, Exhibit—10, Filed on Nov. 22, 2022—Cited in IPR2022-01098, challenging U.S. Pat. No. 11,217,237.

Patent Owner's Preliminary Sur-Reply, Exhibit—10, Filed on May 19, 2022—Cited in IPR2022-00302, challenging U.S. Pat. No. 9,609,424.

Patent Owner's Preliminary Sur-Reply, Exhibit—10, Filed on May 20, 2022—Cited in IPR2022-00324, challenging U.S. Pat. No. 8,254,591.

Patent Owner's Preliminary Sur-Reply, Exhibit—10, Filed on May 31, 2022—Cited in IPR2022-00253, challenging U.S. Pat. No. 9,491,542.

Patent Owner's Preliminary Sur-Reply, Exhibit—10, Filed on Jun. 23, 2022—Cited in IPR2022-00388, challenging U.S. Pat. No. 10,966,015.

Patent Owner's Preliminary Sur-Reply, Exhibit—10, Filed on Jun. 7, 2022—Cited in IPR2022-00281, challenging U.S. Pat. No. 9,270,244.

Patent Owner's Preliminary Sur-Reply, Exhibit—11, Filed on Apr. 29, 2022—Cited in IPR2022-00282, challenging U.S. Pat. No. 8,315,400.

Patent Owner's Preliminary Sur-Reply, Exhibit—11, Filed on Jun. 23, 2022—Cited in IPR2022-00369, challenging U.S. Pat. No. 10,405,082.

Patent Owner's Preliminary Sur-Reply, Exhibit—14, Filed on Apr. 29, 2022—Cited in IPR2022-00243, challenging U.S. Pat. No. 8,111,839.

Patent Owner's Preliminary Sur-Reply, Exhibit—15, Filed on Apr. 29, 2022—Cited in IPR2022-00242, challenging U.S. Pat. No. 8,111,839.

Patent Owner's Preliminary Sur-Reply, Exhibit—9, Filed on Nov. 17, 2022—Cited in IPR2022-01099, challenging U.S. Pat. No. 11,244,666.

Patent Owner's Preliminary Sur-Reply, Exhibit—9, Filed on Nov. 18, 2022—Cited in IPR2022-01078, challenging U.S. Pat. No. 11,057,701.

Patent Owner's Preliminary Sur-Reply, Exhibit—9, Filed on Nov. 18, 2022—Cited in IPR2022-01106, challenging U.S. Pat. No. 11,039,259.

Patent Owner's Preliminary Sur-Reply, Exhibit—9, Filed on Jun. 23, 2022—Cited in IPR2022-00410, challenging U.S. Pat. No. 10,979,836.

Patent Owner's Preliminary Sur-Reply; Exhibit—11, Filed on Apr. 29, 2022—Cited in IPR2022-00234, challenging U.S. Pat. No. 9,124,982.

Patent Owner's Request for Oral Argument, Exhibit—21, Filed on Feb. 3, 2023—Cited in IPR2022-00282, challenging U.S. Pat. No. 8,315,400.

Patent Owner's Request for Oral Argument, Exhibit—21, Filed on Aug. 17, 2023—Cited in IPR2022-01078, challenging U.S. Pat. No. 11,057,701.

Patent Owner's Request for Oral Argument, Exhibit—22, Filed on Feb. 28, 2023—Cited in IPR2022-00302, challenging U.S. Pat. No. 9,609,424.

Patent Owner's Request for Oral Argument, Exhibit—3, Filed on Mar. 1, 2023—Cited in IPR2022-00281, challenging U.S. Pat. No. 9,270,244.

Patent Owner's Request for Oral Argument, Exhibit—24, Filed on Feb. 28, 2023—Cited in IPR2022-00324, challenging U.S. Pat. No. 8,254,591.

Patent Owner's Request for Oral Argument, Exhibit—24, Filed on Mar. 1, 2023—Cited in IPR2022-00253, challenging U.S. Pat. No. 9,491,542.

Patent Owner's Request for Oral Argument, Exhibit—24, Filed on Apr. 4, 2023—Cited in IPR2022-00388, challenging U.S. Pat. No. 10,966,015.

Patent Owner's Request for Oral Argument, Exhibit—25, Filed on Apr. 4, 2023—Cited in IPR2022-00369, challenging U.S. Pat. No. 10,405,082.

Patent Owner's Request for Oral Argument, Exhibit—25, Filed on Aug. 28, 2023—Cited in IPR2022-01106, challenging U.S. Pat. No. 11,039,259.

Patent Owner's Request for Oral Argument, Exhibit—26, Filed on Feb. 7, 2023—Cited in IPR2022-00243, challenging U.S. Pat. No. 8,111,839.

Patent Owner's Request for Oral Argument, Exhibit—27, Filed on Feb. 7, 2023—Cited in IPR2022-00242, challenging U.S. Pat. No. 8,111,839.

Patent Owner's Request for Oral Argument; Exhibit—22, Filed on Feb. 3, 2023—Cited in IPR2022-00234, challenging U.S. Pat. No. 9124982.

Patent Owner's Response, Exhibit—14, Filed on Mar. 23, 2023—Cited in IPR2022-01078, challenging U.S. Pat. No. 11,057,701.

Patent Owner's Response, Exhibit—15, Filed on Sep. 9, 2022—Cited in IPR2022-00282, challenging U.S. Pat. No. 8,315,400.

Patent Owner's Response, Exhibit—16, Filed on Dec. 6, 2024—Cited in IPR2024-00559, challenging U.S. Pat. No. 11,610,587.

Patent Owner's Response, Exhibit—17, Filed on Apr. 10, 2023—Cited in IPR2022-01106, challenging U.S. Pat. No. 11,039,259.

Patent Owner's Response, Exhibit—18, Filed on Oct. 17, 2022—Cited in IPR2022-00302, challenging U.S. Pat. No. 9,609,424.

Patent Owner's Response, Exhibit—18, Filed on Nov. 8, 2022—Cited in IPR2022-00388, challenging U.S. Pat. No. 10,966,015.

Patent Owner's Response, Exhibit—19, Filed on Oct. 19, 2022—Cited in IPR2022-00253, challenging U.S. Pat. No. 9,491,542.

Patent Owner's Response, Exhibit—19, Filed on Oct. 19, 2022—Cited in IPR2022-00281, challenging U.S. Pat. No. 9,270,244.

Patent Owner's Response, Exhibit—19, Filed on Nov. 8, 2022—Cited in IPR2022-00369, challenging U.S. Pat. No. 10,405,082.

Patent Owner's Response, Exhibit—20, Filed on Oct. 17, 2022—Cited in IPR2022-00324, challenging U.S. Pat. No. 8,254,591.

Patent Owner's Response, Exhibit—21, Filed on Sep. 13, 2022—Cited in IPR2022-00243, challenging U.S. Pat. No. 8,111,839.

(56)                    References Cited

OTHER PUBLICATIONS

Patent Owner's Response, Exhibit—22, Filed on Sep. 13, 2022—Cited in IPR2022-00242, challenging U.S. Pat. No. 8,111,839.

Patent Owner's Sur-Reply, Exhibit—19, Filed on Jan. 12, 2023—Cited in IPR2022-00282, challenging U.S. Pat. No. 8,315,400.

Patent Owner's Sur-Reply, Exhibit—19, Filed on Jul. 26, 2023—Cited in IPR2022-01078, challenging U.S. Pat. No. 11,057,701.

Patent Owner's Sur-Reply, Exhibit—21, Filed on Feb. 21, 2023—Cited in IPR2022-00302, challenging U.S. Pat. No. 9,609,424.

Patent Owner's Sur-Reply, Exhibit—22, Filed on Feb. 22, 2023—Cited in IPR2022-00281, challenging U.S. Pat. No. 9,270,244.

Patent Owner's Sur-Reply, Exhibit—22, Filed on Mar. 13, 2023—Cited in IPR2022-00388, challenging U.S. Pat. No. 10,966,015.

Patent Owner's Sur-Reply, Exhibit—23, Filed on Feb. 20, 2023—Cited in IPR2022-00324, challenging U.S. Pat. No. 8,254,591.

Patent Owner's Sur-Reply, Exhibit—23, Filed on Feb. 22, 2023—Cited in IPR2022-00253, challenging U.S. Pat. No. 9,491,542.

Patent Owner's Sur-Reply, Exhibit—23, Filed on Mar. 13, 2023—Cited in IPR2022-00369, challenging U.S. Pat. No. 10,405,082.

Patent Owner's Sur-Reply, Exhibit—23, Filed on Aug. 14, 2023—Cited in IPR2022-01106, challenging U.S. Pat. No. 11,039,259.

Patent Owner's Sur-Reply, Exhibit—25, Filed on Jan. 17, 2023—Cited in IPR2022-00243, challenging U.S. Pat. No. 8,111,839.

Patent Owner's Sur-Reply, Exhibit—26, Filed on Jan. 12, 2023—Cited in IPR2022-00242, challenging U.S. Pat. No. 8,111,839.

Patent Owner's Sur-Reply; Exhibit—21, Filed on Jan. 13, 2023—Cited in IPR2022-00234, challenging U.S. Pat. No. 9,124,982.

Patent Owner's Unopposed Motion To Withdraw and Substitute Counsel Under 37 CFR 11.116, Exhibit—11, Filed on Nov. 13, 2024—Cited in IPR2024-00559, challenging U.S. Pat. No. 11,610,587.

Patent Owner's Unopposed Motion to Withdraw and Substitute Counsel Under 37 CFR 11.116, Exhibit—11, Filed on Nov. 21, 2024—Cited in IPR2024-01003, challenging U.S. Pat. No. 9,191,083.

Patent Owner's Unopposed Motion To Withdraw and Substitute Counsel Under 37 CFR 11.116, Exhibit—11, Filed on Nov. 21, 2024—Cited in IPR2024-01004, challenging U.S. Pat. No. 9,614,943.

Patent Owner's Unopposed Motion To Withdraw and Substitute Counsel Under 37 CFR 11.116, Exhibit—11, Filed on Nov. 21, 2024—Cited in IPR2024-01031, challenging U.S. Pat. No. 7,049,850.

Patent Owner's Unopposed Motion To Withdraw and Substitute Counsel Under 37 CFR 11.116, Exhibit—12, Filed on Nov. 21, 2024—Cited in IPR2024-01034, challenging U.S. Pat. No. 9,279,263.

Patent Owner's Unopposed Motion To Withdraw and Substitute Counsel Under 37 CFR 11.116Paper10, Nov. 21, 2024—Cited in IPR2024-01033, challenging U.S. Pat. No. 8,434,966.

Patent Owner's Updated Exhibit List, Exhibit—23, Filed on Sep. 25, 2023—Cited in IPR2022-01078, challenging U.S. Pat. No. 11,057,701.

Patent Owner's Updated Mandatory Notice under 37 C.F.R. 42.8, Exhibit—15, Filed on Jul. 27, 2022—Cited in IPR2022-00324, challenging U.S. Pat. No. 8,254,591.

Patent Owner's Updated Mandatory Notice under 37 C.F.R. 42.8, Exhibit—17, Filed on Jul. 27, 2022—Cited in IPR2022-00243, challenging U.S. Pat. No. 8,111,839.

Patent Owner's Updated Mandatory Notice under 37 C.F.R. 42.8, Exhibit—18, Filed on Jul. 27, 2022—Cited in IPR2022-00242, challenging U.S. Pat. No. 8,111,839.

Patent Owner's Updated Mandatory Notice under 37 C.F.R. 42.8, Exhibit—8, Filed on Dec. 28, 2021—Cited in IPR2022-00242, challenging U.S. Pat. No. 8,111,839.

Patent Owner's Updated Mandatory Notice under 37 C.F.R. 42.8; Exhibit—14, Filed on Jul. 27, 2022—Cited in IPR2022-00234, challenging U.S. Pat. No. 9,124,982.

Patent Owner's Updated Mandatory Notice under 37 C.F.R. 42.8; Exhibit—7, Filed on Dec. 28, 2021—Cited in IPR2022-00234, challenging U.S. Pat. No. 9,124,982.

Patent Owner's Updated Mandatory Notice, Exhibit—17, Filed on Sep. 13, 2022—Cited in IPR2022-00253, challenging U.S. Pat. No. 9,491,542.

Patent Owner's Updated Mandatory Notice, Exhibit—17, Filed on Sep. 13, 2022—Cited in IPR2022-00281, challenging U.S. Pat. No. 9,270,244.

Patent Owner's Updated Mandatory Notice, Exhibit—18, Filed on Jun. 28, 2023—Cited in IPR2022-01078, challenging U.S. Pat. No. 11,057,701.

Patent Owner's Updated Mandatory Notice, Exhibit—20, Filed on Jun. 28, 2023—Cited in IPR2022-01106, challenging U.S. Pat. No. 11,039,259.

Patent Owner's Updated Mandatory Notice, Exhibit—29, Filed on Jun. 28, 2023—Cited in IPR2022-00282, challenging U.S. Pat. No. 8,315,400.

Patent Owner's Updated Mandatory Notice, Exhibit—29, Filed on Jun. 28, 2023—Cited in IPR2022-00388, challenging U.S. Pat. No. 10,966,015.

Patent Owner's Updated Mandatory Notice, Exhibit—30, Filed on Jun. 28, 2023—Cited in IPR2022-00281, challenging U.S. Pat. No. 9,270,244.

Patent Owner's Updated Mandatory Notice, Exhibit—30, Filed on Jun. 28, 2023—Cited in IPR2022-00369, challenging U.S. Pat. No. 10,405,082.

Patent Owner's Updated Mandatory Notice, Exhibit—31, Filed on Jun. 28, 2023—Cited in IPR2022-00253, challenging U.S. Pat. No. 9,491,542.

Patent Owner's Updated Mandatory Notice, Exhibit—31, Filed on Jun. 28, 2023—Cited in IPR2022-00324, challenging U.S. Pat. No. 8,254,591.

Patent Owner's Updated Mandatory Notice, Exhibit—35, Filed on Jun. 28, 2023—Cited in IPR2022-00302, challenging U.S. Pat. No. 9,609,424.

Patent Owner's Updated Mandatory Notice, Exhibit—36, Filed on Jun. 28, 2023—Cited in IPR2022-00243, challenging U.S. Pat. No. 8,111,839.

Patent Owner's Updated Mandatory Notice, Exhibit—37, Filed on Jun. 28, 2023—Cited in IPR2022-00242, challenging U.S. Pat. No. 8,111,839.

Patent Owner's Updated Mandatory Notice; Exhibit—30, Filed on Jun. 28, 2023—Cited in IPR2022-00234, challenging U.S. Pat. No. 9,124,982.

Patent Owner's Updated Mandatory Notices, Exhibit—15, Filed on Dec. 6, 2024—Cited in IPR2024-00559, challenging U.S. Pat. No. 11,610,587.

Patent Owner's Updated Power of Attorney Pursuant to 37 CFR 41.10(b), Exhibit—14, Filed on Dec. 6, 2024—Cited in IPR2024-00559, challenging U.S. Pat. No. 11,610,587.

Petition : as filed for Inter Partes Review of U.S. Pat. No. 11,610,587, Exhibit—4, Filed on Feb. 9, 2024—Cited in IPR2024-00559, challenging U.S. Pat. No. 11,610,587.

Petition : as filed, Exhibit—3, Filed on Jun. 12, 2024—Cited in IPR2024-01003, challenging U.S. Pat. No. 9,191,083.

Petition : as filed, Exhibit—3, Filed on Jun. 12, 2024—Cited in IPR2024-01004, challenging U.S. Pat. No. 9,614,943.

Petition : as filed, Exhibit—4, Filed on Jun. 25, 2024—Cited in IPR2024-01031, challenging U.S. Pat. No. 7,049,850.

Petition : as filed, Exhibit—5, Filed on Jul. 1, 2024—Cited in IPR2024-01034, challenging U.S. Pat. No. 9,279,263.

Petition : as filedPaper3,Jun. 18, 2024—Cited in IPR2024-01033, challenging U.S. Pat. No. 8,434,966.

Petition for Inter Partes Review of U.S. Pat. No. 11,217,237, Exhibit—4, Filed on Jun. 9, 2022—Cited in IPR2022-01098, challenging U.S. Pat. No. 11,217,237.

Petition for Inter Partes Review of U.S. Pat. No. 11,244,666, Exhibit—3, Filed on Jun. 9, 2022—Cited in IPR2022-01099, challenging U.S. Pat. No. 11,244,666.

Petition for Inter Partes Review of U.S. Pat. No. 8,254,591, Exhibit—3, Filed on Dec. 20, 2021—Cited in IPR2022-00324, challenging U.S. Pat. No. 8,254,591.

Petition for Inter Partes Review of U.S. Pat. No. 10,405,082, Exhibit—3, Filed on Dec. 30, 2021—Cited in IPR2022-00369, challenging U.S. Pat. No. 10,405,082.

Petition for Inter Partes Review of U.S. Pat. No. 10,966,015, Exhibit—3, Filed on Jan. 4, 2022—Cited in IPR2022-00388, challenging U.S. Pat. No. 10,966,015.

(56)                    References Cited

OTHER PUBLICATIONS

Petition for Inter Partes Review of U.S. Pat. No. 10,979,836, Exhibit—3, Filed on Jan. 14, 2022—Cited in IPR2022-00410, challenging U.S. Pat. No. 10,979,836.

Petition for Inter Partes Review of U.S. Pat. No. 11,039,259, Exhibit—3, Filed on Jun. 9, 2022—Cited in IPR2022-01106, challenging U.S. Pat. No. 11,039,259.

Petition for Inter Partes Review of U.S. Pat. No. 8,111,839, Exhibit—3, Filed on Dec. 13, 2021—Cited in IPR2022-00242, challenging U.S. Pat. No. 8,111,839.

Petition for Inter Partes Review of U.S. Pat. No. 8,111,839, Exhibit—3, Filed on Dec, 13, 2021—Cited in IPR2022-00243, challenging U.S. Pat. No. 8,111,839.

Petition for Inter Partes Review of U.S. Pat. No. 9,124,982; Exhibit—3, Filed on Dec, 13, 2021—Cited in IPR2022-00234, challenging U.S. Pat. No. 9,124,982.

Petition for Inter Partes Review of U.S. Pat. No. 9,270,244, Exhibit—3, Filed on Dec. 21, 2021—Cited in IPR2022-00281, challenging U.S. Pat. No. 9,270,244.

Petition for Inter Partes Review of U.S. Pat. No. 9,491,542, Exhibit—3, Filed on Dec. 17, 2021—Cited in IPR2022-00253, challenging U.S. Pat. No. 9,491,542.

Petition for Inter Partes Review of U.S. Pat. No. 9,609,424, Exhibit—3, Filed on Dec. 21, 2021—Cited in IPR2022-00302, challenging U.S. Pat. No. 9,609,424.

Petition of Inter Partes Review of U.S. Pat. No. 11,057,701, Exhibit—3, Filed on Jun. 9, 2022—Cited in IPR2022-01078, challenging U.S. Pat. No. 11,057,701.

Petition with Proposed Corrections in Redline, Exhibit—1042, Filed on Jan. 31, 2022—Cited in IPR2022-00242, challenging U.S. Pat. No. 8,111,839.

Petition with Proposed Corrections in Redline, Exhibit—1042, Filed on Jan. 31, 2022—Cited in IPR2022-00243, challenging U.S. Pat. No. 8,111,839.

Petitioner's Power of Attorney from Samsung Electronics Co., Ltd.; Exhibit—1, Filed on Dec. 13, 2021—Cited in IPR2022-00234, challenging U.S. Pat. No. 9,124,982.

Petitioner's Power of Attorney from Samsung Electronics, America, Inc.; Exhibit—2, Filed on Dec. 13, 2021—Cited in IPR2022-00234, challenging U.S. Pat. No. 9,124,982.

Petitioner's Updated Mandatory Notices, Exhibit—16, Filed on Oct. 13, 2022—Cited in IPR2022-00388, challenging U.S. Pat. No. 10,966,015.

Petitioner's Updated Mandatory Notices, Exhibit—17, Filed on Oct. 13, 2022—Cited in IPR2022-00369, challenging U.S. Pat. No. 10,405,082.

Petitioner's Updated Mandatory Notices; Exhibit—27, Filed on Apr. 3, 2023—Cited in IPR2022-00234, challenging U.S. Pat. No. 9,124,982.

Petitioners Supplemental Brief on Interim Fintiv Guidance, Exhibit—10, Filed on Jul. 1, 2022—Cited in IPR2022-00410, challenging U.S. Pat. No. 10,979,836.

Petitioners Supplemental Brief on Interim Fintiv Guidance, Exhibit—11, Filed on Jul. 1, 2022—Cited in IPR2022-00253, challenging U.S. Pat. No. 9,491,542.

Petitioners Supplemental Brief on Interim Fintiv Guidance, Exhibit—11, Filed on Jul. 1, 2022—Cited in IPR2022-00281, challenging U.S. Pat. No. 9,270,244.

Petitioners Supplemental Brief on Interim Fintiv Guidance, Exhibit—11, Filed on Jul. 1, 2022—Cited in IPR2022-00302, challenging U.S. Pat. No. 9,609,424.

Petitioners Supplemental Brief on Interim Fintiv Guidance, Exhibit—11, Filed on Jul. 1, 2022—Cited in IPR2022-00324, challenging U.S. Pat. No. 8,254,591.

Petitioners Supplemental Brief on Interim Fintiv Guidance, Exhibit—11, Filed on Jul. 1, 2022—Cited in IPR2022-00388, challenging U.S. Pat. No. 10,966,015.

Petitioners Supplemental Brief on Interim Fintiv Guidance, Exhibit—12, Filed on Jul. 1, 2022—Cited in IPR2022-00369, challenging U.S. Pat. No. 10,405,082.

Petitioners' Demonstrative Exhibits for Oral Argument, Exhibit—1019, Filed on Mar. 14, 2023—Cited in IPR2022-00282, challenging U.S. Pat. No. 8,315,400.

Petitioners' Demonstrative Exhibits for Oral Argument; Exhibit—1045, Filed on Mar. 14, 2023—Cited in IPR2022-00234, challenging U.S. Pat. No. 9,124,982.

Petitioners' Motion for Leave to File Corrected Petition, Exhibit—9, Filed on Jan. 31, 2022—Cited in IPR2022-00243, challenging U.S. Pat. No. 8,111,839.

Petitioners' Motion to Submit Supplemental Information Pursuant to 37 C.F.R. §42.123(b), Exhibit—29, Filed on Apr. 13, 2023—Cited in IPR2022-00302, challenging U.S. Pat. No. 9,609,424.

Petitioners' Notice of Appeal, Exhibit—31, Filed on Aug. 11, 2023—Cited in IPR2022-00282, challenging U.S. Pat. No. 8,315,400.

Petitioners' Notice of Appeal, Exhibit—38, Filed on Aug. 11, 2023—Cited in IPR2022-00302, challenging U.S. Pat. No. 9,609,424.

Petitioners' Notice of Cross-Appeal, Exhibit—34, Filed on Sep. 20, 2023—Cited in IPR2022-00281, challenging U.S. Pat. No. 9,270,244.

Petitioners' Notice of Cross-Appeal, Exhibit—35, Filed on Sep. 20, 2023—Cited in IPR2022-00253, challenging U.S. Pat. No. 9,491,542.

Petitioners' Notice of Cross-Appeal, Exhibit—35, Filed on Sep. 20, 2023—Cited in IPR2022-00324, challenging U.S. Pat. No. 8,254,591.

Petitioners' Notice of Cross-Appeal, Exhibit—39, Filed on Aug. 24, 2023—Cited in IPR2022-00242, challenging U.S. Pat. No. 8,111,839.

Petitioners' Notice of Cross-Appeal; Exhibit—32, Filed on Aug. 24, 2023—Cited in IPR2022-00234, challenging U.S. Pat. No. 9,124,982.

Petitioners' Notice of Depo of Chrisotpher Struck, Exhibit —16, Filed on May 15, 2023—Cited in IPR2022-01078, challenging U.S. Pat. No. 11,057,701.

Petitioners' Notice of Deposition of Christopher Struck, Exhibit—19, Filed on Nov. 15, 2022—Cited in IPR2022-00302, challenging U.S. Pat. No. 9,609,424.

Petitioners' Notice of Deposition of Daniel P. Anagnos, Exhibit—23, Filed on Nov. 9, 2022—Cited in IPR2022-00243, challenging U.S. Pat. No. 8,111,839.

Petitioners' Notice of Deposition of Daniel P. Anagnos, Exhibit—24, Filed on Nov. 9, 2022—Cited in IPR2022-00242, challenging U.S. Pat. No. 8,111,839.

Petitioners' Notice of Deposition of Daniel P. Anagnos; Exhibit—19, Filed on Nov. 9, 2022—Cited in IPR2022-00234, challenging U.S. Pat. No. 9,124,982.

Petitioners' Notice of Deposition of David Kleinschmidt, Exhibit—19, Filed on May 24, 2023—Cited in IPR2022-01106, challenging U.S. Pat. No. 11,039,259.

Petitioners' Notice of Objections to Evidence, Exhibit—18, Filed on Apr. 19, 2023—Cited in IPR2022-01106, challenging U.S. Pat. No. 11,039,259.

Petitioners' Notice of Objections to Evidence, Exhibit—22, Filed on Sep. 20, 2022—Cited in IPR2022-00243, challenging U.S. Pat. No. 8,111,839.

Petitioners' Notice of Objections to Evidence, Exhibit—23, Filed on Sep. 20, 2022—Cited in IPR2022-00242, challenging U.S. Pat. No. 8,111,839.

Petitioners' Notice of Objections to Evidence; Exhibit—18, Filed on Sep. 16, 2022—Cited in IPR2022-00234, challenging U.S. Pat. No. 9,124,982.

Petitioners' Preliminary Reply, Exhibit—10, Filed on Apr. 20, 2022—Cited in IPR2022-00282, challenging U.S. Pat. No. 8,315,400.

Petitioners' Preliminary Reply, Exhibit—10, Filed on Jun. 14, 2022—Cited in IPR2022-00369, challenging U.S. Pat. No. 10,405,082.

Petitioners' Preliminary Reply, Exhibit—13, Filed on Apr. 20, 2022—Cited in IPR2022-00243, challenging U.S. Pat. No. 8,111,839.

Petitioners' Preliminary Reply, Exhibit—14, Filed on Apr. 20, 2022—Cited in IPR2022-00242, challenging U.S. Pat. No. 8,111,839.

Petitioners' Preliminary Reply, Exhibit—8, Filed on Nov. 10, 2022—Cited in IPR2022-01078, challenging U.S. Pat. No. 11,057,701.

Petitioners' Preliminary Reply, Exhibit—8, Filed on Nov. 10, 2022—Cited in IPR2022-01099, challenging U.S. Pat. No. 11,244,666.

Petitioners' Preliminary Reply, Exhibit—8, Filed on Nov. 10, 2022—Cited in IPR2022-01106, challenging U.S. Pat. No. 11,039,259.

Petitioners' Preliminary Reply, Exhibit—8, Filed on Jun. 14, 2022—Cited in IPR2022-00410, challenging U.S. Pat. No. 10,979,836.

(56)  References Cited

OTHER PUBLICATIONS

Petitioners' Preliminary Reply, Exhibit—9, Filed on Nov. 15, 2022—Cited in IPR2022-01098, challenging U.S. Pat. No. 11,217,237.

Petitioners' Preliminary Reply, Exhibit—9, Filed on May 10, 2022—Cited in IPR2022-00302, challenging U.S. Pat. No. 9,609,424.

Petitioners' Preliminary Reply, Exhibit—9, Filed on May 11, 2022—Cited in IPR2022-00324, challenging U.S. Pat. No. 8,254,591.

Petitioners' Preliminary Reply, Exhibit—9, Filed on May 20, 2022—Cited in IPR2022-00253, challenging U.S. Pat. No. 9,491,542.

Petitioners' Preliminary Reply, Exhibit—9, Filed on May 27, 2022—Cited in IPR2022-00281, challenging U.S. Pat. No. 9,270,244.

Petitioners' Preliminary Reply, Exhibit—9, Filed on Jun. 14, 2022—Cited in IPR2022-00388, challenging U.S. Pat. No. 10,966,015.

Petitioners' Preliminary Reply; Exhibit—10, Filed on Apr, 20, 2022—Cited in IPR2022-00234, challenging U.S. Pat. No. 9,124,982.

Petitioners' Reply to Patent Owner's Response, Exhibit—17, Filed on Dec. 2, 2022—Cited in IPR2022-00282, challenging U.S. Pat. No. 8,315,400.

Petitioners' Reply to Patent Owner's Response, Exhibit—17, Filed on Jun. 15, 2023—Cited in IPR2022-01078, challenging U.S. Pat. No. 11,057,701.

Petitioners' Reply to Patent Owner's Response, Exhibit—20, Filed on Jan. 10, 2023—Cited in IPR2022-00302, challenging U.S. Pat. No. 9,609,424.

Petitioners' Reply to Patent Owner's Response, Exhibit—20, Filed on Jan. 31, 2023—Cited in IPR2022-00388, challenging U.S. Pat. No. 10,966,015.

Petitioners' Reply to Patent Owner's Response, Exhibit—21, Filed on Jan. 11, 2023—Cited in IPR2022-00281, challenging U.S. Pat. No. 9,270,244.

Petitioners' Reply to Patent Owner's Response, Exhibit—21, Filed on Jan. 31, 2023—Cited in IPR2022-00369, challenging U.S. Pat. No. 10,405,082.

Petitioners' Reply to Patent Owner's Response, Exhibit—21, Filed on Jun. 30, 2023—Cited in IPR2022-01106, challenging U.S. Pat. No. 11,039,259.

Petitioners' Reply to Patent Owner's Response, Exhibit—22, Filed on Jan. 10, 2023—Cited in IPR2022-00324, challenging U.S. Pat. No. 8,254,591.

Petitioners' Reply to Patent Owner's Response, Exhibit—24, Filed on Dec. 6, 2022—Cited in IPR2022-00243, challenging U.S. Pat. No. 8,111,839.

Petitioners' Reply to Patent Owner's Response, Exhibit—25, Filed on Dec. 6, 2022—Cited in IPR2022-00242, challenging U.S. Pat. No. 8,111,839.

Petitioners' Reply to Patent Owner's Response; Exhibit—20, Filed on Dec. 2, 2022—Cited in IPR2022-00234, challenging U.S. Pat. No. 9,124,982.

Petitioners' Reply to Patent Owners Response, Exhibit—21, Filed on Jan. 11, 2023—Cited in IPR2022-00253, challenging U.S. Pat. No. 9,491,542.

Petitioners' Request for Oral Argument, Exhibit—20, Filed on Aug. 17, 2023—Cited in IPR2022-01078, challenging U.S. Pat. No. 11,057,701.

Petitioners' Request for Oral Argument, Exhibit—22, Filed on Feb. 3, 2023—Cited in IPR2022-00282, challenging U.S. Pat. No. 8,315,400.

Petitioners' Request for Oral Argument, Exhibit—23, Filed on Feb. 28, 2023—Cited in IPR2022-00302, challenging U.S. Pat. No. 9,609,424.

Petitioners' Request for Oral Argument, Exhibit—24, Filed on Mar. 1, 2023—Cited in IPR2022-00281, challenging U.S. Pat. No. 9,270,244.

Petitioners' Request for Oral Argument, Exhibit—24, Filed on Aug. 28, 2023—Cited in IPR2022-01106, challenging U.S. Pat. No. 11,039,259.

Petitioners' Request for Oral Argument, Exhibit—25, Filed on Feb. 28, 2023—Cited in IPR2022-00324, challenging U.S. Pat. No. 8,254,591.

Petitioners' Request for Oral Argument, Exhibit—25, Filed on Mar. 1, 2023—Cited in IPR2022-00253, challenging U.S. Pat. No. 9,491,542.

Petitioners' Request for Oral Argument, Exhibit—25, Filed on Apr. 4, 2023—Cited in IPR2022-00388, challenging U.S. Pat. No. 10,966,015.

Petitioners' Request for Oral Argument, Exhibit—26, Filed on Apr. 4, 2023—Cited in IPR2022-00369, challenging U.S. Pat. No. 10,405,082.

Petitioners' Request for Oral Argument, Exhibit—27, Filed on Feb. 7, 2023—Cited in IPR2022-00243, challenging U.S. Pat. No. 8,111,839.

Petitioners' Request for Oral Argument, Exhibit—28, Filed on Feb. 7, 2023—Cited in IPR2022-00242, challenging U.S. Pat. No. 8,111,839.

Petitioners' Request for Oral Argument; Exhibit—23, Filed on Feb. 3, 2023—Cited in IPR2022-00234, challenging U.S. Pat. No. 9,124,982.

Petitioners' Request for Refund of Post-Institution Fee, Exhibit—12, Filed on Mar. 2, 2023—Cited in IPR2022-01099, challenging U.S. Pat. No. 11,244,666.

Petitioners' Request for Refund of Post-Institution Fee, Exhibit—13, Filed on Jan. 18, 2023—Cited in IPR2022-00410, challenging U.S. Pat. No. 10,979,836.

Petitioners' Request for Refund of Post-Institution Fee, Exhibit—13, Filed on Mar. 2, 2023—Cited in IPR2022-01098, challenging U.S. Pat. No. 11,217,237.

Petitioners' Request for Refund of Post-Institution Fees, Exhibit—17, Filed on Dec. 16, 2024—Cited in IPR2024-01003, challenging U.S. Pat. No. 9,191,083.

Petitioners' Request for Refund of Post-Institution Fees, Exhibit—17, Filed on Dec. 16, 2024—Cited in IPR2024-01004, challenging U.S. Pat. No. 9,614,943.

Petitioners' Request for Refund of Post-Institution Fees, Exhibit—17, Filed on Dec. 16, 2024—Cited in IPR2024-01031, challenging U.S. Pat. No. 7,049,850.

Petitioners' Request for Refund of Post-Institution Fees, Exhibit—18, Filed on Dec. 16, 2024—Cited in IPR2024-01034, challenging U.S. Pat. No. 9,279,263.

Petitioners' Request for Refund of Post-Institution FeesPaper16, Dec. 16, 2024—Cited in IPR2024-01033, challenging U.S. Pat. No. 8,434,966.

Petitioners' Submission of Supplemental Information, Exhibit—33, Filed on May 15, 2023—Cited in IPR2022-00302, challenging U.S. Pat. No. 9,609,424.

Petitioners' Sur-Sur-Reply to Patent Owner's Sur-Reply, Exhibit—20, Filed on Jan. 27, 2023—Cited in IPR2022-00282, challenging U.S. Pat. No. 8,315,400.

Petitioners' Sur-Sur-Reply to Patent Owner's Sur-Reply, Exhibit—26, Filed on Mar. 7, 2023—Cited in IPR2022-00281, challenging U.S. Pat. No. 9,270,244.

Petitioners' Sur-Sur-Reply to Patent Owner's Sur-Reply, Exhibit—27, Filed on Mar. 7, 2023—Cited in IPR2022-00253, challenging U.S. Pat. No. 9,491,542.

Petitioners' Updated Exhibit List, Exhibit—10, Filed on Nov. 20, 2024—Cited in IPR2024-01003, challenging U.S. Pat. No. 9,191,083.

Petitioners' Updated Exhibit List, Exhibit—10, Filed on Nov. 20, 2024—Cited in IPR2024-01004, challenging U.S. Pat. No. 9,614,943.

Petitioners' Updated Exhibit List, Exhibit—10, Filed on Nov. 20, 2024—Cited in IPR2024-01031, challenging U.S. Pat. No. 7,049,850.

Petitioners' Updated Exhibit List, Exhibit—11, Filed on Nov. 20, 2024—Cited in IPR2024-01034, challenging U.S. Pat. No. 9,279,263.

Petitioners' Updated Exhibit List, Exhibit—15, Filed on Dec. 11, 2024—Cited in IPR2024-01003, challenging U.S. Pat. No. 9,191,083.

Petitioners' Updated Exhibit List, Exhibit—15, Filed on Dec. 11, 2024—Cited in IPR2024-01004, challenging U.S. Pat. No. 9,614,943.

Petitioners' Updated Exhibit List, Exhibit—15, Filed on Dec. 11, 2024—Cited in IPR2024-01031, challenging U.S. Pat. No. 7,049,850.

Petitioners' Updated Exhibit List, Exhibit—16, Filed on Dec. 11, 2024—Cited in IPR2024-01034, challenging U.S. Pat. No. 9,279,263.

Petitioners' Updated Exhibit List, Exhibit—19, Filed on Dec. 11, 2024—Cited in IPR2024-00559, challenging U.S. Pat. No. 11,610,587.

Petitioners' Updated Exhibit List, Exhibit—24, Filed on Mar. 14, 2023—Cited in IPR2022-00282, challenging U.S. Pat. No. 8,315,400.

Petitioners' Updated Exhibit List, Exhibit—24, Filed on Sep. 26, 2023—Cited in IPR2022-01078, challenging U.S. Pat. No. 11,057,701.

Petitioners' Updated Exhibit List, Exhibit—27, Filed on May 9, 2023—Cited in IPR2022-00388, challenging U.S. Pat. No. 10,966,015.

(56)                    References Cited

OTHER PUBLICATIONS

Petitioners' Updated Exhibit List, Exhibit—28, Filed on Oct. 11, 2023—Cited in IPR2022-01106, challenging U.S. Pat. No. 11,039,259.
Petitioners' Updated Exhibit List, Exhibit—28, Filed on Apr. 11, 2023—Cited in IPR2022-00302, challenging U.S. Pat. No. 9,609,424.
Petitioners' Updated Exhibit List, Exhibit—28, Filed on Apr. 13, 2023—Cited in IPR2022-00281, challenging U.S. Pat. No. 9,270,244.
Petitioners' Updated Exhibit List, Exhibit—28, Filed on May 9, 2023—Cited in IPR2022-00369, challenging U.S. Pat. No. 10,405,082.
Petitioners' Updated Exhibit List, Exhibit—30, Filed on Apr. 12, 2023—Cited in IPR2022-00253, challenging U.S. Pat. No. 9,491,542.
Petitioners' Updated Exhibit List, Exhibit—30, Filed on Apr. 13, 2023—Cited in IPR2022-00302, challenging U.S. Pat. No. 9,609,424.
Petitioners' Updated Exhibit List, Exhibit—30, Filed on Apr. 4, 2023—Cited in IPR2022-00324, challenging U.S. Pat. No. 8,254,591.
Petitioners' Updated Exhibit List, Exhibit—31, Filed on Mar. 16, 2023—Cited in IPR2022-00243, challenging U.S. Pat. No. 8,111,839.
Petitioners' Updated Exhibit List, Exhibit—31, Filed on Apr. 13, 2023—Cited in IPR2022-00302, challenging U.S. Pat. No. 9,609,424.
Petitioners' Updated Exhibit List, Exhibit—32, Filed on Mar. 16, 2023—Cited in IPR2022-00242, challenging U.S. Pat. No. 8,111,839.
Petitioners' Updated Exhibit List; Exhibit—25, Filed on Mar. 14, 2023—Cited in IPR2022-00234, challenging U.S. Pat. No. 9,124,982.
Petitioners' Updated Exhibit ListPaper14, Dec. 11, 2024—Cited in IPR2024-01033, challenging U.S. Pat. No. 8,434,966.
Petitioners' Updated Exhibit ListPaper9, Nov. 20, 2024—Cited in IPR2024-01033, challenging U.S. Pat. No. 8,434,966.
Petitioners' Updated Mandatory Notices, Exhibit—15, Filed on Apr. 3, 2023—Cited in IPR2022-01078, challenging U.S. Pat. No. 11,057,701.
Petitioners' Updated Mandatory Notices, Exhibit—16, Filed on Mar. 28, 2023—Cited in IPR2022-01106, challenging U.S. Pat. No. 11,039,259.
Petitioners' Updated Mandatory Notices, Exhibit—18, Filed on Aug. 10, 2022—Cited in IPR2022-00324, challenging U.S. Pat. No. 8,254,591.
Petitioners' Updated Mandatory Notices, Exhibit—20, Filed on Aug. 10, 2022—Cited in IPR2022-00243, challenging U.S. Pat. No. 8,111,839.
Petitioners' Updated Mandatory Notices, Exhibit—21, Filed on Feb. 8, 2023—Cited in IPR2022-00388, challenging U.S. Pat. No. 10,966,015.
Petitioners' Updated Mandatory Notices, Exhibit—21, Filed on Aug. 10, 2022—Cited in IPR2022-00242, challenging U.S. Pat. No. 8,111,839.
Petitioners' Updated Mandatory Notices, Exhibit—22, Filed on Feb. 8, 2023—Cited in IPR2022-00369, challenging U.S. Pat. No. 10,405,082.
Petitioners' Updated Mandatory Notices, Exhibit—23, Filed on Apr. 3, 2023—Cited in IPR2022-00388, challenging U.S. Pat. No. 10,966,015.
Petitioners' Updated Mandatory Notices, Exhibit—24, Filed on Apr. 3, 2023—Cited in IPR2022-00369, challenging U.S. Pat. No. 10,405,082.
Petitioners' Updated Mandatory Notices, Exhibit—26, Filed on Apr. 3, 2023—Cited in IPR2022-00282, challenging U.S. Pat. No. 8,315,400.
Petitioners' Updated Mandatory Notices, Exhibit—26, Filed on Apr. 3, 2023—Cited in IPR2022-00302, challenging U.S. Pat. No. 9,609,424.
Petitioners' Updated Mandatory Notices, Exhibit—27, Filed on Apr. 3, 2023—Cited in IPR2022-00281, challenging U.S. Pat. No. 9,270,244.
Petitioners' Updated Mandatory Notices, Exhibit—28, Filed on Apr. 3, 2023—Cited in IPR2022-00253, challenging U.S. Pat. No. 9,491,542.
Petitioners' Updated Mandatory Notices, Exhibit—28, Filed on Apr. 3, 2023—Cited in IPR2022-00324, challenging U.S. Pat. No. 8,254,591.
Petitioners' Updated Mandatory Notices, Exhibit—33, Filed on Apr. 3, 2023—Cited in IPR2022-00243, challenging U.S. Pat. No. 8,111,839.
Petitioners' Updated Mandatory Notices, Exhibit—34, Filed on Apr. 3, 2023—Cited in IPR2022-00242, challenging U.S. Pat. No. 8,111,839.
Petitioners' Updated Mandatory Notices, Exhibit—4, Filed on Jan. 6, 2022—Cited in IPR2022-00369, challenging U.S. Pat. No. 10,405,082.
Petitioners' Updated Mandatory Notices, Exhibit—6, Filed on Jan. 20, 2022—Cited in IPR2022-00388, challenging U.S. Pat. No. 10,966,015.
Petitioners' Updated Mandatory Notices, Exhibit—7, Filed on Jan. 20, 2022—Cited in IPR2022-00253, challenging U.S. Pat. No. 9,491,542.
Petitioners' Updated Mandatory Notices, Exhibit—7, Filed on Jan. 20, 2022—Cited in IPR2022-00281, challenging U.S. Pat. No. 9,270,244.
Petitioners' Updated Mandatory Notices, Exhibit—7, Filed on Jan. 20, 2022—Cited in IPR2022-00302, challenging U.S. Pat. No. 9,609,424.
Petitioners' Updated Mandatory Notices, Exhibit—7, Filed on Jan. 20, 2022—Cited in IPR2022-00324, challenging U.S. Pat. No. 8,254,591.
Petitioners' Updated Mandatory Notices, Exhibit—7, Filed on Jan. 20, 2022—Cited in IPR2022-00369, challenging U.S. Pat. No. 10,405,082.
Petitioners' Updated Mandatory Notices, Exhibit—8, Filed on Jan. 20, 2022—Cited in IPR2022-00243, challenging U.S. Pat. No. 8,111,839.
Petitioners' Updated Mandatory Notices, Exhibit—8, Filed on Jan. 20, 2022—Cited in IPR2022-00282, challenging U.S. Pat. No. 8,315,400.
Petitioners' Updated Mandatory Notices, Exhibit—9, Filed on Jan. 20, 2022—Cited in IPR2022-00242, challenging U.S. Pat. No. 8,111,839.
Petitioners' Updated Mandatory Notices; Exhibit—16, Filed on Aug. 10, 2022—Cited in IPR2022-00234, challenging U.S. Pat. No. 9124982.
Petitioners' Updated Mandatory Notices; Exhibit—8, Filed on Jan. 20, 2022—Cited in IPR2022-00234, challenging U.S. Pat. No. 9124982.
PO's Opposition to Motion to File Supplemental Information, Exhibit—32, Filed on Apr. 17, 2023—Cited in IPR2022-00302, challenging U.S. Pat. No. 9,609,424.
PO's Updated Exhibit List, Exhibit—25, Filed on Mar. 14, 2023—Cited in IPR2022-00282, challenging U.S. Pat. No. 8,315,400.
PO's Updated Exhibit List, Exhibit—27, Filed on Oct. 11, 2023—Cited in IPR2022-01106, challenging U.S. Pat. No. 11,039,259.
PO's Updated Exhibit List, Exhibit—27, Filed on Apr. 11, 2023—Cited in IPR2022-00302, challenging U.S. Pat. No. 9,609,424.
PO's Updated Exhibit List, Exhibit—28, Filed on May 9, 2023—Cited in IPR2022-00388, challenging U.S. Pat. No. 10,966,015.
PO's Updated Exhibit List, Exhibit—29, Filed on Apr. 12, 2023—Cited in IPR2022-00253, challenging U.S. Pat. No. 9,491,542.
PO's Updated Exhibit List, Exhibit—29, Filed on Apr. 13, 2023—Cited in IPR2022-00281, challenging U.S. Pat. No. 9,270,244.
PO's Updated Exhibit List, Exhibit—29, Filed on Apr. 4, 2023—Cited in IPR2022-00324, challenging U.S. Pat. No. 8,254,591.
PO's Updated Exhibit List, Exhibit—29, Filed on May 9, 2023—Cited in IPR2022-00369, challenging U.S. Pat. No. 10,405,082.
PO's Updated Exhibit List, Exhibit—30, Filed on Oct. 19, 2023—Cited in IPR2022-01106, challenging U.S. Pat. No. 11,039,259.
PO's Updated Exhibit List, Exhibit—32, Filed on Mar. 16, 2023—Cited in IPR2022-00243, challenging U.S. Pat. No. 8,111,839.
PO's Updated Exhibit List, Exhibit—33, Filed on Mar. 16, 2023—Cited in IPR2022-00242, challenging U.S. Pat. No. 8,111,839.
PO's Updated Exhibit List; Exhibit—26, Filed on Mar. 14, 2023—Cited in IPR2022-00234, challenging U.S. Pat. No. 9124982.
Power of Attorney for Samsung Electronics America, Inc., Exhibit—2, Filed on Dec. 30, 2021—Cited in IPR2022-00369, challenging U.S. Pat. No. 10,405,082.

(56)         References Cited

OTHER PUBLICATIONS

Power of Attorney for Samsung Electronics America, Inc., Exhibit—2, Filed on Jun. 9, 2022—Cited in IPR2022-01078, challenging U.S. Pat. No. 11,057,701.

Power of Attorney for Samsung Electronics America, Inc., Exhibit—2, Filed on Jun. 9, 2022—Cited in IPR2022-01098, challenging U.S. Pat. No. 11,217,237.

Power of Attorney for Samsung Electronics America, Inc., Exhibit—2, Filed on Jun. 9, 2022—Cited in IPR2022-01099, challenging U.S. Pat. No. 11,244,666.

Power of Attorney for Samsung Electronics America, Inc., Exhibit—2, Filed on Jun. 9, 2022—Cited in IPR2022-01106, challenging U.S. Pat. No. 11,039,259.

Power of Attorney for Samsung Electronics Co. Ltd., Exhibit—1, Filed on Jun. 9, 2022—Cited in IPR2022-01078, challenging U.S. Pat. No. 11,057,701.

Power of Attorney for Samsung Electronics Co., Ltd., Exhibit—1, Filed on Dec. 10, 2021—Cited in IPR2022-00282, challenging U.S. Pat. No. 8,315,400.

Power of Attorney for Samsung Electronics Co., Ltd., Exhibit—1, Filed on Dec. 30, 2021—Cited in IPR2022-00369, challenging U.S. Pat. No. 10,405,082.

Power of Attorney for Samsung Electronics Co., Ltd., Exhibit—1, Filed on Jun. 9, 2022—Cited in IPR2022-01098, challenging U.S. Pat. No. 11,217,237.

Power of Attorney for Samsung Electronics Co., Ltd., Exhibit—1, Filed on Jun. 9, 2022—Cited in IPR2022-01099, challenging U.S. Pat. No. 11,244,666.

Power of Attorney for Samsung Electronics Co., Ltd., Exhibit—1, Filed on Jun. 9, 2022—Cited in IPR2022-01106, challenging U.S. Pat. No. 11,039,259.

Power of Attorney for Samsung Electronics, America, Inc., Exhibit—2, Filed on Dec. 10, 2021—Cited in IPR2022-00282, challenging U.S. Pat. No. 8,315,400.

Power of Attorney from Samsung Electronics America, Inc., Exhibit—2, Filed on Jan. 14, 2022—Cited in IPR2022-00410, challenging U.S. Pat. No. 10,979,836.

Power of Attorney from Samsung Electronics America, Inc., Exhibit—2, Filed on Jan. 4, 2022—Cited in IPR2022-00388, challenging U.S. Pat. No. 10,966,015.

Power of Attorney from Samsung Electronics America, Inc., Exhibit—2, Filed on Dec. 13, 2021—Cited in IPR2022-00242, challenging U.S. Pat. No. 8,111,839.

Power of Attorney from Samsung Electronics America, Inc., Exhibit—2, Filed on Dec. 13, 2021—Cited in IPR2022-00243, challenging U.S. Pat. No. 8,111,839.

Power of Attorney from Samsung Electronics America, Inc., Exhibit—2, Filed on Dec. 17, 2021—Cited in IPR2022-00253, challenging U.S. Pat. No. 9,491,542.

Power of Attorney from Samsung Electronics America, Inc., Exhibit—2, Filed on Dec. 20, 2021—Cited in IPR2022-00324, challenging U.S. Pat. No. 8,254,591.

Power of Attorney from Samsung Electronics America, Inc., Exhibit—2, Filed on Dec. 21, 2021—Cited in IPR2022-00281, challenging U.S. Pat. No. 9,270,244.

Power of Attorney from Samsung Electronics America, Inc., Exhibit—2, Filed on Dec. 21, 2021—Cited in IPR2022-00302, challenging U.S. Pat. No. 9,609,424.

Power of Attorney from Samsung Electronics Co., Ltd., Exhibit—1, Filed on Jan. 14, 2022—Cited in IPR2022-00410, challenging U.S. Pat. No. 10,979,836.

Power of Attorney from Samsung Electronics Co., Ltd., Exhibit—1, Filed on Jan. 4, 2022—Cited in IPR2022-00388, challenging U.S. Pat. No. 10,966,015.

Power of Attorney from Samsung Electronics Co., Ltd., Exhibit—1, Filed on Dec. 13, 2021—Cited in IPR2022-00242, challenging U.S. Pat. No. 8,111,839.

Power of Attorney from Samsung Electronics Co., Ltd., Exhibit—1, Filed on dec. 13, 2021—Cited in IPR2022-00243, challenging U.S. Pat. No. 8,111,839.

Power of Attorney from Samsung Electronics Co., Ltd., Exhibit—1, Filed on Dec. 17, 2021—Cited in IPR2022-00253, challenging U.S. Pat. No. 9,491,542.

Power of Attorney from Samsung Electronics Co., Ltd., Exhibit—1, Filed on Dec. 20, 2021—Cited in IPR2022-00324, challenging U.S. Pat. No. 8,254,591.

Power of Attorney from Samsung Electronics Co., Ltd., Exhibit—1, Filed on Dec. 21, 2021—Cited in IPR2022-00281, challenging U.S. Pat. No. 9,270,244.

Power of Attorney from Samsung Electronics Co., Ltd., Exhibit—1, Filed on Dec. 21, 2021—Cited in IPR2022-00302, challenging U.S. Pat. No. 9,609,424.

PR 4-3 JCC Statement, Exhibit—2013, Filed on Jan. 12, 2023—Cited in IPR2022-00282, challenging U.S. Pat. No. 8,315,400.

PR 4-5(d) JCC Chart, Exhibit—2011, Filed on Jan. 12, 2023—Cited in IPR2022-00282, challenging U.S. Pat. No. 8,315,400.

Revised Scheduling Order, Exhibit—22, Filed on Jul. 12, 2023—Cited in IPR2022-01106, challenging U.S. Pat. No. 11,039,259.

Roy Falik, Exhibit—7, Filed on Jul. 18, 2024—Cited in IPR2024-01031, challenging U.S. Pat. No. 7,049,850.

Roy Falik, Exhibit—8, Filed on Jul. 18, 2024—Cited in IPR2024-01034, challenging U.S. Pat. No. 9,279,263.

Sage Journal, The Future of Hearing Aid Technology, Exhibit—2008, Filed on Oct. 17, 2022—Cited in IPR2022-00324, challenging U.S. Pat. No. 8,254,591.

Samsung Elecs. Co., Ltd., et al. v. Staton Techiya, LLC, IPR2022-00302, Paper 11, Exhibit—2006, Filed on Oct. 11, 2022—Cited in IPR2022-01106, challenging U.S. Pat. No. 11,039,259.

Samsung Elecs. Co., Ltd., et al. v. Staton Techiya, LLC, IPR2022-00302, Paper 11, Exhibit—2006, Filed on Oct. 7, 2022—Cited in IPR2022-01078, challenging U.S. Pat. No. 11,057,701.

Samsung Elecs. Co., Ltd., et al. v. Staton Techiya, LLC, IPR2022-00302, Paper 11, Exhibit—2006, Filed on Oct. 7, 2022—Cited in IPR2022-01098, challenging U.S. Pat. No. 11,217,237.

Samsung Elecs. Co., Ltd., et al. v. Staton Techiya, LLC, IPR2022-00302, Paper 11, Exhibit—2006, Filed on Oct. 7, 2022—Cited in IPR2022-01099, challenging U.S. Pat. No. 11,244,666.

Samsung's Claim Construction Brief, Exhibit—2012, Filed on Jan. 12, 2023—Cited in IPR2022-00282, challenging U.S. Pat. No. 8,315,400.

Samsung's Responsive Claim Construction Brief, Exhibit—2012, Filed on Apr. 10, 2023—Cited in IPR2022-01106, challenging U.S. Pat. No. 11,039,259.

Scheduling Order, Exhibit—11, Filed on Jan. 9, 2023—Cited in IPR2022-01106, challenging U.S. Pat. No. 11,039,259.

Scheduling Order, Exhibit—11, Filed on Dec. 30, 2022—Cited in IPR2022-01078, challenging U.S. Pat. No. 11,057,701.

Scheduling Order, Exhibit—14, Filed on Jul. 12, 2022—Cited in IPR2022-00302, challenging U.S. Pat. No. 9,609,424.

Scheduling Order, Exhibit—14, Filed on Jul. 12, 2022—Cited in IPR2022-00324, challenging U.S. Pat. No. 8,254,591.

Scheduling Order, Exhibit—14, Filed on Jul. 15, 2022—Cited in IPR2022-00253, challenging U.S. Pat. No. 9,491,542.

Scheduling Order, Exhibit—14, Filed on Jul. 15, 2022—Cited in IPR2022-00281, challenging U.S. Pat. No. 9,270,244.

Scheduling Order, Exhibit—14, Filed on Aug. 16, 2022—Cited in IPR2022-00388, challenging U.S. Pat. No. 10,966,015.

Scheduling Order, Exhibit—15, Filed on Aug. 16, 2022—Cited in IPR2022-00369, challenging U.S. Pat. No. 10,405,082.

Scheduling Order, Exhibit—16, Filed on Jun. 21, 2022—Cited in IPR2022-00243, challenging U.S. Pat. No. 8,111,839.

Scheduling Order, Exhibit—17, Filed on Jun. 21, 2022—Cited in IPR2022-00242, challenging U.S. Pat. No. 8,111,839.

Scheduling Order, Exhibit—9, Filed on Aug. 22, 2024—Cited in IPR2024-00559, challenging U.S. Pat. No. 11,610,587.

Staton Techiya v Samsung—Docket Control Order, Exhibit—2003, Filed on Apr. 18, 2022—Cited in IPR2022-00253, challenging U.S. Pat. No. 9,491,542.

Staton Techiya v Samsung—Docket Control Order, Exhibit—2003, Filed on Apr. 18, 2022—Cited in IPR2022-00281, challenging U.S. Pat. No. 9,270,244.

(56) References Cited

OTHER PUBLICATIONS

*Staton Techiya* v *Samsung*, Docket Control Order, Exhibit—2003, Filed on Mar. 21, 2022—Cited in IPR2022-00282, challenging U.S. Pat. No. 8,315,400.

*Staton Techiya* v *Samsung*, Docket Control Order, Exhibit—2003, Filed on Apr. 13, 2022—Cited in IPR2022-00302, challenging U.S. Pat. No. 9,609,424.

*Staton Techiya* v *Samsung*, Docket Control Order, Exhibit—2003, Filed on Apr. 13, 2022—Cited in IPR2022-00324, challenging U.S. Pat. No. 8,254,591.

*Staton Techiya* v. *Samsung*, Claim Construction Order, Exhibit—2012, Filed on Mar. 23, 2023—Cited in IPR2022-01078, challenging U.S. Pat. No. 11,057,701.

*Staton Techiya* v. *Samsung*, Docket Control Order, Exhibit—2003, Filed on Mar. 23, 2022—Cited in IPR2022-00242, challenging U.S. Pat. No. 8,111,839.

*Staton Techiya* v. *Samsung*, Docket Control Order, Exhibit—2003, Filed on Mar. 23, 2022—Cited in IPR2022-00243, challenging U.S. Pat. No. 8,111,839.

*Staton Techiya* v. *Samsung*, Docket Control Order, Exhibit—2003, Filed on May 18, 2022—Cited in IPR2022-00369, challenging U.S. Pat. No. 10,405,082.

*Staton Techiya* v. *Samsung*, Docket Control Order, Exhibit—2003, Filed on May 18, 2022—Cited in IPR2022-00388, challenging U.S. Pat. No. 10,966,015.

*Staton Techiya* v. *Samsung*, Docket Control Order, Exhibit—2003, Filed on May 18, 2022—Cited in IPR2022-00410, challenging U.S. Pat. No. 10,979,836.

*Staton Techiya* v. *Samsung*, Docket Control Order; Exhibit—2003, Filed on Mar. 21, 2022—Cited in IPR2022-00234, challenging U.S. Pat. No. 9124982.

*Staton Techiya* v. *Samsung*, Joint Motion to Consolidate, Exhibit—2005, Filed on Apr. 29, 2022—Cited in IPR2022-00242, challenging U.S. Pat. No. 8,111,839.

*Staton Techiya* v. *Samsung*, Joint Mtn to Consolidate, Exhibit—2005, Filed on Apr. 29, 2022—Cited in IPR2022-00243, challenging U.S. Pat. No. 8,111,839.

*Staton Techiya* v. *Samsung*, Joint Mtn to Consolidate, Exhibit—2008, Filed on Apr. 29, 2022—Cited in IPR2022-00282, challenging U.S. Pat. No. 8,315,400.

*Staton Techiya* v. *Samsung*, P.R. 4-5(d) Joint Claim Construction Chart, Exhibit—2011, Filed on Mar. 23, 2023—Cited in IPR2022-01078, challenging U.S. Pat. No. 11,057,701.

*Staton Techiya, LLC* v. *Samsung Elecs. Co., Ltd.*, Appendix B to P.R. 4-3 Statement, Exhibit—2007, Filed on Nov. 8, 2022—Cited in IPR2022-00369, challenging U.S. Pat. No. 10,405,082.

*Staton Techiya, LLC* v. *Samsung Elecs. Co., Ltd.*, Appendix B to P.R. 4-3 Statement, Exhibit—2009, Filed on Nov. 18, 2022—Cited in IPR2022-01078, challenging U.S. Pat. No. 11,057,701.

*Staton Techiya, LLC* v. *Samsung Elecs. Co., Ltd.*, Appendix B to P.R. 4-3 Statement, Exhibit—2010, Filed on Nov. 8, 2022—Cited in IPR2022-00388, challenging U.S. Pat. No. 10,966,015.

*Staton Techiya, LLC* v. *Samsung Elecs. Co., Ltd.*, Appendix B to P.R. 4-3 Statement, Exhibit—2011, Filed on Nov. 18, 2022—Cited in IPR2022-01106, challenging U.S. Pat. No. 11,039,259.

*Staton Techiya, LLC, et al.* v. *Samsung Elecs. Co., Ltd., et al.*, Defendants' P.R. 4-2 Disclosures, Exhibit—2004, Filed on Oct. 11, 2022—Cited in IPR2022-01106, challenging U.S. Pat. No. 11,039,259.

*Staton Techiya, LLC, et al.* v. *Samsung Elecs. Co., Ltd., et al.*, Defendants' P.R. 4-2 Disclosures, Exhibit—2004, Filed on Oct. 7, 2022—Cited in IPR2022-01078, challenging U.S. Pat. No. 11,057,701.

*Staton Techiya, LLC, et al.* v. *Samsung Elecs. Co., Ltd., et al.*, Defendants' P.R. 4-2 Disclosures, Exhibit—2004, Filed on Oct. 7, 2022—Cited in IPR2022-01098, challenging U.S. Pat. No. 11,217,237.

*Staton Techiya, LLC, et al.* v. *Samsung Elecs. Co., Ltd., et al.*, Defendants' P.R. 4-2 Disclosures, Exhibit—2004, Filed on Oct. 7, 2022—Cited in IPR2022-01099, challenging U.S. Pat. No. 11,244,666.

*Staton Techiya, LLC, et al.* v. *Samsung Elecs. Co., Ltd., et al.*, Docket Control Order (Dkt. No. 43), Exhibit—2005, Filed on Oct. 7, 2022—Cited in IPR2022-01078, challenging U.S. Pat. No. 11,057,701.

*Staton Techiya, LLC, et al.* v. *Samsung Elecs. Co., Ltd., et al.*, Docket Control Order (Dkt. No. 43), Exhibit—2005, Filed on Oct. 7, 2022—Cited in IPR2022-01098, challenging U.S. Pat. No. 11,217,237.

*Staton Techiya, LLC, et al.* v. *Samsung Elecs. Co., Ltd., et al.*, Docket Control Order (Dkt. No. 43), Exhibit—2005, Filed on Oct. 7, 2022—Cited in IPR2022-01099, challenging U.S. Pat. No. 11,244,666.

*Staton Techiya, LLC, et al.* v. *Samsung Elecs. Co., Ltd., et al.*, Docket Control Order, Exhibit—2005, Filed on Oct. 11, 2022—Cited in IPR2022-01106, challenging U.S. Pat. No. 11,039,259.

*Staton Techiya, LLC, et al.* v. *Samsung Elecs. Co., Ltd., et al.*, Joint Motion to Consolidate (Dkt. No. 39), Exhibit—2007, Filed on Oct. 7, 2022—Cited in IPR2022-01078, challenging U.S. Pat. No. 11,057,701.

*Staton Techiya, LLC, et al.* v. *Samsung Elecs. Co., Ltd., et al.*, Joint Motion to Consolidate (Dkt. No. 39), Exhibit—2007, Filed on Oct. 7, 2022—Cited in IPR2022-01098, challenging U.S. Pat. No. 11,217,237.

*Staton Techiya, LLC, et al.* v. *Samsung Elecs. Co., Ltd., et al.*, Joint Motion to Consolidate (Dkt. No. 39), Exhibit—2007, Filed on Oct. 7, 2022—Cited in IPR2022-01099, challenging U.S. Pat. No. 11,244,666.

*Staton Techiya, LLC, et al.* v. *Samsung Elecs. Co., Ltd., et al.*, Joint Motion to Consolidate, Exhibit—2007, Filed on Oct. 11, 2022—Cited in IPR2022-01106, challenging U.S. Pat. No. 11,039,259.

*Staton Techiya, LLC, et al.* v. *Samsung Elecs. Co., Ltd., et al.*, Plaintiff's Infringement Contentions, dated Apr. 6, 2022, Exhibit—2008, Filed on Oct. 7, 2022—Cited in IPR2022-01078, challenging U.S. Pat. No. 11,057,701.

*Staton Techiya, LLC, et al.* v. *Samsung Elecs. Co., Ltd., et al.*, Plaintiff's P.R. 4-2 Disclosures, Exhibit—2003, Filed on Oct. 7, 2022—Cited in IPR2022-01099, challenging U.S. Pat. No. 11,244,666.

*Staton Techiya, LLC, et al.* v. *Samsung Elecs. Co., Ltd., et al.*, Plaintiffs' Infringement Contentions dated Apr. 6, 2022, Exhibit—2008, Filed on Oct. 11, 2022—Cited in IPR2022-01106, challenging U.S. Pat. No. 11,039,259.

*Staton Techiya, LLC, et al.* v. *Samsung Elecs. Co., Ltd., et al.*, Plaintiffs' Infringement Contentions, dated Apr. 6, 2022, Exhibit—2008, Filed on Oct. 7, 2022—Cited in IPR2022-01098, challenging U.S. Pat. No. 11,217,237.

*Staton Techiya, LLC, et al.* v. *Samsung Elecs. Co., Ltd., et al.*, Plaintiffs' Infringement Contentions, dated Apr. 6, 2022, Exhibit—2008, Filed on Oct. 7, 2022—Cited in IPR2022-01099, challenging U.S. Pat. No. 11,244,666.

*Staton Techiya, LLC, et al.* v. *Samsung Elecs. Co., Ltd., et al.*, Plaintiffs' P.R. 4-2 Disclosures, Exhibit—2003, Filed on Oct. 11, 2022—Cited in IPR2022-01106, challenging U.S. Pat. No. 11,039,259.

*Staton Techiya, LLC, et al.* v. *Samsung Elecs. Co., Ltd.*, et al., Plaintiffs' P.R. 4-2 Disclosures, Exhibit—2003, Filed on Oct. 7, 2022—Cited in IPR2022-01078, challenging U.S. Pat. No. 11,057,701.

*Staton Techiya, LLC, et al.* v. *Samsung Elecs. Co., Ltd., et al.*, Plaintiffs' P.R. 4-2 Disclosures, Exhibit—2003, Filed on Oct. 7, 2022—Cited in IPR2022-01098, challenging U.S. Pat. No. 11,217,237.

Stipulation Letter dated Apr. 20, 2022, Exhibit—1031, Filed on May 11, 2022—Cited in IPR2022-00324, challenging U.S. Pat. No. 8,254,591.

Stipulation Letter from D. Rokach to J. Snodgrass, Exhibit—1025, Filed on Nov. 10, 2022—Cited in IPR2022-01099, challenging U.S. Pat. No. 11,244,666.

Stipulation Letter from D. Rokach to J. Snodgrass, Exhibit—1027, Filed on Nov. 10, 2022—Cited in IPR2022-01078, challenging U.S. Pat. No. 11,057,701.

Stipulation Letter from D. Rokach to J. Snodgrass, Exhibit—1030, Filed on Nov. 15, 2022—Cited in IPR2022-01098, challenging U.S. Pat. No. 11,217,237.

Stipulation Letter from D. Rokach to J. Snodgrass, Exhibit—1033, Filed on Nov. 10, 2022—Cited in IPR2022-01106, challenging U.S. Pat. No. 11,039,259.

(56) References Cited

OTHER PUBLICATIONS

Stipulation Letter, Exhibit—1015, Filed on Apr. 20, 2022—Cited in IPR2022-00282, challenging U.S. Pat. No. 8,315,400.
Stipulation Letter, Exhibit—1019, Filed on Jun. 14, 2022—Cited in IPR2022-00369, challenging U.S. Pat. No. 10,405,082.
Stipulation Letter, Exhibit—1019, Filed on Jun. 14, 2022—Cited in IPR2022-00388, challenging U.S. Pat. No. 10,966,015.
Stipulation Letter, Exhibit—1020, Filed on Jun. 14, 2022—Cited in IPR2022-00410, challenging U.S. Pat. No. 10,979,836.
Stipulation Letter, Exhibit—1023, Filed on May 10, 2022—Cited in IPR2022-00302, challenging U.S. Pat. No. 9,609,424.
Stipulation Letter, Exhibit—1044, Filed on Apr. 20, 2022—Cited in IPR2022-00242, challenging U.S. Pat. No. 8,111,839.
Stipulation Letter, Exhibit—1044, Filed on Apr. 20, 2022—Cited in IPR2022-00243, challenging U.S. Pat. No. 8,111,839.
Stipulation Letter; Exhibit—1034, Filed on Apr. 20, 2022—Cited in IPR2022-00234, challenging U.S. Pat. No. 9,124,982.
Summary of all applications in the '082 patent family, Exhibit—1018, Filed on Dec. 30, 2021—Cited in IPR2022-00369, challenging U.S. Pat. No. 10,405,082.
Summary of all applications in the '836 patent's family, Exhibit—1019, Filed on Jan. 14, 2022—Cited in IPR2022-00410, challenging U.S. Pat. No. 10,979,836.
Summary of Application in '839 Patent Priority Chain, Exhibit—1041, Filed on Dec. 13, 2021—Cited in IPR2022-00243, challenging U.S. Pat. No. 8,111,839.
Summary of applications in '015 patent family, Exhibit—1018, Filed on Jan. 4, 2022—Cited in IPR2022-00388, challenging U.S. Pat. No. 10,966,015.
Summary of applications in '591 priority chain, Exhibit—1030, Filed on Dec. 20, 2021—Cited in IPR2022-00324, challenging U.S. Pat. No. 8,254,591.
Summary of Applications in '839 Priority Chain, Exhibit—1041, Filed on Dec. 13, 2021—Cited in IPR2022-00242, challenging U.S. Pat. No. 8,111,839.
Summary of Applications in '982 Priority Chain; Exhibit—1032, Filed on Dec. 13, 2021—Cited in IPR2022-00234, challenging U.S. Pat. No. 9,124,982.
Techopedia, Faceplate, Exhibit—2011, Filed on Sep. 13, 2022—Cited in IPR2022-00242, challenging U.S. Pat. No. 8,111,839.
Techopedia, Faceplate; Exhibit—2010, Filed on Sep. 9, 2022—Cited in IPR2022-00234, challenging U.S. Pat. No. 9,124,982.
Termination Decision: Post-DI Settlement, Exhibit—20, Filed on Dec. 12, 2024—Cited in IPR2024-00559, challenging U.S. Pat. No. 11,610,587.
Termination Decision: Pre-DI settlement, Exhibit—16, Filed on Dec. 12, 2024—Cited in IPR2024-01003, challenging U.S. Pat. No. 9,191,083.
Termination Decision: Pre-DI settlement, Exhibit—16, Filed on Dec. 12, 2024—Cited in IPR2024-01004, challenging U.S. Pat. No. 9,614,943.
Termination Decision: Pre-DI settlement, Exhibit—16, Filed on Dec. 12, 2024—Cited in IPR2024-01031, challenging U.S. Pat. No. 7,049,850.
Termination Decision: Pre-DI settlement, Exhibit—17, Filed on Dec. 12, 2024—Cited in IPR2024-01034, challenging U.S. Pat. No. 9,279,263.
Termination Decision: Pre-DI settlementPaper15, Dec. 12, 2024—Cited in IPR2024-01033, challenging U.S. Pat. No. 8,434,966.
Transcript of Deposition of Chris Kyriakakis, Ph.D. taken Oct. 7, 2022, Exhibit—2007, Filed on Oct. 17, 2022—Cited in IPR2022-00302, challenging U.S. Pat. No. 9,609,424.
Transcript of Deposition of Christopher Struck, Exhibit—1028, Filed on Jun. 15, 2023—Cited in IPR2022-01078, challenging U.S. Pat. No. 11,057,701.
Transcript of Deposition of Dr. Les Atlas, Exhibit—2007, Filed on Oct. 17, 2022—Cited in IPR2022-00324, challenging U.S. Pat. No. 8,254,591.

Transcript of Deposition of Dr. Les Atlas; Exhibit—2007, Filed on Sep. 9, 2022—Cited in IPR2022-00234, challenging U.S. Pat. No. 9,124,982.
Transcript of Deposition of Les Atlas, Ph.D., Aug. 18, 2022, Exhibit—2007, Filed on Sep. 13, 2022—Cited in IPR2022-00242, challenging U.S. Pat. No. 8,111,839.
Transcript of Deposition of Les Atlas, Ph.D., Aug. 18, 2022, Exhibit—2007, Filed on Sep. 13, 2022—Cited in IPR2022-00243, challenging U.S. Pat. No. 8,111,839.
Transcript of Deposition of Les Atlas, Ph.D., Exhibit—2016, Filed on Apr. 10, 2023—Cited in IPR2022-01106, challenging U.S. Pat. No. 11,039,259.
Transcript of Deposition of Nathaniel Polish, Ph.D., taken Sep. 29, 2022, Exhibit—2007, Filed on Oct. 19, 2022—Cited in IPR2022-00253, challenging U.S. Pat. No. 9,491,542.
Transcript of Deposition of Nathaniel Polish, Ph.D., taken Sep. 29, 2022, Exhibit—2007, Filed on Oct. 19, 2022—Cited in IPR2022-00281, challenging U.S. Pat. No. 9,270,244.
Transcript of Deposition of Richard M. Stern, Exhibit—2010, Filed on Mar. 23, 2023—Cited in IPR2022-01078, challenging U.S. Pat. No. 11,057,701.
Transcript of Deposition of Richard M. Stern, Ph.D., taken Oct. 27, 2022, Exhibit—2009, Filed on Nov. 8, 2022—Cited in IPR2022-00369, challenging U.S. Pat. No. 10,405,082.
Transcript of Deposition of Richard M. Stern, Ph.D., taken Oct. 27, 2022, Exhibit—2009, Filed on Nov. 8, 2022—Cited in IPR2022-00388, challenging U.S. Pat. No. 10,966,015.
Transcript of Deposition of Richard Stern, Ph.D., Exhibit—2010, Filed on Sep. 9, 2022—Cited in IPR2022-00282, challenging U.S. Pat. No. 8,315,400.
U.S. Appl. No. 09/653,869, Exhibit—1007, Filed on Dec. 20, 2021—Cited in IPR2022-00324, challenging U.S. Pat. No. 8,254,591.
U.S. Pat. No. 10,405,082, Exhibit—1001, Filed on Dec. 30, 2021—Cited in IPR2022-00369, challenging U.S. Pat. No. 10,405,082.
U.S. Appl. No. 61/778,737, Exhibit—1008, Filed on Dec. 21, 2021—Cited in IPR2022-00281, challenging U.S. Pat. No. 9,270,244.
U.S. Appl. No. 62/575,713, Exhibit—1006, Filed on Dec. 30, 2021—Cited in IPR2022-00369, challenging U.S. Pat. No. 10,405,082.
U.S. Appl. No. 62/575,713, Exhibit—1006, Filed on Jan. 4, 2022—Cited in IPR2022-00388, challenging U.S. Pat. No. 10,966,015.
Wikipedia, Apple headphones, Exhibit—2010, Filed on Sep. 13, 2022—Cited in IPR2022-00243, challenging U.S. Pat. No. 8,111,839.
Wikipedia, Microphone, Exhibit—2012, Filed on Sep. 13, 2022—Cited in IPR2022-00242, challenging U.S. Pat. No. 8,111,839.
Wikipedia, Microphone; Exhibit—2011, Filed on Sep. 9, 2022—Cited in IPR2022-00234, challenging U.S. Pat. No. 9,124,982.
Wiley Elec and Elecs Eng Dictionary (excerpts), Exhibit—2004, Filed on Mar. 21, 2022—Cited in IPR2022-00282, challenging U.S. Pat. No. 8,315,400.
Wiley Electrical and Electronics Engineering Dictionary (excerpt), Exhibit—2009, Filed on Oct. 7, 2022—Cited in IPR2022-01098, challenging U.S. Pat. No. 11,217,237.
3M/Aearo Technologies' E-A-RFitTM Dual-Ear Validation System ("E-A-RFit"), Sept. 4, 2015 WayBack Machine capture of 3M's website contains an image of the E-A-RFit and states "[t]he 3M™ E-A-Rfit™ Dual Ear Validation System makes . . . " https://web.archive.org/web/20150904132810/ http:/solutions.3m.com/wps/portal/3M/en_US/3M-PPE-Safety-Solutions/Personal- Protective-Equipment/safety-management/safety-training/hearing- protection-fit-testing/?WT.mc_id=www.3m.com/EARfitDe mo/ (SAM-TECH_00052276; SAM- TECH ; SAM-TECH 00052239), 2 pgs.
A Dual-Mode Human-Machine Interface for Robotic Control Based on Acoustic Sensitivity of the Aural Cavity Claim Chart (Exhibit N49 to Samsung's Invalidity Contentions), 2006, 7 pages.
Chung, Challenges and Recent Developments in Hearing Aids, Trends in Amplification, 2004, pp. 125-164, vol. 8, No. 4, 42 pages.
Declaration and Affirmation of Debbie Montgomery, as presented in *Samsung* v. *Techiya*, IPR2022-00410 as Exhibit 1018, including that Declaration's attached Exhibit A (2022), 10 pages.
Ex. I10 to Samsung's Invalidity Contentions and P.R. 3-3 And 3-4 Disclosures for U.S. Pat. Nos. 8,111,839, 8,254,591, 8,315,400,

(56) References Cited

OTHER PUBLICATIONS 9,124,982, 9,270,244, 9,491,542, 9,609,424, 10,405,082, 10,966,015 (Case No. 2:22-CV-00053-JRG-RSP), served May 18, 2022, 161 pages.
Ex. I11 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022, 219 pages.
Ex. I12 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022, 182 pages.
Ex. I15 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022, 219 pages.
Ex. I16 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022, 112 pages.
Ex. I17 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022, 190 pages.
Ex. I18 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022, 120 pages.
Ex. I2 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022, 183 pages.
Ex. I3 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022, 121 pages.
Ex. I4 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022, 73 pages.
Ex. I5 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022, 138 pages.
Ex. I6 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022, 79 pages.
Ex. I7 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022, 87 pages.
Ex. I8 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022, 48 pages.

Ex. I9 to Samsung's Invalidity Contentions and P.R. 3-3 And 3-4 Disclosures for U.S. Pat. Nos. 8,111,839, 8,254,591, 8,315,400, 9,124,982, 9,270,244, 9,491,542, 9,609,424, 10,405,082, 10,966,015 (Case No. 2:22-CV-00053-JRG-RSP), served May 18, 2022, 86 pages.
Exhbit-1001—U.S. Pat. No. 11,589,329, filed by Steven W. Goldstein, Assignee: Staton Techiya LLC, IPR2024-01300, filed on Apr. 20, 2021, pp. 1-19.
Exhbit-1001—U.S. Pat. No. 8,805,692, filed by Steven Wayne Goldstein, Assignee: Personics Holdings, LLC, IPR2024-01301, filed on Jan. 7, 2014, pp. 1-17.
Exhbit-1004—U.S. Patent No. 7,570, 158, filed by Michael S. Denny, Assignee: AT&T Intellectual Property I, L.P., IPR2024-01300, filed on Aug. 17, 2006, pp. 1-22.
Exhbit-1004—U.S. Publication No. 20060132382, filed by James H. Jannard, IPR2024-01301, filed on Dec. 22, 2004, pp. 1-79.
Exhbit-1005—U.S. Pat. No. 7,529,677, filed by John W. Wittenberg, Assignee: ITT Manufacturing Enterprises, Inc.,, IPR2024-01301, filed on Jan. 21, 2005, pp. 1-10.
Exhbit-1006—U.S. Publication No. 20070038395, filed by David John Green, IPR2024-01300, filed on Sep. 2, 2004, pp. 1-8.
Exhbit-1007—U.S. Publication No. 20060020960, filed by Sandeep Relan, IPR2024-01301, filed on Sep. 6, 2005, pp. 1-39.
Exhbit-1009—U.S. Pat. No. 6,219,645, filed by Charles Calvin Byers, Assignee: Lucent Technologies, Inc., IPR2024-01300, filed on Dec. 2, 1999, pp. 1-20.
Exhbit-1009—U.S. Publication No. 20030130852, filed by Shinichi Tanaka, Assignee: Kabushiki Kaisha Toshiba, IPR2024-01301, filed on Jan. 2, 2003, pp. 1-41.
Exhbit-1010—U.S. Publication No. 20100311390, filed by Gerald R. Black, IPR2024-01301, filed on Sep. 22, 2008, pp. 1-40.
Exhbit-1011—U.S. Publication No. 20070165875, filed by Behrooz Rezvani, IPR2024-01301, filed on Dec. 1, 2006, pp. 1-18.
Exhbit-1012—Introduction to Computer Network, Source: A.S. Tanenbaum: Computer Networks, 3rd. Edition, *Harman* v. *ST Cases Tech*, under Case IPR2024-01300, 1997, pp. 1-7.
Exhbit-1012—United States District Courts National Judicial Caseload Profile, filed by *Harman* v. *ST CasesTech*, Under Case IPR2024-01301, Dated Aug. 30, 2024, pp. 1-95.
Exhbit-1013—"Architecture & Terminology Overview: Specification of the Bluetooth System Wireless connections made easy", Specification vol. 1, Version 1.2, IPR2024-01300, Nov. 5, 2003, pp. 1-31.
Exhbit-1013—U.S. Publication No. 20060136378, filed by Anthony G. Martin, IPR2024-01301, filed on Dec. 17, 2004, pp. 1-13.
Exhbit-1014—Australian Patent Application No. 2005201979, filed by NEC Corporation, IPR2024-01301, filed on May 10, 2005, pp. 1-50.
Exhbit-1014—U.S. Pat. No. 7,529,677, filed by John W. Wittenberg, Assignee: ITT Manufacturing Enterprises, Inc., IPR2024-01300, filed on Jun. 21, 2005, pp. 1-10.
Exhbit-1015—Computer Dictionary, 2nd Edition, The Comprehensive Standard for Business, School, Library, and Home, software engineering, *Harman* v. *ST CasesTech*, Under Case IPR2024-01301, 1994, pp. 1-5.
Exhbit-1015—U.S. Pat. No. 7,769,591, filed by George M. White, IPR2024-01300, filed on Aug. 31, 2006, pp. 1-22.
Exhbit-1016—U.S. Pat. No. 5,251,263, filed by Douglas Andrea, Assignee: Andrea Electronics Corporation, IPR2024-01301, filed on May 22, 1992, pp. 1-33.
Exhbit-1019—Complaint for Patent Infringement filed by *Staton Techiya, LLC*, v. *Harman International Industries, Incorporated and Harman-Kardon, Inc.*, Case 1:23-cv-00802-UNA, Under IPR2024-01301, Jul. 26, 2023, pp. 1-252.
Exhibit-10—Term Order filed by *Harman International Industries, Inc.*, v. *ST Casestech, LLC*, for IPR2024-01299 (U.S. Pat. No. 8,319,620 B2) IPR2024-01300 (U.S. Pat. No. 11,589,329 B1) IPR2024-01301 (U.S. Pat. No. 8,805,692 B2) IPR2024-01302 (U.S. Pat. No. 8,150,044 B2) IPR2024-01303 (U.S. Pat. No. 11,521,632 B2)1, Dated Jan. 14, 2025, 5 pages.
Exhibit-11—Notice of Refund, Filed by *Harman International Industries, Inc.*, vs. *ST Casestech, LLC*, for U.S. Pat. No. 8,805,692 Under Case IPR2024-01301, Mailed on Jan. 17, 2024, 2 pages.

(56)　　　　　References Cited

OTHER PUBLICATIONS

Exhibit-12—Notice of Refund filed by *Harman International Industries, Inc.,* vs. *ST Casestech, LLC,* for U.S. Pat. No. 11,589,329 under Case IPR2024-01300, Mailed on Jan. 17, 2024, 2 pages.

Exhibit-9—Term Order filed by *Harman International Industries, Inc.,* v. *ST Casestech, LLC,* for IPR2024-01299 (U.S. Pat. No. 8,319,620 B2) IPR2024-01300 (U.S. Pat. No. 11,589,329 B1) IPR2024-01301 (U.S. Pat. No. 8,805,692 B2) IPR2024-01302 (U.S. Pat. No. 8,150,044 B2) IPR2024-01303 (U.S. Pat. No. 11,521,632 B2)1, Dated Jan. 14, 2025, 5 pages.

Exhibit E9—Invalidity of U.S. Pat. No. 9,270,244 ("the '244 Patent") in view of U.S. Pat. No. 6,567,524 ("Svean"), pp. 1-55 (date not available), 55 pages.

Exhibit F5—Invalidity of U.S. Pat. No. 9,491,542 ("the '542 Patent") in view of U.S. Pat. App. Pub. 2011/0293103 ("Park"), pp. 1-81 (date not available), 81 pages.

Exhibit H5—Invalidity of U.S. Pat. No. 10,405,082 ("the '082 Patent") in view of U.S. Pat. Appl. Pub. No. 2014/0163976, pp. 1-151 (date not available), 151 pages.

Exhibit-3001—Email from Trials Subject Patent Owner Staton Techiya IPR Request, Under IPR2024-01299, -01300, -01301, -01302, -01303, Mailed on Dec. 4, 2024, 4 pages.

Exhibit-1002—File History of U.S. Appl. No. 14/148,752 Under IPR2024-01301, Dated Aug. 30, 2024, pp. 1-268.

Exhibit-1002—File History of U.S. Appl. No. 17/235,130 Under IPR2024-01300, Dated Aug. 30, 2024, pp. 1-730.

Exhibit-1003—Declaration of Dr. Michael T. Johnson In Support of Petition For Inter Partes Review of U.S. Pat. No. 8,805,692 filed by *Harman International Industries, Incorporated,* v. *St Casestech LLC,* for U.S. Pat. No. 8,805,692 Under Case IPR2024-01301, Aug. 30, 2024, pp. 1-161.

Exhibit-1003—Declaration of Dr. Sayfe Kiaei in Support of Petition for Inter Partes Review of U.S. Pat. No. 11,589,329, filed by *Harman International Industries, Inc.* v. *St Casestech, LLC,* for U.S. Pat. No. 11,589,329 Under IPR2024-01300, filed on Aug. 30, 2024, pp. 1-177.

Exhibit-1005—U.S. Publication No. 20080132199 filed by Kazuko Hirata, Assignee: Jupiter Net Incorporated, IPR2024-01300, filed on Aug. 30, 2024, pp. 1-28.

Exhibit-1006, U.S. Appl. No. 11/038,426, filed by *Harman v. ST CasesTech,* titled Methods and Apparatus for Remotely Processing Locally Generated Commands To Control a Local Device, filed on Jan. 21, 2005, pp. 1-34.

Exhibit-1007—Translation of Japanese Patent Application Publication No. 2004-212544, filed by *Harman v. ST CasesTech,* Under IPR2024-01300, filed on Aug. 30, 2024, pp. 1-63.

Exhibit-1008—Original Copy of Japanese Publication No. 2004-212544, filed by *Harman v. ST CasesTech,* Under IPR2024-01300, filed on Aug. 30, 2024, pp. 1-33.

Exhibit-1010—United States District Courts—National Judicial Caseload Profile filed by *Harman v. ST CasesTech,* Under IPR2024-01300, filed on Aug. 30, 2024, pp. 1-95.

Exhibit-1011—Complaint for Patent Infringement filed by *Staton Techiya, LLC,* v. *Harman International Industries,* Incorporated Case 1:23-cv-00801-UNA, IPR2024-01300 filed on Jul. 25, 2023, pp. 1-86.

Exhibit-1016—File History of U.S. Appl. No. 16/736,820 Under IPR2024-01300, Dated Jan. 8, 2020, 151 pages.

Exhibit-1017—File History for U.S. Appl. No. 16/055,488, filed by *Herman v. ST Cases Tech,* IPR2024-01300, filed on Aug. 30, 2024, pp. 1-165.

Exhibit-1017, File History of U.S. Appl. No. 60/806,769, filed by *Harman v. ST CasesTech,* titled Personalized Services delivered to a Personal Audio Assistant (PAA), filed on Jul. 8, 2006, pp. 1-44.

Exhibit-1018—File History of U.S. Appl. No. 13/976,636 Under IPR2024-01300, filed on Aug. 30, 2024, 572 pages.

Exhibit-1019—Declaration of Jonathan Bradford in Support Of Petition for Inter Partes Review of U.S. Pat. No. 11,589,329 filed by

*Harman International Industries, Inc.,* v. *ST Casestech, LLC,* for U.S. Pat. No. 11,589,329 Under Case IPR2024-01300, Aug. 30, 2024, pp. 1-7.

Exhibit-1020—Declaration of Jonathan Bradford in Support Of Petition for Inter Partes Review of U.S. Pat. No. 8,805,692 filed by *Harman International Industries, Inc.,* v. *ST Casestech, LLC,* for U.S. Pat. No. 8,805,692 Under Case IPR2024-01301, Aug. 30, 2024, pp. 1-7.

Exhibit-5—Notice of Filing Date Accorded to Petition and Time for Filing Patent Owner Preliminary Response filed by *Harman International Industries, Inc.,* v. *ST Casestech LLC,* for U.S. Pat. No. 8,805,692 Under IPR2024-01301, Mailed on Oct. 15, 2024, 6 pages.

Exhibit-6—Notice of Filing Date Accorded to Petition and Time for Filing Patent Owner Preliminary Response filed by *Harman International Industries, Inc.,* v. *ST Casestech LLC,* for U.S. Pat. No. 11,589,329 Under IPR2024-01300, Mailed on Oct. 10, 2024, 6 pages.

File History of corresponding Reexamination U.S. Patent Application No. 90/015,146, filed Oct. 28, 2022, 1270 pages.

File History of corresponding Reexamination U.S. Patent Application No. 90/019,169, filed Feb. 24, 2023, Reexamination Certificate Issued Oct. 11, 2023 as U.S. Pat. No. 11,244,666 C1., 998 pages.

Joint Motion to Terminate Proceeding filed by *Harman International Industries, Inc.,* v. *ST Casestech, LLC,* for U.S. Pat. No. 11,589,329 Under Case IPR2024-01300, Dated Dec. 19, 2024, 8 pages.

Joint Motion to Terminate Proceeding filed by *Harman International Industries, Inc.,* v. *ST Casestech, LLC,* for U.S. Pat. No. 8,805,692 Under Case IPR2024-01301, Dated Dec. 19, 2024, 8 pages.

Joint Request to Treat Settlement Agreement as Business Confidential Information filed by *Harman International Industries, Inc.,* v. *ST Casestech, LLC,* for U.S. Pat. No. 11,589,329 under Case IPR2024-01300, Dated Dec. 19, 2024, 5 pages.

Joint Request to Treat Settlement Agreement as Business Confidential Information filed by *Harman International Industries, Inc.,* v. *ST Casestech, LLC,* for U.S. Pat. No. 8,805,692 under Case IPR2024-01301, Dated Dec. 19, 2024, 5 pages.

Mueller, There's less talking in barrels, but the occlusion effect is still with US, The Hearing Journal, Aug. 2003, pp. 10-16, vol. 56, No. 8.

Muggleton, Nacre's QUIETPRO+ Intelligent Hearing System: Delivering Performance and Hearing Protection Now for the Future of the Soldier, SoldierMod Jan. 2009, pp. 28-29, vol. 2.

NACRE QuietPro, Mar. 9, 2005, WayBack Machine capture of Nacre's website contains an image of the NACRE QuietPro and states that "Nacre has secured MNOK 27,5 from a consortium led by Ferd Venture" and that "[m]ost of the money will be spent to boost efforts within sales and marketing of QUIETPRO in the global military market.", (Sam-TECH_00054131) 2 pages.

Patent Owner'S Unopposed Motion to Withdraw And Substitute Counsel Under 37 C.F.R. § 11.116 filed by *Harman International Industries, Inc.,* v. *ST Casestech, LLC* for U.S. Pat. No. 11,589,329 Under Case No. IPR2024-01300, Nov. 21, 2024, 4 pages.

Patent Owner'S Unopposed Motion to Withdraw And Substitute Counsel Under 37 C.F.R. § 11.116 filed by *Harman International Industries, Inc.,* v. *ST Casestech, LLC* for U.S. Pat. No. 8,805,692 Under Case No. IPR2024-01301, Nov. 21, 2024, 4 pages.

Petition for Inter Partes Review filed by *Harman International Industries, Inc.* v. *ST Casestech, LLC,* for U.S. Pat. No. 11,589,329 Under Case IPR2024-01300, Dated Aug. 30, 2024, 78 pages.

Petition For Inter Partes Review filed by *Harman International Industries, Inc.,* v. *ST Casestech LLC,* U.S. Pat. No. 8,805,692 under Case IPR2024-01301, dated Aug. 30, 2024, 85 pages.

Petitioner Harman International Industries, Inc. Corrected Power of Attorney filed by *Harman International Industries, Inc.* v. *ST Casestech LLC1,* for U.S. Pat. No. 11,589,329 Under Case IPR2024-01300, Dated Aug. 31, 2024, 5 pages.

Petitioner Harman International Industries, Inc. Power Of Attorney U.S. Pat. No. 11,589,329 filed by *Harman International Industries, Inc.* v. *Staton Techiya, LLC,* for U.S. Pat. No. 11,589,329 Under Case IPR2024-01300 Dated Aug. 26, 2024, 3 pages.

(56)   References Cited

OTHER PUBLICATIONS

Petitioner Harman International Industries, Inc. Power Of Attorney U.S. Pat. No. 8,805,692 filed by *Harman International Industries, Inc.*, v. *ST Casestech LLC*, for U.S. Pat. No. 8,805,692 Under Case IPR2024-01301, Dated Aug. 26, 2024, 3 pages.
Petitioner'S Request for Refund of Post-Institution Fees filed by *Harman International Industries, Inc.* v. *ST Casestech, LLC*, for U.S. Pat. No. 11,589,329 under Case IPR2024-01300, dated Jan. 16, 2025, 3 pages.
Petitioner'S Request for Refund of Post-Institution Fees filed by *Harman International Industries, Inc.* v. *ST Casestech, LLC*, for U.S. Pat. No. 8,805,692 under Case IPR2024-01301, dated Jan. 16, 2025, 3 pages.
Samsung's Invalidity Contentions and P.R. 3-3 And 3-4 Disclosures for U.S. Pat. Nos. 11,039,259, 11,057,701, 11,217,237, and 11,244,666 (Case No. 2:22-CV-00053-JRG-RSP), served Jul. 6, 2022, 1009 pages.
Samsung's Motion for Summary Judgment of Invalidity under 35 U.S.C. §112 of the '666 Patent (Redacted), Jun. 26, 2023, 78 pages.
Samsung's Reply in Support of Its Motion for Summary Judgment of Invalidity under 35 U.S.C. § 112 of the '666 Patent (Redacted), Aug. 7, 2023, 22 pages.
St Casestech, LLC Power of Attorney filed by *Harman International Industries, Inc.* v. *ST Casestech, LLC*, for U.S. Pat. No. 11,589,329 Under Case No. IPR2024-01300, Dated Sep. 20, 2024, 4 pages.
St Casestech, LLC Power of Attorney filed by *Harman International Industries, Inc.* v. *ST Casestech, LLC*, for U.S. Pat. No. 8,805,692 Under Case No. IPR2024-01301, Dated Sep. 20, 2024, 4 pages.
St Casestech, LLC'S Mandatory Notices Pursuant to 37 C.F.R. § 42.8(b) filed by *Harman International Industries, Inc.* v. *ST Casestech, LLC*, for U.S. Pat. No. 11,589,329 Under Case No. IPR2024-01300, Dated Sep. 20, 2024, 8 pages.
St Casestech, LLC'S Mandatory Notices Pursuant to 37 C.F.R. § 42.8(b) filed by *Harman International Industries, Inc.* v. *ST Casestech, LLC*, for U.S. Pat. No. 8,805,692 Under Case No. IPR2024-01301, Dated Sep. 20, 2024, 8 pages.
Strand, et al. On the Feasibility of ASR in Extreme Noise Using the Parat Earplug Communication Terminal, IEEE, 2003, pp. 315-320.
Techiya's Opposition to Samsung's Motion for Summary Judgment of Invalidity under 35 U.S.C. § 112 of the '666 Patent (Redacted), Jul. 24, 2023, 30 pages.
Techiya's Sur-Reply to Samsung's Motion for Summary Judgment of Invalidity under 35 U.S.C. § 112 of the '666 Patent, Aug. 21, 2023, 5 pages.
Vraalsen, A Multimodal Context Aware Mobile Maintenance Terminal for Noisy Environments, 2004, pp. 79-92.

* cited by examiner

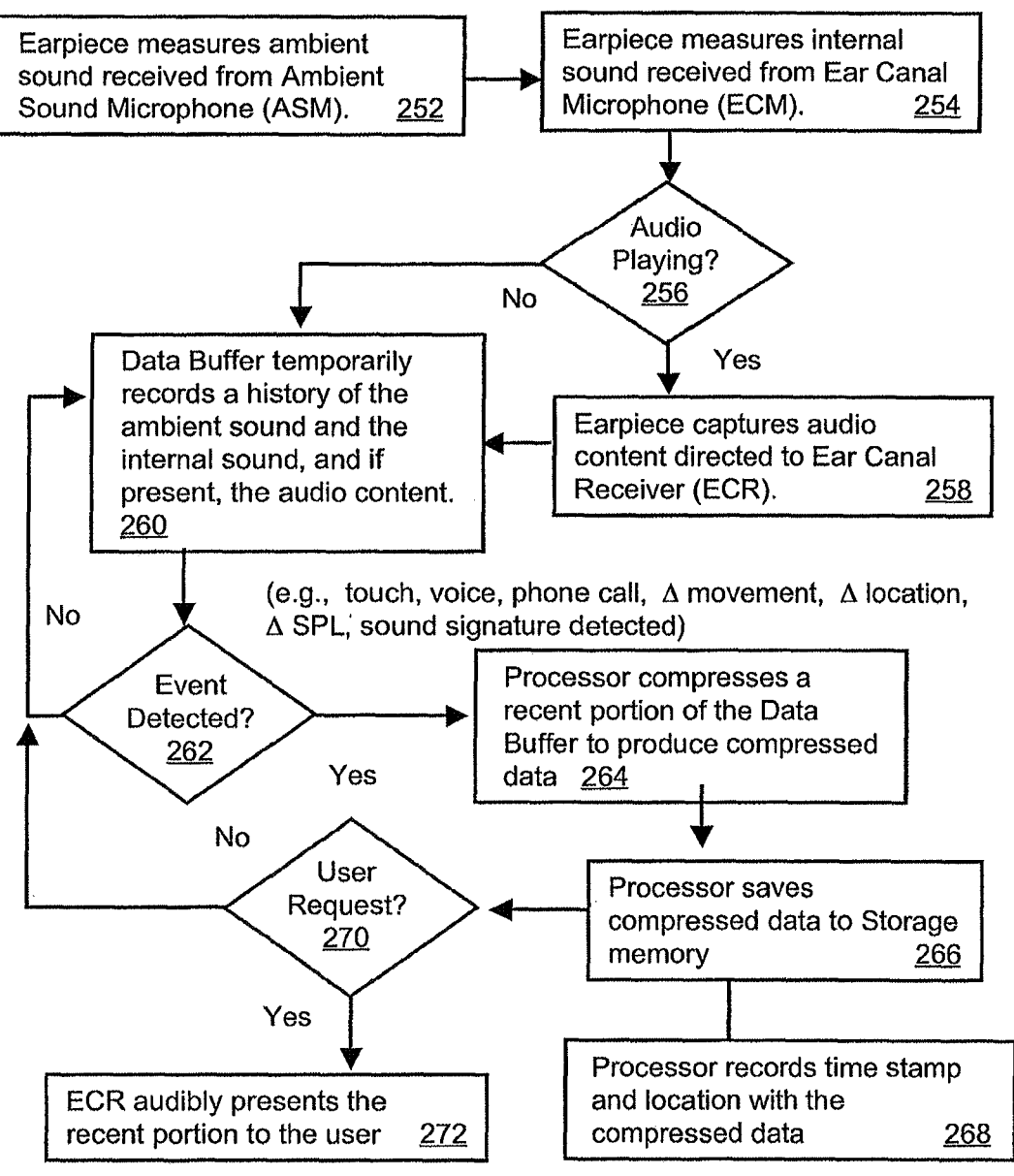

Earpiece measures ambient sound received from Ambient Sound Microphone (ASM).          252

Earpiece measures internal sound received from Ear Canal Microphone (ECM).          254

Audio Playing?          256

No

Yes

Data Buffer temporarily records a history of the ambient sound and the internal sound, and if present, the audio content.          260

Earpiece captures audio content directed to Ear Canal Receiver (ECR).          258

(e.g., touch, voice, phone call, Δ movement, Δ location, Δ SPL, sound signature detected)

No

Event Detected?          262

Yes

Processor compresses a recent portion of the Data Buffer to produce compressed data          264

No

User Request?          270

Processor saves compressed data to Storage memory          266

Yes

ECR audibly presents the recent portion to the user          272

Processor records time stamp and location with the compressed data          268

METHOD AND DEVICE FOR AUDIO RECORDING

CROSS-REFERENCE TO RELATED APPLICATION(S)

This application is a continuation of U.S. patent application Ser. No. 17/973,536, filed 26 Oct. 2022, which is a continuation of U.S. patent application Ser. No. 17/061,722, filed 2 Oct. 2020, which is a continuation of U.S. patent application Ser. No. 16/781,286, filed 4 Feb. 2020, now U.S. Pat. No. 10,856,092, which is a continuation of U.S. patent application Ser. No. 16/260,454 filed 29 Jan. 2019, now U.S. Pat. No. 10,616,702, which is a continuation of U.S. patent application Ser. No. 15/790,771, filed on Oct. 23, 2017, now U.S. Pat. No. 10,212,528, which is a continuation of U.S. patent application Ser. No. 15/137,730, filed on Apr. 25, 2016, now U.S. Pat. No. 9,900,718, which is a continuation of U.S. patent application Ser. No. 14/576,236, filed Dec. 19, 2014, now U.S. Pat. No. 9,323,899, which is a continuation of U.S. patent application Ser. No. 14/048,324, filed on Oct. 8, 2013, now U.S. Pat. No. 8,918,141, which is a divisional of U.S. patent application Ser. No. 13/556,509, filed on Jul. 24, 2012, now U.S. Pat. No. 8,582,782, which is a continuation of and claims priority to U.S. patent application Ser. No. 12/024,842 filed on Feb. 1, 2008, now U.S. Pat. No. 8,254,591, which claims the benefit of U.S. Provisional Patent Application Ser. No. 60/887,800, filed on Feb. 1, 2007, all of which are herein incorporated by reference in their entireties and to which the present application claims priority benefit to.

FIELD OF THE INVENTION

The present invention is generally directed to the detection and recording of acoustic events, and in particular, though not exclusively, to the detection and recording of acoustic events as measured by an earpiece.

BACKGROUND OF THE INVENTION

The human auditory system has been increasingly stressed to tolerate high noise and sound levels. However, excessive high level exposure over long durations can damage hearing. Moreover, a user's attention to sounds within the environment can be compromised when media devices such as music players, cell phones, and Bluetooth™ earpieces deliver audio to the ear.

In industrial environments where noise is frequently present, workers can be subject to loud excessive noises over long periods of time in addition to the sounds presented by the media devices. Although earplugs help suppress the noise and mitigate the physiological and psychological effects of the noise on the workers, there are few accurate indications of the noise exposure to which the workers are subjected.

A need therefore can be appreciated for assessing sound exposure levels in various environmental settings.

SUMMARY

Embodiments in accordance with the present invention provide a method and device for audio recording.

At least one exemplary embodiment is directed to the detection and recording of acoustic events, and in at least one exemplary embodiment is further directed to a device for sound reproduction, sound recording, audio forensics and audio communications using earpieces.

At least one exemplary embodiment is directed to a multiple earpiece device (e.g., a headset) which can include a left earpiece, a right earpiece, a memory and a processor. The left earpiece can include a left Ambient Sound Microphone (LASM) to capture ambient sound in an environment, and a left Ear Canal Microphone (LECM) to capture internal sound in a left ear canal. The right earpiece can include a right Ambient Sound Microphone (RASM) to capture the ambient sound in the environment and a right Ear Canal Microphone (RECM) to capture internal sound in a right ear canal. The internal sound can be an ambient sound, speech, or audio content portion resident in the ear canal. The memory (e.g., RAM) can record a history (e.g., Sound pressure level (SPL) as a function of time) of the ambient sound and the internal sound, and the processor can save a recent portion of the history responsive to an event. The event can be a touching of the headset, a recognizing of a voice command, a starting or ending of a phone call, or a scheduled time. In one configuration, the processor can trigger the event responsive to detecting an abrupt movement of the headset, or a change in location of the earpiece.

The memory can include a data buffer to temporarily capture the ambient sound and the internal sound, and a storage memory to save from the data buffer the recent portion of the history in a compressed data format responsive to a directive by the processor. In one configuration, the data buffer can be a circular buffer that temporarily stores the ambient sound and the internal sound at a current time point to a previous time point. The processor can save a last two minutes of the history, and audibly present the last two minutes responsive to a user request. The history can be at least one among a conversation, a voice mail, and an audio recording. Additionally, the history can record data (e.g., SPL values) from both earpieces. Also note that in at least one exemplary embodiment a single earpiece can be used. The earpiece can include an audio interface communicatively coupled to the processor to deliver audio content by way of a left Ear Canal Receiver (LECR) and a right ECR, wherein the memory records a history of the audio content with the residual sound and the internal sound. In one arrangement, at least a portion of the left earpiece and a portion of the right earpiece can constitute a microphone array, and the processor can increase a signal to noise ratio of the audio content with respect to the ambient sound using the microphone array. The processor can binaurally record the ambient sound and the internal sound from the left earpiece and the right earpiece.

At least one further exemplary embodiment is directed to an earpiece at least partially occluding an ear canal, which can include an Ambient Sound Microphone (ASM) to capture ambient sound in an environment, an Ear Canal Microphone (ECM) to capture internal sound in the ear canal, a memory to record a history of the ambient sound and the internal sound, and a processor operatively coupled to the ASM, the ECM and the memory to save a recent portion of the history responsive to an event. The event can be a touching of the headset, a recognizing of a voice command, a starting or ending of a phone call, a scheduled time, or an abrupt movement of the headset. The processor can save the history of at least one among a conversation, a voice mail, and an audio recording responsive to the event. In another arrangement, the processor can monitor the ambient sound for a Sound Pressure Level (SPL) change, and in response to detecting the SPL change commit the history to the memory.

At least one further exemplary embodiment is directed to an earpiece at least partially occluding an ear canal, which can include an Ambient Sound Microphone (ASM) to capture ambient sound in an environment, an Ear Canal Microphone (ECM) to capture internal sound in the ear canal, an Ear Canal Receiver (ECR) to deliver audio content to an ear canal, a memory to record a history of the ambient sound, the internal sound, and the audio content, and a processor operatively coupled to the ASM, the ECM and the memory to save a recent portion of the history responsive to an event. The processor can continually record the history in the memory. The event can be a touching of the headset, a recognizing of a voice command, a starting or ending of a phone call, or an abrupt movement of the headset.

At least one exemplary embodiment is directed to a method for audio recording, which can include the steps of measuring ambient sound in an environment, measuring internal sound in an ear canal, continually recording a history of the ambient sound and the internal sound, and saving a recent portion of the history responsive to detecting an event. The step of continually recording can include temporarily saving the history to a circular data buffer based on a chosen data management scheme (e.g., first-in first-out (FIFO)). A time stamp, a location, and the earpiece (e.g., if there are multiple earpieces) can also be recorded with the history. The method can include recording an audio content delivered to the ear canal with the history in a compressed data format. The event can be a touching of the headset, a recognizing of a voice command, a starting or ending of a phone call, an abrupt movement of the headset, or a scheduled time.

At least one further exemplary embodiment is directed to a method for audio recording, which can include measuring ambient sound in an environment, measuring internal sound in an ear canal, measuring audio content delivered to the ear canal, continually recording a history of the ambient sound, the internal sound and the audio content, and saving a recent portion of the history responsive to detecting an event that is at least one among a touching of the headset, a recognizing of a voice command, a starting or ending of a phone call, or an abrupt movement of the headset. The method can further include data compressing the recent portion of the history in a memory, and issuing a warning message to inform a user when a remaining memory receiving the recent portion of the history is below a predetermined value. The recent portion of the history can be audibly presented responsive to a user request.

BRIEF DESCRIPTION OF THE DRAWINGS

FIG. 3 is a flowchart of a method for audio recording in accordance with at least one exemplary embodiment;

4

Figure 9:
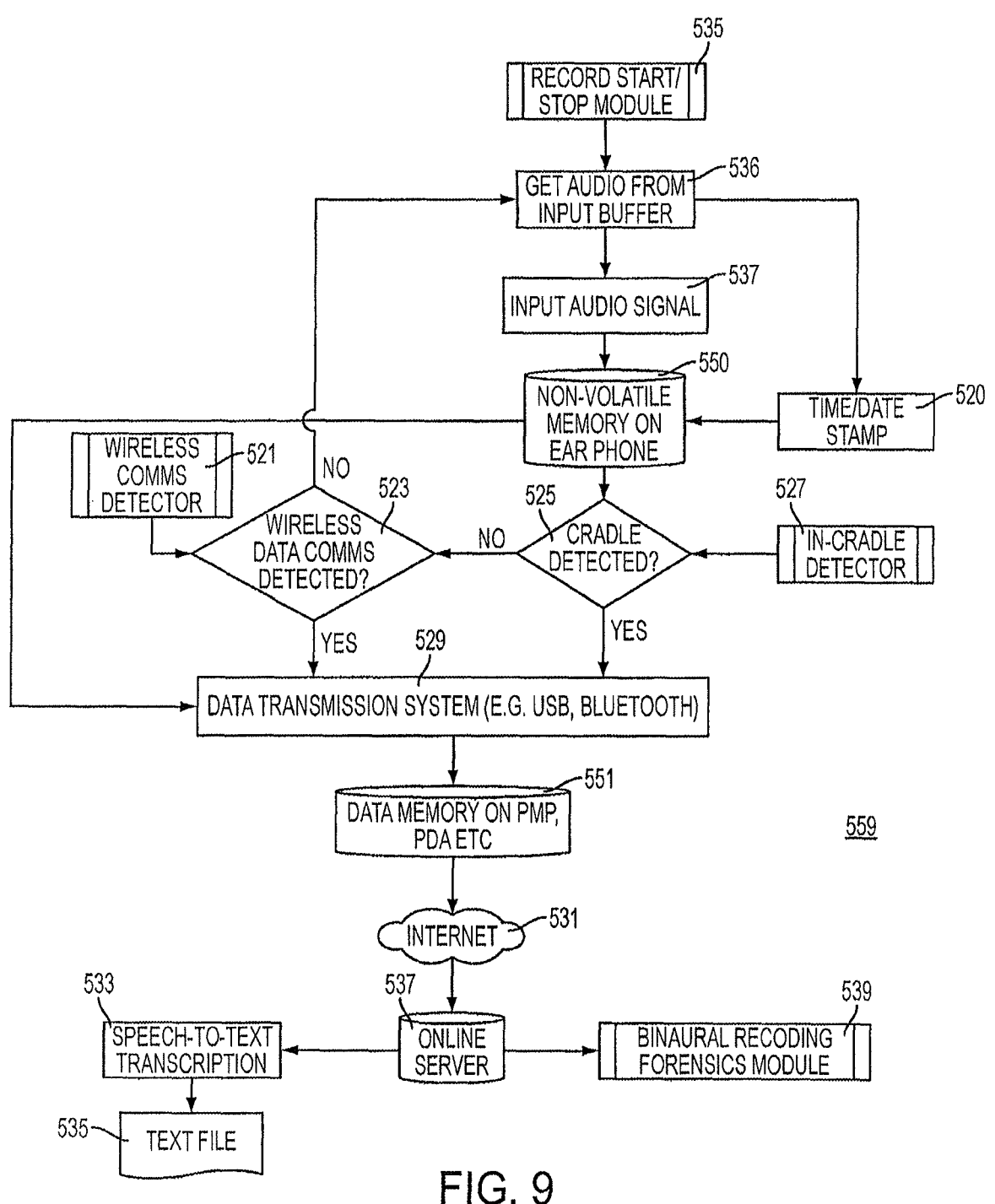
Figure 10:
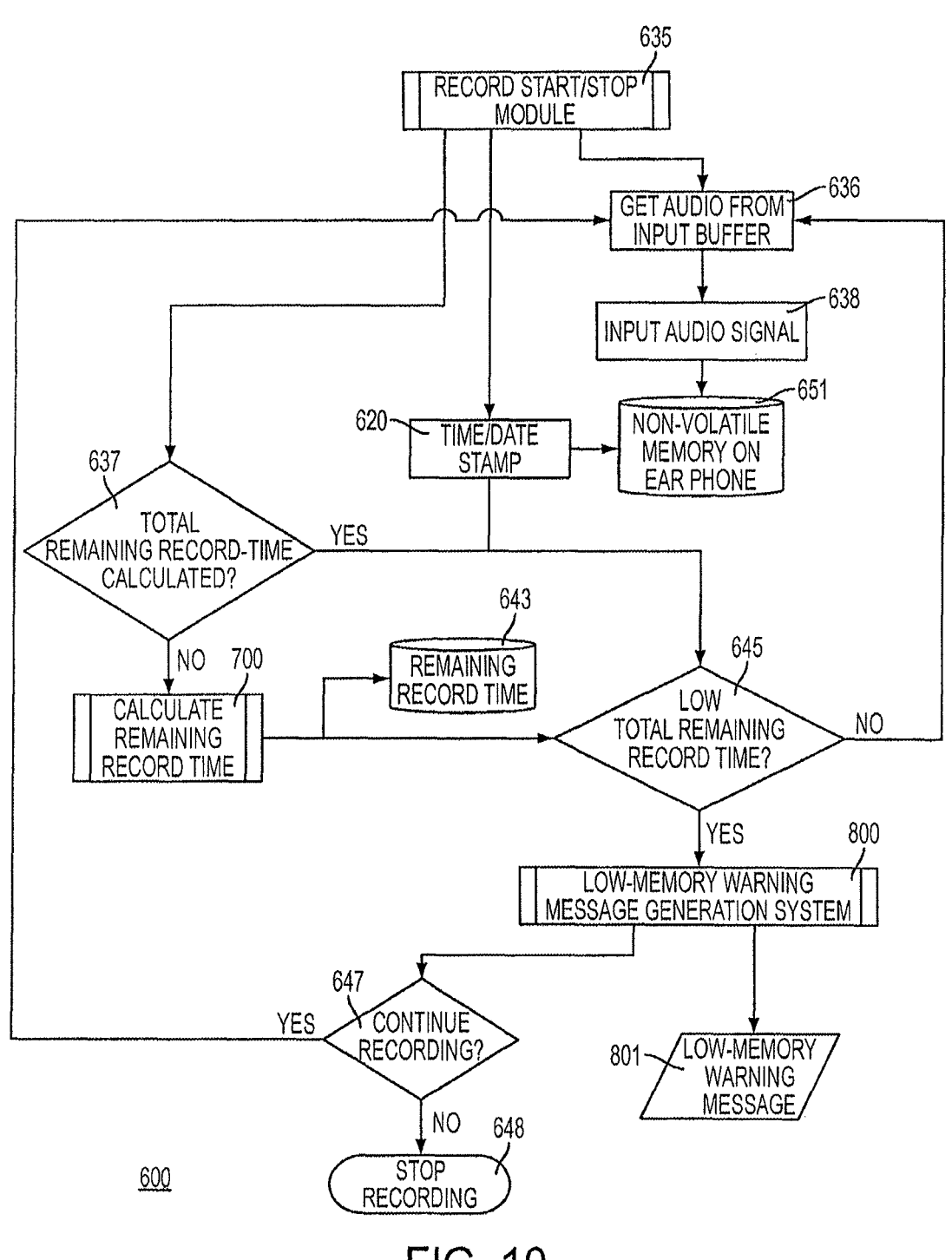
Figure 11:
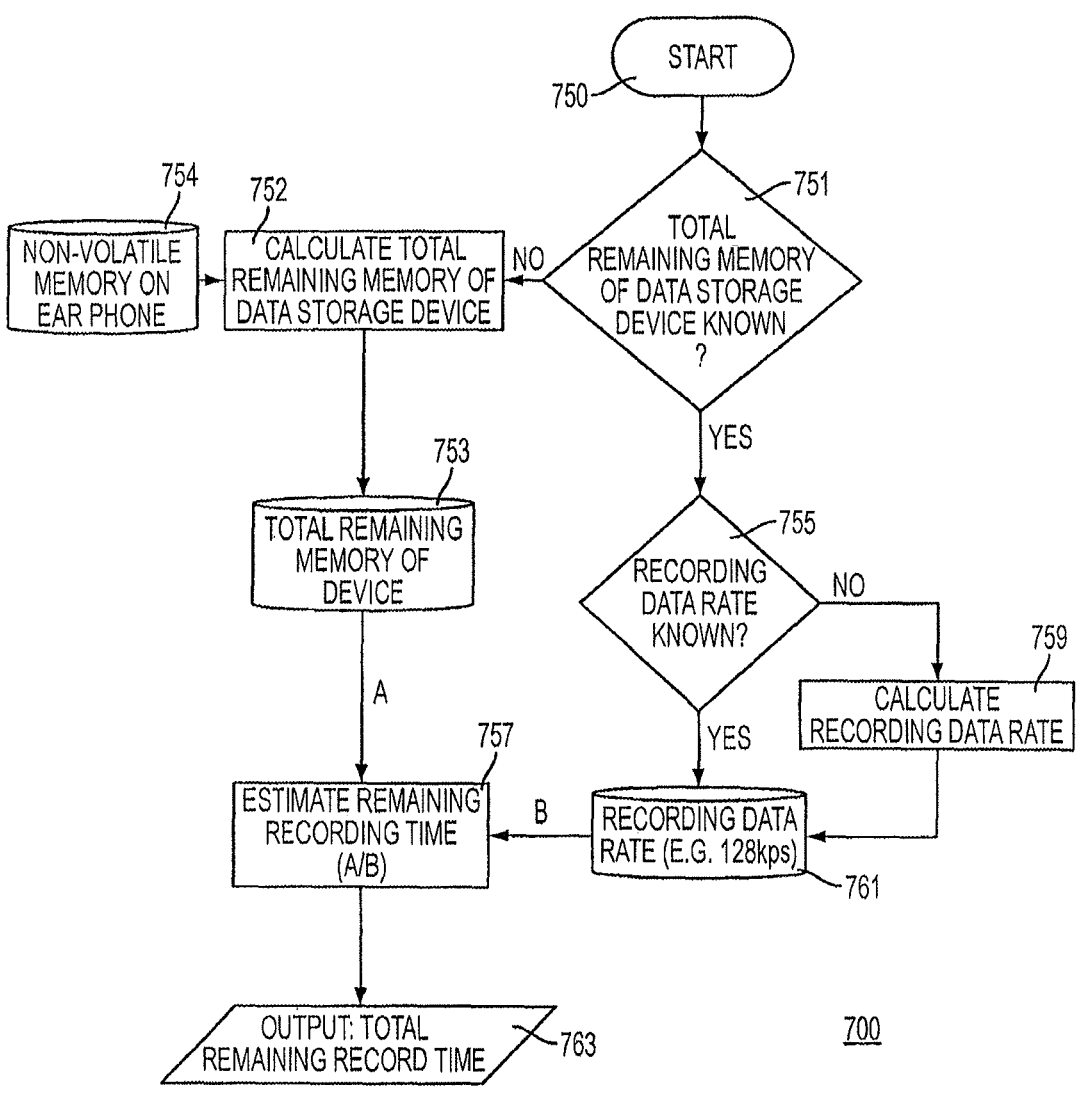
Figure 12:
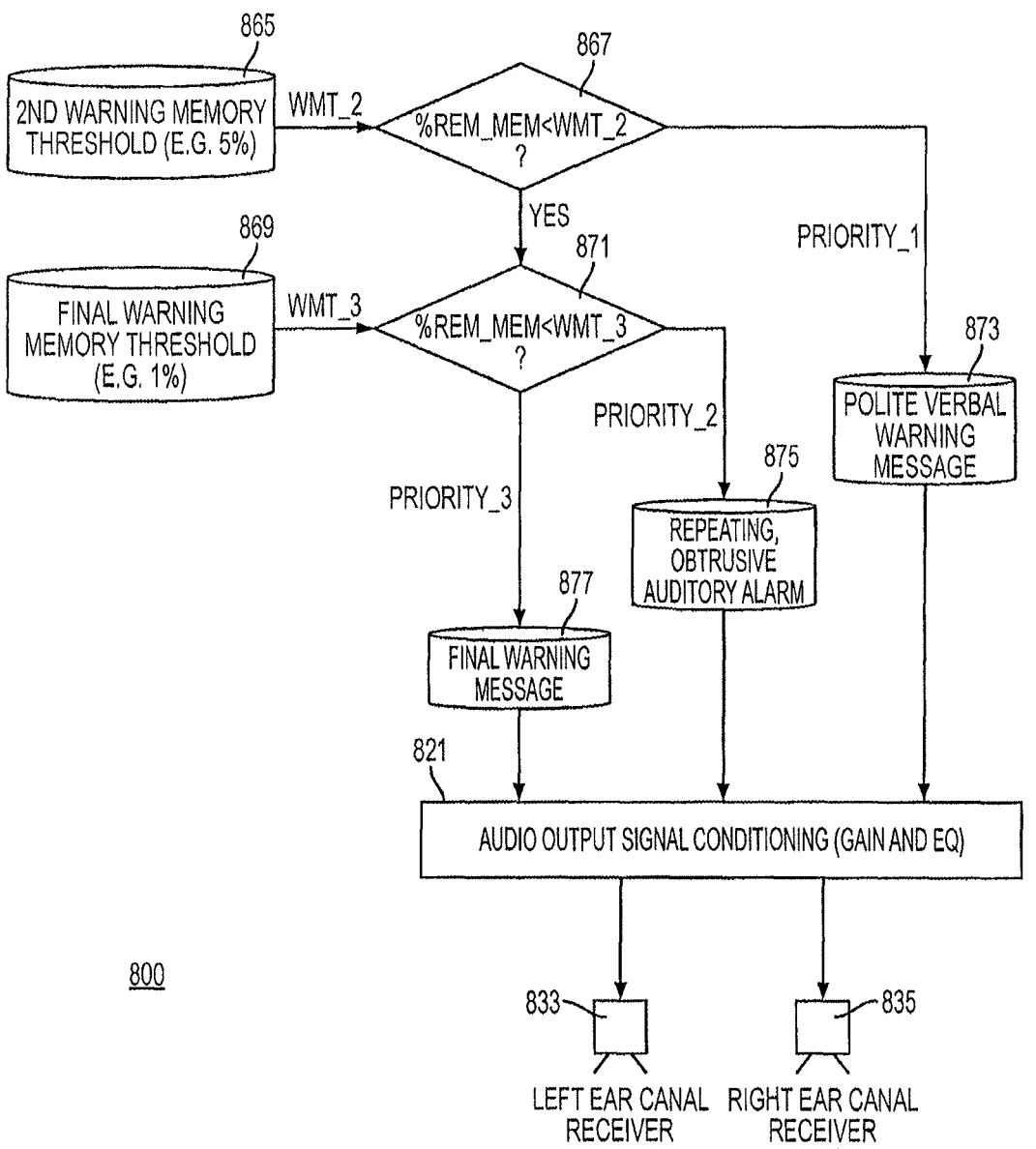

FIG. 9 is a flowchart of a method for forensic audio evaluation in accordance with at least one exemplary embodiment;

FIG. 10 is a flowchart of a method for low remaining-memory warning in accordance with at least one exemplary embodiment;

FIG. 11 is a flowchart of a method for remaining record-time in accordance with at least one exemplary embodiment; and FIG. 12 is a flowchart of a method for remaining memory in accordance with at least one exemplary embodiment.

DETAILED DESCRIPTION

The following description of at least one exemplary embodiment is merely illustrative in nature and is in no way intended to limit the invention, its application, or uses.

Processes, techniques, apparatus, and materials as known by one of ordinary skill in the relevant art may not be discussed in detail but are intended to be part of the enabling description where appropriate, for example the fabrication and use of transducers.

In all of the examples illustrated and discussed herein, any specific values, for example the sound pressure level change, should be interpreted to be illustrative only and non-limiting. Thus, other examples of the exemplary embodiments could have different values.

Note that similar reference numerals and letters refer to similar items in the following figures, and thus once an item is defined in one figure, it may not be discussed for following figures.

Note that herein when referring to correcting or preventing an error or damage (e.g., hearing damage), a reduction of the damage or error and/or a correction of the damage or error are intended.

Figure 1:
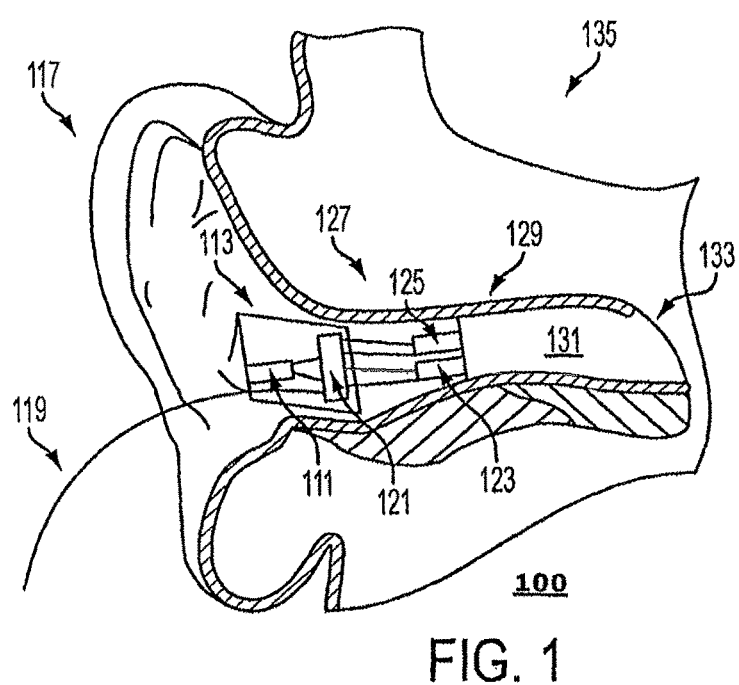
FIG. 1 is a pictorial diagram of an earpiece in accordance with at least one exemplary embodiment.

At least one exemplary embodiment of the invention is directed to an earpiece for ambient sound monitoring and warning detection. Reference is made to FIG. 1 in which an earpiece device, generally indicated as earpiece 100, is constructed and operates in accordance with at least one exemplary embodiment of the invention. As illustrated, earpiece 100 depicts an electro-acoustical assembly 113 for an in-the-ear acoustic assembly, as it would typically be placed in the ear canal 131 of a user 135. The earpiece 100 can be an in the ear earpiece, behind the ear earpiece, receiver in the ear, open-fit device, or any other suitable earpiece type. The earpiece 100 can be partially or fully occluded in the ear canal 131, and is suitable for use with users having healthy or abnormal auditory functioning.

Earpiece 100 includes an Ambient Sound Microphone (ASM) Ill to capture ambient sound, an Ear Canal Receiver (ECR) 125 to deliver audio to an ear canal 131, and an Ear Canal Microphone (ECM) 123 to assess a sound exposure level within the ear canal 131. The earpiece 100 can partially or fully occlude the ear canal 131 to provide various degrees of acoustic isolation. The assembly is designed to be inserted into the users ear canal 131, and to form an acoustic seal with the walls 129 of the ear canal at a location 127 between the entrance 117 to the ear canal 131 and the tympanic membrane (or ear drum) 133. Such a seal is typically achieved by means of a soft and compliant housing of assembly 113. Such a seal creates a closed cavity 131 of approximately 5 cc between the in-ear assembly 113 and the tympanic membrane 133. As a result of this seal, the ECR (speaker) 125 is able to generate a full range bass response when reproducing sounds for the user. This seal also serves to significantly reduce the sound pressure level at the user's eardrum 133 resulting from the sound field at the entrance to the ear canal 131. This seal is also a basis for a sound isolating performance of the electro-acoustic assembly 113.

Located adjacent to the ECR 125, is the ECM 123, which is acoustically coupled to the (closed) ear canal cavity 131. One of its functions is that of measuring the sound pressure level in the ear canal cavity 131 as a part of testing the hearing acuity of the user as well as confirming the integrity of the acoustic seal and the working condition of the earpiece 100. In one arrangement, the ASM 111 can be housed in the assembly 113 to monitor sound pressure at the entrance to the occluded or partially occluded ear canal 131. All transducers shown can receive or transmit audio signals to a processor 121 that undertakes audio signal processing and provides a transceiver for audio via the wired or wireless communication path 119.

Figure 2:
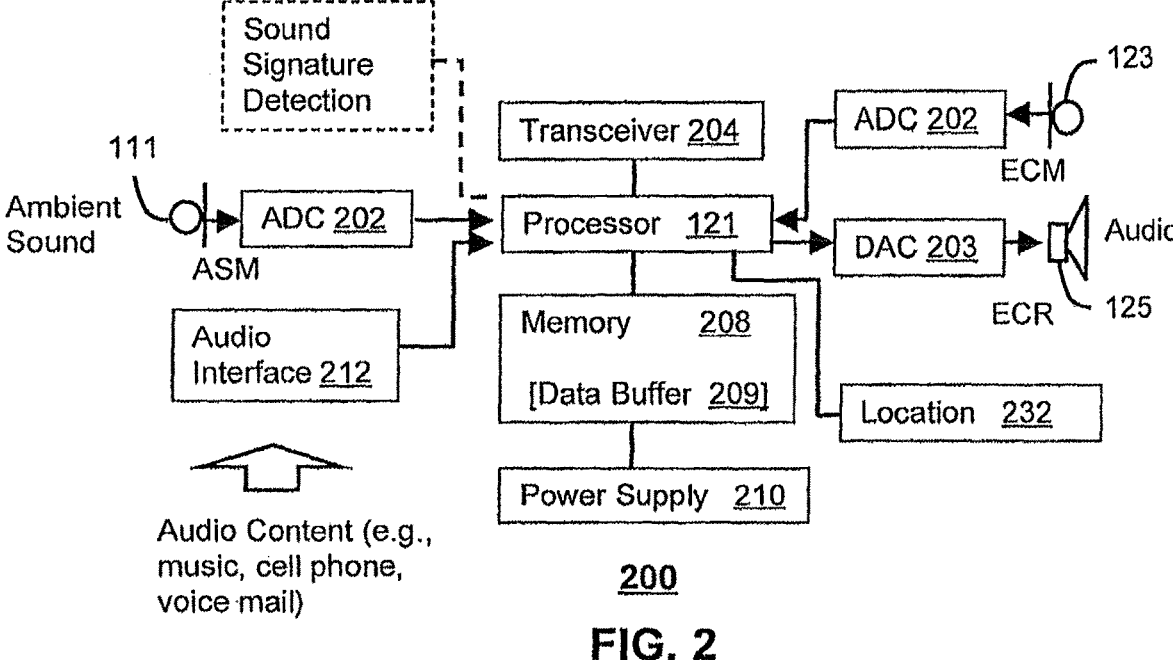
FIG. 2 is a block diagram of the earpiece in accordance with at least one exemplary embodiment.

Referring to FIG. 2, a block diagram 200 of the earpiece 100 in accordance with an exemplary embodiment is shown. As illustrated, the earpiece 100 can include the processor 121 operatively coupled to the ASM 111, ECR 125, and ECM 123 via one or more Analog to Digital Converters (ADC) 202 and Digital to Analog Converters (DAC) 203. The processor 121 can utilize computing technologies such as a microprocessor, Application Specific Integrated Chip (ASIC), and/or digital signal processor (DSP) with associated storage memory 208 such as Flash, ROM, RAM, SRAM, DRAM or other memory based technologies for controlling operations of the earpiece device 100. The processor 121 can also include a clock to record a time stamp.

The memory 208 can store program instructions for execution on the processor 121 as well as captured audio processing data. For instance, memory 208 can be off-chip and external to the processor 121, and include a data buffer 209 to temporarily capture the ambient sound and the internal sound as a history, and a storage memory to save from the data buffer the recent portion of the history in a compressed data format responsive to a directive by the processor. The data buffer 209 can be a circular buffer that temporarily stores audio sound at a current time point to a previous time point. It should also be noted that the data buffer 209 can in one configuration reside on the processor 121 to provide high speed data access. The storage memory 208 can be non-volatile memory such as SRAM to store captured or compressed data format.

The earpiece 100 can include an audio interface 212 operatively coupled to the processor 121 to receive audio content, for example from a media player or cell phone, and deliver the audio content to the processor 121. The processor 121 responsive to detecting events can among various operations save the history in the data buffer 209 to the longer term storage memory 208. The processor 121 by way of the ECM 123 can also actively monitor the internal sound exposure level inside the ear canal 131 and adjust the audio to within a safe and subjectively optimized listening level range.

The earpiece 100 can further include a transceiver 204 that can support singly or in combination any number of wireless access technologies including without limitation Bluetooth™, Wireless Fidelity (WiFi), Worldwide Interoperability for Microwave Access (WiMAX), and/or other short or long range communication protocols. The transceiver 204 can also provide support for dynamic downloading over-the-air to the earpiece 100. It should be noted that next generation access technologies can also be applied to the present disclosure.

The location receiver 232 can utilize common technology such as a common GPS (Global Positioning System) receiver that can intercept satellite signals and therefrom determine a location fix of the earpiece 100.

The power supply 210 can utilize common power management technologies such as replaceable batteries, supply regulation technologies, and charging system technologies for supplying energy to the components of the earpiece 100 and to facilitate portable applications. A motor (not shown) can be a single supply motor driver coupled to the power supply 210 to improve sensory input via haptic vibration. As an example, the processor 121 can direct the motor to vibrate responsive to an action, such as a detection of a warning sound or an incoming voice call.

The earpiece 100 can further represent a single operational device or a family of devices configured in a master-slave arrangement, for example, a mobile device and an earpiece. In the latter embodiment, the components of the earpiece 100 can be reused in different form factors for the master and slave devices.

FIG. 3 is a flowchart of a method 250 for audio recording in accordance with an exemplary embodiment. The method 250 can be practiced with more or less than the number of steps shown and is not limited to the order shown. To describe the method 250, reference will be made to components of FIG. 1 and FIG. 2, although it is understood that the method 250 can be implemented in any other manner using other suitable components. The method 250 can be implemented in a single earpiece, a pair of earpieces, headphones, or other suitable headset audio delivery device.

The method 250 can start in a state wherein the earpiece 100 has been inserted and powered on. As shown in step 252, the earpiece 100 can measure ambient sounds in the environment received at the ASM 111. Ambient sounds correspond to sounds within the environment such as the sound of traffic noise, street noise, conversation babble, or any other acoustic sound. Ambient sounds can also correspond to industrial sounds present in an industrial setting, such as factory noise, lifting vehicles, automobiles, and robots to name a few.

Although the earpiece 100 when inserted in the ear can partially occlude the ear canal, the earpiece 100 may not completely attenuate the ambient sound. During the measuring of ambient sounds in the environment, the earpiece 100 can also measure internal sounds, such as ear canal levels, via the ECM 123 as shown in step 254. The passive aspect of the earpiece 100, due to the mechanical and sealing properties, can provide upwards of a 22 dB noise reduction. However, portions of ambient sounds higher than the noise reduction level may still pass through the earpiece 100 into the ear canal thereby producing residual sounds. For instance, high energy low frequency sounds may not be completely attenuated. Accordingly, residual sound may be resident in the ear canal producing internal sounds that can be measured by the ECM 123. Internal sounds can also correspond to spoken voice when the user is speaking or audio content delivered by the ECR 125 to the ear canal 131 by way of the audio interface 212.

If at step 256, audio is playing (e.g., music, cell phone, etc.), the earpiece 100 at step 258 can capture audio content directed to the ECR 125. Portions of the audio content can be saved in the data buffer 209 with the ambient sound and internal sounds. For instance, the audio interface 212 can deliver sound to the occluded ear canal 131 via the ECR 125. The audio interface 212 can receive the audio content from at least one among a portable music player, a cell phone, and a portable communication device. For instance, a user can elect to play music through the earpiece 100 which can be audibly presented to the ear canal 131 for listening. The user can also elect to receive voice communications (e.g., cell phone, voice mail, messaging) via the earpiece 100. The user can receive audio content for voice mail or a phone call directed to the ear canal via the ECR 125.

At step 260, the data buffer 209 temporarily records a history of the ambient sound and the internal sound; and if present, the audio content. The internal sound can correspond to residual ambient sound in the ear canal, speech generated by the user wearing the earpiece 100 when talking, or audio content delivered from the audio interface 212 from a media device (e.g., iPod®, cell phone, radio, etc.). The history can correspond to at least one among a conversation, a voice mail, and an audio recording. For instance, the portions of audio data from a voice mail can be stored for later retrieval (e.g., phone number, address, names, etc.).

Notably, the data buffer 209 stores the ambient sound from the ASM 111 and internal sound from the ECM 123 only temporarily until an event is detected. In one arrangement, the data buffer 209 can temporarily store at least 2 minutes of recording history. The data buffer 209 continually buffers in data while the last data samples in time (unable to be stored in the data buffer 209 due to limited memory) are discarded from the data buffer 209 to make room for the new data. The processor 121 can also interleave the data onto the data buffer 209 during real-time continuous data acquisition.

If at step 262, an event is detected the processor can proceed to save a history of the ambient sound, internal sound, and audio content in the data buffer 209 to the memory 208. An event can correspond to a user event such as a touching of the headset, a recognizing of a voice command, a starting or ending of a phone call, or a scheduled event. The event can also be due to a change in Sound Pressure Level (SPL) or a detected sound signature; that is, a specific sound within the ambient sound (e.g., "horn", "siren", "help"). The processor 121 can monitor the ambient sound for a Sound Pressure Level (SPL) change event, and in response to detecting the SPL change event commits the audio history on the data buffer 209 to the memory 208. For instance, the earpiece 100 can commit recently captured data on the data buffer 209 to the memory 208 responsive to detecting a loud explosion or crashing sound. The earpiece 100 can continue back to step 260 if an event is not detected, while continuing to monitor for events at step 262.

The event can also correspond to an abrupt movement or a change in location of the earpiece 100. For instance, the processor can trigger the event responsive to detecting an abrupt movement of the headset, for instance, due to an accident, or a change in location of the earpiece, for instance, an abrupt aggregated movement. In such regard, the earpiece 100 performs as a black box to record the few minutes prior to an event. Notably, this audio history is available on the data buffer 209 at the time of the event. Moreover, if dual earpieces are used (e.g., headphones), the processor 121 can binaurally record the ambient sound and the internal sound (and, if present, the audio content) from a left earpiece and a right earpiece. The binaural data can be further analyzed to identify a location of sound sources triggering the event.

Upon detecting the event at step 262, the processor 121 can apply data compression techniques to reduce the dimensionality of the data as shown in step 264. The processor 121 can retrieve data from the data buffer 209, compress the data, and store the data in the storage memory 208 as shown in step 266. For instance, the processor 121 can implement a voice coding (vocoder) operation to compress the data from Pulse Code Modulation (PCM) format to a smaller memory footprint format (e.g., EFR723, EFR726, EFR729). If audio content is present, the processor 121 can stream the data from audio interface 212 in an already compressed format (e.g., MP3, AAC, WMA, etc.) Other audio compression techniques can be used for storing the data to the memory 208.

The processor 121 can also time stamp the data (e.g., D/M/Y, hh:mm:ss, etc.) and record a location (e.g., latitude, longitude, elevation, degrees) of the earpiece at the time of the event, as shown in step 268. For instance, in response to an abrupt movement of the earpiece 100 due to an accident, the processor 121 can capture the history of the audio prior to the accident, as well as the time and the location. This information can then be reported to a system that monitors the earpiece 100 for reporting a potential accident or alarming incident. The processor 121, can also tag the data in the storage memory 208 with a filename or header that reflects the condition of the user event. For instance, the header can be saved with the history and include the time stamp, location, and event type (user initiated, abrupt movement, location change, etc.).

If at step 270 a user request (or any other request) is initiated to retrieve stored data, the earpiece 100 can audibly present the recent portion of the history to the user via the ECR 125, as shown in step 272. The recent portion can include any historic audio data previously captured (by way of ASM, ECM, ECR) and stored to the memory 208. Notably, the processor 121 can keep track (e.g., look-up table) of the recent portions stored in the memory 208. For instance, a first entry in the memory 208 can correspond to a recording at 1 PM, and a second entry can correspond to a recording at 1:40 PM. The earpiece 100 can continue back to step 260 if a user request is not received, and continue to monitor for a user request.

The user request can also correspond to a system request to retrieve audio data from the earpiece 100. For instance, the user can subscribe to a service that stores the audio data when memory capacity is reached. Upon the processor determining that memory capacity is full, the earpiece 100 by way of the transceiver 204 can inform the service to retrieve (upload) data from the earpiece. A service provider of the service can then download the data from the earpiece 100 and forensically analyze content within the audio (e.g., spoken commands, passing sounds, voice identification, etc.)

Figure 4:
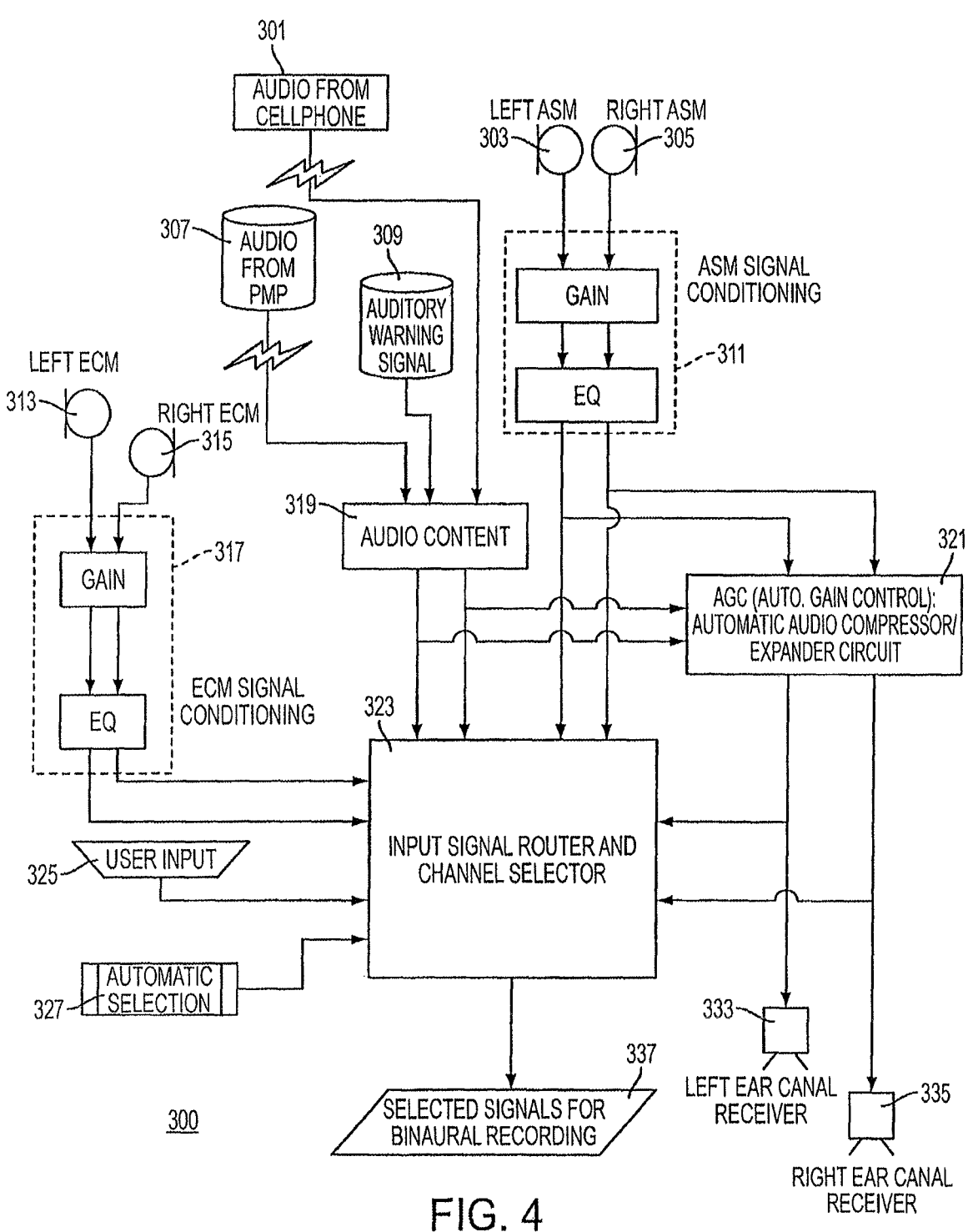
FIG. 4 is a block diagram for audio selection in accordance with at least one exemplary embodiment.

FIG. 4 is a block diagram 300 for audio selection in accordance with an exemplary embodiment. To describe the block diagram 300, reference will be made to components of FIG. 2, although it is understood that the block diagram 300 can be implemented in any other manner using other suitable components. The block diagram 300 can be implemented in a single earpiece, a pair of earpieces, headphones, or other suitable headset audio delivery device.

Block diagram 300 describes an input audio channel selection system to select which audio signals are recorded using an "Always-on" Binaural Recording System (AO-BRS). Input signals to the AOBRS comprise the signal generated by one or both the Ear Canal Microphones (left ECM 313 and right ECM 315), which are processed using gain and equalizer (EQ) circuitry 317 (which may be implemented using analog or digital electronics). Other input signals may comprise one or both Ambient Sound Microphones (left ASM 303 and right ASM 305) from separate left and right headset electroacoustic assemblies, or from the output of multiple ASM signals in the same right headset electroacoustic assembly. The ASM signals are processed using gain and equalizer circuitry 311 (which may be implemented using analog or digital electronics) housed in assembly 113. Audio Content 319 can be recorded during simultaneous reproduction with left and right Ear Canal Receivers 333, 335, via the automatic gain control (AGC) circuitry 321 (which may comprise either or both analog or digital signal processing). Audio Content 319 may be, for example, from a cell-phone 301; a Personal Media Player (PMP) 307; or an auditory warning signal 309 such as a low battery alarm generated by the AOBRS or from a second device such as a second data storage system. The audio signals from circuitry 317, 319, 311, and 321 are selected for recording 337 using the switching assembly 323, and configured either manually with user input system 325 (e.g. using buttons mounted on the electroacoustic headset system) or with automatic selection 327 which may be initiated in response to a specific record start/stop command, for example, generated by the system 449 described in FIG. 6.

Figure 5:
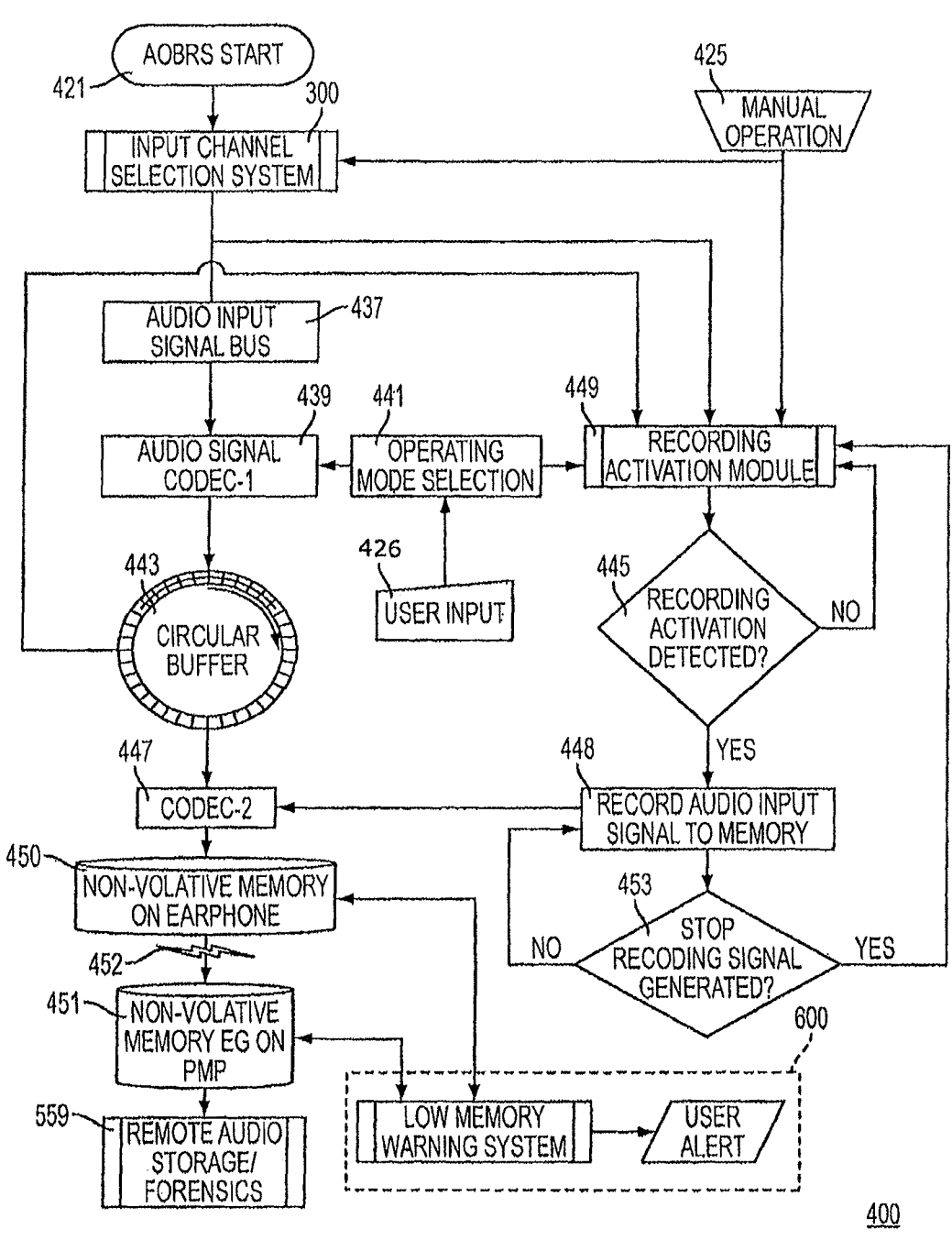
FIG. 5 is a block diagram for always-on binaural recording in accordance with at least one exemplary embodiment.

FIG. 5 is a block diagram 400 for an "Always-On" Binaural Recording System (AOBRS) in accordance with an exemplary embodiment. To describe the block diagram 400, reference will be made to components of FIG. 2, although it is understood that the block diagram 400 can be implemented in any other manner using other suitable components. The block diagram 400 can be implemented in a single earpiece, a pair of earpieces, headphones, or other suitable headset audio delivery device.

Figure 6:
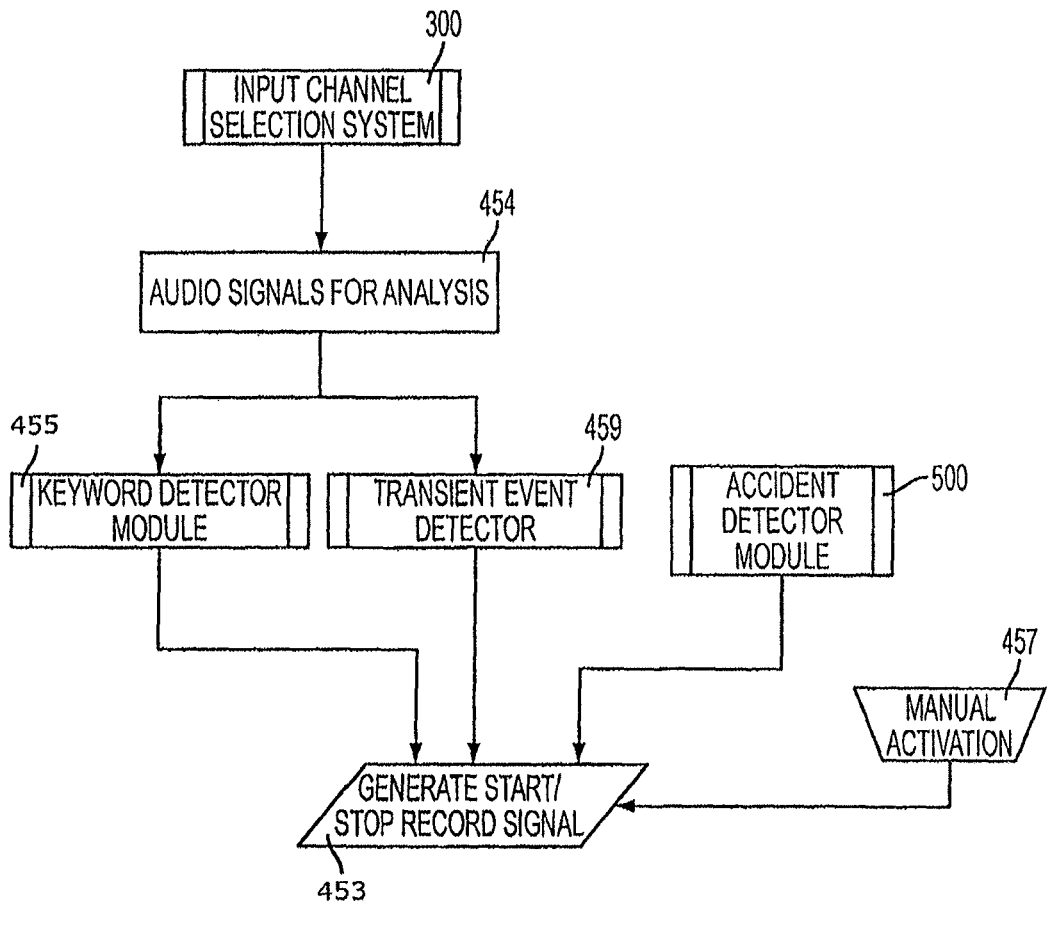
FIG. 6 is a block diagram for activating audio recording in accordance with at least one exemplary embodiment.

Following activation at step 421 and selection (300 shown in FIG. 4) of the audio signals to be recorded (for example, by manual operation 425), the selected audio signals 437 are analyzed by the recording activation circuitry 449 described in FIG. 6. Depending on the operating mode selected 441 (for example, by user input 426), the audio input audio signals 437 are first processed by an optional audio signal CODEC 439, which may reduce the data bit-rate of the signal using either a lossy or lossless data compression system. The audio data is then continuously recorded to a circular data buffer 443 which in the preferred embodiment is housed within the earpiece 100, or on a second device such as a Personal media player (PMP). The circular buffer 443 consists of computer memory, and is a familiar device for those skilled in the art. Following recording activation determined by decision unit 445, the contents of the circular data buffer 443 are recorded to a second non-volatile memory 450, which may be at a compressed data rate using audio signal CODEC 447 (which may use a lossy or loss-less data compression system) receiving recorded audio 448. The recording may continue until a stop recording signal is generated 453. With either a wired or wireless data communication system 452, the contents of the data storage 450 may be stored on a separate data memory device 451, such as a portable hard drive. The remaining data memory of either or both systems 450 and 451 are monitored using a low memory warning system (see 600 FIG. 10), which alert the user when remaining memory is low. A remote audio forensic analysis system 559 described in FIG. 9 can analyze the contents of the first 450 or second 451 audio data storage system, for example, following a detected accident.

FIG. 6 is a block diagram for activating audio recording by recording activation circuitry 449 in accordance with an exemplary embodiment. To describe the block diagram, reference will be made to components of FIG. 2, although it is understood that the block diagram can be implemented in any other manner using other suitable components. The block diagram can be implemented in a single earpiece, a pair of earpieces, headphones, or other suitable headset audio delivery device.

The input audio signal for analysis is selected with the input channel selection system 300 described in FIG. 4. The signals 454 comprise the ASM signals from one or both earphones (though different audio signals may be recorded to data memory for storage). A keyword detector module 455 analyzes the input signals 454 and activates or deactivates recording 453 if specific verbal commands are detected (e.g. "Start", "Stop", which may be in multiple languages). Alternatively, or additionally, a method 459 for Transient Event Detection (described in FIG. 7) generates a stop or start signal to the system 300 in response to a detected transient in signal 454 with a particular temporal envelope profile. Alternatively, or additionally, an accident detector module 500 (see FIG. 8) generates a stop or start signal to the system 300 in response to a particular user biological state or movement. Alternately or additionally, a stop or start signal 453 is generated to the system 300 in response to a manual user activation 457, such as with a switch mounted on the earphone assembly.

Figure 7:
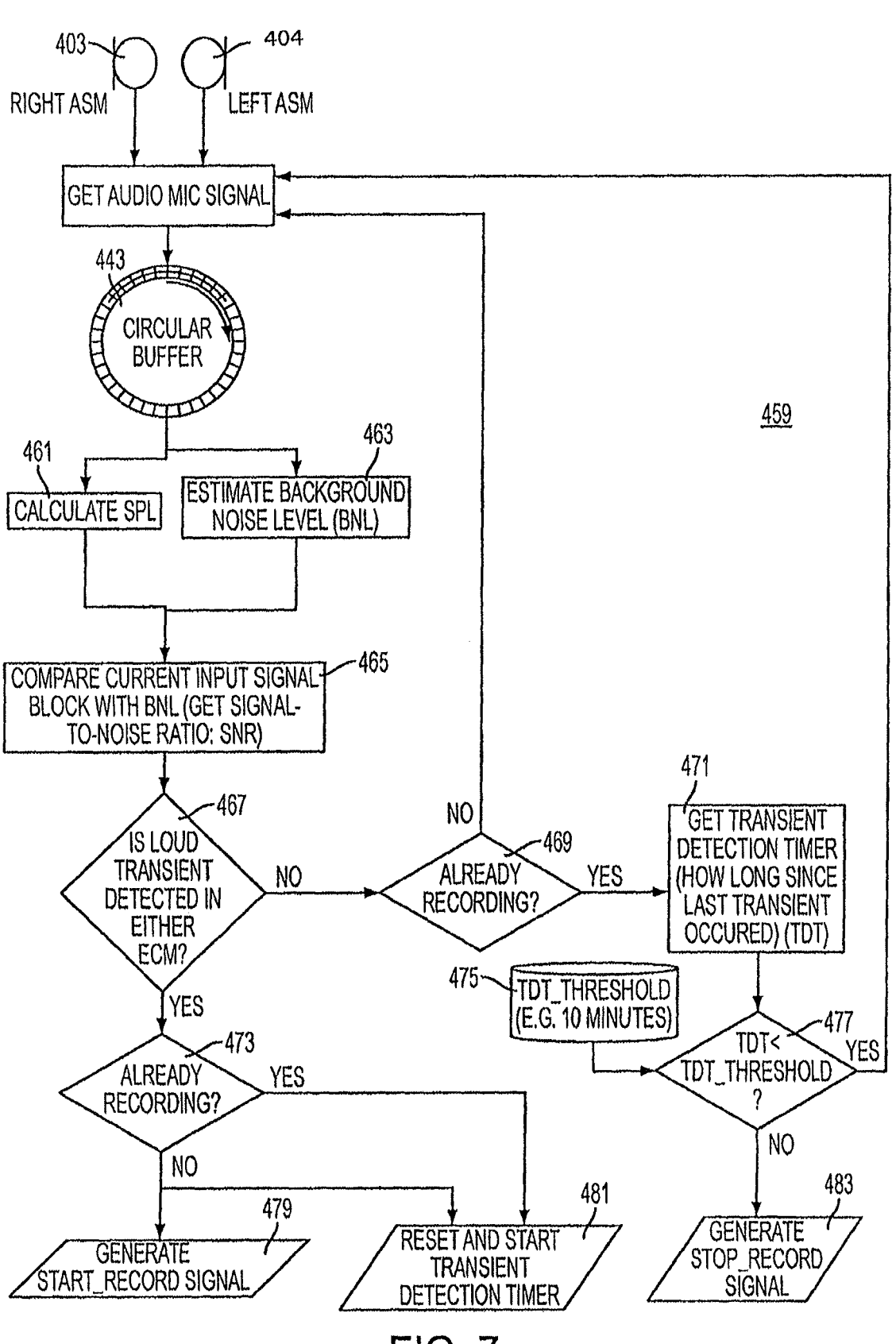
FIG. 7 is a flowchart of a method for transient event detection in accordance with at least one exemplary embodiment.

FIG. 7 is a flowchart further detailing the method 459 for transient event detection in accordance with an exemplary embodiment. The method 459 can include more or less than the number of steps shown and is not limited to the order of the steps. To describe the method 459, reference will be made to components of FIG. 2, although it is understood that the method 459 can be implemented in any other manner using other suitable components. The method 459 can be implemented in a single earpiece, a pair of earpieces, headphones, or other suitable headset audio delivery device.

Transient Event detection generates a stop or start signal to the system 300 in response to a detected transient in either or both the ASM signals 403, 404 (which may be from the same or different earphones). The audio data is continuously recorded to a circular data buffer 443, and a recent history of data samples (e.g. the past 10 ms) is used to estimate the SPL 461 at the entrance to the occluded ear canal 131 (e.g. in dB). The Background Noise Level (BNL) is also estimated at step 463 from a running time-smoothed average of the SPL, which may use circuitry to remove transient peaks in the SPL to calculate the BNL. If the decision unit 467 deems that the difference between the SPL 461 and BNL 463 is less than a predefined amount (which may be determined on a frequency selective basis)—as calculated with unit 465— then the recording is stopped 469 if it is already activated. If the recording is already active, then the Transient Detection Timer (TDT) 471 (which is the time since recording was activated) is compared with a predefined constant 475 using comparator 477, and if the TDT 471 is greater than the threshold 475 then recording is stopped 483. Alternatively, if a loud transient is detected 467, then the TDT clock is started 479 and recording of the circular buffer 443 to a second data storage device is initiated; and if recording is already activated (as determined at step 473), the TDT clock is reset and restarted, at step 481.

Figure 8:
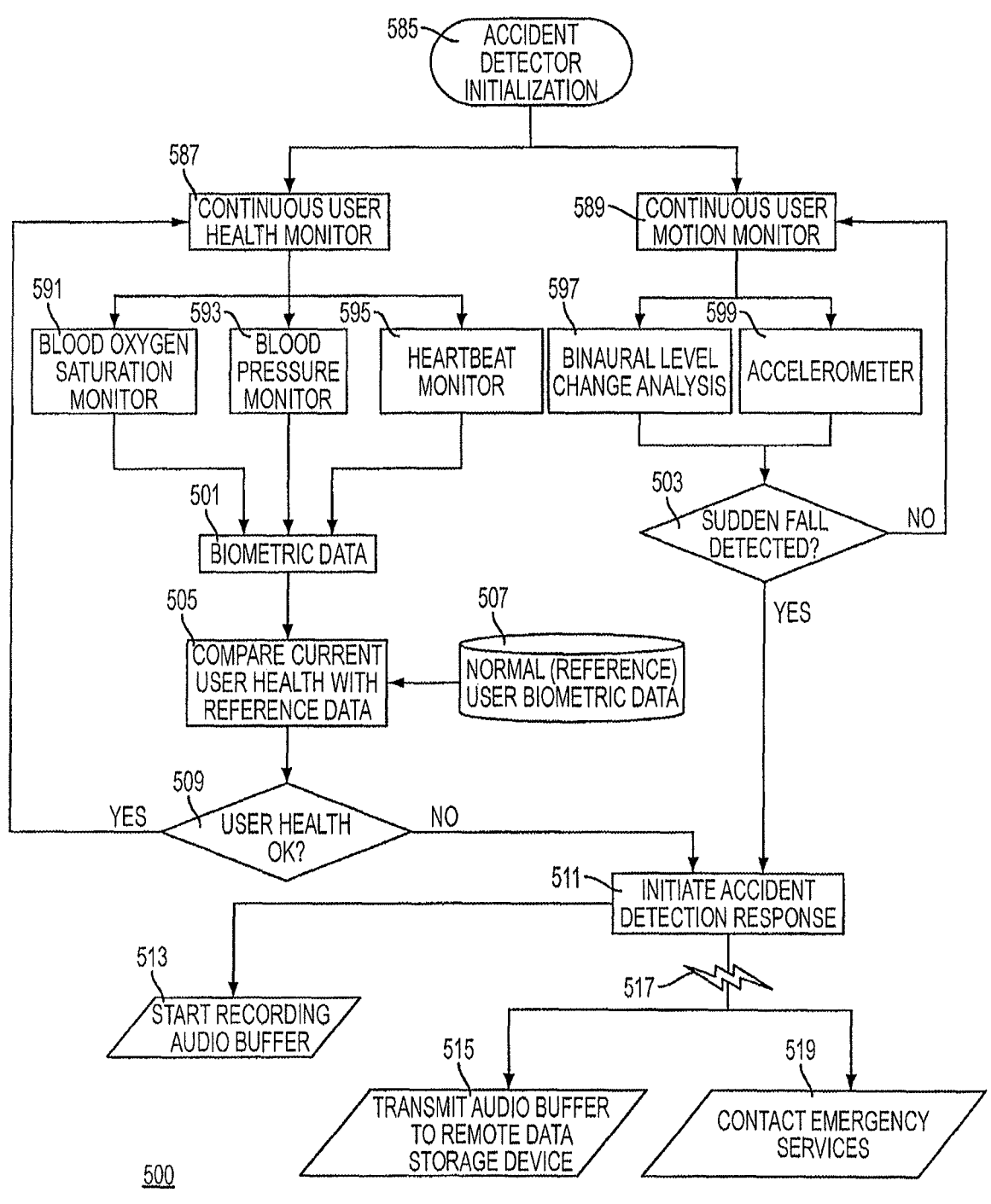
FIG. 8 is a flowchart of a method for event detection in accordance with at least one exemplary embodiment.

FIG. 8 is a flowchart of a method 500 for event detection in accordance with an exemplary embodiment. The method 500 can include more or less than the number of steps shown and is not limited to the order of the steps. To describe the method 500, reference will be made to components of FIG. 2, although it is understood that the method 500 can be implemented in any other manner using other suitable components. The method 500 can be implemented in a single earpiece, a pair of earpieces, headphones, or other suitable headset audio delivery device.

In one embodiment, the method 500 describes an accident detection platform, with the purpose of recording the audio signals selected in the system 300 process in FIG. 4 in response to a detected accident involving an AOBRS user. Following activation of accident detection 585, aspects of both the User's health 587 and physical motion 589 can be simultaneously and continuously monitored. Aspects of user health may include (but are not limited to) blood oxygen saturation 591, blood pressure 593 and heart-rate 595. These health aspects may be monitored using a probe mounted on the earphone device. The resulting biometric data 501 is compared SOS with a set of reference (normal, healthy) data 507, which may be from a database adapted to the particular user, or from a database generalized for users of a similar age, sex etc. If the comparison SOS of current biometric data 501 and reference data 507 indicates a sudden discrepancy, such as a drop in blood pressure 593, then decision unit 509 initiates a specific response 511. The user motion sensor system 589 monitors the location of the user using either of or a combination of analysis of the sound level at each earphone 597 using the output of the ASMs 403, 404 in both the left and right earphone; and/or an analysis of the spatial acceleration of the earphone device using accelerometers 599 and or internal sensors housed within the earphone assembly. If either or both the motion sensors 597, 599 indicate a sudden movement indicative of a fall, then decision unit 503 initiates a specific response 511. Such specific responses include starting the binaural recording system 513, and transmitting selected audio signals (see FIG. 4) to a second data storage device 515, which may involve a wireless data communication system 517, and may automatically invoke a system to alert the emergency services of a detected accident involving the AOBRS user 519.

FIG. 9 is a flowchart of a method 559 for forensic audio evaluation in accordance with an exemplary embodiment. The method 559 can include more or less than the number of steps shown and is not limited to the order of the steps. To describe the method 559, reference will be made to components of FIG. 2, although it is understood that the method 559 can be implemented in any other manner using other suitable components. The method 559 can be implemented in a single earpiece, a pair of earpieces, headphones, or other suitable headset audio delivery device.

Method 559 describes an audio forensics system for transferring recording audio data 537 from memory on the earphone 550 or a second data storage system 551 to an online server 537 for analysis 539 (for example, via Internet 531), or automatic speech-to-text processing 533, 535. The recorded audio data 536, (responsive to record start/stop module 535), is time-stamped 520 to mark when the recording commenced, and time-stamps may be embedded in the recorded data stream at regular intervals or to mark significant events such as detected transient events (FIG. 7). Transmission of data 529 recorded on non-volatile memory in the earphone 550 to a second data system may be invoked automatically by decision unit 525 when an in-cradle detection system 527 detects that the earphones are located in a docking station (e.g., for recharging batteries). Alternatively, or additionally, transmission of data 529 recorded on non-volatile memory in the earphone 550 to a second data system 551 may be invoked automatically whenever the AOBRS detects 523 the presence of a wireless communication system 521, such as Wifi or Bluetooth.

FIG. 10 is a flowchart of a method 600 for low remaining-memory warning in accordance with an exemplary embodiment. The method 600 can include more or less than the number of steps shown and is not limited to the order of the steps. To describe the method 600, reference will be made to components of FIG. 2, although it is understood that the method 600 can be implemented in any other manner using other suitable components. The method 600 can be implemented in a single earpiece, a pair of earpieces, headphones, or other suitable headset audio delivery device.

The method 600 can inform the user when the remaining data memory for storage of audio signals in the system 300 is critically low (similar to a low battery alarm). The record start/stop module 635 can get audio from the input buffer at step 636, and input the audio signal at step 638, to the non-volatile memory 208 on the earpiece 100 as shown in 651. A time stamp 620 can be included with the recorded audio signal.

During recording, the processor 121 at step 637 proceeds to determine if a total remaining record time is available. If the remaining record time is not available, the processor 121 can calculate it as shown in step 700 (see FIG. 11) and store the remaining record time to memory at step 643. At step 645 the processor 121 then determines if the total remaining record time is low. If the total record time is not low, the method proceeds back to step 636 to get the next audio from the input buffer. If, however, the total record time is low, a low-memory warning message generation system 800 (see FIG. 12) generates a low memory warning message at step 801. Upon delivering the low-memory warning message, a determination is made at step 647 to continue recording. The recording can stop at step 648, for example, in response to a user request or automatic event detection. The method 600 can proceed back to step 636 to get the next audio data if the recording is continued.

FIG. 11 is a flowchart of a method 700 for remaining record-time in accordance with an exemplary embodiment. The method 700 can include more or less than the number of steps shown and is not limited to the order of the steps. To describe the method 700, reference will be made to components of FIG. 2, although it is understood that the method 700 can be implemented in any other manner using other suitable components. The method 700 can be implemented in a single earpiece, a pair of earpieces, headphones, or other suitable headset audio delivery device.

At step 750, the method 700 can start. At step 751, the processor 121 can determine if a total remaining memory of data storage of a device is known. If the total remaining memory is known, and the recording data rate is known at step 755, the data can be recorded at a designated recording rate as shown in step 761 based on the remaining memory and the data rate. If the recording rate is not known at step 755, the processor 121 can calculate the recording data rate at step 759 (e.g., 512 kps).

If however, at step 751, the total remaining memory is not known, the processor 121 can calculate a total remaining memory of data storage at step 752 using the non-volatile memory on the earpiece 100 from step 754. At step 753, the total remaining memory of the device can be used in step 757 to estimate a remaining recording time (A/B). At step 763, the total remaining recording time can be output. For instance, upon the completion of method 700, the earpiece 100 can present a warning indication with the total remaining recording time left on the earpiece 100.

FIG. 12 is a flowchart of a method 800 for remaining memory in accordance with an exemplary embodiment. The method 800 can include more or less than the number of steps shown and is not limited to the order of the steps. To describe the method 800, reference will be made to components of FIG. 2, although it is understood that the method 800 can be implemented in any other manner using other suitable components. The method 800 can be implemented in a single earpiece, a pair of earpieces, headphones, or other suitable headset audio delivery device.

Briefly, method 800 prioritizes warning levels for reporting based on memory usage and remaining memory capacity. The method 800 can start when the "always-on" binaural recording feature is running on the earpiece 100. Notably, the memory 208 will be filled as recent portions of audio history are committed to the memory 208. The processor 121 can periodically check the memory capacity to determine when, and a type of warning message, to be sent to the user.

At step 867, the processor 121 can compare the remaining memory to a warning memory threshold (WMT_2) indicated in a database 865. For instance, the WMT_2 can be set to 5% remaining capacity. If the remaining memory is greater than the WMT_2 (>95% used capacity), the processor 121 can assign a priority level 1 and generate a polite verbal warning message to the user at step 873. The audio output of the warning message can be conditioned (e.g., gain, EQ) at step 821 and delivered to the user via the left ECR 833 and right ECR 835 of the earpiece. If however at step 871, the remaining memory is less than the WMT_2, but greater than a WMT_3, the processor 121 can assign a priority level2 and generate a repeating warning message (obtrusive auditory alarm) audibly presented to the user as shown in step 875. If however at step 871, the remaining memory is less than a WMT_3 retrieved from data base 869, the processor 121 can assign a priority level 3 and generate a final verbal warning message to the user at step 877.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

We claim:

1. A headset, comprising:
a left earpiece including:
    a first left Ambient Sound Microphone (L1 ASM) configured to capture a first ambient sound,
    a second left Ambient Sound Microphone (L2ASM) configured to capture a second ambient sound,
    a left Ear Canal Microphone (LECM) configured to capture a first internal sound in a left ear canal, wherein the L1ASM, L2ASM, and the LECM are part of a single left earpiece, wherein the LECM is placed so that it is closer to a user's left ear canal than the placement of the L1ASM when the left earpiece is being worn by user, and wherein the LECM captures the first internal sound through a first opening in the left earpiece that is within the left ear canal when the left earpiece is worn by the user, and
    a left speaker configured to play a first audio content into the user's left ear canal;
a right earpiece including:
    a first right Ambient Sound Microphone (R1 ASM) configured to capture a third ambient sound,
    a second right Ambient Sound Microphone (R2ASM) configured to capture a fourth ambient sound, and

a right Ear Canal Microphone (RECM) configured to capture a second internal sound in a right ear canal, wherein the R1ASM, R2ASM, and the RECM are part of a single right earpiece wherein the RECM is placed so that it is closer to a user's right ear canal than the placement of the R1ASM when the right earpiece is being used by user, and wherein the RECM captures the second internal sound through a second opening in the right earpiece that Is within the right ear canal when the right earpiece is worn by the user, and
    a right speaker configured to play a second audio content into the user's right ear canal, wherein the first audio content and the second audio content are played at the same time;
a memory, wherein the memory is configured to record at least one of the first ambient sound or the third ambient sound and at least one of the first internal sound or the second internal sound, and
a processor operatively coupled to the left earpiece, the right earpiece and the memory, the processor configured to save, when the processor detects the user is speaking, a first portion of the second ambient sound or second portion of the fourth ambient sound or a combination of both, wherein the processor is configured to save, when the processor detects the user is speaking, a third portion of the first internal sound or a fourth portion of the second internal sound or a combination of both, wherein the processor detects whether the user is speaking by using at least one of the first internal sound, the second internal sound, a motion sensor, or a combination of both, wherein the processor detects an event, if the user is speaking, by analyzing at least one of the first portion or the second portion or a combination of both, and wherein the left earpiece, the right earpiece, the memory and the processor are part of a single headset.

2. The headset of claim 1, wherein the processor detects whether the user is speaking by using the motion sensor, wherein the motion sensor is an accelerometer.

3. The headset of claim 1, wherein the processor also detects the event when the processor detects at least one of an abrupt movement of the headset, or a touching of the left earpiece, or a touching of the right earpiece, or a voice command, or a starting of a phone call, or an ending of a phone call or a change in location of the headset or a combination thereof.

4. The headset of claim 1, wherein the memory comprises:
a data buffer to temporarily capture the at least one of the first ambient sound or the third ambient sound and the at least one of the first internal sound or the second internal sound; and
a storage memory to save from the data buffer the first portion or the second portion or both.

5. The headset of claim 4, wherein the data buffer is a circular buffer that temporarily stores data from at least one of the first ambient sound or the third ambient sound and at least one of the first internal sound or the second internal sound, wherein the time span of the data is from a current time point to a previous time point.

6. The headset of claim 5, wherein the time span is two minutes.

7. The headset of claim 1, wherein at least one of the first internal sound or the second internal sound is an ambient sound, speech, or audio content.

8. The headset of claim 1, wherein the left earpiece and the right earpiece constitute a microphone array, and the processor increases a signal to noise ratio of audio content delivered to the headset with respect to the first or second ambient sound or a combination thereof using the microphone array.

9. The headset of claim 1, wherein the processor binaurally records the first ambient sound and the third ambient sound.

10. The headset of claim 1, further comprising:

an audio interface communicatively coupled to the processor to deliver the first audio content and the second audio content.

11. The headset of claim 1, wherein at least one of either the left or right earpiece is wirelessly connected to a communication device, wherein the earpiece not wirelessly connected to the communication device is wirelessly connected to the earpiece that is wirelessly connected to the communication device.

12. An earpiece, comprising:

a first Ambient Sound Microphone (ASM1) configured to capture a first ambient sound;

a second Ambient Sound Microphone (ASM2) configured to capture a second ambient sound;

an Ear Canal Microphone (ECM) configured to capture internal sound in an ear canal;

a memory; and a processor operatively coupled to the ECM and the memory, wherein the ASM1, the ASM2, and the ECM are part of a single earpiece, wherein the ECM is placed so that it is closer to a user's ear canal than the placement of the ASM1 when the earpiece is being worn by the user, and wherein the ECM captures the internal sound through an opening in the earpiece that is within the left ear canal when the earpiece is being worn by the user; and a speaker configured to play an audio content into the user's ear canal while the ASM1 captures the first ambient sound and while the ASM2 captures the second ambient sound, wherein the processor saves a first portion of the captured first ambient sound and saves a second portion of the captured internal sound when the processor detects that the user is speaking, wherein the processor detects whether the user is speaking by using the internal sound and the first ambient sound, and wherein the processor detects an event, if the user is speaking, by analyzing the first ambient sound or the second ambient sound.

13. The earpiece of claim 12, wherein the event is detected when a modified portion of the first ambient sound matches a stored sonic signature of the event within a threshold.

14. The earpiece of claim 13, wherein the modified portion is a sonic signature of part of the ambient sound.

15. The earpiece of claim 14, wherein the event is a touching of the earpiece.

16. The earpiece according to claim 14, wherein the event is a voice command.

17. The earpiece according to claim 13, wherein the event is a starting or ending of a phone call.

18. The earpiece according to claim 13, wherein the event is an abrupt movement of the earpiece.

19. A method comprising:

receiving a first sound measured from a first microphone;

receiving a second sound measured from a second microphone;

receiving a third sound measured from a third microphone;

storing the first sound into memory;

receiving motion data from a motion sensor;

storing the second sound into memory;

storing the third sound into memory;

receiving audio content from a communication device;

analyzing at least one of the first sound or the second sound or the motion data to detect a user speaking, wherein a processor performs the analysis, wherein the first microphone, the second microphone, the third microphone, the memory, the processor and a speaker are part of a single wearable device, wherein the third microphone is located closer to the user than the first or second microphones when the wearable device is worn or carried by the user;

saving a first portion of the first sound and a second portion of the second sound and a third portion of the third sound if the processor detects the user speaking; and analyzing at least one of the first portion or the second portion or the third portion to detect a voice command.

20. The method according to claim 19, wherein the voice command is detected when a modified first portion or a modified second portion or a modified third portion matches a stored sonic signature within a threshold.

* * * * *